United States Patent
Hansen et al.

(10) Patent No.: US 11,965,181 B2
(45) Date of Patent: Apr. 23, 2024

(54) INCREASED BIOSYNTHESIS OF BENZYLISOQUINOLINE ALKALOIDS AND BENZYLISOQUINOLINE ALKALOID PRECURSORS IN A RECOMBINANT HOST CELL

(71) Applicant: RIVER STONE BIOTECH LLC, Wilmington, DE (US)

(72) Inventors: Esben Halkjaer Hansen, Frederiksbeg (DK); Markus Schwab, Lorrach (DE); Philipp Berninger, Basel (CH); Fanny Delgrange, Hagenthal-le-Haut (FR); Franziska Grassinger, Basel (CH)

(73) Assignee: RIVER STONE BIOTECH, INC., Wilmington, DE (US)

( * ) Notice: Subject to any disclaimer, the term of this patent is extended or adjusted under 35 U.S.C. 154(b) by 0 days.

(21) Appl. No.: 17/351,381

(22) Filed: Jun. 18, 2021

(65) Prior Publication Data
US 2021/0340505 A1    Nov. 4, 2021

Related U.S. Application Data

(62) Division of application No. 16/324,284, filed as application No. PCT/EP2017/070253 on Aug. 9, 2017, now Pat. No. 11,060,071.

(60) Provisional application No. 62/524,120, filed on Jun. 23, 2017, provisional application No. 62/372,356, filed on Aug. 9, 2016.

(51) Int. Cl.
| | | |
|---|---|---|
| *C12N 9/04* | (2006.01) | |
| *C12N 9/02* | (2006.01) | |
| *C12P 17/12* | (2006.01) | |

(52) U.S. Cl.
CPC ......... *C12N 9/0006* (2013.01); *C12N 9/0008* (2013.01); *C12P 17/12* (2013.01); *C12Y 101/01001* (2013.01); *C12Y 101/01006* (2013.01); *C12Y 101/01021* (2013.01); *C12Y 101/01026* (2013.01); *C12Y 101/01034* (2013.01); *C12Y 101/01035* (2013.01); *C12Y 101/01041* (2013.01); *C12Y 101/01046* (2013.01); *C12Y 101/01049* (2013.01); *C12Y 101/01076* (2013.01); *C12Y 101/0109* (2013.01); *C12Y 101/05003* (2013.01)

(58) Field of Classification Search
None
See application file for complete search history.

(56) References Cited

FOREIGN PATENT DOCUMENTS

| | | |
|---|---|---|
| WO | WO 2011/058446 A2 | 5/2011 |
| WO | WO 2015/066642 A1 | 7/2015 |
| WO | WO 2016/179296 A1 | 11/2016 |
| WO | WO 2016/183023 A1 | 11/2016 |

OTHER PUBLICATIONS

Accession Q04894. Nov. 1, 1997. (Year: 1997).*
Accession D6W0E6. Nov. 1, 1997. (Year: 1997).*
Chenna et al. Multiple sequence alignment with the Clustal series of programs. Nucl. Acids Res. Vol. 31, No. 13, pp. 3497-3500 (2003).
Fossati et al. Synthesis of Morphinan Alkaloids in *Saccharomyces cerevisiae*. PLoS ONE 10(4): e0124459 (2015).
Hagel JM & P. Facchini. Benzylisoquinoline Alkaloid Metabolism: A Century of Discovery and a Brave New World. Plant Cell Physiol. 54(5): 647-672 (2013).
Hawkins K.M. & C.D. Smolke. Production of benzylisoquinoline alkaloids in *Saccharomyces cerevisiae*. Nat Chem. Biol., 4:564-573 (2008).
Hawkins, Metabolic Engineering of *Saccharomyces cerevisiae* for the Production of Benzylisoquinoline Alkaloids. PHD Thesis, CaltechTHESIS, XP055361294, p. 1-154 (Jan. 1, 2009).
Lari et al. Structural Basis of Enzymatic (S)-Norcoclaurine Biosynthesis. J Biol. Chem. Vol.284, No. 2, pp. 897-904 (2009).
Mnaimneh et al. Exploration of Essential Gene Functions via Titratable Promoter Alleles. Cell., vol. 118, 31-44 2004).
Nakagawa et al. (R,S)-Tetrahydropapaveroline production by stepwise fermentation using engineered *Escherichia coli*. Sci. Rep., 4:6695 (2014).
Nakagawa et al. A bacterial platform for fermentative production of plant alkaloids. Nature Communications. 2:326 (2011).
Thodey et al. A microbial biomanufacturing platform for natural and semisynthetic opioids. Nat Chem. Biol., 10 (10) 837-844 (2014).
Chica et al., Curr Opin Biotechnol. Aug. 2005; 16(4):378-84. (Year 2005).
Singh et al. Curr Protein Pept Sci. 2017, 18, 1-11 (Year: 2017).
Kizer et al. Appl Environ Microbiol. May 2008; 74(10):3229-41. (Year 2008).
Prather et al. Curr Opin Biotechnol. Oct. 2008; 19(5):468-74. (Year: 2008).
Accession P53111. Oct. 1, 1996 (Year: 1996).
Acession Q12068. Oct. 25, 2004 (Year: 2004).

* cited by examiner

*Primary Examiner* — Christian L Fronda
(74) *Attorney, Agent, or Firm* — McDonnell Boehnen Hulbert & Berghoff LLP

(57) ABSTRACT

Recombinant microorganisms, plants, and plant cells are disclosed that have been engineered to have reduced levels or activity of one or more alcohol dehydrogenases or aldehyde reductases thereby increasing the production of benzylisoquinoline alkaloids and/or benzylisoquinoline alkaloid precursors.

20 Claims, 4 Drawing Sheets

Specification includes a Sequence Listing.

INCREASED BIOSYNTHESIS OF BENZYLISOQUINOLINE ALKALOIDS AND BENZYLISOQUINOLINE ALKALOID PRECURSORS IN A RECOMBINANT HOST CELL

CROSS-REFERENCE TO RELATED APPLICATIONS

This application is a divisional of U.S. application Ser. No. 16/324,284, filed Feb. 8, 2019, which is a national stage application under 35 U.S.C. § 371 of International Application No. PCT/EP2017/070253, filed Aug. 9, 2017, which claims the benefit of U.S. Provisional Application Ser. No. 62/372,356, filed Aug. 9, 2016, and U.S. Provisional Application Ser. No. 62/524,120, filed Jun. 23, 2017, the disclosures of each of which are explicitly incorporated herein by reference in their entirety.

SEQUENCE LISTING STATEMENT

A computer readable form of the Sequence Listing is filed with this application by electronic submission and is incorporated into this application by reference in its entirety. The Sequence Listing is contained in the file created on Jun. 16, 2021 having the file name "15-992-WO-US-DIV_Sequence-Listing_ST25.txt" and is 182 kb in size.

BACKGROUND OF THE INVENTION

Field of the Invention

The invention disclosed herein relates generally to the field of genetic engineering. Particularly, the invention disclosed herein provides methods for biosynthetic production of benzylisoquinoline alkaloid compounds and benzylisoquinoline alkaloid precursors in a genetically modified cell.

Description of Related Art

Benzylisoquinoline alkaloids (BIAs) are a broad class of plant secondary metabolites with diverse pharmaceutical properties including, for example, analgesic, antimicrobial, antitussive, antiparasitic, cytotoxic, and anticancer properties (Hagel & Facchini, 2013, Plant Cell Physiol. 54(5); 647-672). Thousands of distinct BIAs have been identified in plants, each of which derive from a common precursor: (S)-norcoclaurine (see e.g., Hagel & Facchini, 2013, Plant Cell Physiol. 54(5); 647-672; Fossati et al., 2015, PLoS ONE 10(4): e0124459).

While BIAs are widely used in human health and nutrition, current production is achieved mainly by extraction from plants. However, extraction of these compounds from plants often provides low yields due, in part, to low levels of the metabolites within the plant cells (Nakagawa et al., 2011, Nature Communications, 2:326; DOI:10.1028/ncomms1327). Extraction of sufficient quantities of just the opiate morphine, a widely-prescribed analgesic BIA, to meet medical needs requires industrial processing of tens to hundreds of thousand tons of *Papaver somniferum* (opium poppy) biomass per year (Thodey and Smolke, 2014, Nat Chem Biol., 10(10):837-844). Chemical synthesis of BIAs is not a viable alternative for commercial production due to the complex regio- and stereochemistry of BIAs (see e.g., Thodey and Smolke, 2014; Hagel and Facchini, 2013).

Recently, synthesis of BIA branch point intermediate reticuline has been reported from simple carbon sources in *E. coli* (Nakagawa et al., 2014, Sci Rep., 4:6695) and from (R,S)-norlaudanosoline in *S. cerevisiae* (Hawkins and Smolke, 2008, Nat Chem Biol., 4:564-573), and production of morphine and semi-synthetic opioids from thebaine in *S. cerevisiae* was also recently reported (Thodey et al., 2014, Nat Chem Biol., 10:837-844). However, low yields of intermediates at the beginning of the BIA pathway and the corresponding inability to reconstitute a complete BIA pathway from a low cost substrate currently prevent BIA synthesis from being a viable microbial process (Fossati et al., 2015, PLoS ONE 10(4): e0124459). One such problem to be resolved is the extreme inefficiency in yeast of the initial conversion of dopamine and 4-HPAA (4-hydroxyphenylacetaldehyde) (or 3,4-DHPAA (3,4-Dihydroxyphenylacetaldehyde) in the alternative pathway) via norcoclaurine synthase (NCS), which results in low yields of intermediate (S)-Norcoclaurine ((S)-Norlaudanosoline in the alternative pathway) (see e.g., Hawkins and Smolke, 2008, Nat Chem Biol., 4:564-573). This inefficiency has resulted in requiring fed dopamine concentrations of approximately 100 mM, or bypassing the reaction altogether in favor of using Norcoclaurine or Norlaudanosoline as the initial substrate for conversion to (S)-Reticuline (see Hawkins and Smolke, 2008, Nat Chem Biol., 4:564-573).

There is thus a need in this art to increase production of metabolic intermediates at the beginning of the BIA pathway to enable production of valuable products of the BIA pathway more efficiently and economically.

SUMMARY OF THE INVENTION

It is against the above background that this invention provides certain advantages and advancements over the prior art.

Although this invention disclosed herein is not limited to specific advantages or functionality, the invention disclosed herein provides recombinant host cells capable of increased production of one or more benzylisoquinoline alkaloids or benzylisoquinoline alkaloid precursors, or both, having:
(a) reduced or eliminated enzymatic activity of a first alcohol dehydrogenase or aldehyde reductase; and, optionally,
(b) reduced or eliminated enzymatic activity of one or more second alcohol dehydrogenases or aldehyde reductases, or a combination thereof, wherein the activity of each of the enzymes in (a) and (b) is reduced or eliminated by having disrupted or deleted one or more genes encoding said enzyme, and whereby the host cell is thereby capable of increased production of one or more benzylisoquinoline alkaloids or benzylisoquinoline alkaloid precursors, or both, than are produced in wild-type cell.

The invention further provides methods for producing a benzylisoquinoline alkaloid or a benzylisoquinoline alkaloid precursor, comprising:
(a) providing a recombinant host that has reduced or eliminated activity of (i) a first alcohol dehydrogenase or aldehyde reductase and, optionally, (ii) one or more second alcohol dehydrogenases or aldehyde reductases, or a combination thereof, wherein the activity of each of the enzymes in (i) and (ii) is reduced or eliminated by disrupting or deleting one or more genes encoding said enzyme, wherein said cell has been genetically engineered to produce a benzylisoquinoline alkaloid and/or a benzylisoquinoline alkaloid precursor;

(b) cultivating said recombinant host for a time sufficient for said recombinant host to produce a benzylisoquinoline alkaloid and/or a benzylisoquinoline alkaloid precursor; and, optionally, (c) isolating the benzylisoquinoline alkaloid and/or a benzylisoquinoline alkaloid precursor from said recombinant host or from the cultivation supernatant, thereby producing a benzylisoquinoline alkaloid and/or a benzylisoquinoline alkaloid precursor.

In certain embodiments of the recombinant host cells or the methods disclosed herein, the cells produce one or more benzylisoquinoline alkaloid precursors. Particular benzylisoquinoline alkaloid precursors produced in said embodiments are (S)-reticuline or (S)-norcoclaurine.

In some aspects, the first alcohol dehydrogenase is Alcohol Dehydrogenase 3 (ADH3) (SEQ ID NOs: 29 & 30), Alcohol Dehydrogenase 4 (ADH4) (SEQ ID NOs: 31 & 32), Alcohol Dehydrogenase 5 (ADH5) (SEQ ID NOs:1 & 2), Alcohol Dehydrogenase 6 (ADH6) (SEQ ID NOs: 3 & 4), Alcohol Dehydrogenase 7 (ADH7) (SEQ ID NOs: 5 & 6), Genes de Respuesta a Estres 2 (GRE2) (SEQ ID NOs: 7 & 8), Aryl-alcohol Dehydrogenase 3 (AAD3) (SEQ ID NOs: 25 & 26), Aryl-alcohol Dehydrogenase 4 (AAD4) (SEQ ID NOs: 27 & 28), Butanediol dehydrogenase 1 (BDH1) (SEQ ID NOs: 35 & 36), medium-chain alcohol dehydrogenase BDH2 (SEQ ID NOs: 37 & 38), arabinose dehydrogenase ARA1 (SEQ ID NOs: 61 & 62), glycerol dehydrogenase GCY1 (SEQ ID NOs: 41 & 42), 3-hydroxyacyl-CoA dehydrogenase FOX2 (SEQ ID NOs: 39 & 40), Aryl-alcohol Dehydrogenase YPL088W (SEQ ID NOs: 59 & 60), glucose-6-phosphate dehydrogenase ZWF1 (SEQ ID NOs: 57 & 58), Glycerol-3-Phosphate Dehydrogenase (GPD1) (SEQ ID NOs: 45 & 46), HIS4 (SEQ ID NOs: 47 & 48), NADP-specific Isocitrate Dehydrogenase (IDP1) (SEQ ID NOs: 51 & 52), homo-isocitrate dehyrogenases (LYS12) (SEQ ID NOs: 53 & 54), or a homolog thereof.

In some aspects, the first aldehyde reductase is Aldehyde Reductase Intermediate 1 (ARI1) (SEQ ID NOs: 15 & 16), Genes de Respuesta a Estres 3 (GRE3) (SEQ ID NOs: 9 & 10), aldehyde reductase YCR102C (SEQ ID NOs: 19 & 20), aldehyde reductase YDR541C (SEQ ID NOs: 11 & 12), SER33 (SEQ ID NOs: 55 & 56), aldehyde reductase YGL039W (SEQ ID NOs: 17 & 18), aldehyde reductase YLR460C (SEQ ID NOs: 13 & 14), aldehyde reductase YPR127W (SEQ ID NOs: 21 & 22), aldehyde dehydrogenase 6 (ALD6) (SEQ ID NOs: 33 & 34), GlyOxylate Reductase (GOR1) (SEQ ID NOs: 43 & 44), 3-Hydroxy-3-MethylGlutaryl-coenzyme a reductase (HMG1) (SEQ ID NOs: 49 & 50), or a homolog thereof.

In some aspects, the one or more second alcohol dehydrogenases or aldehyde reductases, or a combination thereof, is ADH3 (SEQ ID NOs: 29 & 30), ADH4 (SEQ ID NOs: 31 & 32), ADH5 (SEQ ID NOs:1 & 2), ADH6 (SEQ ID NOs: 3 & 4), ADH7 (SEQ ID NOs: 5 & 6), GRE2 (SEQ ID NOs: 7 & 8), AAD3 (SEQ ID NOs: 25 & 26), AAD4 (SEQ ID NOs: 27 & 28), BDH1(SEQ ID NOs: 35 & 36), BDH2 (SEQ ID NOs: 37 & 38), ARA1 (SEQ ID NOs: 61 & 62), GCY1 (SEQ ID NOs: 41 & 42), FOX2 (SEQ ID NOs: 39 & 40), Aryl-alcohol Dehydrogenase YPL088W (SEQ ID NOs: 59 & 60), glucose-6-phosphate dehydrogenase ZWF1 (SEQ ID NOs: 57 & 58), GPD1 (SEQ ID NOs: 45 & 46), HIS4 (SEQ ID NOs: 47 & 48), IDP1 (SEQ ID NOs: 51 & 52), LYS12 (SEQ ID NOs: 53 & 54), ARI1 (SEQ ID NOs: 15 & 16), GRE3 (SEQ ID NOs: 9 & 10), aldehyde reductase YCR102C (SEQ ID NOs: 19 & 20), aldehyde reductase YDR541C (SEQ ID NOs: 11 & 12), SER33 (SEQ ID NOs: 55 & 56), aldehyde reductase YGL039W (SEQ ID NOs: 17 & 18), aldehyde reductase YLR460C (SEQ ID NOs: 13 & 14), aldehyde reductase YPR127W (SEQ ID NOs: 21 & 22), ALD6 (SEQ ID NOs: 33 & 34), GOR1 (SEQ ID NOs: 43 & 44), HMG1 (SEQ ID NOs: 49 & 50), or a homolog thereof.

In some aspects of the recombinant host cell or methods disclosed herein, the recombinant host is a microorganism.

In some aspects of the recombinant host cell or methods disclosed herein, the microorganism is *Saccharomyces cerevisiae, Schizosaccharomyces pombe, Escherichia coli*, or *Yarrowia lipolytica*.

In some aspects of the recombinant host cell or methods disclosed herein, the recombinant host is a plant, an alga, or a cell thereof.

These and other features and advantages of this invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of this invention can be best understood when read in conjunction with the following drawings.

FIG. 1 includes biosynthesis of (S)-Reticuline via the natural plant pathway, the alternative pathway in bacteria (with bacterial enzymes italicized and underlined), and yeast, which can utilize both the plant and bacterial pathways. Enzymatic examples (with GenBank accession numbers) and other protein abbreviations within FIG. 1 are as follows: TYDC (Tyrosine decarboxylase) of *Papaver somniferum* (GenBank accession nos. P54768 or U08597) or *Thalictrum flavum* (GenBank accession no. AF314150); TYR (Tyrosinase) of *Rattus norvegicus* (GenBank accession no. NM012740) or *Streptomyces castaneoglobisporus* (ScTYR containing tyrosinase and adaptor protein, ORF378, GenBank accession nos. AY254101 and AY254102); HPPDC (hydroxyphenylpyruvate decarboxylase) of *S. cerevisiae* (GenBank accession no. NP_010668.3); DODC (aromatic-L-amino-acid decarboxylase) of *Pseudomonas putida* (GenBank accession no. AE015451); MAO (monoamine oxidase) of *Micrococcus luteus* (GenBank accession no. AB010716); NCS ((S)-norcoclaurine synthase) of *Coptis japonica* (GenBank accession no. AB267399.2) and *S. cerevisiae* codon-optimized (SEQ ID NOs: 23 & 24); 6OMT (Norcoclaurine 6-O-methyltransferase) of *P. somniferum* (GenBank accession no. Q6WUC1) or *C. japonica* (GenBank accession no. D29811); SAM (S-adenosyl-L-methionine); CNMT (Coclaurine-N-methyltransferase) of *C. japonica* (GenBank accession no. Q948P7) or *T. flavum* (GenBank accession no. AY610508) or *P. somniferum* (GenBank accession no. AY217336); CYP80B (N-methylcoclaurine 3'-monooxygenase) of *P. somniferum* (GenBank accession no. 064899); 4'OMT (3'-hydrozy-N-methyl-(S)-coclaurine 4'-O-methyltransferase) of *C. japonica* (GenBank accession no. Q9LEL5); STORR ((S)-to-(R)-reticuline) of *P. somniferum* (GenBank accession no. P0DKI7); SAS (salutaridine synthase) of *P. somniferum* (GenBank accession no. EF451150); SAR (salutaridine reductase) of *P. somniferum* (GenBank accession no. DQ316261); NADPH (nicotinamide adenine dinucleotide phosphate); SAT (salutaridinol acetyl transferase) with acetyl-CoA of *P. somniferum* (GenBank accession no. AF339913); T6ODM (thebaine 6-O-demethylase) of *P. somniferum* (GenBank accession no. GQ500139); 2-OG (2-oxoglutarate); CODM (codeine 3-O-demethylase) of *P. somniferum* (GenBank accession no. GQ500141); NADH (nicotinamide adenine dinucleotide); morA (morphine 6-dehydrogenase) of *Pseudomonas putida* (GenBank accession no. T2HEI8); morB (morphinone reductase) of *P. putida* (GenBank accession no. Q51990); COR (codeinone reductase) of *P. somniferum* (GenBank accession no. AF108432); CODM (codeine 3-O-demethylase) of *P. somniferum* (GenBank accession no. D4N502).

DETAILED DESCRIPTION OF THE INVENTION

All publications, patents and patent applications cited herein are hereby expressly incorporated by reference for all purposes.

Methods well known to those skilled in the art can be used to construct genetic expression constructs and recombinant cells according to this invention. These methods include in vitro recombinant DNA techniques, synthetic techniques, in vivo recombination techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

Before describing this invention in detail, a number of terms are defined. As used herein, the singular forms "a", "an", and "the" include plural referents unless the context clearly dictates otherwise. For example, reference to a "nucleic acid" means one or more nucleic acids.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of this invention.

For the purposes of describing and defining this invention it is noted that the terms "reduced", "reduction", "increase", "increases", "increased", "greater", "higher", and "lower" are utilized herein to represent comparisons, values, measurements, or other representations to a stated reference or control.

For the purposes of describing and defining this invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the terms "polynucleotide", "nucleotide", "oligonucleotide", and "nucleic acid" can be used interchangeably to refer to nucleic acid comprising DNA, RNA, derivatives thereof, or combinations thereof.

Synthesis of Benzylisoquinoline Alkaloids

Figure 1:
FIG. 1 is a schematic of biosynthesis of benzylisoquinoline alkaloids and benzylisoquinoline alkaloid precursors from L-tyrosine.

With reference to the metabolic pathway illustrated in FIG. 1, in plants, BIA synthesis proceeds through condensation of the L-tyrosine derivatives L-dopamine and 4-hydroxyphenylacetaldehyde (4-HPAA) to produce (S)-norcoclaurine, which is catalyzed by the enzyme norcoclaurine synthase (NCS) of *Coptis japonica* (GenBank accession no. AB267399.2) (*S. cerevisiae* codon-optimized: SEQ ID NOs: 23 & 24) (see e.g., Fossati et al., 2015, PLoS ONE 10(4): e0124459; Ilari et al., *J Biol Chem,* 2009, 284:897-904; FIG. 1). (S)-Norcoclaurine is then converted to (S)-Coclaurine by the enzyme 6-O-methyltransferase (6-OMT) of *P. somniferum* (GenBank accession no. Q6WUC1) or *C. japonica* (GenBank accession no. D29811), followed by conversion of (S)-Coclaurine to (S)-N-Methylcoclaurine by (CNMT) of *C. japonica* (GenBank accession no. Q948P7) or *T. flavum* (GenBank accession no. AY610508) or *P. somniferum* (GenBank accession no. AY217336); conversion of (S)-N-Methylcoclaurine to (S)-3'-Hydroxy-N-methylcoclaurine by N-methylcoclaurine 3'-hydroxylase (CYP80B) of *P. somniferum* (GenBank accession no. 064899); and finally conversion of (S)-3'-Hydroxy-N-methylcoclaurine to the branch point intermediate (S)-reticuline via 4'-O-methyltransferase (4'OMT) of *C. japonica* (GenBank accession no. Q9LEL5). Yeast can also utilize the pathway traditionally used by plants.

An alternative pathway to biosynthesis of (S)-Reticuline also set forth in FIG. 1 has been developed in bacteria, but which yeast are also able to utilize, in which the L-tyrosine derivatives L-dopamine and 3,4-Dihydroxyphenylacetaldehyde (3,4-DHPAA) are condensed by norcoclaurine synthase (NCS) of *Coptis japonica* (GenBank accession no. AB267399.2) and *S. cerevisiae* codon-optimized (SEQ ID NOs: 23 & 24) to produce (S)-Norlaudanosoline. This alternative pathway continues to produce (S)-Reticuline via conversion of (S)-Norlaudanosoline to (S)-3'-Hydroxycoclaurine by 6-OMT of *P. somniferum* (GenBank accession no. Q6WUC1) or *C. japonica* (GenBank accession no. D29811); conversion of (S)-3'-Hydroxycoclaurine to (S)-3'-Hydroxy-N-methylcoclaurine by CNMT of *C. japonica* (GenBank accession no. Q948P7) or *T. flavum* (GenBank accession no. AY610508) or *P. somniferum* (GenBank accession no. AY217336); and, finally, conversion of (S)-3'-Hydroxy-N-methylcoclaurine to (S)-Reticuline by 4'OMT of *C. japonica* (GenBank accession no. Q9LEL5) (FIG. 1). In plants and microorganisms, synthesis of BIAs from the intermediate (S)-Reticuline proceeds via known enzymatic reactions (see FIG. 1).

As disclosed herein, disrupting or knocking out certain enzymes, including alcohol dehydrogenases, and/or aldehyde reductases, or similar enzymes, decreases the amount of 4-hydroxyphenylacetaldehyde (4-HPAA) that is reduced to the byproduct 4-hydroxyphenylacetalcohol. See FIG. 1. This is of commercial importance because retention of 4-HPAA in the plant reticuline pathway, or 3,4-DHPAA in the alternative bacterial reticuline pathway improves conversion of dopamine and 4-HPAA or 3,4-DHPAA to (S)-Norcoclaurine and (S)-Norlaudanosoline, respectively, via norcoclaurine synthase (NCS).

This invention provides a recombinant host that is capable of producing increased amounts of benzylisoquinoline alkaloids (BIAs) and/or benzylisoquinoline alkaloid (BIA) precursors, as disclosed herein, and does not produce, or has reduced production of, one or more alcohol dehydrogenases and/or, one or more aldehyde reductases. A recombinant host that produces or is capable of producing BIAs and/or BIA precursors as disclosed herein is a host cell that expresses the necessary biosynthetic enzymes to produce BIAs and/or BIA precursor from a primary substrate, e.g., glucose, or from an intermediate molecule, e.g., L-tyrosine. See e.g., Fossati et al., 2015, PLoS ONE 10(4): e0124459; Ilari et al., *J Biol Chem*, 2009, 284:897-904; Hawkins and Smolke, 2008, Nat Chem Biol., 4:564-573; FIG. 1.

As used herein a recombinant host that fails to produce an enzyme, has reduced production of an enzyme, or lacks a functional enzyme, includes an organism that has been recombinantly modified such that the gene encoding the enzyme is knocked out, an organism in which the gene encoding the enzyme contains one or more mutations that reduce or diminish the activity of the enzyme compared to a wild-type organism, or an organism wherein the promoter of the gene encoding the enzyme has been modified or deleted so that the enzyme is expressed at a reduced level compared to a wild-type organism or is not expressed.

Many methods for genetic modification of target genes are known to one skilled in the art and may be used to create recombinant hosts of this invention. Modifications that may be used to reduce or eliminate expression of a target enzyme are disruptions that include, but are not limited to, deletion of the entire gene or a portion of the gene encoding an enzyme; inserting a DNA fragment into a gene encoding the enzyme (in either the promoter or coding region) so that the enzyme is not expressed or expressed at lower levels; introducing a mutation into the coding region for the enzyme, which adds a stop codon or frame shift such that a functional enzyme is not expressed; and introducing one or more mutations, including insertions and deletions, into the coding region of an enzyme to alter amino acids so that a non-functional or a less enzymatically active enzyme is expressed. In addition, expression of an enzyme can be blocked by expression of an antisense RNA or an interfering RNA, and constructs can be introduced that result in co-suppression. In addition, the synthesis or stability of the transcript can be lessened by mutation. Similarly, the efficiency by which an enzyme is translated from mRNA can be modulated by mutation. All of these methods can be readily practiced by one skilled in the art making use of the known sequences encoding the alcohol dehydrogenases and/or aldehyde reductases of this invention.

Alcohol dehydrogenase and aldehyde reductase sequences from a variety of organisms are known in the art and selection of target gene(s) is dependent upon the host selected. Representative alcohol dehydrogenase (ADH) and aldehyde reductase sequences, which can be targeted in accordance with this invention are listed in Table 1. One skilled in the art can choose specific modification strategies to eliminate or lower the expression of an alcohol dehydrogenase and/or aldehyde reductase as desired to facilitate production of BIAs and/or BIA precursors.

TABLE 1

| | | Amino Acid Sequence | | Nucleotide Sequence | |
|---|---|---|---|---|---|
| Target | | Accession No. | SEQ ID NO: | Accession No. | SEQ ID NO: |
| S. cerevisiae | ADH5 | NP_009703 | 1 | NM_001178493 | 2 |
| S. cerevisiae | ADH6 | NP_014051 | 3 | NM_001182831 | 4 |
| S. cerevisiae | ADH7 | NP_010030 | 5 | NM_001178812 | 6 |
| S. cerevisiae | GRE2 | NP_014490 | 7 | NM_001183405 | 8 |
| S. cerevisiae | GRE3 | NP_011972 | 9 | NM_001179234 | 10 |
| S. cerevisiae | YDR541C | NP_010830 | 11 | NM_001180849 | 12 |
| S. cerevisiae | YLR460C | NP_013565 | 13 | NM_001182348 | 14 |
| S. cerevisiae | ARI1 | NP_011358 | 15 | NM_001181022 | 16 |
| S. cerevisiae | YCR102C | NP_010026 | 19 | NM_001178809 | 20 |
| S. cerevisiae | YPR127W | NP_015452 | 21 | NM_001184224 | 22 |

In some aspects, the recombinant host cell disclosed herein has reduced or zero activity of a first alcohol dehydrogenase or aldehyde reductase and, optionally, reduced or zero activity of one or more second alcohol dehydrogenases, one or more aldehyde dehyrogenases, or a combination thereof, wherein the activity of each of the alcohol dehydrogenases or aldehyde reductases is reduced or eliminated by having disrupted or deleted one or more genes encoding the enzyme, and whereby the host cell is capable of increased production of one or more benzylisoquinoline alkaloids or benzylisoquinoline alkaloid precursors, or both, than are produced in wild-type cell capable of producing one or more benzylisoquinoline alkaloids or benzylisoquinoline alkaloid precursors.

In some aspects, a first alcohol dehydrogenase is ADH6 or a homolog thereof, e.g., CAD9, CAD3 or CAD2 from *A. thaliana*. In some aspects, one or more second alcohol dehydrogenases are ADH7, GRE2 (Genes de Respuesta a Estres 2), or a homolog thereof, e.g., AT1G51410 or AT5G19440; and the aldehyde reductase is ARI1 (Aldehyde Reductase Intermediate 1), Aldehyde Reductase YGL039W, or a homolog thereof, e.g., SPAC513.07 or YDR541C).

DNA sequences surrounding one or more of the above-referenced sequences are also useful in some modification procedures and are available for yeasts such as for *Saccharomyces cerevisiae* in the complete genome sequence coordinated by NCBI (National Center for Biotechnology Information) with identifying BioProject Nos. PRJNA128, PRJNA13838, PRJNA43747, PRJNA48559, PRJNA52955, PRJNA48569, PRJNA39317. Additional examples of yeast genomic sequences include that of *Schizosaccharomyces*

*pombe*, which is included in BioProject Nos. PRJNA127, PRJNA13836, and PRJNA20755. Genomic sequences of plants are also known in the art and the genomic sequence of *Arabidopsis thaliana* is included in BioProject Nos. PRJNA116, PRJNA10719, PRJNA13190, and PRJNA30811. Other genomic sequences can be readily found by one of skill in the art in publicly available databases.

In particular, DNA sequences surrounding an alcohol dehydrogenase or aldehyde reductase coding sequence are useful for modification methods using homologous recombination. For example, sequences flanking the gene of interest are placed on either side of a selectable marker gene to mediate homologous recombination whereby the marker gene replaces the gene of interest. Also partial gene sequences and flanking sequences bounding a selectable marker gene may be used to mediate homologous recombination whereby the marker gene replaces a portion of the target gene. In addition, the selectable marker may be bounded by site-specific recombination sites, so that following expression of the corresponding site-specific recombinase, the resistance gene is excised from the gene of interest without reactivating the latter. The site-specific recombination leaves behind a recombination site which disrupts expression of the alcohol dehydrogenase or aldehyde reductase. A homologous recombination vector can be constructed to also leave a deletion in the gene of interest following excision of the selectable marker, as is well known to one skilled in the art.

Deletions can be made using mitotic recombination as described in Wach et al. (1994, Yeast 10:1793-1808). This method involves preparing a DNA fragment that contains a selectable marker between genomic regions that may be as short as 20 bp, and which bind a target DNA sequence. This DNA fragment can be prepared by PCR amplification of the selectable marker gene using as primers oligonucleotides that hybridize to the ends of the marker gene and that include the genomic regions that can recombine with the yeast genome. The linear DNA fragment can be efficiently transformed into yeast and recombined into the genome resulting in gene replacement including with deletion of the target DNA sequence.

Moreover, promoter replacement methods may be used to change endogenous transcriptional control elements allowing another means to modulate expression such as described in Mnaimneh et al. (2004, Cell 118:31-44).

Hosts cells of use in this invention include any organism capable of producing BIAs and/or BIA precursors as disclosed herein, either naturally or synthetically, e.g., by recombinant expression of one or more genes of the BIA biosynthetic pathway (FIG. 1). A number of prokaryotes and eukaryotes are suitable for use in constructing the recombinant microorganisms described herein, e.g., gram-negative bacteria, gram-positive bacteria, yeast or other fungi. A species and strain selected for use as a BIA and/or BIA precursor production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species may be suitable. For example, suitable species may be in a genus *Agaricus, Aspergillus, Bacillus, Candida, Corynebacterium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces, Yarrowia* and *Lactobacillus*. Exemplary species from such genera include *Lentinus tigrinus, Laetiporus sulphureus, Phanerochaete chrysosporium, Pichia pastoris, Physcomitrella patens, Rhodoturula glutinis* 32, *Rhodoturula mucilaginosa, Phaffia rhodozyma* UBV-AX, *Xanthophyllomyces dendrorhous, Fusarium fujikuroi/Gibberella fujikuroi, Candida utilis* and *Yarrowia lipolytica*. In some aspects, a microorganism can be an Ascomycete such as *Gibberella fujikuroi, Kluyveromyces lactis, Schizosaccharomyces pombe, Aspergillus niger*, or *Saccharomyces cerevisiae*. In some aspects, a microorganism can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of BIAs and/or BIA precursors.

In some aspects, the recombinant host used with this invention is *S. cerevisiae*, which can be genetically engineered as described herein. *S. cerevisiae* is a widely used organism in synthetic biology, and can be used as the recombinant microorganism platform herein. There are libraries of mutants, plasmids, detailed computer models of metabolism and other information available for *S. cerevisiae*, permitting rational design of various modules to enhance product yield. Methods are known for making recombinant microorganisms. In some aspects, the *S. cerevisiae* strain is S288C (Mortimer and Johnston, 1986, Genetics 113:35-43).

*Aspergillus* species such as *A. oryzae, A. niger* and *A. sojae* are widely used microorganisms in food production, and can also be used as the recombinant microorganism platform. Thus, the recombinant host may be *Aspergillus* spp. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies.

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Rhodobacter* can be used as the recombinant microorganism platform. Similar to *E. coli*, there are libraries of mutants available as well as suitable plasmid vectors, allowing for rational design of various modules to enhance product yield. Methods similar to those described above for *E. coli* can be used to make recombinant *Rhodobacter* microorganisms.

*Physcomitrella* mosses, when grown in suspension culture, have characteristics similar to yeast or other fungal cultures. These genera are becoming an important type of cell for production of plant secondary metabolites, which can be difficult to produce in other types of cells. Thus, the recombinant host may be a *Physcomitrella* spp.

In some aspects, the recombinant host is a plant or plant cells that includes a sufficient number of genes from the BIA biosynthetic pathway set forth in FIG. 1 to produce one or more benzylisoquinoline alkaloids or benzylisoquinoline alkaloid precursors, or both. As disclosed herein, a plant or plant cell modified to express the BIA biosynthetic pathway can also contain a knockout of one or more alcohol dehydrogenases and/or aldehyde reductases to advantageously increase the yield thereof. Plant or plant cells can be stably transformed to retain the introduced nucleic acid with each cell division. A plant or plant cell can also be transiently transformed such that the heterologous nucleic acid is not integrated into its genome. Transiently transformed cells typically lose all or some portion of the introduced nucleic acid with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a heterologous nucleic acid, for example a recombinant nucleic acid construct into other lines, to transfer a heterologous nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Certain transgenic plants or plant cells can be grown in suspension culture. For the purposes of this invention, solid and/or liquid culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation; see U.S. Pat. Nos. 5,538,880; 5,204,253; 6,329,571; and 6,013,863. If a cell or cultured tissue is used as the recipient tissue for transformation, plants can be regenerated from transformed cultures if desired, by techniques known to those skilled in the art.

A population of transgenic plants can be screened and/or selected for those members of the population that have a trait or phenotype conferred by expression of the transgene. For example, a population of progeny of a single transformation event can be screened for those plants having a desired level of expression of a polypeptide or nucleic acid described herein. Physical and biochemical methods can be used to identify expression levels. These include Southern analysis or PCR amplification for detection of a polynucleotide; northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, western blots, immunoprecipitation, and enzyme-linked immunoassays to detect polypeptides. Other techniques such as in situ hybridization, enzyme staining, and immunostaining also can be used to detect the presence or expression of polypeptides and/or nucleic acids. Methods for performing all of the referenced techniques are known.

As an alternative, a population of plants with independent transformation events can be screened for those plants having a desired trait, such as production of BIAs and/or BIA precursors, and/or lack of conversion of 4-HPAA and/or 3,4-DHPAA to 4-hydroxyphenylacetalcohol and 3,4-Di hydroxyphenylacetalcohol, respectively. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant.

Depending on the particular organism used in this invention, the recombinant host cell can naturally or recombinantly express genes encoding a 6-OMT (6-O-methyltransferase) of *P. somniferum* (GenBank accession no. Q6WUC1) or *C. japonica* (GenBank accession no. D29811), CNMT (Coclaurine N-methyltransferase) of *C. japonica* (GenBank accession no. Q948P7) or *T. flavum* (GenBank accession no. AY610508) or *P. somniferum* (GenBank accession no. AY217336), CYP80B (N-methylcoclaurine 3'-hydroxylase) of *P. somniferum* (GenBank accession no. 064899), or 4'OMT (4'-O-methyltransferase) of *C. japonica* (GenBank accession no. Q9LEL5) (FIG. 1).

As used herein, "recombinant expression" means that the genome of a host cell has been augmented through the introduction of one or more recombinant genes, which include regulatory sequences that facilitate the transcription and translation of a protein of interest. While embodiments include stable introduction of recombinant genes into the host genome, autonomous or replicative plasmids or vectors can also be used within the scope of this invention. Moreover, this invention can be practiced using a low copy number, e.g., a single copy, or high copy number (as exemplified herein) plasmid or vector.

Generally, the introduced recombinant gene is not originally resident in the host that is the recipient of the recombinant gene, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, plant cells, and plants.

The term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA.

A recombinant gene encoding a polypeptide described herein includes the coding sequence for that polypeptide, operably linked, in sense orientation, to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. The term "heterologous nucleic acid" as used herein, refers to a nucleic acid introduced into a recombinant host, wherein said nucleic acid is not naturally present in said host or members of the host species. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically includes at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes, for example one or more heterologous nucleic acids, can be combined in a recombinant nucleic acid construct in "modules" useful for a discrete aspect of BIA and/or BIA precursor production. Combining a plurality of genes or heterologous nucleic acids in a module facilitates the use of the module in a variety of species. For example, a BIA and/or BIA precursor gene cluster can be combined such that each coding sequence is operably linked to a separate regulatory region, to form a BIA and/or BIA precursor module for production in eukaryotic organisms. Alternatively, the module can express a polycistronic message for production of BIAs and/or BIA precursors in prokaryotic hosts such as species of Rodobacter, *E. coli, Bacillus* or *Lactobacillus*. In addition to genes useful for production of BIAs and/or BIA precursors, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

Functional Homologs

Functional homologs of the polypeptides described herein are also suitable for use in producing benzylisoquinoline alkaloid compounds and benzylisoquinoline alkaloid precursors in a recombinant host. A functional homolog is a polypeptide that has sequence similarity to a reference polypeptide, and that carries out one or more of the biochemical or physiological function(s) of the reference polypeptide. A functional homolog and the reference polypeptide can be a naturally occurring polypeptide, and the sequence similarity can be due to convergent or divergent evolutionary events. As such, functional homologs are sometimes designated in the literature as homologs or orthologs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of benzylisoquinoline alkaloid compounds and benzylisoquinoline alkaloid precursors. Amino acid sequence similarity allows for conservative amino acid substitutions, such as inter alia substitution of one hydrophobic residue for another or substitution of one polar residue for another. If desired, manual inspection of such candidates can be carried out in order to narrow the number of candidates to be further evaluated.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 125% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program ClustalW (version 1.83, default parameters), which allows alignments of nucleic acid or polypeptide sequences to be carried out across their entire length (global alignment). See, Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method:% age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine %-identity of a candidate nucleic acid or amino acid sequence to a reference sequence, the sequences are aligned using ClustalW, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

To demonstrate expression and activity of one or more of the above-referenced enzymes expressed by the recombinant host, levels of products, substrates and intermediates, e.g., 4-HPAA, 3,4-DHPAA, (S)-Norcoclaurine, (S)-Norlaudanosoline, L-Tyrosine, Dopamine, and/or benzylisoquinoline alkaloids produced by the recombinant host can be determined by extracting samples from culture media for analysis according to published methods.

Recombinant hosts described herein can be used in methods to produce BIAs and/or BIA precursors. For example, if the recombinant host is a microorganism, the method can include growing a recombinant microorganism genetically engineered to produce BIAs and/or BIA precursors in a culture medium under conditions in which biosynthesis genes for BIAs and/or BIA precursors are expressed. The recombinant microorganism may be grown in a batch, fed batch or continuous process or combinations thereof. Typically, the recombinant microorganism is grown in a fermenter at a defined temperature(s) in the presence of a suitable nutrient source, e.g., a carbon source, for a desired period of time to produce a desired amount of BIAs and/or BIA precursors.

Therefore, this invention also provides an improved method for producing BIAs and/or BIA precursors as disclosed herein by providing a recombinant host that produces BIAs and/or BIA precursors as disclosed herein and has reduced production or activity of at least one alcohol dehydrogenase, at least one aldehyde reductase, or at least one alcohol dehydrogenase and at least one aldehyde reductase; cultivating said recombinant host, e.g., in the presence of a suitable carbon source, for a time sufficient for said recombinant host to produce BIAs and/or BIA precursors as disclosed herein; and isolating BIAs and/or BIA precursors as disclosed herein from said recombinant host or from the cultivation supernatant. In some aspects, the recombinant host produces a reduced amount of 4-hydroxyphenylacetalcohol or 3,4-dihydroxyphenylacetalcohol in comparison to a host that expresses the one or more functional alcohol dehydrogenases or one or more aldehyde reductases.

The level of 4-hydroxyphenylacetaldehyde (4-HPAA) and 4-hydroxyphenylacetalcohol, and/or 3,4-dihydroxyphenylacetaldehyde (3,4-DHPAA) and 3,4-dihydroxyphenylacetalcohol may be determined by any suitable method useful for detecting these compounds. Such methods include, for example, HPLC. Similarly, the level of a specific BIA and/or BIA precursor, such as but not limited to, Dopamine, 4-HPAA, 3,4-DHPAA, (S)-Norcoclaurine, (S)-Norlaudanosoline, and (S)-Reticuline may be determined using any suitable method useful for detecting these compounds. Such methods include, for example, HPLC.

Carbon sources of use in the method of this invention include any molecule that can be metabolized by a suitably modified recombinant host cell to facilitate growth and/or production of BIAs and/or BIA precursors as disclosed herein. Examples of suitable carbon sources include, but are not limited to, sucrose (e.g., as found in molasses), fructose, xylose, ethanol, glycerol, glucose, cellulose, starch, cellobiose or other glucose containing polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

After a suitably modified recombinant host has been grown in culture for the desired period of time, BIAs and/or BIA precursors can then be recovered from the culture using various techniques known in the art, e.g., isolation and purification by extraction, vacuum distillation and multi-stage re-crystallization from aqueous solutions and ultrafiltration (Böddeker, et al. (1997) *J. Membrane Sci.* 137:155-158; Borges da Silva, et al. (2009) *Chem. Eng. Des.* 87:1276-1292). If the recombinant host is a plant or plant cells, BIAs and/or BIA precursors can be extracted from the plant tissue using various techniques known in the art.

In some embodiments, BIAs and/or BIA precursors can be produced using suitably modified whole cells that are fed raw materials that contain precursor molecules. The raw materials may be fed during cell growth or after cell growth. The whole cells may be in suspension or immobilized. The whole cells may be in fermentation broth or in a reaction buffer. In some embodiments a permeabilizing agent may be required for efficient transfer of substrate into the cells.

In some aspects, a BIA and/or BIA precursor is isolated and purified to homogeneity (e.g., at least 90%, 92%, 94%, 96%, or 98% pure). In some aspects, the BIA and/or BIA precursor is isolated as an extract from a suitably modified recombinant host. In this respect, BIA and/or BIA precursor may be isolated, but not necessarily purified to homogeneity. Desirably, the amount of BIA and/or BIA precursor produced can be from about 1 mg/l to about 20,000 mg/L or higher. For example about 1 to about 100 mg/L, about 30 to about 100 mg/L, about 50 to about 200 mg/L, about 100 to about 500 mg/L, about 100 to about 1,000 mg/L, about 250 to about 5,000 mg/L, about 1,000 to about 15,000 mg/L, or about 2,000 to about 10,000 mg/L of BIA and/or BIA precursor can be produced. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of suitably modified recombinant microorganisms is used, they can be grown in a mixed culture to produce BIAs and/or BIA precursors.

Extracts of isolated, and optionally purified, BIAs and/or BIA precursors find use in a wide variety of pharmaceutical compositions.

The invention is further described in the following examples, which do not limit the scope of the invention described in the claims.

EXAMPLES

Example 1: Identification of Gene Candidates

Figure 2A:
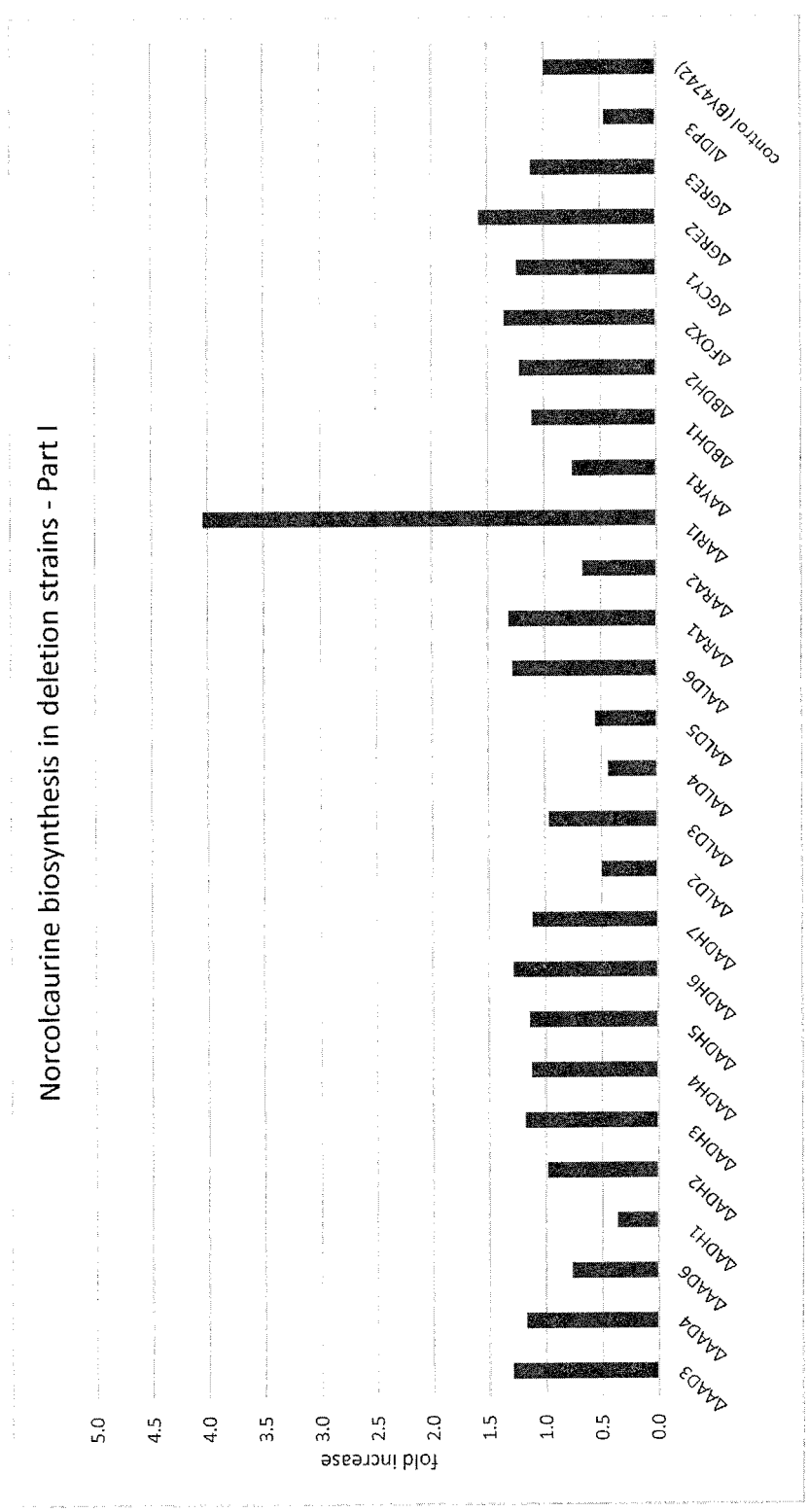
FIG. 2(A) provides results from a first part of a data set of fold-increase of norcoclaurine over the control strain (EVST25620, MATalpha his3Δ1 leu2Δ0 lys2Δ0 ura3Δ0 [ARS/CEN/URA3/pPGK1-Cj_NCS_co-tADH1]). Norcoclaurine concentrations were measured in duplicate cultures by LC/MS in cell culture supernatants of norcoclaurine synthase expressing single gene deletion strains. Positives singe gene deletions in this dataset with an increase of norcolaurine biosynthesis of at least 10%: ΔAAD3, ΔAAD4, ΔADH3, ΔADH4, ΔADH5, ΔADH6, ΔADH7, ΔARA1, ΔARI1, ΔALD6, ΔBDH1, ΔBDH2, ΔFOX2, ΔGCY1, ΔGRE2, ΔGRE3.
Figure 2B:
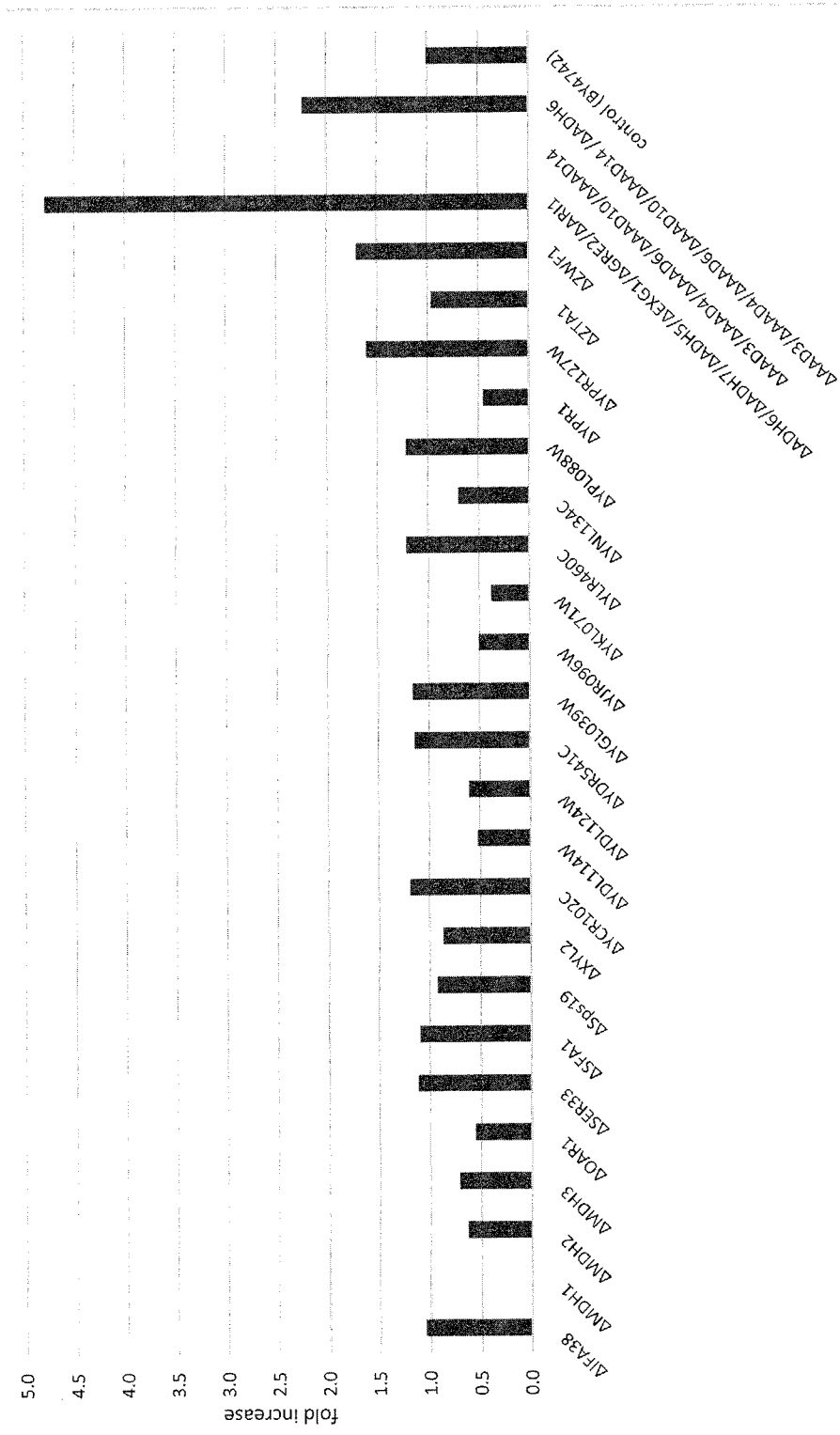
FIG. 2(B) provides results from the remaining part of data set of fold increase of norcoclaurine over the control strain (EVST25620, MATalpha his3Δ1 leu2Δ0 lys2Δ0 ur3Δ0 [ARS/CEN/URA3/pPGK1-Cj_NCS_co-tADH1]). Norcoclaurine concentrations were measured in duplicate cultures by LC/MS in cell culture supernatants of norcoclaurine synthase expressing single gene deletion strains and multiple deletion strains. Positives single gene deletions in this dataset with an increase of norcolaurine biosynthesis of at least 10%: ΔSER33, ΔYCR102C, ΔYDR541C, ΔYGL039W, ΔYLR460C, ΔYPL088W, ΔYPR127, ΔZWF1. Positive combinations of gene deletions in this data set: 4ΔDH6/ΔADH7/ΔADH5/ΔBGL1/ΔGRE2/ΔARI1, ΔAAD3/ΔAAD4/ΔAAD6/ΔAAD10/ΔAAD14/ΔADH6.
Figure 3:
FIG. 3 provides the fold-increase of norcoclaurine concentration in the cell culture supernatant measured by LC/MS over the control strain (EVST25620, MATalpha his3Δ1 leu2Δ0 lys2Δ0 ura3Δ0 [ARS/CEN/URA3/pPGK1-Cj_NCS_co-tADH1]). Norcoclaurine concentrations were measured after 72 h of cultivation in two independent experiments, average fold increase of norcoclaurine concentrations was calculated. Positive single gene deletions in this dataset with an increase of norcolaurine biosynthesis of at least 10%: ΔGOR1, ΔGPD1, ΔHIS4, ΔHMG1, ΔIDP1, ΔLYS12.

Gene candidates shown in FIGS. 2A and 2B were identified in the *S. cerevisiae* genome either by annotated information on alcohol- and/or aldehyde dehydrogenases in the *Saccharomyces* Genome Database (http://www.yeastgenome.org/) or by sequence homology searches against the *S. cerevisiae* genome. In addition, all RefSeq Protein sequences were downloaded from NCBI on Nov. 13, 2015 (totally 5915 Sequences). Those sequences were scanned with PRIAM (Claudel-Renard et al. 2003, Nucleic Acids Res. 31(22):6633-39) for hits to EC 1.1.1 in order to identify further candidates (FIG. 3). Seventy-two single gene deletions (generated as described in Example 2) were tested and list of the single gene deletions which were shown to work is presented in Table 2 and gene combinations are shown in Table 3.

TABLE 2

Single gene deletions shown to increase norcoclaurine biosynthesis.

| Standard Name | Systematic Name | Strain number | Annotation |
|---|---|---|---|
| AAD3 | YCR107W | EVST25702 | Putative aryl-alcohol dehydrogenase |
| AAD4 | YDL243C | EVST25704 | Putative aryl-alcohol dehydrogenase |
| ADH3 | YMR083W | EVST25572 | Mitochondrial alcohol dehydrogenase isozyme III |
| ADH4 | YGL256W | EVST25573 | Alcohol dehydrogenase isoenzyme type IV |
| ADH5 | YBR145W | EVST25574 | Alcohol dehydrogenase isoenzyme V |
| ADH6 | YMR318C | EVST25575 | NADPH-dependent medium chain alcohol dehydrogenase |
| ADH7 | YCR105W | EVST25576 | NADPH-dependent medium chain alcohol dehydrogenase |
| ALD6 | YPL061W/ | EVST25611 | Cytosolic aldehyde dehydrogenase |
| ARA1 | YBR149W | EVST25591 | NADP+ dependent arabinose dehydrogenase |
| ARI1 | YGL157W | EVST25577 | NADPH-dependent aldehyde reductase |
| BDH1 | YAL060W | EVST25586 | NAD-dependent (R,R)-butanediol dehydrogenase |
| BDH2 | YAL061W | EVST25587 | Putative medium-chain alcohol dehydrogenase with similarity to BDH1 |
| FOX2 | YKR009C | EVST25593 | 3-hydroxyacyl-CoA dehydrogenase and enoyl-CoA hydratase |
| GCY1 | YOR120W | EVST25594 | Glycerol dehydrogenase |
| GOR1 | YNL274C | EVST27673 | Glyoxylate reductase |
| GPD1 | YDL022W | EVST27687 | NAD-dependent glycerol-3-phosphate dehydrogenase |
| GRE2 | YOL151W | EVST25578 | 3-methylbutanal reductase and NADPH-dependent methylglyoxal reductase |
| GRE3 | YHR104W | EVST25579 | Aldose reductase |
| HIS4 | YCL030C | EVST27654 | Multifunctional enzyme containing phosphoribosyl-ATP pyrophosphatase, phosphoribosyl-AMP cyclohydrolase, and histidinol dehydrogenase activities |
| HMG1 | YML075C | EVST27685 | HMG-CoA reductase |
| IDP1 | YDL066W | EVST27690 | Mitochondrial NADP-specific isocitrate dehydrogenase |
| LYS12 | YIL094C | EVST27692 | Homo-isocitrate dehydrogenase |
| SER33 | YIL074C | EVST25600 | 3-phosphoglycerate dehydrogenase and alpha-ketoglutarate reductase |
| ZWF1 | YNL241C | EVST25705 | Glucose-6-phosphate dehydrogenase |
| | YCR102C | EVST25581 | Putative protein of unknown function |
| | YDR541C | EVST25582 | Aldehyde reductase |
| | YGL039W | EVST25583 | Aldehyde reductase |

TABLE 2-continued

Single gene deletions shown to increase norcoclaurine biosynthesis.

| Standard Name | Systematic Name | Strain number | Annotation |
|---|---|---|---|
| | YLR460C | EVST25584 | Member of the quinone oxidoreductase family |
| | YPL088W | EVST25701 | Putative aryl alcohol dehydrogenase |
| | YPR127W | EVST25698 | Putative pyridoxine 4-dehydrogenase |

TABLE 3

Multiple Gene Deletions tested for increase of norcoclaurine biosynthesis.

| Standard Name | Systematic Name | Strain | Annotation |
|---|---|---|---|
| ADH6/ADH7/ ADH5/EXG1/ GRE2/ARI1 | YMR318C/ YCR105W/ YBR145W/ YLR300W/ YOL151W/ YGL157W | EVST25619 | Combination of alcohol dehydrogenases and aldehyde reductases |
| AAD3/AAD4/ AAD6/AAD10/ AAD14/ADH6 | YCR107W/ YDL243C/ YFL056C/ YJR155W/ YNL331C | EVST25618 | Combination of putative aryl-alcohol dehydrogenases with alcohol dehydrogenase |

Example 2: Construction and Cultivation of Assay Strains

All single gene deletion strains were constructed from the Yeast MATalpha Collection YSC1054 (GE Dharmacon) which is based on the strain BY4742 with the genotype MAT alpha his3Δ1 leu2Δ0 lys2Δ0 ura3Δ0 (GenBank accession no. JRIR00000000). Deletion strains were generated using homologous recombination methods, by deletion of the respective target gene, as identified for each strain in Table 2. As an indirect measure for 4-hydroyxphenyl acetaldehyde (4-HPAA), strains overexpressing norcoclaurine synthase from a plasmid were generated. Control strain EVST25620 (MAT alpha his3Δ1 leu2Δ0 lys2Δ0 ura3Δ0 [ARS/CEN/URA3/pPGK1-Cj_NCS_co-tADH1]) was prepared accordingly in the BY4742 background, as described above, that did not carry any additional deletions.

Multiple deletion strains EVST25618 and EVST25619 were constructed from the previously described strain YSC1054 (based on strain BY4742; genotype MAT alpha his3Δ1 leu2Δ0 lys2Δ0 ura3Δ0). Deletion strains were generated using homologous recombination methods, with sequential deletion of either the genes: (1) AAD3, AAD4, AAD6, (Putative aryl-alcohol dehydrogenase 6; YFL056C), AAD10 (Putative aryl-alcohol dehydrogenase 10), AAD14 (Putative aryl-alcohol dehydrogenase), ADH6; or (2) ADH6, ADH7, ADH5, EXG1 (EXo-1,3-beta-Glucanase), GRE2, ARI1, respectively.

Coptis japonica norcoclaurine synthase (GenBank accession number AB267399.2) was codon optimized for S. cerevisiae (SEQ ID NOs: 23 & 24) and synthesized de novo (GeneArt). An open reading frame flanked by HindIII and SacII restriction enzyme recognition sites was cloned into HindIII/SacII linearized vector backbone pEVE2120 (SEQ ID NO: 63) resulting in plasmid pEV27735 (SEQ ID NO: 64). Clones were verified by sequencing, and the yeast single deletion mutant strains, as well as the non-deleted control strain, were transformed with plasmid pEV27735 (SEQ ID NO: 64). Single clones grown on selective SC-agar plates lacking uracil were singled out on selective SC-agar plates. One single clone in duplicates was used to inoculate 500 µl SC minus uracil selective media, supplemented with 1 mM tyrosine and 9.8 mM dopamine, in single wells of 96-deep well plates. Cultures were grown for 72 h at 30° C. with shaking at 300 rpm. Optical density of the cultures was measured at 600 nm either by a standard method using a spectrophotometer or a plate reader. For analysis of norcoclaurine biosynthesis the plates were centrifuged for 5 min at 3000 rpm and 100 µl of the supernatant were withdrawn.

TABLE 4

Average absorption values ($OD_{600}$) of duplicate cultures after cultivation time of 72 h measured with a standard spectrophotometer.

| Gene deletion | Average $OD_{600}$ |
|---|---|
| ΔAAD3 | 12.3 |
| ΔAAD4 | 12.5 |
| ΔADH3 | 12.0 |
| ΔADH4 | 12.8 |
| ΔADH5 | 13.3 |
| ΔADH6 | 13.0 |
| ΔADH7 | 12.3 |
| ΔALD6 | 13.8 |
| ΔARA1 | 12.8 |
| ΔARI1 | 13.0 |
| ΔBDH1 | 11.8 |
| ΔBDH2 | 13.8 |
| ΔFOX2 | 13.8 |
| ΔGCY1 | 11.5 |
| ΔGRE2 | 13.5 |
| ΔGRE3 | 12.3 |
| control (BY4742) | 13.3 |

TABLE 5

Average absorption values ($OD_{600}$) of duplicate cultures after cultivation time of 72 h measured with a standard spectrophotometer.

| Gene deletion | Average final $OD_{600}$ |
|---|---|
| ΔYGL039W | 11.8 |
| ΔYLR460C | 13.5 |
| ΔYPL088W | 11.8 |
| ΔSER33 | 12.3 |
| ΔYPR127W | 8.9 |
| ΔZWF1 | 13.0 |
| ΔYCR102C | 15.3 |
| ΔADH6/ΔADH7/ΔADH5Δ/EXG1/ΔGRE2/ΔARI1 | 14.3 |
| ΔAAD3/ΔAAD4/ΔAAD6/ΔAAD10/ΔAAD14/ ΔADH6 | 6.0 |
| control (BY4742) | 13.3 |

TABLE 6

Absorption values ($OD_{600}$) of cultures of one of the two independent experiments carried out in this study after a cultivation time of 72 h measured with a standard plate reader.

| Genotype | Absorption |
|---|---|
| ΔGOR1 | 6.1 |
| ΔGPD1 | 9.7 |
| ΔLYS12 | 5.5 |
| ΔHIS4 | 5.2 |
| ΔHMG1 | 5.7 |
| ΔIDP1 | 6.0 |
| control BY4742 | 5.2 |

Example 3: Measurement of Norcoclaurine in Cell Culture Media

Norcoclaurine analysis was carried out on an Acquity UPLC-SQD apparatus (Waters) equipped with an Acquity BEH C18 1.7 µm 2.1×100 mm reverse phase column (Waters) kept at 35° C. 5 µl of culture supernatant were loaded onto the column and separated using a gradient from 2% Solvent B to 30% Solvent B in 5 min, then washed with 100% Solvent B for 1 minute and reconditioned at 2% Solvent B for another minute. Solvent A consisted of water with 0.1% formic acid and Solvent B consisted of acetonitrile with 0.1% formic acid. The flow rate was 0.4 ml/min. Norcoclaurine was quantified by single ion monitoring of m/z 272 [M+H]$^+$ at 2.42 min and a calibration curve prepared in culture medium covering the concentration range of 78 µg/L to 10 mg/L.

Norcoclaurine concentrations were normalized to the optical density ($OD_{600}$) of the cultures after cultivation (72 h), and fold increase of norcoclaurine concentrations were calculated from the normalized results. The control strain (EVST25620, MATalpha his3Δ1 Leu2Δ0 lys2Δ0 ura3Δ0 [ARS/CEN/URA3/pPGK1-Cj_NCS_co-tADH1]) was set at a fold increase of 1.0. Positives singe gene deletions with an increase of norcolaurine biosynthesis of at least 10% were shown for: ΔAAD3, ΔAAD4, ΔADH3, ΔADH4, ΔADH5, ΔADH6, ΔADH7, ΔARA1, ΔARI1, ΔALD6, ΔBDH1, ΔBDH2, ΔFOX2, ΔGCY1, ΔGRE2, ΔGRE3, ΔSER33, ΔYCR102C, ΔYDR541C, ΔYGL039W, ΔYLR460C, ΔYPL088W, ΔYPR127, ΔZWF1, ΔGOR1, ΔGPD1, ΔHIS4, ΔHMG1, ΔIDP1, ΔLYS12 (FIGS. 2 and 3).

TABLE 7

| Disclosed Nucleic Acid and Amino Acid Sequences |
| --- |
| SEQ ID NO: 1    Protein sequence from alcohol dehydrogenase 5 (ADH5) of *Saccharomyces cerevisiae*<br>MPSQVIPEKQKAIVFYETDGKLEYKDVTVPEPKPNEILVHVKYSGVCHSDLHAWHGDWP<br>FQLKFPLIGGHEGAGVVVKLGSNVKGWKVGDFAGIKWLNGTCMSCEYCEVGNESQCP<br>YLDGTGFTHDGTFQEYATADAVQAAHIPPNVNLAEVAPILCAGITVYKALKRANVIPGQW<br>VTISGACGGLGSLAIQYALAMGYRVIGIDGGNAKRKLFEQLGGEIFIDFTEEKDIVGAIIKA<br>TNGGSHGVINVSVSEAAIEASTRYCRPNGTVVLVGMPAHAYCNSDVFNQVVKSISIVGS<br>CVGNRADTREALDFFARGLIKSPIHLAGLSDVPEIFAKMEKGEIVGRYVVETSK |
| SEQ ID NO: 2    DNA sequence encoding alcohol dehydrogenase 5 (ADH5) of *Saccharomyces cerevisiae*<br>ATGCCTTCGCAAGTCATTCCTGAAAAACAAAAGGCTATTGTCTTTTATGAGACAGATG<br>GAAAATTGGAATATAAAGACGTCACAGTTCCGGAACCTAAGCCTAACGAAATTTTAG<br>TCCACGTTAAATATTCTGGTGTTTGTCATAGTGACTTGCACGCGTGGCACGGTGATT<br>GGCCATTTCAATTGAAATTTCCATTAATCGGTGGTCACGAAGGTGCTGGTGTTGTTG<br>TTAAGTTGGGATCTAACGTTAAGGGCTGGAAAGTCGGTGATTTTGCAGGTATAAAT<br>GGTTGAATGGGACTTGCATGTCCTGTGAATATTGTGAAGTAGGTAATGAATCTCAAT<br>GTCCTTATTTGGATGGTACTGGCTTCACACATGATGGTACTTTTCAAGAATACGCAA<br>CTGCCGATGCCGTTCAAGCTGCCCATATTCCACCAAACGTCAATCTTGCTGAAGTTG<br>CCCCAATCTTGTGTGCAGGTATCACTGTTTATAAGGCGTTGAAAAGAGCCAATGTGA<br>TACCAGGCCAATGGGTCACTATATCCGGTGCATGCGGTGGCTTGGGTTCTCTGGCA<br>ATCCAATACGCCCTTGCTATGGGTTACAGGGTCATTGGTATCGATGGTGGTAATGCC<br>AAGCGAAAGTTATTTGAACAATTAGGCGGAGAAATATTCATCGATTTCACGGAAGAA<br>AAAGACATTGTTGGTGCTATAATAAAGGCCACTAATGGCGGTTCTCATGGAGTTATT<br>AATGTGTCTGTTTCTGAAGCAGCTATCGAGGCTTCTACGAGGTATTGTAGGCCCAAT<br>GGTACTGTCGTCCTGGTTGGTATGCCAGCTCATGCTTACTGCAATTCCGATGTTTTC<br>AATCAAGTTGTAAAATCAATCTCCATCGTTGGATCTTGTGTTGGAAATAGAGCTGATA<br>CAAGGGAGGCTTTAGATTTCTTCGCCAGAGGTTTGATCAAATCTCCGATCCACTTAG<br>CTGGCCTATCGGATGTTCCTGAAATTTTTGCAAAGATGGAGAAGGGTGAAATTGTTG<br>GTAGATATGTTGTTGAGACTTCTAAATGA |
| SEQ ID NO: 3    Protein sequence from alcohol dehydrogenase 6 (ADH6) of *Saccharomyces cerevisiae*<br>MSYPEKFEGIAIQSHEDWKNPKKTKYDPKPFYDHDIDIKIEACGVCGSDIHCAAGHWGN<br>MKMPLVVGHEIVGKVVKLGPKSNSGLKVGQRVGVGAQVFSCLECDRCKNDNEPYCTK<br>FVTTYSQPYEDGYVSQGGYANYVRVHEHFVVPIPENIPSHLAAPLLCGGLTVYSPLVRN<br>GCGPGKKVGIVGLGGIGSMGTLISKAMGAETYVISRSSRKREDAMKMGADHYIATLEEG<br>DWGEKYFDTFDLIVVCASSLTDIDFNIMPKAMKVGGRIVSISIPEQHEMLSLKPYGLKAVS<br>ISYSALGSIKELNQLLKLVSEKDIKIWVETLPVGEAGVHEAFERMEKGDVRYRFTLVGYD<br>KEFSD |
| SEQ ID NO: 4    DNA sequence encoding alcohol dehydrogenase 6 (ADH6) of *Saccharomyces cerevisiae*<br>ATGTCTTATCCTGAGAAATTTGAAGGTATCGCTATTCAATCACACGAAGATTGGAAAA<br>ACCCAAAGAAGACAAAGTATGACCCAAAACCATTTTACGATCATGACATTGACATTAA<br>GATCGAAGCATGTGGTGTCTGCGGTAGTGATATTCATTGTGCAGCTGGTCATTGGG<br>GCAATATGAAGATGCCGCTAGTCGTTGGTCATGAAATCGTTGGTAAAGTTGTCAAGC<br>TAGGGCCCAAGTCAAACAGTGGGTTGAAAGTCGGTCAACGTGTTGGTGTAGGTGCT<br>CAAGTCTTTTCATGCTTGGAATGTGACCGTTGTAAGAATGATAATGAACCATACTGCA<br>CCAAGTTTGTTACCACATACAGTCAGCCTTATGAAGACGGCTATGTGTCGCAGGGTG<br>GCTATGCAAACTACGTCAGAGTTCATGAACATTTTGTGGTGCCTATCCCAGAGAATA<br>TTCCATCACATTTGGCTGCTCCACTATTATGTGGTGGTTTGACTGTGTACTCTCCATT<br>GGTTCGTAACGGTTGCGGTCCAGGTAAAAAAGTTGGTATAGTTGGTCTTGGTGGTAT<br>CGGCAGTATGGGTACATTGATTTCCAAAGCCATGGGGGCAGAGACGTATGTTATTTC<br>TCGTTCTTCGAGAAAAAGAGAAGATGCAATGAAGATGGGCGCCGATCACTACATTG<br>CTACATTAGAAGAAGGTGATTGGGGTGAAAAGTACTTTGACACCTTCGACCTGATTG<br>TAGTCGTGTGCTTCCTCCCCTTACCGACATTGACTTCAACATTATGCCAAAGGCTATGAA |

TABLE 7-continued

Disclosed Nucleic Acid and Amino Acid Sequences

```
GGTTGGTGGTAGAATTGTCTCAATCTCTATACCAGAACAACACGAAATGTTATCGCT
AAAGCCATATGGCTTAAAGGCTGTCTCCATTTCTTACAGTGCTTTAGGTTCCATCAAA
GAATTGAACCAACTCTTGAAATTAGTCTCTGAAAAAGATATCAAATTTGGGTGGAAA
CATTACCTGTTGGTGAAGCCGGCGTCCATGAAGCCTTCGAAAGGATGGAAAAGGGT
GACGTTAGATATAGATTTACCTTAGTCGGCTACGACAAAGAATTTTCAGACTAG
```

SEQ ID NO: 5     Protein sequence from alcohol dehydrogenase 7
(ADH7) of *Saccharomyces cerevisiae*

```
MLYPEKFQGIGISNAKDWKHPKLVSFDPKPFGDHDVDVEIEACGICGSDFHIAVGNWGP
VPENQILGHEIIGRVVKVGSKCHTGVKIGDRVGVGAQALACFECERCKSDNEQYCTNDH
VLTMWTPYKDGYISQGGFASHVRLHEHFAIQIPENIPSPLAAPLLCGGITVFSPLLRNGC
GPGKRVGIVGIGGIGHMGILLAKAMGAEVYAFSRGHSKREDSMKLGADHYIAMLEDKG
WTEQYSNALDLLVVCSSSLSKVNFDSIVKIMKIGGSIVSIAAPEVNEKLVLKPLGLMGVSIS
SSAIGSRKEIEQLLKLVSEKNVKIWVEKLPISEEGVSHAFTRMESGDVKYRFTLVDYDKK
FHK
```

SEQ ID NO: 6     DNA sequence encoding alcohol dehydrogenase 7
(ADH7) of *Saccharomyces cerevisiae*

```
ATGCTTTACCCAGAAAAATTTCAGGGCATCGGTATTTCCAACGCAAAGGATTGGAAG
CATCCTAAATTAGTGAGTTTTGACCCAAAACCCTTTGGCGATCATGACGTTGATGTT
GAAATTGAAGCCTGTGGTATCTGCGGATCTGATTTTCATATAGCCGTTGGTAATTGG
GGTCCAGTCCCAGAAAATCAAATCCTTGGACATGAAATAATTGGCCGCGTGGTGAA
GGTTGGATCCAAGTGCCACACTGGGGTAAAAATCGGTGACCGTGTTGGTGTTGGTG
CCCAAGCCTTGGCGTGTTTTGAGTGTGAACGTTGCAAAAGTGACAACGAGCAATACT
GTACCAATGACCACGTTTTGACTATGTGGACTCCTTACAAGGACGGCTACATTTCAC
AAGGAGGCTTTGCCTCCACGTGAGGCTTCATGAACACTTTGCTATTCAAATACCAG
AAAATATTCCAAGTCCGCTAGCCGCTCCATTATTGTGTGGTGGTATTACAGTTTTCTC
TCCACTACTAAGAAATGGCTGTGGTCCAGGTAAGAGGGTAGGTATTGTTGGCATCG
GTGGTATTGGGCATATGGGGATTCTGTTGGCTAAAGCTATGGGAGCCGAGGTTTAT
GCGTTTTCGCGAGGCCACTCCAAGCGGGAGGATTCTATGAAACTCGGTGCTGATCA
CTATATTGCTATGTTGGAGGATAAAGGCTGGACAGAACAATACTCTAACGCTTTGGA
CCTTCTTGTCGTTTGCTCATCATCTTTGTCGAAAGTTAATTTTGACAGTATCGTTAAG
ATTATGAAGATTGGAGGCTCCATCGTTTCAATTGCTGCTCCTGAAGTTAATGAAAAG
CTTGTTTTAAAACCGTTGGGCCTAATGGGAGTATCAATCTCAAGCAGTGCTATCGGA
TCTAGGAAGGAAATCGAACAACTATTGAAATTAGTTTCCGAAAAGAATGTCAAAATAT
GGGTGGAAAAACTTCCGATCAGCGAAGAAGGCGTCAGCCATGCCTTTACAAGGATG
GAAAGCGGAGACGTCAAATACAGATTTACTTTGGTCGATTATGATAAGAAATTCCATA
AATAG
```

SEQ ID NO: 7     Protein sequence from Genes de Respuesta a
Estres 2 (GRE2) of *Saccharomyces cerevisiae*

```
MSVFVSGANGFIAQHIVDLLLKEDYKVIGSARSQEKAENLTEAFGNNPKFSMEVVPDISK
LDAFDHVFQKHGKDIKIVLHTASPFCFDITDSERDLLIPAVNGVKGILHSIKKYAADSVERV
VLTSSYAAVFDMAKENDKSLTFNEESWNPATWESCQSDPVNAYCGSKKFAEKAAWEF
LEENRDSVKFELTAVNPVYVFGPQMFDKDVKKHLNTSCELVNSLMHLSPEDKIPELFGG
YIDVRDVAKAHLVAFQKRETIGQRLIVSEARFTMQDVLDILNEDFPVLKGNIPVGKPGSG
ATHNTLGATLDNKKSKKLLGFKFRNLKETIDDTASQILKFEGRI
```

SEQ ID NO: 8     DNA sequence encoding Genes de Respuesta a
Estres 2 (GRE2) of *Saccharomyces cerevisiae*

```
ATGTCAGTTTTCGTTTCAGGTGCTAACGGGTTCATTGCCCAACACATTGTCGATCTC
CTGTTGAAGGAAGACTATAAGGTCATCGGTTCTGCCAGAAGTCAAGAAAAGGCCGA
GAATTTAACGGAGGCCTTTGGTAACAACCCAAAATTCTCCATGGAAGTTGTCCCAGA
CATATCTAAGCTGGACGCATTTGACCATGTTTTCCAAAAGCACGGCAAGGATATCAA
GATAGTTCTACATACGGCCTCTCCATTCTGCTTTGATATCACTGACAGTGAACGCGA
TTTATTAATTCCTGCTGTGAACGGTGTTAAGGGAATTCTCCACTCAATTAAAAAATAC
GCCGCTGATTCTGTAGAACGTGTAGTTCTCACCTCTTCTTATGCAGCTGTGTTCGAT
ATGGCAAAAGAAAACGATAAGTCTTTAACATTTAACGAAGAATCCTGGAACCCAGCT
ACCTGGGAGAGTTGCCAAAGTGACCCAGTTAACGCCTACTGTGGTTCTAAGAAGTTT
GCTGAAAAAGCAGCTTGGGAATTTCTAGAGGAGAATAGAGACTCTGTAAAATTCGAA
TTAACTGCCGTTAACCCAGTTTACGTTTTTGGTCCGCAAATGTTTGACAAAGATGTGA
AAAAACACTTGAACACATCTTGCGAACTCGTCAACAGCTTGATGCATTTATCACCAG
AGGACAAGATACCGGAACTATTTGGTGGATACATTGATGTTCGTGATGTTGCAAAGG
CTCATTTAGTTGCCTTCCAAAAGAGGGAAACAATTGGTCAAAGACTAATCGTATCGG
AGGCCAGATTTACTATGCAGGATGTTCTCGATATCCTTAACGAAGACTTCCCTGTTC
TAAAAGGCAATATTCCAGTGGGGAAACCAGGTTCTGGTGCTACCCATAACACCCTTG
GTGCTACTCTTGATAATAAAAAGAGTAAGAAATTGTTAGGTTTCAAGTTCAGGAACTT
GAAAGAGACCATTGACGACACTGCCTCCCAAATTTTAAAATTTGAGGGCAGAATATA
A
```

SEQ ID NO: 9     Protein sequence from Genes de Respuesta a
Estres 3 (GRE3) of *Saccharomyces cerevisiae*

```
MSSLVTLNNGLKMPLVGLGCWKIDKKVCANQIYEAIKLGYRLFDGACDYGNEKEVGEGI
RKAISEGLVSRKDIFVVSKLWNNFHHPDHVKLALKKTLSDMGLDYLDLYYIHFPIAFKYVP
FEEKYPPGFYTGADDEKKGHITEAHVPIIDTYRALEECVDEGLIKSIGVSNFQGSLIQDLL
RGCRIKPVALQIEHHPYLTQEHLVEFCKLHDIQVVAYSSFGPQSFIEMDLQLAKTTPTLFE
NDVIKKVSQNHPGSTTSQVLLRWATQRGIAVIPKSSKKERLLGNLEIEKKFTLTEQELKDI
SALNANIRFNDPWTWLDGKFPTFA
```

TABLE 7-continued

Disclosed Nucleic Acid and Amino Acid Sequences

SEQ ID NO: 10   DNA sequence encoding Genes de Respuesta a
                Estres 3 (GRE3) of *Saccharomyces cerevisiae*

ATGTCTTCACTGGTTACTCTTAATAACGGTCTGAAAATGCCCCTAGTCGGCTTAGGG
TGCTGGAAAATTGACAAAAAAGTCTGTGCGAATCAAATTTATGAAGCTATCAAATTAG
GCTACCGTTTATTCGATGGTGCTTGCGACTACGGCAACGAAAAGGAAGTTGGTGAA
GGTATCAGGAAAGCCATCTCCGAAGGTCTTGTTTCTAGAAAGGATATATTTGTTGTTT
CAAAGTTATGGAACAATTTTCACCATCCTGATCATGTAAAATTAGCTTTAAAGAAGAC
CTTAAGCGATATGGGACTTGATTATTTAGACCTGTATTATATTCACTTCCCAATCGCC
TTCAAATATGTTCCATTTGAAGAGAAATACCCTCCAGGATTCTATACGGGCGCAGAT
GACGAGAAGAAAGGTCACATCACCGAAGCACATGTACCAATCATAGATACGTACCG
GGCTCTGGAAGAATGTGTTGATGAAGGCTTGATTAAGTCTATTGGTGTTTCCAACTT
TCAGGGAAGCTTGATTCAAGATTTATTACGTGGTTGTAGAATCAAGCCCGTGGCTTT
GCAAATTGAACACCATCCTTATTTGACTCAAGAACACCTAGTTGAGTTTGTAAATTA
CACGTATATCCAAGTAGTTGCTTACTCCTCCTTCGGTCCTCAATCATTCATTGAGATG
GACTTACAGTTGGCAAAAACCACGCCAACTCTGTTCGAGAATGATGTAATCAAGAAG
GTCTCACAAAACCATCCAGGCAGTACCACTTCCCAAGTATTGCTTAGATGGGCAACT
CAGAGAGGCATTGCCGTCATTCCAAAATCTTCCAAGAAGGAAAGGTTACTTGGCAAC
CTAGAAATCGAAAAAAAGTTCACTTTAACGGAGCAAGAATTGAAGGATATTTCTGCA
CTAAATGCCAACATCAGATTTAATGATCCATGGACCTGGTTGGATGGTAAATTCCCC
ACTTTTGCCTGA

SEQ ID NO: 11   Protein sequence from carbonyl reductase
                (NADPH-dependent) (YDR541C) of *Saccharomyces
                cerevisiae*

MSNTVLVSGASGFIALHILSQLLKQDYKVIGTVRSHEKEAKLLRQFQHNPNLTLEIVPDIS
HPNAFDKVLQKRGREIRYVLHTASPPHYDTTEYEKDLLIPALEGTKNILNSIKKYAADTVE
RVVVTSSCTAIITLAKMDDPSVVFTEESWNEATWESCQIDGINAYFASKKFAEKAAWEFT
KENEDHIKFKLTTVNPSLLFGPQLFDEDVHGHLNTSCEMINGLIHTPVNASVPDFHSIFID
VRDVALAHLYAFQKENTAGKRLVVTNGKFGNQDILDILNEDFPQLRGLIPLGKPGTGDQV
IDRGSTTDNSATRKILGFEFRSLHESVHDTAAQILKKQNRL

SEQ ID NO: 12   DNA sequence encoding carbonyl reductase
                (NADPH-dependent) (YDR541C) of *Saccharomyces
                cerevisiae*

ATGTCTAATACAGTTCTAGTTTCTGGCGCTTCAGGTTTTATTGCCTTGCATATCCTGT
CACAATTGTTAAAACAAGATTATAAGGTTATTGGAACTGTGAGATCCCATGAAAAAGA
AGCAAAATTGCTAAGACAATTTCAACATAACCCTAATTTAACTTTAGAAATTGTTCCG
GACATTTCTCATCCAAATGCTTTCGATAAGGTTCTGCAGAAACGTGGACGTGAGATT
AGGTATGTTCTACACACGGCCTCTCCTTTTCATTATGATACTACCGAATATGAAAAAG
ACTTATTGATTCCCGCGTTAGAAGGTACAAAAAACATCCTAAATTCTATCAAGAAATA
TGCAGCAGACACTGTAGAGCGTGTTGTTGTGACTTCTTCTTGTACTGCTATTATAAC
CCTTGCAAAGATGGACGATCCCAGTGTGGTTTTTACAGAAGAGAGTTGGAACGAAG
CAACCTGGGAAAGCTGTCAAATTGATGGGATAAATGCTTACTTTGCATCCAAGAAGT
TTGCTGAAAAGGCTGCCTGGGAGTTCACAAAAGAGAATGAAGATCACATCAAATTCA
AACTAACAACAGTCAACCCTTCTCTTCTTTTTGGTCCTCAACTTTTCGATGAAGATGT
GCATGGCCATTTGAATACTTCTTGCGAAATGATCAATGGCCTAATTCATACCCCAGT
AAATGCCAGTGTTCCTGATTTTCATTCCATTTTTATTGATGTAAGGGATGTGGCCCTA
GCTCATCTGTATGCTTTCCAGAAGGAAAATACCGCGGGTAAAAGATTAGTGGTAACT
AACGGTAAATTTGGAAACCAAGATATCCTGGATATTTTGAACGAAGATTTTCCACAAT
TAAGAGGTCTCATTCCTTTGGGTAAGCCTGGCACAGGTGATCAAGTCATTGACCGC
GGTTCAACTACAGATAATAGTGCAACGAGGAAAATACTTGGCTTTGAGTTCAGAAGT
TTACACGAAAGTGTCCATGACTACTGCTGCCCAAATTTTGAAGAAGCAGAACAGATTA
TGA

SEQ ID NO: 13   Protein sequence from YLR460C of *Saccharomyces
                cerevisiae*

MQVAIPETMKAVVIEDGKAVVKEGIPIPELEEGFVLIKTLAVAGNPTDWAHIDYKIGPQGSI
LGCDAAGQIVKLGPAVNPKDFSIGDYIYGFIHGSSVRFPSNGAFAEYSAISTVVAYKSPN
ELKFLGEDVLPAGPVRSLEGVATIPVSLTTAGLVLTYNLGLDLKWEPSTPQRKGPILLWG
GATAVGQSLIQLANKLNGFTKIIVVASRKHEKLLKEYGADELFDYHDIDVVEQIKHKYNNIS
YLVDCVANQDTLQQVYKCAADKQDATIVELKNLTEENVKKENRRQNVTIDIIRLYSIGGH
EVPFGNITLPADSEARKAAIKFPIKFINPKINDGQIRHIPVRVYKNGLCDVPHILKDIKYGKNS
GEKLVAVLN

SEQ ID NO: 14   DNA sequence encoding YLR460C of *Saccharomyces
                cerevisiae*

ATGCAAGTTGCAATTCCAGAAACCATGAAGGCTGTCGTCATTGAAGACGGTAAAGC
GGTTGTTAAAGAGGGCATTCCCATTCCTGAATTGGAAGAAGGATTCGTATTGATTAA
GACACTCGCTGTTGCTGGTAACCCCACTGATTGGGCACACATTGACTACAAGATCG
GCCTCAAGGATCTATTCTGGGATGTGATGCTGCTGGCCAAATTGTCAAATTGGGC
CCAGCTGTCAATCCTAAAGACTTTTCTATCGGTGATTATATTTATGGGTTCATTCACG
GATCTTCCGTAAGGTTTCCTTCCAATGGTGCTTTTGCTGAATATTCTGCTATTTCAA
TGTGGTTGCCTACAAATCACCCAATGAACTCAAATTTTTGGGTGAGGATGTTCTACC
TGCCGGCCCTGTCAGGTCTTTGGAAGGTGTAGCCACTATCCCAGTGTCACTGACCA
CAGCCGGCTTGGTGTTGACCTATAACTTGGGCTTGGACCTGAAGTGGGAGCCATCA
ACCCCACAAAGAAAGGCCCCATCTTATTATGGGCGGTGCAACTGCAGTAGGTCA
GTCGCTCATCCAATTAGCCAATAAAATTGAATGGCTTCACCAAGATCATTGTTGTGGC

TABLE 7-continued

Disclosed Nucleic Acid and Amino Acid Sequences

TTCTCGGAAGCACGAAAAACTTTTGAAAGAATATGGTGCTGATGAATTATTTGATTAT
CATGATATTGACGTGGTAGAACAAATTAAACACAAGTACAACAATATCTCGTATTTAG
TCGACTGTGTCGCGAATCAAGATACGCTTCAACAAGTGTACAAATGTGCGGCCGATA
AACAGGATGCTACAATTGTTGAATTAAAAAATTTGACAGAAGAAAACGTCAAAAAAGA
GAACAGGAGACAAAACGTTACTATTGACATAATAAGGCTATATTCAATAGGTGGCCA
TGAAGTACCATTTGGAAACATTACTTTACCAGCCGACTCAGAAGCTAGGAAAGCTGC
AATAAAATTTATCAAATTCATCAATCCAAAGATTAATGATGGACAAATTCGCCATATTC
CAGTAAGGGTCTATAAGAACGGGCTTTGTGATGTTCCTCATATCCTAAAAGACATCA
AATATGGTAAGAACTCTGGTGAAAAACTCGTTGCCGTATTAAACTAG

SEQ ID NO: 15    Protein sequence from carbonyl reductase
                 (NADPH-dependent) (ARI1) of Saccharomyces
                 cerevisiae
MTTDTTVFVSGATGFIALHIMNDLLKAGYTVIGSGRSQEKNDGLLKKFNNNPKLSMEIVE
DIAAPNAFDEVFKKHGKEIKIVLHTASPFHFETTNFEKDLLTPAVNGTKSILEAIKKYAADT
VEKVIVTSSTAALVTPTDMNKGDLVITEESWNKDTWDSCQANAVAAYCGSKKFAEKTA
WEFLKENKSSVKFTLSTINPGFVFGPQMFADSLKHGINTSSGIVSELIHSKVGGEFYNYC
GPFIDVRDVSKAHLVAIEKPECTGQRLVLSEGLFCCQEIVDILNEEFPQLKGKIATGEPAT
GPSFLEKNSCKFDNSKTKKLLGFQFYNLKDCIVDTAAQMLEVQNEA SEQ ID NO: 16    DNA sequence encoding carbonyl reductase
                 (NADPH-dependent) (ARI1) of Saccharomyces
                 cerevisiae
ATGACTACTGATACCACTGTTTTCGTTTCTGGCGCAACCGGTTTCATTGCTCTACACA
TTATGAACGATCTGTTGAAAGCTGGCTATACAGTCATCGGCTCAGGTAGATCTCAAG
AAAAAAATGATGGCTTGCTCAAAAAATTTAATAACAATCCCAAACTATCGATGGAAAT
TGTGGAAGATATTGCTGCTCCAAACGCCTTTGATGAAGTTTTCAAAAAACATGGTAA
GGAAATTAAGATTGTGCTACACACTGCCTCCCCATTCCATTTTGAAACTACCAATTTT
GAAAAGGATTTACTAACCCCTGCAGTGAACGGTACAAAATCTATCTTGGAAGCGATT
AAAAAATATGCTGCAGACACTGTTGAAAAGTTATTGTTACTTCGTCTACTGCTGCTC
TGGTGACACCTACAGACATGAACAAAGGAGATTTGGTGATCACGGAGGAGAGTTGG
AATAAGGATACATGGGACAGTTGTCAAGCCAACGCCGTTGCCGCATATTGTGGCTC
GAAAAAGTTTGCTGAAAAAACTGCTTGGGAATTTCTTAAAGAAAACAAGTCTAGTGTC
AAATTCACACTATCCACTATCAATCCGGGATTCGTTTTTGGTCCTCAAATGTTTGCAG
ATTCGCTAAAACATGGCATAAATACCTCCTCAGGGATCGTATCTGAGTTAATTCATTC
CAAGGTAGGTGGAGAATTTTATAATTACTGTGGCCCATTTATTGACGTGCGTGACGT
TTCTAAAGCCCACCTAGTTGCAATTGAAAAACCAGAATGTACCGGCCAAAGATTAGT
ATTGAGTGAAGGTTTATTCTGCTGTCAAGAAATCGTTGACATCTTGAACGAGGAATT
CCCTCAATTAAAGGGCAAGATAGCTACAGGTGAACCTGCGACCGGTCCAAGCTTTTT
AGAAAAAAACTCTTGCAAGTTTGACAATTCTAAGACAAAAAAACTACTGGGATTCCAG
TTTTACAATTTAAAGGATTGCATAGTTGACACCGCGGCGCAAATGTTAGAAGTTCAAA
ATGAAGCCTAA SEQ ID NO: 17    Protein sequence from carbonyl reductase
                 (NADPH-dependent) (YGL039W) of Saccharomyces
                 cerevisiae
MTTEKTVVFVSGATGFIALHVVDDLLKTGYKVIGSGRSQEKNDGLLKKFKSNPNLSMEIV
EDIAAPNAFDKVFQKHGKEIKVVLHIASPVHFNTTDFEKDLLIPAVNGTKSILEAIKNYAAD
TVEKVVITSSVAALASPGDMKDTSFVVNEESWNKDTWESCQANAVSAYCGSKKFAEKT
AWDFLEENQSSIKFTLSTINPGFVFGPQLFADSLRNGINSSSAIIANLVSYKLGDNFYNYS
GPFIDVRDVSKAHLLAFEKPECAGQRLFLCEDMFCSQEALDILNEEFPQLKGKIATGEPG
SGSTFLTKNCCKCDNRKTKNLLGFQFNKFRDCIVDTASQLLEVQSKS SEQ ID NO: 18    DNA sequence encoding carbonyl reductase
                 (NADPH-dependent) (YGL039W) of Saccharomyces
                 cerevisiae
ATGACTACTGAAAAAACCGTTGTTTTTGTTTCTGGTGCTACTGGTTTCATTGCTCTAC
ACGTAGTGGACGATTTATTAAAAACTGGTTACAAGGTCATCGGTTCGGGTAGGTCCC
AAGAAAAAGAATGATGGATTGCTGAAAAAATTTAAGAGCAATCCCAACCTTTCAATGG
AGATTGTCGAAGACATTGCTGCTCCAAACGCTTTTGACAAAGTTTTTCAAAAGCACG
GCAAAGAGATCAAGGTTGTCTTGCACATAGCTTCTCCGGTTCACTTCAACACCACTG
ATTTCGAAAGGATCTGCTAATTCCTGCTGTGAATGGTACCAAGTCCATTCTAGAAG
CAATCAAAAATTATGCCGCAGACACAGTCGAAAAAGTCGTTATTACTTCTTCTGTTGC
TGCCCTTGCATCTCCCGGAGATATGAAGGACACTAGTTTCGTTGTCAATGGAAGAAG
TTGGAACAAAGATACTTGGGAAGTTGTCAAGCTAACGCGGTTTCCGCATACTGTGG
TTCCAAGAAATTTGCTGAAAAACTGCTTGGGATTTTCTCGAGGAAAACCAATCAAG
CATCAAATTTACGCTATCAACCATCAACCCAGGATTTGTTTTGGCCCTCAGCTATTT
GCCGACTCTCTTAGAAATGGAATAAATAGCTCTTCAGCCATTATTGCCAATTTGGTTA
GTTATAAATTAGGCGACAATTTTTATAATTACAGTGGTCCTTTTATTGACGTTCGCGA
TGTTTCAAAAGCTCATTTACTTGCATTTGAGAAACCCGAATGCGCTGGCCAAAGACT
ATTCTTATGTGAAGATATGTTTTGCTCTCAAGAAGCGCTGGATATCTTGAATGAGGAA
TTTCCACAGTTAAAAGGCAAGATAGCAACTGGCGAACCTGGTAGCGGCTCAACCTTT
TTGACAAAAAACTGCTGCAAGTGCGACAACCGCAAAACCAAAAATTTATTAGGATTC
CAATTTAATAAGTTCAGAGATTGCATTGTCGATACTGCCTCGCAATTACTAGAAGTTC
AAAGTAAAAGCTAA TABLE 7-continued Disclosed Nucleic Acid and Amino Acid Sequences SEQ ID NO: 19  Protein sequence from YCR102C of *Saccharomyces cerevisiae*
MKAVVIEDGKAVVKEGVPIPELEEGFVLIKTLAVAGNPTDWAHIDYKVGPQGSILGCDAA
GQIVKLGPAVDPKDFSIGDYIYGFIHGSSVRFPSNGAFAEYSAISTVVAYKSPNELKFLGE
DVLPAGPVRSLEGAATIPVSLTTAGLVLTYNLGLNLKWEPSTPQRNGPILLWGGATAVG
QSLIQLANKLNGFTKIIVVASRKHEKLLKEYGADQLFDYHDIDVVEQIKHKYNNISYLVDCV
ANQNTLQQVYKCAADKQDATVVELTNLTEENVKKENRRQNVTIDRTRLYSIGGHEVPFG
GITFPADPEARRAATEFVKFINPKISDGQIHHIPARVYKNGLYDVPRILEDIKIGKNSGEKL
VAVLN SEQ ID NO: 20  DNA sequence encoding YCR102C of *Saccharomyces cerevisiae*
ATGAAGGCTGTCGTCATTGAAGACGGTAAAGCGGTTGTCAAAGAGGGCGTTCCCAT
TCCTGAATTGGAAGAAGGATTCGTATTGATTAAGACACTCGCTGTTGCTGGTAACCC
GACTGATTGGGCACACATTGACTACAAGGTCGGGCCTCAAGGATCTATTCTGGGAT
GTGACGCTGCCGGCCAAATTGTCAAATTGGGCCCAGCCGTCGATCCTAAAGACTTT
TCTATTGGTGATTATATTTATGGGTTCATTCACGGATCTTCCGTAAGGTTTCCTTCCA
ATGGTGCTTTTGCTGAATATTCTGCTATTTCAACTGTGGTTGCCTACAAATCACCCAA
TGAACTCAAATTTTTGGGTGAAGATGTTCTACCTGCCGGCCCTGTCAGGTCTTTGGA
AGGGGCAGCCACTATCCCAGTGTCACTGACCACAGCTGGCTTGGTGTTGACCTATA
ACTTGGGCTTGAACCTGAAGTGGGAGCCATCAACCCCACAAAGAAACGGCCCCATC
TTATTATGGGGCGGTGCAACTGCAGTAGGTCAGTCGCTCATCCAATTAGCCAATAAA
TTGAATGGCTTCACCAAGATCATTGTTGTGGCTTCTCGGAAACACGAAAAACTGTTG
AAAGAATATGGTGCTGATCAACTATTTGATTACCATGATATTGACGTGGTAGAACAAA
TTAAACACAAGTACAACAATATCTCGTATTTAGTCGACTGTGTCGCGAATCAAAATAC
GCTTCAACAAGTGTACAAATGTGCGGCCGATAAACAGGATGCTACCGTTGTCGAATT
AACTAATTTGACAGAAGAAAACGTCAAAAAGGAGAATAGGAGGCAAAATGTCACTAT
TGACAGAACAAGACTGTATTCAATAGGCGGCCATGAAGTACCATTTGGTGGCATTAC
TTTCCCTGCTGACCCAGAAGCCAGGAGAGCTGCCACCGAATTCGTCAAGTTCATCA
ATCCAAAGATTAGTGATGGGCAAATTCACCATATTCCAGCAAGGGTCTATAAGAACG
GGCTTTACGATGTTCCTCGTATCCTGGAAGACATTAAAATCGGTAAGAACTCTGGTG
AAAAACTAGTTGCCGTATTAAACTAG SEQ ID NO: 21  Protein sequence from pyridoxine 4-dehydrogenase (YPR127W) of *Saccharomyces cerevisiae*
MSVADLKNNIHKLDTGYGLMSLTWRAEPIPQSQAFEAMHRVVELSRERGHKAFFNVGE
FYGPDFINLSYVHDFFAKYPDLRKDVVISCKGGADNATLTPRGSHDDVVQSVKNSVSAI
GGYIDIFEVARIDTSLCTKGEVYPYESFEALAEMISEGVIGGISLSEVNEEQIRAIHKDWGK
FLTCVEVELSLFSNDILHNGIAKTCAELGLSIICYSPLGRGLLTGQLKSNADIPEGDFRKSL
KRFSDESLKKNLTLVRFLQEEIVDKRPQNNSITLAQLALGWVKHWNKVPEYSGAKFIPIP
SGSSISKVNENFDEQKTKLTDQEFNAINKYLTTFHTVGDRYEMA SEQ ID NO: 22  DNA sequence encoding pyridoxine 4-dehydrogenase (YPR127W) of *Saccharomyces cerevisiae*
ATGTCTGTCGCCGATTTGAAAAACAACATCCACAAGTTAGATACTGGCTATGGTTTAA
TGAGTTTGACTTGGAGAGCCGAGCCTATCCCTCAGTCGCAGGCTTTCGAGGCCATG
CACAGAGTGGTTGAGTTATCCAGAGAACGTGGGCACAAGGCCTTTTTCAACGTTGG
TGAATTCTATGGTCCCGATTTTATTAATTTGTCGTATGTTCACGACTTCTTTGCGAAAT
ACCCAGATTTGAGAAAGGATGTGGTTATCAGTTGTAAAGGTGGTGCAGACAATGCTA
CCTTAACCCCCAGAGGCAGTCACGATGATGTTGTACAAAGCGTAAAGAATTCAGTTA
GTGCTATTGGTGGCTACATCGACATCTTCGAAGTCGCAAGAATCGACACTTCCCTAT
GCACGAAAGGAGAGGTCTACCCCTACGAATCGTTCGAAGCGCTTGCTGAGATGATC
TCCGAAGGCGTTATTGGCGGTATTTCATTAAGTGAAGTTAATGAAGAGCAAATTAGA
GCTATTCACAAGGATTGGGGAAAGTTTTTGACCTGCGTTGAAGTGGAACTTTCTTTG
TTCAGTAATGACATTTTACACAACGGAATTGCTAAAACATGTGCTGAATTGGGGTTGT
CCATCATCTGCTACTCCCCACTGGGCAGAGGATTGTTGACAGGTCAATTGAAGTCAA
ACGCTGATATCCCTGAGGGTGACTTTAGAAAGTCGTTAAAGAGATTTAGCGACGAGT
CTTTGAAAAAAAACCTGACCTTGGTCAGGTTTCTACAGGAAGAAATAGTCGACAAGC
GCCCACAAAACAACTCCATTACTCTTGCACAACTGGCTTTGGGATGGGTTAAGCACT
GGAACAAAGTTCCGGAATACAGTGGCGCCAAATTTATCCCAATTCCAAGTGGCTCTT
CTATTTCCAAGGTTAATGAAAACTTTGATGAACAGAAAACCAAACTTACCGATCAAGA
GTTCAATGCCATTAACAAATATTTGACTACTTTCCATACTGTTGGTGACAGATACGAA
ATGGCGTAA SEQ ID NO: 23  DNA sequence encoding norcoclaurine synthase of *Coptis japonica*, codon optimized for *S. cerevisiae* with HindIII and SacII cloning sites
AAGCTTAAAATGAGAATGGAAGTCGTCTTGGTCGTTTTCTTGATGTTCATTGGTACTA
TCAACTGCGAAAGATTGATCTTCAATGGTAGACCTTTGTTGCACAGAGTTACCAAAG
AAGAAACCGTTATGTTGTACCACGAATTGGAAGTTGCTGCTTCTGCTGATGAAGTTT
GGTCTGTTGAAGGTTCTCCAGAATTGGGTTTACATTTGCCAGATTTGTTGCCAGCTG
GTATTTTTGCCAAGTTCGAAATTACTGGTGATGGTGGTGAAGGTTCCATTTTGGATAT
GACTTTTCCACCAGGTCAATTCCCACATCATTACAGAGAAAAGTTCGTCTTTTTCGAC
CACAAGAACAGATACAAGTTGGTCGAACAAATCGATGGTGATTTCTTCGATTTGGGT
GTTACTTACTACATGGACACCATTAGAGTTGTTGCTACTGGTCCAGATTCTTGCGTTA
TTAAGTCTACTACTGAATACCACGTCAAGCCAGAATTTGCTAAAATCGTTAAGCCATT
GATCGATACCGTTCCATTGGCTATTATGTCTGAAGCTATTGCCAAGGTTGTCTTGGA TABLE 7-continued Disclosed Nucleic Acid and Amino Acid Sequences

AAACAAACACAAGTCATCTGAATGAAAGACTCCGCGG

SEQ ID NO: 24   Protein sequence from norcoclaurine synthase of
                Coptis japonica
MRMEVVLVVFLMFIGTINCERLIFNGRPLLHRVTKEETVMLYHELEVAASADEVWSVEGS
PELGLHLPDLLPAGIFAKFEITGDGGEGSILDMTFPPGQFPHHYREKFVFFDHKNRYKLV
EQIDGDFFDLGVTYYMDTIRVVATGPDSCVIKSTTEYHVKPEFAKIVKPLIDTVPLAIMSEA
IAKVVLENKHKSSE SEQ ID NO: 25   Protein sequence from Aryl-alcohol Dehydrogenase
                3 (AAD3) of Saccharomyces cerevisiae
MIGSASDSSSKLGRLRFLSETAAIKVSPLILGEVSYDGARSDFLKSMNKNRAFELLDTFYE
AGGNFIDAANNCQNEQSEEWIGEWIQSRRLRDQIVIATKFIKSDKKYKAGESNTANYCGN
HKRSLHVSVRDSLRKLQTDWIDILYVHWWDYMSSIEEFMDSLHILVQQGKVLYLGVSDTP
AWVVSAANYYATSYGKTPFSIYQGKWNVLNRDFERDIIPMARHFGMALAPWDVMGGGR
FQSKKAMEERRKNGEGIRSFVGASEQTDAEIKISEALAKIAEEHGTESVTAIAIAYVRSKAK
NFFPSVEGGKIEDLKENIKALSIDLTPDNIKYLESIVPFDIGFPNNFIVLNSLTQKYGTNNV SEQ ID NO: 26   DNA sequence encoding Aryl-alcohol Dehydrogenase
                3 (AAD3) of Saccharomyces cerevisiae
ATGATTGGGTCCGCGTCCGACTCATCTAGCAAGTTAGGACGCCTCCGATTTCTTTCT
GAAACTGCCGCTATTAAAGTATCCCCGTTAATCCTAGGAGAAGTCTCATACGATGGA
GCACGTTCGGATTTTCTCAAATCAATGAACAAGAATCGAGCTTTTGAATTGCTTGATA
CTTTTTACGAGGCAGGTGGAAATTTCATTGATGCCGCAAACAACTGCCAAAACGAGC
AATCAGAAGAATGGATTGGTGAATGGATACAGTCCAGAAGGTTACGTGATCAAATTG
TCATTGCAACCAAGTTTATAAAAGCGATAAAAAGTATAAAGCAGGTGAAAGTAACAC
TGCCAACTACTGTGGTAATCACAAGCGTAGTTTACATGTGAGTGTGAGGGATTCTCT
CCGCAAATTGCAAACTGATTGGATTGATATACTTTACGTTCACTGGTGGGATTATATG
AGTTCAATCGAAGAATTTATGGATAGTTTGCATATTCTGGTCCAGCAGGGCAAGGTC
CTCTATTTGGGTGTATCTGATACACCTGCTTGGGTTGTTTCTGCGGCAAACTACTACG
CTACATCTTATGGTAAAACTCCCTTTAGTATCTACCAAGGTAAATGGAACGTGTTGAA
CAGAGATTTTGAGCGTGATATTATTCCAATGGCTAGGCATTTCGGTATGGCCCTCGC
CCCATGGGATGTCATGGGAGGTGGAAGATTTCAGAGTAAAAAAGCAATGGAGGAAC
GGAGGAAGAATGGAGAGGGTATTCGTTCTTTCGTTGGCGCCTCCGAACAAACAGAT
GCAGAAATCAAGATTAGTGAAGCATTGGCCAAGATTGCTGAGGAACATGGCACTGAG
TCTGTTACTGCTATTGCTATTGCCTATGTTCGCTCTAAGGCGAAAAATTTTTTTCCGTC
GGTTGAAGGAGGAAAAATTGAGGATCTCAAAGAGAACATTAAGGCTCTCAGTATCGA
TCTAACGCCAGACAATATAAAATACTTAGAAAGTATAGTTCCTTTTGACATCGGATTTC
CTAATAATTTTATCGTGTTAAATTCCTTGACTCAAAAATATGGTACGAATAATGTTTAG SEQ ID NO: 27   Protein sequence from Aryl-alcohol Dehydrogenase
                4 (AAD4) of Saccharomyces cerevisiae
MGSMNKEQAFELLDAFYEAGGNCIDTANSYQNEESEIWIGEWMKSRKLRDQIVIATKFTG
DYKKYEVGGGKSANYCGNHKHSLHVSVRDSLRKLQTDWIDILYVHWWDYMSSIEEVMD
SLHILVQQGKVLYLGVSDTPAWVVSAANYYATSHGKTPFSIYQGKWNVLNRDFERDIIPM
ARHFGMALAPWDVMGGGRFQSKKAMEERKKNGEGLRTVSGTSKQTDKEVKISEALAKV
AEEEHGTESVTAIAIAYVRSKAKNVFPLVGGRKIEHLKQNIEALSIKLTPEQIEYLESIIPFDVG
FPTNFIGDDPAVTKKASLLTAMSAQISFD SEQ ID NO: 28   DNA sequence encoding Aryl-alcohol Dehydrogenase
                4 (AAD4) of Saccharomyces cerevisiae
ATGGGCTCTATGAATAAGGAACAGGCTTTTGAACTTCTTGATGCTTTTTATGAAGCAG
GAGGTAATTGCATTGATACTGCAAACAGTTACCAAAATGAAGAGTCAGAGATTTGGAT
AGGTGAATGGATGAAATCAAGAAAGTTGCGTGACCAAATTGTAATTGCCACCAAGTTT
ACCGGAGATTATAAGAAGTATGAAGTAGGTGGCGGTAAAAGTGCCAACTATTGTGGT
AATCACAAGCATAGTTTACATGTGAGTGTGAGGGATTCTCTCCGCAAATTGCAAACTG
ATTGGATTGATATACTTTACGTTCACTGGTGGGATTATATGAGTTCAATCGAAGAAGT
TATGGATAGTTTGCATATTTTAGTTCAGCAGGGCAAAGTCCTCTATTTGGGTGTGTCT
GATACACCTGCTTGGGTTGTTTCTGCGGCAAACTACTACGCCACATCTCATGGGAAA
ACTCCTTTTAGTATCTATCAAGGTAAATGGAATGTGTTGAACAGGGACTTTGAGCGCG
ATATCATTCCAATGGCCAGACATTTTGGTATGGCTCTAGCCCCATGGGATGTTATGG
GAGGTGGAAGATTTCAGAGTAAAAAAGCAATGGAGGAACGGAAGAAGAATGGAGAG
GGTCTGCGTACTGTTTCGGGTACTTCTAAACAGACGGATAAAGAGGTTAAGATCAGT
GAAGCATTGGCCAAGGTTGCTGAGGAACATGGCACTGAGTCTGTTACTGCTATTGCT
ATTGCCTATGTTCGCTCTAAGGCGAAAAATGTTTTCCCATTGGTTGGTGGAAGGAAAA
TTGAACACCTCAAACAGAACATTGAGGCTTTAAGTATCAAACTGACACCAGAACAGAT
AGAATACTTAGAAAGTATTATTCCTTTTGATGTTGGTTTTCCTACTAATTTTATCGGTG
ATGATCCGGCTGTTACCAAGAAGGCTTCACTTCTCACGGCAATGTCTGCGCAGATTT
CCTTCGATTAA SEQ ID NO: 29   Protein sequence from Mitochondrial alcohol
                dehydrogenase isozyme III (ADH3) of Saccharomyces
                cerevisiae
MLRTSTLFTRRVQPSLFSRNILRLQSTAAIPKTQKGVIFYENKGKLHYKDIPVPEPKPNEIL
INVKYSGVCHTDLHAWHGDWPLPVKLPLVGGHEGAGVVVKLGSNVKGWKVGDLAGIK
WLNGSCMTCEFCESGHESNCPDADLSGYTHDGSFQQFATADAIQAAKIQQGTDLAEVA
PILCAGVTVYKALKEADLKAGDWVAISGAAGGLGSLAVQYATAMGYRVLGIDAGEEKEK
LFKKLGGEVFIDFTKTKNMVSDIQEATKGGPHGVINVSVSEAAISLSTEYVRPCGTVVLV TABLE 7-continued Disclosed Nucleic Acid and Amino Acid Sequences

GLPANAYVKSEVFSHVVKSINIKGSYVGNRADTREALDFFSRGLIKSPIKIVGLSELPKVY
DLMEKGKILGRYVVDTSK

SEQ ID NO: 30   DNA sequence encoding Mitochondrial alcohol
                dehydrogenase isozyme III (ADH3) of *Saccharomyces
                cerevisiae*

ATGTTGAGAACGTCAACATTGTTCACCAGGCGTGTCCAACCAAGCCTATTTTCTAGA
AACATTCTTAGATTGCAATCCACAGCTGCAATCCCTAAGACTCAAAAAGGTGTCATCT
TTTATGAGAATAAGGGGAAGCTGCATTACAAAGATATCCCTGTCCCCGAGCCTAAGC
CAAATGAAATTTTAATCAACGTTAAATATTCTGGTGTATGTCACACCGATTTACATGC
TTGGCACGGCGATTGGCCATTACCTGTTAAACTACCATTAGTAGGTGGTCATGAAGG
TGCTGGTGTAGTTGTCAAACTAGGTTCCAATGTCAAGGGCTGGAAAGTCGGTGATTT
AGCAGGTATCAAATGGCTGAACGGTTCTTGTATGACATGCGAATTCTGTGAATCAGG
TCATGAATCAAATTGTCCAGATGCTGATTTATCTGGTTACACTCATGATGGTTCTTTC
CAACAATTTGCGACCGCTGATGCTATTCAAGCCGCCAAAATTCAACAGGGTACCGAC
TTGGCCGAAGTAGCCCCAATATTATGTGCTGGTGTTACTGTATATAAAGCACTAAAA
GAGGCAGACTTGAAAGCTGGTGACTGGGTTGCCATCTCTGGTGCTGCAGGTGGCTT
GGGTTCCTTGGCCGTTCAATATGCAACTGCGATGGGTTACAGAGTTCTAGGTATTGA
TGCAGGTGAGGAAAAGGAAAAACTTTTCAAGAAATTGGGGGGTGAAGTATTCATCGA
CTTTACTAAAACAAAGAATATGGTTTCTGACATTCAAGAAGCTACCAAAGGTGGCCC
TCATGGTGTCATTAACGTTTCCGTTTCTGAAGCCGCTATTTCTCTATCTACGGAATAT
GTTAGACCATGTGGTACCGTCGTTTTGGTTGGTTTGCCCGCTAACGCCTACGTTAAA
TCAGAGGTATTCTCTCATGTGGTGAAGTCCATCAATATCAAGGGTTCTTATGTTGGTA
ACAGAGCTGATACGAGAGAAGCCTTAGACTTCTTTAGCAGAGGTTTGATCAAATCAC
CAATCAAATTGTTGGATTATCTGAATTACCAAAGGTTTATGACTTGATGGAAAAGGG
CAAGATTTTGGGTAGATACGTCGTCGATACTAGTAAATAA

SEQ ID NO: 31   Protein sequence from Alcohol dehydrogenase
                isoenzyme type IV (ADH4) of *Saccharomyces
                cerevisiae*

MSSVTGFYIPPISFFGEGALEETADYIKNKDYKKALIVTDPGIAAIGLSGRVQKMLEERDL
NVAIYDKTQPNPNIANVTAGLKVLKEQNSEIVVSIGGGSAHDNAKAIALLATNGGEIGDYE
GVNQSKKAALPLFAINTTAGTASEMTRFTIISNEEKKIKMAIIDNNVTPAVAVNDPSTMFGL
PPALTAATGLDALTHCIEAYVSTASNPITDACALKGIDLINESLVAAYKDGKDKKARTDMC
YAEYLAGMAFNNASLGYVHALAHQLGGFYHLPHGVCNAVLLPHVQEANMQCPKAKKRL
GEIALHFGASQEDPEETIKALHVLNRTMNIPRNLKELGVKTEDFEILAEHAMHDACHLTN
PVQFTKEQVVAIIKKAYEY

SEQ ID NO: 32   DNA sequence encoding Alcohol dehydrogenase
                isoenzyme type IV (ADH4) of *Saccharomyces
                cerevisiae*

ATGTCTTCCGTTACTGGGTTTTACATTCCACCAATCTCTTTCTTTGGTGAAGGTGCTTT
AGAAGAAACCGCTGATTACATCAAAAACAAGGATTACAAAAAGGCTTTGATCGTTACT
GATCCTGGTATTGCAGCTATTGGTCTCTCCGGTAGAGTCCAAAAGATGTTGGAAGAA
CGTGACTTAAACGTTGCTATCTATGACAAAACTCAACCAAACCCAAATATTGCCAATG
TCACAGCTGGTTTGAAGGTTTTGAAGGAACAAAACTCTGAAATTGTTGTTTCCATTGG
TGGTGGTTCTGCTCACGACAATGCTAAGGCCATTGCTTTATTGGCTACTAACGGTGG
GGAAATCGGAGACTATGAAGGTGTCAATCAATCTAAGAAGGCTGCTTTACCACTATTT
GCCATCAACACTACTGCTGGTACTGCTTCCGAAATGACCAGATTCACTATTATCTCTA
ATGAAGAAAAGAAAATCAAGATGGCTATCATTGACAACAACGTCACTCCAGCTGTTGC
TGTCAACGATCCATCTACCATGTTTGGTTTGCCACCTGCTTTGACTGCTGCTACTGGT
CTAGATGCTTTGACTCACTGTATCGAAGCTTATGTTTCCACCGCCTCTAACCCAATCA
CCGATGCCTGTGCTTTGAAGGGTATTGATTTGATCAATGAAAGCTTAGTCGCTGCATA
CAAAGACGGTAAAGACAAGAAGGCCAGAACTGACATGTGTTACGCTGAATACTTGGC
AGGTATGGCTTTCAACAATGCTTCTCTAGGTTATGTTCATGCCCTTGCTCATCAACTT
GGTGGTTTCTACCACTTGCCTCATGGTGTTTGTAACGCTGTCTTGTTGCCTCATGTTC
AAGAGGCCAACATGCAATGTCCAAAGGCCAAGAAGAGATTAGGTGAAATTGCTTTGC
ATTTCGGTGCTTCTCAAGAAGATCCAGAAGAAACCATCAAGGCTTTGCACGTTTTAAA
CAGAACCATGAACATTCCAAGAAACTTGAAAGAATTAGGTGTTAAAACCGAAGATTTT
GAAATTTTGGCTGAACACGCCATGCATGATGCCTGCCATTTGACTAACCCAGTTCAAT
TCACCAAAGAACAAGTGGTTGCCATTATCAAGAAAGCCTATGAATATTAA

SEQ ID NO: 33   Protein sequence from Cytosolic aldehyde
                dehydrogenase (ALD6) of *Saccharomyces
                cerevisiae*

MTKLHFDTAEPVKITLPNGLTYEQPTGLFINNKFMKAQDGKTYPVEDPSTENTVCEVSSA
TTEDVEYAIECADRAFHDTEWATQDPRERGRLLSKLADELESQIDLVSSIEALDNGKTLA
LARGDVTIAINCLRDAAAYADKVNGRTINTGDGYMNFTTLEPIGVCGQIIPWNFPIMMLA
WKIAPALAMGNVCILKPAAVTPLNALYFASLCKKVGIPAGVVNIVPGPGRTVGAALTNDP
RIRKLAFTGSTEVGKSVAVDSSESNLKKITLELGGKSAHLVFDDANIKKTLPNLVNGIFKN
AGQICSSGSRIYVQEGIYDELLAAFKAYLETEIKVGNPFDKANFQGAITNRQQFDTIMNYI
DIGKKEGAKILTGGEKVGDKGYFIRPTVFYDVNEDMRIVKEEIFGPVVTVAKFKTLEEGVE
MANSSEFGLGSGIETESLSTGLKVAKMLKAGTVWINTYNDFDSRVPFGGVKQSGYGRE
MGEEVYHAYTEVKAVRIKL

TABLE 7-continued

Disclosed Nucleic Acid and Amino Acid Sequences

SEQ ID NO: 34     DNA sequence encoding Cytosolic aldehyde
                  dehydrogenase (ALD6) of *Saccharomyces*
                  *cerevisiae*
ATGACTAAGCTACACTTTGACACTGCTGAACCAGTCAAGATCACACTTCCAAATGGT
TTGACATACGAGCAACCAACCGGTCTATTCATTAACAACAAGTTTATGAAAGCTCAA
GACGGTAAGACCTATCCCGTCGAAGATCCTTCCACTGAAAACACCGTTTGTGAGGT
CTCTTCTGCCACCACTGAAGATGTTGAATATGCTATCGAATGTGCCGACCGTGCTTT
CCACGACACTGAATGGGCTACCCAAGACCCAAGAGAAAGAGGCCGTCTACTAAGTA
AGTTGGCTGACGAATTGGAAAGCCAAATTGACTTGGTTTCTTCCATTGAAGCTTTGG
ACAATGGTAAAACTTTGGCCTTAGCCCGTGGGGATGTTACCATTGCAATCAACTGTC
TAAGAGATGCTGCTGCCTATGCCGACAAAGTCAACGGTAGAACAATCAACACCGGT
GACGGCTACATGAACTTCACCACCTTAGAGCCAATCGGTGTCTGTGGTCAAATTATT
CCATGGAACTTTCCAATAATGATGTTGGCTTGGAAGATCGCCCCAGCATTGGCCATG
GGTAACGTCTGTATCTTGAAACCCGCTGCTGTCACACCTTTAAATGCCCTATACTTT
GCTTCTTTATGTAAGAAGGTTGGTATTCCAGCTGGTGTCGTCAACATCGTTCCAGGT
CCTGGTAGAACTGTTGGTGCTGCTTTGACCAACGACCCAAGAATCAGAAAGCTGGC
TTTTACCGGTTCTACAGAAGTCGGTAAGAGTGTTGCTGTCGACTCTTCTGAATCTAA
CTTGAAGAAAATCACTTTGGAACTAGGTGGTAAGTCCGCCCATTTGGTCTTTGACGA
TGCTAACATTAAGAAGACTTTACCAAATCTAGTAAACGGTATTTTCAAGAACGCTGGT
CAAATTTGTTCCTCTGGTTCTAGAATTTACGTTCAAGAAGGTATTTACGACGAACTAT
TGGCTGCTTTCAAGGCTTACTTGGAAACCGAAATCAAAGTTGGTAATCCATTTGACA
AGGCTAACTTCCAAGGTGCTATCACTAACCGTCAACAATTCGACACAATTATGAACT
ACATCGATATCGGTAAGAAAGAAGGCGCCAAGATCTTAACTGGTGGCGAAAAAGTT
GGTGACAAGGGTTACTTCATCAGACCAACCGTTTTCTACGATGTTAATGAAGACATG
AGAATTGTTAAGGAAGAAATTTTTGGACCAGTTGTCACTGTCGCAAAGTTCAAGACTT
TAGAAGAAGGTGTCGAAATGGCTAACAGCTCTGAATTCGGTCTAGGTTCTGGTATCG
AAACAGAATCTTTGAGCACAGGTTTGAAGGTGGCCAAGATGTTGAAGGCCGGTACC
GTCTGGATCAACACATACAACGATTTTGACTCCAGAGTTCCATTCGGTGGTGTTAAG
CAATCTGGTTACGGTAGAGAAATGGGTGAAGAAGTCTACCATGCATACACTGAAGTA
AAAGCTGTCAGAATTAAGTTGTAA SEQ ID NO: 35     Protein sequence from NAD-dependent
                  (R,R)-butanediol dehydrogenase (BDH1) of
                  *Saccharomyces cerevisiae*
MRALAYFKKGDIHFTNDIPRPEIQTDDEVIIDVSWCGICGSDLHEYLDGPIFMPKDGECHK
LSNAALPLAMGHEMSGIVSKVGPKVTKVKVGDHVVVDAASSCADLHCWPHSKFYNSKP
CDACQRGSENLCTHAGFVGLGVISGGFAEQVVVSQHHIIPVPKEIPLDVAALVEPLSVTW
HAVKISGFKKGSSALVLGAGPIGLCTILVLKGMGASKIVVSEIAERRIEMAKKLGVEVFNP
SKHGHKSIEILRGLTKSHDGFDYSYDCSGIQVTFETSLKALTFKGTATNIAVWGPKPVPF
QPMDVTLQEKVMTGSIGYVVEDFEEVVRAIHNGDIAMEDCKQLITGKQRIEDGWEKGFQ
ELMDHKESNVKILLTPNNHGEMK SEQ ID NO: 36     DNA sequence encoding NAD-dependent
                  (R,R)-butanediol dehydrogenase (BDH1) of
                  *Saccharomyces cerevisiae*
ATGAGAGCTTTGGCATATTTCAAGAAGGGTGATATTCACTTCACTAATGATATCCCTA
GGCCAGAAATCCAAACCGACGATGAGGTTATTATCGACGTCTCTTGGTGTGGGATTT
GTGGCTCGGATCTTCACGAGTACTTGGATGGTCCAATCTTCATGCCTAAAGATGGAG
AGTGCCATAAATTATCCAACGCTGCTTTACCTCTGGCAATGGGCCATGAGATGTCAG
GAATTGTTTCCAAGGTTGGTCCTAAAGTGACAAAGGTGAAGGTTGGCGACCACGTGG
TCGTTGATGCTGCCAGCAGTTGTGCGGACCTGCATTGCTGGCCACACTCCAAATTTT
ACAATTCCAAACCATGTGATGCTTGTCAGAGGGGCAGTGAAAATCTATGTACCCACG
CCGGTTTTGTAGGACTAGGTGTGATCAGTGGTGGCTTTGCTGAACAAGTCGTAGTCT
CTCAACATCACATTATCCCGGTTCCAAAGGAAATTCCTCTAGATGTGGCTGCTTTAGT
TGAGCCTCTTTCTGTCACCTGGCATGCTGTTAAGATTTCTGGTTTCAAAAAAGGCAGT
TCAGCCTTGGTTCTTGGTGCAGGTCCCATTGGGTTGTGTACCATTTTGGTACTTAAG
GGAATGGGGGCTAGTAAAATTGTAGTGTCTGAAATTGCAGAGAGAAGAATAGAAATG
GCCAAGAAACTGGGCGTTGAGGTGTTCAATCCCTCCAAGCACGGTCATAAATCTATA
GAGATACTACGTGGTTTGACCAAGAGCCATGATGGGTTTGATTACAGTTATGATTGTT
CTGGTATTCAAGTTACTTTCGAAACCTCTTTGAAGGCATTAACATTCAAGGGGACAGC
CACCAACATTGCAGTTTGGGGTCCAAAACCTGTCCCATTCCAACCAATGGATGTGAC
TCTCCAAGAGAAGTTATGACTGGTTCGATCGGCTATGTTGTCGAAGACTTCGAAGA
AGTTGTTCGTGCCATCCACAACGGAGACATCGCCATGGAAGATTGTAAGCAACTAAT
CACTGGTAAGCAAAGGATTGAGGACGGTTGGGAAAAGGGATTCCAAGAGTTGATGG
ATCACAAGGAATCCAACGTTAAGATTCTATTGACGCCTAACAATCACGGTGAAATGAA
GTAA SEQ ID NO: 37     Protein sequence from Putative medium-chain
                  alcohol dehydrogenase with similarity to BDH2
                  (BDH2) of *Saccharomyces cerevisiae*
MRALAYFGKGNIRFTNHLKEPHIVAPDELVIDIEWCGICGTDLHEYTDGPIFFPEDGHTHE
ISHNPLPQAMGHEMAGTVLEVGPGVKNLKVGDKVVVEPTGTCRDRYRWPLSPNVDKE
WCAACKKGYYNICSYLGLCGAGVQSGGFAERVVMNESHCYKVPDFVPLDVAALIQPLA
VCWHAIRVCEFKAGSTALIIGAGPIGLGTILALNAAGCKDIVVSEPAKVRRELAEKMGARV
YDPTAHAAKESIDYLRSIADGDGFDYTFDCSGLEVTLNAAIQCLTFRGTAVNLAMWGH
HKIQFSPMDITLHERKYTGSMCYTHHDFEAVIEALEEGRIDIDRARHMITGRVNIEDGLDG
AIMKLINEKESTIKIILTPNNHGELNREADNEKKEISELSSRKDQERLRESINEAKLRHT TABLE 7-continued Disclosed Nucleic Acid and Amino Acid Sequences SEQ ID NO: 38   DNA sequence encoding Putative medium-chain
                alcohol dehydrogenase with similarity to BDH2
                (BDH2) of *Saccharomyces cerevisiae*

```
ATGAGAGCCTTAGCGTATTTCGGTAAAGGTAACATCAGATTCACCAACCATTTAAAGG
AGCCACATATTGTGGCGCCCGATGAGCTTGTGATTGATATCGAATGGTGTGGTATTT
GCGGTACGGACCTGCATGAGTACACAGATGGTCCTATCTTTTTCCCAGAAGATGGAC
ACACACATGAGATTAGTCATAACCCATTGCCACAGGCGATGGGCCACGAAATGGCTG
GTACCGTTTTGGAGGTGGGCCCTGGTGTGAAAAACTTGAAAGTGGGAGACAAGGTA
GTTGTCGAGCCCACAGGTACATGCAGAGACCGGTATCGTTGGCCCCTGTCGCCAAA
CGTTGACAAGGAATGGTGCGCTGCTTGCAAAAAGGGCTACTATAACATTTGTTCATAT
TTGGGGCTTTGTGGTGCGGGTGTGCAGAGCGGTGGATTTGCAGAACGTGTTGTGAT
GAACGAATCTCACTGCTACAAAGTACCGGACTTCGTGCCCTTAGACGTTGCAGCTTT
GATTCAACCGTTGGCTGTGTGCTGGCATGCAATTAGAGTCTGCGAGTTCAAAGCAGG
CTCTACGGCTTTGATCATTGGTGCTGGCCCCATCGGACTGGGCACGATACTGGCGTT
GAACGCTGCAGGTTGCAAGGACATCGTCGTTTCAGAGCCTGCCAAGGTAAGAAGAG
AACTGGCTGAAAAAATGGGTGCCAGGGTTTACGACCCAACTGCGCACGCTGCCAAG
GAGAGCATTGATTATCTGAGGTCGATTGCTGATGGTGGAGACGGCTTCGATTACACA
TTTGATTGCTCCGGGTTGGAAGTCACATTGAATGCTGCTATTCAGTGTCTCACTTTCA
GAGGCACCGCAGTGAACTTGGCCATGTGGGGCCATCACAAGATACAGTTTTCTCCG
ATGGACATCACATTGCATGAAAGAAAGTACACAGGGTCCATGTGCTACACACACCAC
GATTTTGAGGCAGTAATAGAAGCTTTGGAAGAAGGCAGGATTGACATTGATAGAGCA
AGACATATGATAACGGGCAGAGTCAACATTGAGGACGGCCTTGATGGCGCCATCAT
GAAGCTGATAAACGAGAAGGAGTCTACAATCAAGATTATTCTGACTCCAAACAATCAC
GGAGAGTTGAACAGGGAAGCCGATAATGAGAAGAAAGAAATTTCCGAGCTGAGCAG
TCGGAAAGATCAAGAAAGACTACGAGAATCAATAAACGAGGCTAAACTGCGTCACAC
ATGA
```

SEQ ID NO: 39   Protein sequence from 3-hydroxyacyl-CoA
                dehydrogenase and enoyl-CoA hydratase (FOX2) of
                *Saccharomyces cerevisiae*

```
MPGNLSFKDRVVVITGAGGGLGKVYALAYASRGAKVVVNDLGGTLGGSGHNSKAADLV
VDEIKKAGGIAVANYDSVNENGEKIIETAIKEFGRVDVLINNAGILRDVSFAKMTEREFASV
VDVHLTGGYKLSRAAWPYMRSQKFGRIINTASPAGLFGNFGQANYSAAKMGLVGLAET
LAKEGAKYNINVNSIAPLARSRMTENVLPPHILKQLGPEKIVPLVLYLTHESTKVSNSIFEL
AAGFFGQLRWERSSGQIFNPDPKTYTPEAILNKWKEITDYRDKPFNKTQHPYQLSDYND
LITKAKKLPPNEQGSVKIKSLCNKVVVVTGAGGGLGKSHAIWFARYGAKVVVNDIKDPFS
VVEEINKLYGEGTAIPDSHDVVTEAPLIIQTAISKFQRVDILVNNAGILRDKSFLKMKDEEW
FAVLKVHLFSTFSLSKAVWPIFTKQKSGFIINTTSTSGIYGNFGQANYAAAKAAILGFSKTI
ALEGAKRGIIVNVIAPHAETAMTKTIFSEKELSNHFDASQVSPLVVLLASEELQKYSGRRV
IGQLFEVGGGWCGQTRWQRSSGYVSIKETIEPEEIKENWNHITDFSRNTINPSSTEESS
MATLQAVQKAHSSKELDDGLFKYTTKDCILYNLGLGCTSKELKYTYENDPDFQVLPTFA
VIPFMQATATLAMDNLVDNFNYAMLLHGEQYFKLCTPTMPSNGTLKTLAKPLQVLDKNG
KAALVVGGFETYDIKTKKLIAYNEGSFFIRGAHVPPEKEVRDGKRAKFAVQNFEVPHGKV
PDFEAEISTNKDQAALYRLSGDFNPLHIDPTLAKAVKFPTPILHGLCTLGISAKALFEHYG
PYEELKVRFTNVVFPGDTLKVKAWKQGSVVVFQTIDTTRNVIVLDNAAVKLSQAKSKL
```

SEQ ID NO: 40   DNA sequence encoding 3-hydroxyacyl-CoA
                dehydrogenase and enoyl-CoA hydratase (FOX2) of
                *Saccharomyces cerevisiae*

```
ATGCCTGGAAATTTATCCTTCAAAGATAGAGTTGTTGTAATCACGGGCGCTGGAGGG
GGCTTAGGTAAGGTGTATGCACTAGCTTACGCAAGCAGAGGTGCAAAAGTGGTCGT
CAATGATCTAGGTGGCACTTTGGGTGGTTCAGGACATAACTCCAAAGCTGCAGACTT
AGTGGTGGATGAGATAAAAAAAGCCGGAGGTATAGCTGTGGCAAATTACGACTCTGT
TAATGAAAATGGAGAGAAATAATTGAAACGGCTATAAAAGAATTCGGCAGGGTTGAT
GTACTAATTAACAACGCTGGAATATTAAGGGATGTTTCATTTGCAAAGATGACAGAAC
GTGAGTTTGCATCTGTGGTAGATGTTCATTTGACAGGTGGCTATAAGCTATCGCGTG
CTGCTTGGCCTTATATGCGCTCTCAGAAATTTGGTAGAATCATTAACACCGCTTCCCC
TGCCGGTCTATTTGGAAATTTTGGTCAAGCTAATTATTCAGCAGCTAAATGGGCTTA
GTTGGTTTGGCGGAAACCCTCGCGAAGGAGGGTGCCAAATACAACATTAATGTTAAT
TCAATTGCGCCATTGGCTAGATCACGTATGACAGAAAACGTGTTACCACCACATATCT
TGAAACAGTTAGGACCGGAAAAAATTGTTCCCTTAGTACTCTATTTGACACACGAAAG
TACGAAAGTGTCAAACTCCATTTTTGAACTCGCTGCTGGATTCTTTGGACAGCTCAGA
TGGGAGAGGTCTTCTGGACAAATTTTCAATCCAGACCCCAAGACATATACTCCTGAA
GCAATTTTAAATAAGTGGAAGGAAATCACAGACTATAGGGACAAGCCATTTAACAAAA
CTCAGCATCCATATCAACTCTCGGATTATAATGATTTAATCACCAAAGCAAAAAAATTA
CCTCCCAATGAACAAGGCTCAGTGAAAATCAAGTCGCTTTGCAACAAAGTCGTAGTA
GTTACGGGTGCAGGAGGTGGTCTTGGGAAGTCTCATGCAATCTGGTTTGCACGGTA
CGGTGCGAAGGTAGTTGTAAATGACATCAAGGATCCTTTTTCAGTTGTTGAAGAAATA
AATAAACTATATGGTGAAGGCACAGCCATTCCAGATTCCCATGATGTGGTCACCGAA
GCTCCTCTCATTATCCAAACTGCAATAAGTAAGTTTCAGAGAGTAGACATCTTGGTCA
ATAACGCTGGTATTTTGCGTGACAAATCTTTTTTAAAAATGAAAGATGAGGAATGGTTT
GCTGTCCTGAAAGTCCACCTTTTTTCCACATTTTCATTGTCAAAAGCAGTATGGCCAA
TATTTACCAAACAAAAGTCTGGATTTATTATCAATACTACTTCTACCTCAGGAATTTAT
GGTAATTTTGGACAGGCCAATTATGCCGCTGCAAAAGCCGCCATTTTAGGATTCAGT
AAAACTATTGCACTGGAAGGTGCCAAGAGAGGAATTATTGTTAATGTTATCGCTCCTC
ATGCAGAAACGGCTATGACAAAGACTATATTCTCGGAGAAGGAATTATCAAACCACTT
TGATGCATCTCAAGTCTCCCCACTTGTTGTTTTGTTGGCATCTGAAGAACTACAAAAG
```

TABLE 7-continued

Disclosed Nucleic Acid and Amino Acid Sequences

TATTCTGGAAGAAGGGTTATTGGCCAATTATTCGAAGTTGGCGGTGGTTGGTGTGGG
CAAACCAGATGGCAAAGAAGTTCCGGTTATGTTTCTATTAAAGAGACTATTGAACCGG
AAGAAATTAAAGAAATTGGAACCACATCACTGATTTCAGTCGCAACACTATCAACCC
GAGCTCCACAGAGGAGTCTTCTATGGCAACCTTGCAAGCCGTGCAAAAGCGCACT
CTTCAAAGGAGTTGGATGATGGATTATTCAAGTACACTACCAAGGATTGTATCTTGTA
CAATTTAGGACTTGGATGCACAAGCAAAGAGCTTAAGTACACCTACGAGAATGATCC
AGACTTCCAAGTTTTGCCCACGTTCGCCGTCATTCCATTTATGCAAGCTACTGCCACA
CTAGCTATGGACAATTTAGTCGATAACTTCAATTATGCAATGTTACTGCATGGAGAAC
AATATTTTAAGCTCTGCACGCCGACAATGCCAAGTAATGGAACTCTAAAGACACTTGC
TAAACCTTTACAAGTACTTGACAAGAATGGTAAAGCCGCTTTAGTTGTTGGTGGCTTC
GAAACTTATGACATTAAAACTAAGAAACTCATAGCTTATAACGAAGGATCGTTCTTCAT
CAGGGGCGCACATGTACCTCCAGAAAAGGAAGTGAGGGATGGGAAAAGAGCCAAGT
TTGCTGTCCAAAATTTTGAAGTGCCACATGGAAAGGTACCAGATTTTGAGGCGGAGA
TTTCTACGAATAAAGATCAAGCCGCATTGTACAGGTTATCTGGCGATTTCAATCCTTT
ACATATCGATCCCACGCTAGCCAAAGCAGTTAAATTTCCTACGCCAATTCTGCATGG
GCTTTGTACATTAGGTATTAGTGCGAAAGCATTGTTTGAACATTATGGTCCATATGAG
GAGTTGAAAGTGAGATTTACCAATGTTGTTTTCCCAGGTGATACTCTAAAGGTTAAAG
CTTGGAAGCAAGGCTCGGTTGTCGTTTTTCAAACAATTGATACGACCAGAAACGTCAT
TGTATTGGATAACGCCGCTGTAAAACTATCGCAGGCAAAATCTAAACTATAA

SEQ ID NO: 41     Protein sequence from Glycerol dehydrogenase
                  (GCY1) of Saccharomyces cerevisiae
MPATLHDSTKILSLNTGAQIPQIGLGTWQSKENDAYKAVLTALKDGYRHIDTAAIYRNED
QVGQAIKDSGVPREEIFVTTKLWCTQHHEPEVALDQSLKRLGLDYVDLYLMHWPARLD
PAYIKNEDILSVPTKKDGSRAVDITNWNFIKTWELMQELPKTGKTKAVGVSNFSINNLKDL
LASQGNKLTPAANQVEIHPLLPQDELINFCKSKGIVVEAYSPLGSTDAPLLKEPVILEIAKK
NNVQPGHVVISWHVQRGYVVLPKSVNPDRIKTNRKIFTLSTEDFEAINNISKEKGEKRVV
HPNWSPFEVFK SEQ ID NO: 42     DNA sequence encoding Glycerol dehydrogenase
                  (GCY1) of Saccharomyces cerevisiae
ATGCCTGCTACTTTACATGATTCTACGAAAATCCTTTCTCTAAATACTGGAGCCCAAAT
CCCTCAAATAGGTTTAGGTACGTGGCAGTCGAAAGAGAACGATGCTTATAAGGCTGT
TTTAACCGCTTTGAAAGATGGCTACCGACACATTGATACTGCTGCTATTTACCGTAAT
GAAGACCAAGTCGGTCAAGCCATCAAGGATTCAGGTGTTCCTCGGGAAGAAATCTTT
GTTACTACAAAGTTATGGTGTACACAACACCACGAACCTGAAGTAGCGCTGGATCAA
TCACTAAAGAGGTTAGGATTGGACTACGTAGACTTATATTTGATGCATTGGCCTGCCA
GATTAGATCCAGCCTACATCAAAAATGAAGACATCTTGAGTGTGCCAACAAAGAAGG
ATGGTTCTCGTGCAGTGGATATCACCAATTGGAATTTCATCAAAACCTGGGAATTAAT
GCAGGAACTACCAAAGACTGGTAAAACTAAGGCCGTTGGAGTCTCCAACTTTTCTAT
AAATAACCTGAAAGATCTATTAGCATCTCAAGGTAATAAGCTTACGCCAGCTGCTAAC
CAAGTCGAAATACATCCATTACTACCTCAAGACGAATTGATTAATTTTTGTAAAAGTAA
AGGCATTGTGGTTGAAGCTTATTCTCCGTTAGGTAGTACCGATGCTCCACTATTGAAG
GAACCGGTTATCCTTGAAATTGCAAGAAAAATAACGTTCAACCCGGACACGTTGTTA
TTAGCTGGCACGTCCAAAGAGGTTATGTTGTCTTGCCAAAATCTGTGAATCCCGATC
GAATCAAAACGAACAGGAAATATTTACTTTGTCTACTGAGGACTTTGAAGCTATCAA
TAACATATCGAAGGAAAAGGGCGAAAAAAGGGTTGTACATCCAAATTGGTCTCCTTTC
GAAGTATTCAAGTAA SEQ ID NO: 43     Protein sequence from Glyoxylate reductase
                  (GOR1) of Saccharomyces cerevisiae
MSKKPIVLKLGKDAFGDQAWGELEKIADVITIPESTTREQFLREVKDPQNKLSQVQVITRT
ARSVKNTGRFDEELALALPSSVVAVCHTGAGYDQIDVEPFKKRHIQVANVPDLVSNATA
DTHVFLLLGALRNFGIGNRRLIEGNWPEAGPACGSPFGYDPEGKTVGILGLRIGRCILE
RLKPFGFENFIYHNRHQLPSEEEHGCEYVGFEEFLKRSDIVSVNVPLNHNTHHLINAETIE
KMKDGVVIVNTARGAVIDEQAMTDALRSGKIRSAGLDVFEYEPKISKELLSMSQVLGLPH
MGTHSVETRKKMEELVVENAKNVILTGKVLTIVPELQNEDWPNESKPLV SEQ ID NO: 44     DNA sequence encoding Glyoxylate reductase
                  (GOR1) of Saccharomyces cerevisiae
ATGAGTAAGAAACCAATTGTTTTGAAATTAGGAAAGGATGCCTTTGGTGACCAAGCC
TGGGGGGAATTGGAAAAGATTGCGGATGTAATTACCATCCCTGAATCCACCACTAGA
GAACAGTTTTTGCGGGAGGTAAAAGACCCACAAAATAAGCTCTCCCAAGTACAAGTC
ATTACTAGAACAGCAAGGAGTGTGAAAAACACCGGTAGATTTGATGAAGAGCTTGCT
CTTGCTTTGCCCTCCTCCGTAGTGGCTGTATGTCATACTGGTGCTGGTTATGACCAA
ATTGATGTTGAGCCATTCAAGAAAAGGCACATCCAGGTTGCCAATGTTCCTGATTTA
GTTAGCAATGCTACCGCTGATACGCATGTATTTTTGCTATTGGGTGCCCTAAGAAAC
TTCGGTATTGGTAACAGAAGGTTGATCGAGGGAAACTGGCCGGAGGCAGGACCCG
CATGTGGTTCTCCCTTTGGATACGACCCTGAAGGGAAACAGTTGGATACTGGGTC
TAGGTAGGATTGGTCGTTGTATTTTAGAGAGATTGAAGCCGTTTGGGTTCGAGAATT
TCATATATCATAACAGACACCAGCTTCCTTCCGAAGAAGAGCATGGTTGTGAATATG
TAGGATTCGAGGAGTTTTTGAAGCGTTCTGATATAGTATCTGTAAACGTCCCACTGA
ACCACAATACTCACCATCTAATCAATGCAGAGACTATTGAAAAAATGAAAGATGGTGT
AGTTATTGTTAACACAGCGCGTGGTGCCGTGATAGACGAACAAGCCATGACTGATG
CTTTGCGTTCTGGAAAGATTAGAAGTGCTGGTTTGGACGTTTTCGAATATGAGCCAA
AAATATCCAAAGAGTTATTATCGATGTCCCAAGTCTTAGGACTGCCTCATATGGGCA
CACATAGTGTAGAAACAAGAAAGAAAATGGAAGAACTGGTCGTTGAAAATGCAAAGA TABLE 7-continued Disclosed Nucleic Acid and Amino Acid Sequences

```
ATGTGATATTGACCGGGAAAGTCTTGACTATTGTTCCGGAATTACAAAATGAAGACT
GGCCCAATGAATCTAAGCCATTAGTTTGA
```

SEQ ID NO: 45    Protein sequence from NAD-dependent glycerol-3-
                 phosphate dehydrogenase (GPD1) of Saccharomyces
                 cerevisiae

```
MSAAADRLNLTSGHLNAGRKRSSSSVSLKAAEKPFKVTVIGSGNWGTTIAKVVAENCKG
YPEVFAPIVQMWVFEEEINGEKLTEIINTRHQNVKYLPGITLPDNLVANPDLIDSVKDVDII
VFNIPHQFLPRICSQLKGHVDSHVRAISCLKGFEVGAKGVQLLSSYITEELGIQCGALSGA
NIATEVAQEHWSETTVAYHIPKDFRGEGKDVDHKVLKALFHRPYFHVSVIEDVAGISICG
ALKNVVALGCGFVEGLGWGNNASAAIQRVGLGEIIRFGQMFFPESREETYYQESAGVA
DLITTCAGGRNVKVARLMATSGKDAWECEKELLNGQSAQGLITCKEVHEWLETCGSVE
DFPLFEAVYQIVYNNYPMKNLPDMIEELDLHED
```

SEQ ID NO: 46    DNA sequence encoding NAD-dependent glycerol-3-
                 phosphate dehydrogenase (GPD1) of Saccharomyces
                 cerevisiae

```
ATGTCTGCTGCTGCTGATAGATTAAACTTAACTTCCGGCCACTTGAATGCTGGTAGAA
AGAGAAGTTCCTCTTCTGTTTCTTTGAAGGCTGCCGAAAAGCCTTTCAAGGTTACTGT
GATTGGATCTGGTAACTGGGGTACTACTATTGCCAAGGTGGTTGCCGAAAATTGTAA
GGGATACCCAGAAGTTTTCGCTCCAATAGTACAAATGTGGGTGTTCGAAGAAGAGAT
CAATGGTGAAAAATTGACTGAAATCATAAATACTAGACATCAAAACGTGAAATACTTG
CCTGGCATCACTCTACCCGACAATTTGGTTGCTAATCCAGACTTGATTGATTCAGTCA
AGGATGTCGACATCATCGTTTTCAACATTCCACATCAATTTTTGCCCCGTATCTGTAG
CCAATTGAAAGGTCATGTTGATTCACACGTCAGAGCTATCTCCTGTCTAAAGGGTTTT
GAAGTTGGTGCTAAAGGTGTCCAATTGCTATCCTCTTACATCACTGAGGAACTAGGTA
TTCAATGTGGTGCTCTATCTGGTGCTAACATTGCCACCGAAGTCGCTCAAGAACACT
GGTCTGAAACAACAGTTGCTTACCACATTCCAAAGGATTTCAGAGGCGAGGGCAAGG
ACGTCGACCATAAGGTTCTAAAGGCCTTGTTCCACAGACCTTACTTCCACGTTAGTGT
CATCGAAGATGTTGCTGGTATCTCCATCTGTGGTGCTTTGAAGAACGTTGTTGCCTTA
GGTTGTGGTTTCGTCGAAGGTCTAGGCTGGGGTAACAACGCTTCTGCTGCCATCCAA
AGAGTCGGTTTGGGTGAGATCATCAGATTCGGTCAAATGTTTTTCCCAGAATCTAGA
GAAGAAACATACTACCAAGAGTCTGCTGGTGTTGCTGATTTGATCACCACCTGCGCT
GGTGGTAGAAACGTCAAGGTTGCTAGGCTAATGGCTACTTCTGGTAAGGACGCCTG
GGAATGTGAAAAGGAGTTGTTGAATGGCCAATCCGCTCAAGGTTTAATTACCTGCAA
AGAAGTTCACGAATGGTTGGAAACATGTGGCTCTGTCGAAGACTTCCCATTATTTGAA
GCCGTATACCAAATCGTTTACAACAACTACCCAATGAAGAACCTGCCGGACATGATT
GAAGAATTAGATCTACATGAAGATTAG
```

SEQ ID NO: 47    Protein sequence from Multifunctional enzyme
                 containing phosphoribosyl-ATP pyrophosphatase,
                 phosphoribosyl-AMP cyclohydrolase, and histidinol
                 dehydrogenase activities (HIS4) of Saccharomyces
                 cerevisiae

```
MVLPILPLIDDLASWNSKKEYVSLVGQVLLDGSSLSNEEILQFSKEEEVPLVALSLPSGKF
SDDEIIAFLNNGVSSLFIASQDAKTAEHLVEQLNVPKERVVVEENGVFSNQFMVKQKFSQ
DKIVSIKKLSKDMLTKEVLGEVRTDRPDGLYTTLVVDQYERCLGLVYSSKKSIAKAIDLGR
GVYYSRSRNEIWIKGETSGNGQKLLQISTDCDSDALKFIVEQENVGFCHLETMSCFGEF
KHGLVGLESLLKQRLQDAPEESYTRRLFNDSALLDAKIKEEAEELTEAKGKKELSWEAA
DLFYFALAKLVANDVSLKDVENNLNMKHLKVTRRKGDAKPKFVGQPKAEEEKLTGPIHL
DVVKASDKVGVQKALSRPIQKTSEIMHLVNPIIENVRDKGNSALLEYTEKFDGVKLSNPV
LNAPFPEEYFEGLTEEMKEALDLSIENVRKFHAAQLPTETLEVETQPGVLCSRFPRPIEK
VGLYIPGGTAILPSTALMLGVPAQVAQCKEIVFASPPRKSDGKVSPEVVYVAEKVGASKI
VLAGGAQAVAAMAYGTETIPKVDKILGPGNQFVTAAKMYVQNDTQALCSIDMPAGPSEV
LVIADEDADVDFVASDLLSQAEHGIDSQVILVGVNLSEKKIQEIQDAVHNQALQLPRVDIV
RKCIAHSTIVLCDGYEEALEMSNQYAPEHLILQIANANDYVKLVDNAGSVFVGAYTPESC
GDYSSGTNHTLPTYGYARQYSGANTATFQKFITAQNITPEGLENIGRAVMCVAKKEGLD
GHRNAVKIRMSKLGLIPKDFQ
```

SEQ ID NO: 48    DNA sequence Multifunctional enzyme containing
                 phosphoribosyl-ATP pyrophosphatase, phosphoribosyl-
                 AMP cyclohydrolase, and histidinol dehydrogenase
                 activities (HIS4) of Saccharomyces cerevisiae

```
ATGGTTTTGCCGATTCTACCGTTAATTGATGATCTGGCCTCATGGAATAGTAAGAAG
GAATACGTTTCACTTGTTGGTCAGGTACTTTTGGATGGCTCGAGCCTGAGTAATGAA
GAGATTCTCCAGTTCTCCAAAGAGGAAGAAGTTCCATTGGTGGCTTTGTCCTTGCCA
AGTGGTAAATTCAGCGATGATGAAATCATTGCCTTCTTGAACAACGGAGTTTCTTCTC
TGTTCATTGCTAGCCAAGATGCTAAAACAGCCGAACACTTGGTTGAACAATTGAATG
TACCAAAGGAGCGTGTTGTTGTGGAAGAGAACGGTGTTTTCTCCAATCAATTCATGG
TAAAACAAAAATTCTCGCAAGATAAAATTGTGTCCATAAAGAAATTAAGCAAGGATAT
GTTGACCAAAGAAGTGCTTGGTGAAGTACTACAGACCGTCCTGACGGTTTATATAC
CACCCTAGTTGTCGACCAATATGAGCGTTGTCTAGGGTTGGTGTATTCTTCGAAGAA
ATCTATAGCAAAGGCCATCGATTTGGGTCGTGGCGTTTATTATTCTCGTTCTAGGAA
TGAAATCTGGATCAAGGGTGAAACTTCTGGCAATGGCCAAAAGCTTTTACAAATCTC
TACTGACTGTGATTCGGATGCCTTAAAGTTTATCGTTGAACAAGAAACGTTGGATTT
TGCCACTTGGAGACCATGTCTTGCTTTGGTGAATTCAAGCATGGTTTGGTGGGGCTA
GAATCTTTACTAAAACAAAGGCTACAGGACGCTCCAGAGGAATCTTATACTAGAAGA
CTATTCAACGACTCTGCATTGTTAGATGCCAAGATCAAGGAAGAAGCTGAAGAACTG
```

TABLE 7-continued

Disclosed Nucleic Acid and Amino Acid Sequences

```
ACTGAGGCAAAGGGTAAGAAGGAGCTTTCTTGGGAGGCTGCCGATTTGTTCTACTTT
GCACTGGCCAAATTAGTGGCCAACGATGTTTCATTGAAGGACGTCGAGAATAATCTG
AATATGAAGCATCTGAAGGTTACAAGACGGAAAGGTGATGCTAAGCCAAAGTTTGTT
GGACAACCAAAGGCTGAAGAAGAAAAACTGACCGGTCCAATTCACTTGGACGTGGT
GAAGGCTTCCGACAAAGTTGGTGTGCAGAAGGCTTTGAGCAGACCAATCCAAAAGA
CTTCTGAAATTATGCATTTAGTCAATCCGATCATCGAAAATGTTAGAGACAAAGGTAA
CTCTGCCCTTTTGGAGTACACAGAAAAAGTTTGATGGTGTAAAATTATCCAATCCTGTT
CTTAATGCTCCATTCCCAGAAGAATACTTTGAAGGTTTAACCGAGGAAATGAAGGAA
GCTTTGGACCTTTCAATTGAAAACGTCCGCAAATTCCATGCTGCTCAATTGCCAACA
GAGACTCTTGAAGTTGAAACCCAACCTGGTGTCTTGTGTTCCAGATTCCCTCGTCCT
ATTGAAAAAGTTGGTTTGTATATCCCTGGTGGCACTGCCATTTTACCAAGTACTGCAT
TAATGCTTGGTGTTCCAGCACAAGTTGCCCAATGTAAGGAGATTGTGTTTGCATCTC
CACCAAGAAAATCTGATGGTAAAGTTTCACCCGAAGTTGTTTATGTCGCAGAAAAG
TTGGCGCTTCCAAGATTGTTCTAGCTGGTGGTGCCCAAGCCGTTGCTGCTATGGCT
TACGGGACAGAAACTATTCCTAAAGTGGATAAGATCTTGGGTCCAGGTAATCAATTT
GTGACTGCCGCCAAAATGTATGTTCAAAATGACACTCAAGCTCTATGTTCCATTGATA
TGCCAGCTGGCCCAAGTGAAGTTTTGGTTATTGCCGATGAAGATGCCGATGTGGAT
TTTGTTGCAAGTGATTTGCTATCGCAAGCTGAACACGGTATTGACTCCCAAGTTATC
CTTGTTGGTGTTAACTTGAGCGAAAAGAAAATTCAAGAGATTCAAGATGCTGTCCAC
AATCAAGCTTTACAACTGCCACGTGTGGATATTGTTCGTAAATGTATTGCTCACAGTA
CGATCGTTCTTTGTGACGGTTACGAAGAAGCCCTTGAAATGTCCAACCAATATGCAC
CAGAACATTTGATTCTACAAATCGCCAATGCTAACGATTATGTTAAATTGGTTGACAA
TGCAGGGTCCGTATTTGTGGGTGCTTACACTCCAGAATCGTGCGGTGACTATTCAA
GTGGTACTAACCATACATTACCAACCTATGGTTACGCTAGGCAGTACAGTGGTGCCA
ACACTGCAACCTTCCAAAAGTTTATCACTGCCCAAAACATTACCCCTGAAGGTTTAG
AAAACATCGGTAGAGCTGTTATGTGCGTTGCCAAGAAGGAGGGTCTAGACGGTCAC
AGAAACGCTGTGAAAATCAGAATGAGTAAGCTTGGGTTGATCCCAAAGGATTTCCAG
TAG
```

SEQ ID NO: 49    Protein sequence from HMG-CoA reductase (HMG1) of
                 Saccharomyces cerevisiae
MPPLFKGLKQMAKPIAYVSRFSAKRPIHIILFSLIISAFAYLSVIQYYFNGWQLDSNSVFET
APNKDSNTLFQECSHYYRDSSLDGWVSITAHEASELPAPHHYYLLNLNFNSPNETDSIP
ELANTVFEKDNTKYILQEDLSVSKEISSTDGTKWRLRSDRKSLFDVKTLAYSLYDVFSEN
VTQADPFDVLIMVTAYLMMFYTIFGLFNDMRKTGSNFWLSASTVVNSASSLFLALYVTQ
CILGKEVSALTLFEGLPFIVVVVGFKHKIKIAQYALEKFERVGLSKRITTDEIVFESVSEEG
GRLIQDHLLCIFAFIGCSMYAHQLKTLTNFCILSAFILIFELILTPTFYSAILALRLEMNVIHRS
TIIKQTLEEDGVVPSTARIISKAEKKSVSSFLNLSVVVIIMKLSVILLFVFINFYNFGANWVN
DAFNSLYFDKERVSLPDFITSNASENFKEQAIVSVTPLLYYKPIKSYQRIEDMVLLLLRNVS
VAIRDRFVSKLVLSALVCSAVINVYLLNAARIHTSYTADQLVKTEVTKKSFTAPVQKASTP
VLTNKTVISGSKVKSLSSAQSSSSGPSSSSEEDSRDIESLDKKIRPLEELEALLSSGNTK
QLKNKEVAALVIHGKLPLYALEKKLGDTTRAVAVRRKALSILAEAPVLASDRLPYKNYDY
DRVFGACCENVIGYMPLPVGVIGPLVIDGTSYHIPMATTEGCLVASAMRGCKAINAGGG
ATTVLTKDGMTRGPVVRFPTLKRSGACKIWLDSEEGQNAIKKAFNSTSRFARLQHIQTC
LAGDLLFMRFRTTTGDAMGMNMISKGVEYSLKQMVEEYGWEDMEVVSVSGNYCTDKK
PAAINWIEGRGKSVVAEATIPGDVVRKVLKSDVSALVELNIAKNLVGSAMAGSVGGFNA
HAANLVTAVFLALGQDPAQNVESSNCITLMKEVDGDLRISVSMPSIEVGTIGGGTVLEPQ
GAMLDLLGVRGPHATAPGTNARQLARIVACAVLAGELSLCAALAAGHLVQSHMTHNRK
PAEPTKPNNLDATDINRLKDGSVTCIKS SEQ ID NO: 50    DNA sequence encoding HMG-CoA reductase (HMG1) of
                 Saccharomyces cerevisiae
ATGCCGCCGCTATTCAAGGGACTGAAACAGATGGCAAAGCCAATTGCCTATGTTTCA
AGATTTTCGGCGAAACGACCAATTCATATAATACTTTTTTCTCTAATCATATCCGCATT
CGCTTATCTATCCGTCATTCAGTATTACTTCAATGGTTGGCAACTAGATTCAAATAGT
GTTTTTGAAACTGCTCCAAATAAAGACTCCAACACTCTATTTCAAGAATGTTCCCATTA
CTACAGAGATTCCTCTCTAGATGGTTGGGTATCAATCACCGCGCATGAAGCTAGTGA
GTTACCAGCCCCACACCATTACTATCTATTAAACCTGAACTTCAATAGTCCTAATGAA
ACTGACTCCATTCCAGAACTAGCTAACACGGTTTTTGAGAAAGATAATACAAAATATA
TTCTGCAAGAAGATCTCAGTGTTTCCAAAGAAATTTCTTCTACTGATGGAACGAAATG
GAGGTTAAGAAGTGACAGAAAAAGTCTTTTCGACGTAAAGACGTTAGCATATTCTCTC
TACGATGTATTTTCAGAAAATGTAACCCAAGCAGACCCGTTTGACGTCCTTATTATGG
TTACTGCCTACCTAATGATGTTCTACACCATATTCGGCCTCTTCAATGACATGAGGAA
GACCGGGTCAAATTTTGGTTGAGCGCCTCTACAGTGGTCAATTCTGCATCATCACTT
TTCTTAGCATTGTATGTCACCCAATGTATTCTAGGCAAAGAAGTTTCCGCATTAACTCT
TTTTGAAGGTTTGCCTTTCATTGTAGTTGTTGTTGGTTTCAAGCACAAAATCAAGATTG
CCCAGTATGCCCTGGAGAAATTTGAAAGAGTCGGTTTATCTAAAAGGATTACTACCGA
TGAAATCGTTTTTGAATCCGTGAGCGAAGAGGGTGGTCGTTTGATTCAAGACCATTT
GCTTTGTATTTTTGCCTTTATCGGATGCTCTATGTATGCTCACCAATTGAAGACTTTGA
CAAACTTCTGCATATTATCAGCATTTATCCTAATTTTTGAATTGATTTTAACTCCTACAT
TTTATTCTGCTATCTTAGCGCTTAGACTGGAAATGAATGTTATCCACAGATCTACTATT
ATCAAGCAAACATTAGAAGAAGACGGTGTTGTTCCATCTACAGCAAGAATCATTTCTA
AAGCAGAAAAGAAATCCGTATCTTCTTTCTTAAATCTCAGTGTGGTTGTCATTATCATG
AAACTCTCTGTCATACTGTTGTTTGTCTTCATCAACTTTTATAACTTTGGTGCAAATTG
GGTCAATGATGCCTTCAATTCATTGTACTTCGATAAGGAACGTGTTTCTCTACCAGAT
TTTATTACCTCGAATGCCTCTGAAAACTTTAAAGAGCAAGCTATTGTTAGTGTCACCC
CATTATTATATTACAAACCCATTAAGTCCTACCAACGCATTGAGGATATGGTTCTTCTA
TTGCTTCGTAATGTCAGTGTTGCCATTCGTGATAGGTTCGTCAGTAAATTAGTTCTTT
```

TABLE 7-continued

Disclosed Nucleic Acid and Amino Acid Sequences

```
CCGCCTTAGTATGCAGTGCTGTCATCAATGTGTATTTATTGAATGCTGCTAGAATTCA
TACCAGTTATACTGCAGACCAATTGGTGAAAACTGAAGTCACCAAGAAGTCTTTTACT
GCTCCTGTACAAAAGGCTTCTACACCAGTTTTAACCAATAAAACAGTCATTTCTGGAT
CGAAAGTCAAAAGTTTATCATCTGCGCAATCGAGCTCATCAGGACCTTCATCATCTAG
TGAGGAAGATGATTCCCGCGATATTGAAAGCTTGGATAAGAAAATACGTCCTTTAGAA
GAATTAGAAGCATTATTAAGTAGTGGAAATACAAAACAATTGAAGAACAAAGAGGTCG
CTGCCTTGGTTATTCACGGTAAGTTACCTTTGTACGCTTTGGAGAAAAAATTAGGTGA
TACTACGAGAGCGGTTGCGGTACGTAGGAAGGCTCTTTCAATTTTGGCAGAAGCTCC
TGTATTAGCATCTGATCGTTTACCATATAAAAATTATGACTACGACCGCGTATTTGGC
GCTTGTTGTGAAAATGTTATAGGTTACATGCCTTTGCCCGTTGGTGTTATAGGCCCT
TGGTTATCGATGGTACATCTTATCATATACCAATGGCAACTACAGAGGGTTGTTTGGT
AGCTTCTGCCATGCGTGGCTGTAAGGCAATCAATGCTGGCGGTGGTGCAACAACTG
TTTTAACTAAGGATGGTATGACAAGAGGCCCAGTAGTCCGTTTCCCAACTTTGAAAAG
ATCTGGTGCCTGTAAGATATGGTTAGACTCAGAAGAGGGACAAAACGCAATTAAAAA
AGCTTTTAACTCTACATCAAGATTTGCACGTCTGCAACATATTCAAACTTGTCTAGCA
GGAGATTTACTCTTCATGAGATTTAGAACAACTACTGGTGACGCAATGGGTATGAATA
TGATTTCTAAAGGTGTCGAATACTCATTAAAGCAAATGGTAGAAGAGTATGGCTGGGA
AGATATGGAGGTTGTCTCCGTTTCTGGTAACTACTGTACCGACAAAAAACCAGCTGC
CATCAACTGGATCGAAGGTCGTGGTAAGAGTGTCGTCGCAGAAGCTACTATTCCTGG
TGATGTTGTCAGAAAAGTGTTAAAAAGTGATGTTTCCGCATTGGTTGAGTTGAACATT
GCTAAGAATTTGGTTGGATCTGCAATGGCTGGGTCTGTTGGTGGATTTAACGCACAT
GCAGCTAATTTAGTGACAGCTGTTTTCTTGGCATTAGGACAAGATCCTGCACAAAATG
TTGAAAGTTCCAACTGTATAACATTGATGAAAGAAGTGGACGGTGATTTGAGAATTTC
CGTATCCATGCCATCCATCGAAGTAGGTACCATCGGTGGTGGTACTGTTCTAGAACC
ACAAGGTGCCATGTTGGACTTATTAGGTGTAAGAGGCCCGCATGCTACCGCTCCTGG
TACCAACGCACGTCAATTAGCAAGAATAGTTGCCTGTGCCGTCTTGGCAGGTGAATT
ATCCTTATGTGCTGCCCTAGCAGCCGGCCATTTGGTTCAAAGTCATATGACCCACAA
CAGGAAACCTGCTGAACCAACAAAACCTAACAATTTGGACGCCACTGATATAAATCGT
TTGAAAGATGGGTCCGTCACCTGCATTAAATCCTAA
```

SEQ ID NO 51   Protein sequence from Mitochondrial NADP-specific
               isocitrate dehydrogenase (IPD1) of Saccharomyces
               cerevisiae

```
MSMLSRRLFSTSRLAAFSKIKVKQPVVELDGDEMTRIIWDKIKKKLILPYLDVDLKYYDLS
VESRDATSDKITQDAAEAIKKYGVGIKCATITPDEARVKEFNLHKMWKSPNGTIRNILGGT
VFREPIVIPRIPRLVPRWEKPIIIGRHAHGDQYKATDTLIPGPGSLELVYKPSDPTTAQPQT
LKVYDYKGSGVAMAMYNTDESIEGFAHSSFKLAIDKKLNLFLSTKNTILKKYDGRFKDIFQ
EVYEAQYKSKFEQLGIHYEHRLIDDMVAQMIKSKGGFIMALKNYDGDVQSDIVAQGFGS
LGLMTSILVTPDGKTFESEAAHGTVTRHYRKYQKGEETSTNSIASIFAWSRGLLKRGELD
NTPALCKFANILESATLNTVQQDGIMTKDLALACGNNERSAYVTTEEFLDAVEKRLQKEI
KSIE
```

SEQ ID NO: 52   DNA sequence encoding Mitochondrial NADP-specific
                isocitrate dehydrogenase (IPD1) of Saccharomyces
                cerevisiae

```
ATGAGTATGTTATCTAGAAGATTATTTTCCACCTCTCGCCTTGCTGCTTTCAGTAAGAT
TAAGGTCAAACAACCCGTTGTCGAGTTGGACGGTGATGAAATGACCCGTATCATTTG
GGATAAGATCAAGAAGAAATTGATTCTACCCTACTTGGACGTAGATTTGAAGTACTAC
GACTTATCTGTCGAATCTCGTGACGCCACCTCCGACAAGATTACTCAGGATGCTGCT
GAGGCGATCAAGAAGTATGGTGTTGGTATCAAATGTGCCACCATCACTCCTGATGAA
GCTCGTGTGAAGGAATTCAACCTGCACAAGATGTGGAAATCTCCTAATGGTACCATC
AGAAACATTCTCGGCGGTACAGTGTTCAGAGAGCCCATTGTGATTCCTAGAATTCCT
AGACTGGTCCCACGTTGGGAAAAACCAATCATTATTGGAAGACACGCCCACGGTGAT
CAATATAAAGCTACGGACACACTGATCCCAGGCCCAGGATCTTTGGAACTGGTCTAC
AAGCCATCCGACCCTACGACTGCTCAACCACAAACTTTGAAAGTGTATGACTACAAG
GGCAGTGGTGTGGCCATGGCCATGTACAATACTGACGAATCCATCGAAGGGTTTGCT
CATTCGTCTTTCAAGCTGGCCATTGACAAAAAGCTAAATCTTTTCTTGTCAACCAAGA
ACACTATTTTGAAGAAATATGACGGTCGGTTCAAAGACATTTTCCAAGAAGTTTATGA
AGCTCAATATAAATCCAAATTCGAACAACTAGGGATCCACTATGAACACCGTTTAATT
GATGATATGGTCGCTCAAATGATAAAATCTAAAGGTGGCTTTATCATGGCGCTAAAGA
ACTATGACGGTGATGTCCAATCTGACATCGTCGCTCAAGGATTTGGCTCCTTAGGTTT
GATGACTTCTATCTTAGTTACACCAGACGGTAAAACTTTCGAAAGTGAAGCTGCTCAT
GGTACCGTGACAAGACATTATAGAAAGTACCAAAAGGGTGAAGAAACTTCTACAAAC
TCCATTGCATCCATTTTCGCGTGGTCGAGAGGTCTATTGAAGAGAGGTGAATTGGAC
AATACTCCTGCTTTGTGTAAATTTGCCAATATTTTGGAATCCGCCACTTTGAACACAGT
TCAGCAAGACGGTATCATGACGAAGGACTTGGCTTTGGCTTGCGGTAACAACGAAAG
ATCTGCTTATGTTACCACAGAAGAATTTTTGGATGCCGTTGAAAAAGACTACAAAAA
GAAATCAAGTCGATCGAGTAA
```

SEQ ID NO: 53   Protein sequence from Homo-isocitrate dehydrogenase
                (LYS12) of Saccharomyces cerevisiae

```
MFRSVATRLSACRGLASNAARKSLTIGLIPGDGIGKEVIPAGKQVLENLNSKHGLSFNFID
LYAGFQTFQETGKALPDETVKVLKEQCQGALFGAVQSPTTKVEGYSSPIVALRREMGLF
ANVRPVKSVEGEKGKPIDMVIVRENTEDLYIKIEKTYIDKATGTRVADATKRISEIATRRIAT
IALDIALKRLQTRGQATLTVTHKSNVLSQSDGLFREICKEVYESNKDKYGQIKYNEQIVDS
MVYRLFREPQCFDVIVAPNLYGDILSDGAAALVGSLGVVPSANVGPEIVIGEPCHGSAPD
IAGKGIANPIATIRSTALMLEFLGHNEAAQDIYKAVDANLREGSIKTPDLGGKASTQQVVD
DVLSRL
```

TABLE 7-continued

Disclosed Nucleic Acid and Amino Acid Sequences

SEQ ID NO: 54    DNA sequence encoding Homo-isocitrate dehydrogenase
                 (LYS12) of *Saccharomyces cerevisiae*
ATGTTTAGATCTGTTGCTACTAGATTATCTGCCTGCCGTGGGTTAGCATCTAACGCT
GCTCGCAAATCACTCACTATTGGTCTTATCCCCGGTGACGGTATCGGTAAGGAAGTC
ATTCCTGCTGGTAAGCAAGTTTTGGAAAACCTTAACTCCAAGCACGGCCTAAGCTTC
AACTTTATTGATCTCTACGCCGGTTTCCAAACATTCCAAGAAACAGGAAAGGCGTTG
CCTGATGAGACTGTTAAAGTGTTGAAGGAACAATGTCAAGGTGCTCTTTTCGGTGCA
GTTCAGTCTCCAACTACTAAGGTGGAAGGTTACTCCTCACCAATTGTTGCTCTAAGG
AGGGAAATGGGCCTTTTCGCTAATGTTCGTCCTGTTAAGTCTGTAGAGGGAGAAAAG
GGTAAACCAATTGACATGGTTATCGTCAGAGAAAATACTGAGGACCTGTACATTAAA
ATTGAAAAAACATACATTGACAAGGCCACAGGTACAAGAGTTGCTGATGCCACAAAG
AGAATATCCGAATTGCAACAAGAAGAATTGCAACCATTGCATTAGATATTGCCTTGA
AAAGATTACAAACAAGAGGCCAAGCCACTTTGACAGTGACTCATAAATCAAATGTTC
TATCTCAAAGTGATGGTCTATTCAGAGAAATCTGTAAGGAAGTCTACGAATCTAACAA
GGACAAGTACGGTCAAATCAAATATAACGAACAAATTGTGGATTCCATGGTTTATAG
GCTGTTCAGAGAACCACAATGTTTTGATGTGATAGTGGCACCAAACCTATCGGGGA
TATATTATCTGACGGTGCTGCTGCTTTAGTCGGTTCATTAGGTGTTGTTCCAAGCGC
CAACGTAGGTCCAGAAATTGTCATTGGTGAACCATGCCATGGTTCTGCACCAGATAT
TGCTGGTAAAGGTATTGCTAACCCAATCGCCACTATAAGATCTACTGCTTTGATGTT
GGAATTCTTGGGCCACAACGAAGCTGCCCAAGATATCTACAAGGCTGTTGATGCTAA
CTTAAGAGAGGGTTCTATCAAGACACCAGATTTAGGTGGTAAGGCTTCTACTCAACA
AGTCGTTGACGACGTTTTGTCGAGATTATAG SEQ ID NO: 55    Protein sequence from 3-phosphoglycerate
                 dehydrogenase and alpha-ketoglutarate reductase
                 (SER33) of *Saccharomyces cerevisiae*
MSYSAADNLQDSFQRAMNFSGSPGAVSTSPTQSFMNTLPRRVSITKQPKALKPFSTGD
MNILLLENVNATAIKIFKDQGYQVEFHKSSLPEDELIEKIKDVHAIGIRSKTRLTEKILQHAR
NLVCIGCFCIGTNQVDLKYAASKGIAVFNSPFSNSRSVAELVIGEIISLARQLGDRSIELHT
GTWNKVAARCWEVRGKTLGIIGYHIGSQLSVLAEAMGLHVLYYDIVTIMALGTARQVST
LDELLNKSDFVTLHVPATPETEKMLSAPQFAAMKDGAYVINASRGTVVDIPSLIQAVKAN
KIAGAALDVYPHEPAKNGEGSFNDELNSWTSELVSLPNIILTPHIGGSTEEAQSSIGIEVA
TALSKYINEGNSVGSVNFPEVSLKSLDYDQENTVRVLYIHRNVPGVLKTVNDILSDHNIEK
QFSDSHGEIAYLMADISSVNQSEIKDIYEKLNQTSAKVSIRLLY SEQ ID NO: 56    DNA sequence encoding 3-phosphoglycerate
                 dehydrogenase and alpha-ketoglutarate reductase
                 (SER33) of *Saccharomyces cerevisiae*
ATGTCTTATTCAGCTGCCGATAATTTACAAGATTCATTCCAACGTGCCATGAACTTTTC
TGGCTCTCCTGGTGCAGTCTCAACCTCACCAACTCAGTCATTTATGAACACACTACCT
CGTCGTGTAAGCATTACAAAGCAACCAAAGGCTTTAAAACCTTTTTCTACTGGTGACA
TGAATATTCTACTGTTGGAAAATGTCAATGCAACTGCAATCAAAATCTTCAAGGATCA
GGGTTACCAAGTAGAGTTCCACAAGTCTTCTCTACCTGAGGATGAATTGATTGAAAA
ATCAAAGACGTACACGCTATCGGTATAAGATCTCAAAACTAGATTGACTGAAAAATAC
TACAGCATGCCAGGAATCTAGTTTGTATTGGTTGTTTTTGCATAGGTACCAATCAAGT
AGACCTAAAATATGCCGCTAGTAAAGGTATTGCTGTTTTCAATTCGCCATTCTCCAAT
TCAAGATCCGTAGCAGAATTGGTAATTGGTGAGATCATTAGTTTAGCAAGACAATTAG
GTGATAGATCCATTGAACTGCATACAGGTACATGGAATAAAGTCGCTGCTAGGTGTT
GGGAAGTAAGAGGGAAAAACTCTCGGTATTATTGGGTATGGTCACATTGGTTCGCAAT
TATCAGTTCTTGCAGAAGCTATGGGCCTGCATGTGCTATACTATGATATCGTGACAAT
TATGGCCTTAGGTACTGCCAGACAAGTTTCTACATTAGATGAATTGTTGAATAAATCT
GATTTTGTAACACTACATGTACCAGCTACTCCAGAAACTGAAAAAATGTTATCTGCTC
CACAATTCGCTGCTATGAAGGACGGGGCTTATGTTATTAATGCCTCAAGAGGTACTG
TCGTGGACATTCCATCTCTGATCCAAGCCGTCAAGGCCAACAAAATTGCAGGTGCTG
CTTTAGATGTTTATCCACATGAACCAGCTAAGAACGGTGAAGGTTCATTTAACGATGA
ACTTAACAGCTGGACTTCTGAGTTGGTTTCATTACCAAATATAATCCTGACACCACAT
ATTGGTGGCTCTACAGAAGAAGCTCAAAGTTCAATCGGTATTGAGGTGGCTACTGCA
TTGTCCAAATACATCAATGAAGGTAACTCTGTCGGTTCTGTGAACTTCCCAGAAGTCA
GTTTGAAGTCTTTGGACTACGATCAAGAGAACACAGTACGTGTCTTGTATATTCATCG
TAACGTTCCTGGTGTTTTGAAGACCGTTAATGATATCTTATCCGATCATAATATCGAG
AAACAGTTTTCTGATTCTCACGGCGAGATCGCTTATCTAATGGCAGACATCTCTTCTG
TTAATCAAAGTGAAATCAAGGATATATATGAAAAGTTGAACCAAACTTCTGCCAAAGTT
TCCATCAGGTTATTATACTAA SEQ ID NO: 57    Protein sequence from Glucose-6-phosphate
                 dehydrogenase (ZWF1) of *Saccharomyces cerevisiae*
MSEGPVKFEKNTVISVFGASGDLAKKKTFPALFGLFREGYLDPSTKIFGYARSKLSMEED
LKSRVLPHLKKPHGEADDSKVEQFFKMVSYISGNYDTDEGFDELRTQIEKFEKSANVDV
PHRLFYLALPPSVFLTVAKQIKSRVYAENGITRVIVEKPFGHDLASARELQKNLGPLFKEE
ELYRIDHYLGKELVKNLLVLRFGNQFLNASWNRDNIQSVQISFKERFGTEGRGGYFDSIG
IIRDVMQNHLLQIMTLLTMERPVSFDPESIRDEKVKVLKAVAPIDTDDVLLGQYGKSEDGS
KPAYVDDDTVDKDSKCVTFAAMTFNIENERWEGVPIMMRAGKALNESKVEIRLQYKAVA
SGVFKDIPNNELVIRVQPDAAVYLKFNAKTPGLSNATQVTDLNLTYASRYQDFWIPEAYE
VLIRDALLGDHSNFVRDDELDISWGIFTPLLKHIERPDGPTPEIYPYGSRGPKGLKEYMQ
KHKYVMPEKHPYAWPVTKPEDTKDN TABLE 7-continued Disclosed Nucleic Acid and Amino Acid Sequences SEQ ID NO: 58    DNA sequence encoding Glucose-6-phosphate
                 dehydrogenase (ZWF1) of *Saccharomyces cerevisiae*
ATGAGTGAAGGCCCCGTCAAATTCGAAAAAAATACCGTCATATCTGTCTTTGGTGCGT
CAGGTGATCTGGCAAAGAAGAAGACTTTTCCCGCCTTATTTGGGCTTTTCAGAGAAG
GTTACCTTGATCCATCTACCAAGATCTTCGGTTATGCCCGGTCCAAATTGTCCATGGA
GGAGGACCTGAAGTCCCGTGTCCTACCCCACTTGAAAAAACCTCACGGTGAAGCCG
ATGACTCTAAGGTCGAACAGTTCTTCAAGATGGTCAGCTACATTTCGGGAAATTACGA
CACAGATGAAGGCTTCGACGAATTAAGAACGCAGATCGAGAAATTCGAGAAAGTGC
CAACGTCGATGTCCCACACCGTCTCTTCTATCTGGCCTTGCCGCCAAGCGTTTTTTT
GACGGTGGCCAAGCAGATCAAGAGTCGTGTGTACGCAGAGAATGGCATCACCCGTG
TAATCGTAGAGAAACCTTTCGGCCACGACCTGGCCTCTGCCAGGGAGCTGCAAAAAA
ACCTGGGGCCCTCTTTAAAGAAGAAGAGTTGTACAGAATTGACCATTACTTGGGTA
AAGAGTTGGTCAAGAATCTTTTAGTCTTGAGGTTCGGTAACCAGTTTTTGAATGCCTC
GTGGAATAGAGACAACATTCAAAGCGTTCAGATTTCGTTTAAAGAGAGGTTCGGCAC
CGAAGGCCGTGGCGGCTATTTCGACTCTATAGGCATAATCAGAGACGTGATGCAGAA
CCATCTGTTACAAATCATGACTCTCTTGACTATGGAAAGACCGGTGTCTTTTGACCCG
GAATCTATTCGTGACGAAAAGGTTAAGGTTCTAAAGGCCGTGGCCCCATCGACACG
GACGACGTCCTCTTGGGCCAGTACGGTAAATCTGAGGACGGGTCTAAGCCCGCCTA
CGTGGATGATGACACTGTAGACAAGGACTCTAAATGTGTCACTTTTGCAGCAATGAC
TTTCAACATCGAAAACGAGCGTTGGGAGGGCGTCCCCATCATGATGCGTGCCGGTA
AGGCTTTGAATGAGTCCAAGGTGGAGATCAGACTGCAGTACAAAGCGGTCGCATCG
GGTGTCTTCAAAGACATTCCAAATAACGAACTGGTCATCAGAGTGCAGCCCGATGCC
GCTGTGTACCTAAAGTTTAATGCTAAGACCCCTGGTCTGTCAAATGCTACCCAAGTCA
CAGATCTGAATCTAACTTACGCAAGCAGGTACCAAGACTTTTGGATTCCAGAGGCTTA
CGAGGTGTTGATAAGAGACGCCCTACTGGGTGACCATTCCAACTTTGTCAGAGATGA
CGAATTGGATATCAGTTGGGGCATATTCACCCCATTACTGAAGCACATAGAGCGTCC
GGACGGTCCAACACCGGAAATTTACCCCTACGGATCAAGAGGTCCAAAGGGATTGA
AGGAATATATGCAAAAACACAAGTATGTTATGCCCGAAAAGCACCCTTACGCTTGGC
CCGTGACTAAGCCAGAAGATACGAAGGATAATTAG SEQ ID NO: 59    Protein sequence from Putative aryl alcohol
                 dehydrogenase (YPL088W) of *Saccharomyces
                 cerevisiae*
MVLVKQVRLGNSGLKISPIVIGCMSYGSKKWADWVIEDKTQIFKIMKHCYDKGLRTFDTA
DFYSNGLSERIIKEFLEYYSIKRETVVIMTKIYFPVDETLDLHHNFTLNEFEELDLSNQRGL
SRKHIIAGVENSVKRLGTYIDLLQIHRLDHETPMKEIMKALNDVVEAGHVRYIGASSMLAT
EFAELQFTADKYGWFQFISSQSYYNLLYREDERELIPFAKRHNIGLLPWSPNARGMLTR
PLNQSTDRIKSDPTFKSLHLDNLEEEQKEIINRVEKVSKDKKVSMAMLSIAWVLHKGCHPI
VGLNTTARVDEAIAALQVTLTEEEIKYLEEPYKPQRQRC SEQ ID NO: 60    DNA sequence encoding Putative aryl alcohol
                 dehydrogenase (YPL088W) of *Saccharomyces
                 cerevisiae*
ATGGTTTTAGTTAAGCAGGTAAGACTCGGTAACTCAGGTCTTAAGATATCACCGATA
GTGATAGGATGTATGTCATACGGGTCCAAGAAATGGGCGGACTGGGTCATAGAGGA
CAAGACCCAAATTTTCAAGATTATGAAGCATTGTTACGATAAAGGTCTTCGTACTTTT
GACACAGCAGATTTTTATTCTAATGGTTTGAGTGAAAGAATAATTAAGGAGTTTCTGG
AGTACTACAGTATAAAGAGAGAAACGGTGGTGATTATGACCAAAATTTACTTCCCAG
TTGATGAAACGCTTGATTTGCATCATAACTTCACTTTAAATGAATTTGAAGAATTGGA
CTTGTCCAACCAGCGGGGTTTATCCAGAAAGCATATAATTGCTGGTGTCGAGAACTC
TGTGAAAAGACTGGGCACATATATAGACCTTTTACAAATTCACAGATTAGATCATGAA
ACGCCAATGAAAGAGATCATGAAGGCATTGAATGATGTTGTTGAAGCGGGCCACGT
TAGATACATTGGGGCTTCGAGTATGTTGGCAACTGAATTTGCAGAACTGCAGTTCAC
AGCCGATAAATATGGCTGGTTTCAGTTCATTTCTTCGCAGTCTTACTACAATTTGCTC
TATCGTGAAGATGAACGCGAATTGATTCCTTTTGCCAAAAGACACAATATTGGTTTAC
TTCCATGGTCTCCTAACGCACGAGGCATGTTGACTCGTCCTCTGAACCAAAGCACG
GACAGGATTAAGAGTGATCCAACTTTCAAGTCGTTACATTTGGATAATCTCGAAGAA
GAACAAAAGGAAATTATAAATCGTGTGGAAAAGGTGTCGAAGGACAAAAAAAGTCTCG
ATGGCTATGCTCTCCATTGCATGGGTTTTGCATAAAGGATGTCACCCTATTGTGGGA
TTGAACACTACAGCAAGAGTAGACGAAGCGATTGCCGCACTACAAGTAACTCTAACA
GAAGAAGAGATAAAGTACCTCGAGGAGCCCTACAAACCCCAGAGGCAAAGATGTTA
A SEQ ID NO: 61    Protein sequence NADP+ dependent arabinose
                 dehydrogenase (ARA1) of *Saccharomyces cerevisiae*
MSSSVASTENIVENMLHPKTTEIYFSLNNGVRIPALGLGTANPHEKLAETKQAVKAAIKAG
YRHIDTAWAYETEPFVGEAIKELLEDGSIKREDLFITTKVWPVLWDEVDRSLNESLKALG
LEYVDLLLQHWPLCFEKIKDPKGISGLVCRVKPTVNQVETHPHLPQMELRKFCFMHDILLTAYS
PLGSHGAPNLKIPLVKKLAEKYNVTGNDLLISYHIRQGTIVIPRSLNPVRISSSIEFASLTKD
ELQELNDFGEKYPVRFIDEPFAAILPEFTGNGPNLDNLKY SEQ ID NO: 62    DNA Encoding NADP+ dependent arabinose
                 dehydrogenase (ARA1) of *Saccharomyces cerevisiae*
ATGTCTTCTTCAGTAGCCTCAACCGAAAACATAGTCGAAATATGTTGCATCCAAAGA
CTACAGAAATATACTTTTCACTCAACAATGGTGTTCGTATCCCAGCACTGGGTTTGGG
GACAGCAAATCCTCACGAAAAGTTAGCTGAAACAAAACAAGCCGTAAAAGCTGCAAT TABLE 7-continued Disclosed Nucleic Acid and Amino Acid Sequences CAAAGCTGGATACAGGCACATTGATACTGCTTGGGCCTACGAGACAGAGCCATTCGT
AGGTGAAGCCATCAAGGAGTTATTAGAAGATGGATCTATCAAAAGGGAGGATCTTTT
CATAACCACAAAAGTGTGGCCGGTTCTATGGGACGAAGTGGACAGATCATTGAATGA
ATCTTTGAAAGCTTTAGGCTTGGAATACGTCGACTTGCTCTTGCAACATTGGCCGCTA
TGTTTTGAAAAGATTAAGGACCCTAAGGGGATCAGCGGACTGGTGAAGACTCCGGTT
GATGATTCTGGAAAAACAATGTATGCTGCCGACGGTGACTATTTAGAAACTTACAAGC
AATTGGAAAAAATTTACCTTGATCCTAACGATCATCGTGTGAGAGCCATTGGTGTCTC
AAATTTTTCCATTGAGTATTTGGAACGTCTCATTAAGGAATGCAGAGTTAAGCCAACG
GTGAACCAAGTGGAAACTCACCCTCACTTACCACAAATGGAACTAAGAAAGTTCTGC
TTTATGCACGACATTCTGTTAACAGCATACTCACCATTAGGTTCCCATGGCGCACCAA
ACTTGAAAATCCCACTAGTGAAAAAGCTTGCCGAAAAGTACAATGTCACAGGAAATGA
CTTGCTAATTTCTTACCATATTAGACAAGGCACTATCGTAATTCCGAGATCCTTGAATC
CAGTTAGGATTTCCTCGAGTATTGAATTCGCATCTTTGACAAAGGATGAATTACAAGA
GTTGAACGACTTCGGTGAAAAATACCCAGTGAGATTCATCGATGAGCCATTTGCAGC
CATCCTTCCAGAGTTTACTGGTAACGGACCAAACTTGGACAATTTAAAGTATTAA SEQ ID NO: 63    DNA sequence from vector pEVE2120
CTGCATTAATGAATCGGCCAACGCGCGGGGAGAGGCGGTTTGCGTATTGGGCGCT
CTTCCGCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGGATAACG
CAGGAAAGAACATGTGAGCAAAAGGCCAGCAAAAGGCCAGGAACCGTAAAAAGGC
CGCGTTGCTGGCGTTTTTCCATAGGCTCCGCCCCCTGACGAGCATCACAAAAATC
GACGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTA
GGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCC
GGTAAGACACGACTTATCGCCACTGGCAGCAGCCACTGGTAACAGGATTAGCAGAG
CGAGGTATGTAGGCGGTGCTACAGAGTTCTTGAAGTGGTGGCCTAACTACGGCTAC
ACTAGAAGGACAGTATTTGGTATCTGCGCTCTGCTGAAGCCAGTTACCTTCGGAAAA
AGAGTTGGTAGCTCTTGATCCGGCAAACAAACCACCGCTGGTAGCGGTGGTTTTTT
GTTTGCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTTGGTC
ATGAGATTATCAAAAAGGATCTTCACCTAGATCCTTTTAAATTAAAAATGAAGTTTTAA
ATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCC
GTCGTGTAGATAACTACGATACGGGAGGGCTTACCATCTGGCCCCAGTGCTGCAAT
GATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCT
ATTAATTGTTGCCGGGAAGCTAGAGTAAGTAGTTCGCCAGTTAATAGTTTGCGCAAC
GTTGTTGCCATTGCTACAGGCATCGTGGTGTCACGCTCGTCGTTTGGTATGGCTTCA
TTCAGCTCCGGTTCCCAACGATCAAGGCGAGTTACATGATCCCCCATGTTGTGCAAA
AAAGCGGTTAGCTCCTTCGGTCCTCCGATCGTTGTCAGAAGTAAGTTGGCCGCAGT
GTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATG
CGGCGACCGAGTTGCTCTTGCCCGGCGTCAATACGGGATAATACCGCGCCACATAG
CAGAACTTTAAAAGTGCTCATCATTGGAAAACGTTCTTCGGGGCGAAAACTCTCAAG
GATCTTACCGCTGTTGAGATCCAGTTCGATGTAACCCACTCGTGCACCCAACTGATC
TTCAGCATCTTTTACTTTCACCAGCGTTTCTGGGTGAGCAAAAACAGGAAGGCAAAA
TGCCGCAAAAAAGGGAATAAGGGCGACACGGAAATGTTGAATACTCATACTCTTCCT
TTTTCAATATTATTGAAGCATTTATCAGGGTTATTGTCTCATGAGCGGATACATATTTG
AATGTATTTAGAAAAATAAACAAATAGGGGTTCCGCGCACATTTCCCCGAAAAGTGC
CACCTGGGTCCTTTTCATCACGTGCTATAAAAATAATTATAATTTAAATTTTTTAATAT
AAATATATAAATTAAAAATAGAAAGTAAAAAAAGAAATTAAAGAAAAATAGTTTTTGT
TTTCCGAAGATGTAAAAGACTCTAGGGGGATCGCCAACAAATACTACCTTTTATCTT
GCTCTTCCTGCTCTCAGGTATTAATGCCGAATTGTTTCATCTTGTCTGTGTAGAAGAC
CACACACGAAAATCCTGTGATTTTACATTTTACTTATCGTTAATCGAATGTATATCTAT
TTAATCTGCTTTTCTTGTCTAATAAATATATATGTAAAGTACGCTTTTTGTTGAAATTTT
TTAAACCTTTGTTTATTTTTTTTCTTCATTCCGTAACTCTTCTACCTTCTTTATTTACT
TTCTAAAATCCAAATACAAAACATAAAAATAAATAAACACAGATAAATTCCCAAATTA
TTCCATCATTAAAAGATACGAGGCGCGTGTAAGTTACAGGCAAGCGATCCGTCCTAA
GAAACCATTATTATCATGACATTAACCTATAAAAATAGGCGTATCACGAGGCCCTTTC
GTCTCGCGCGTTTCGGTGATGACGGTGAAAACCTCTGACACATGCAGCTCCCGGAG
ACGGTCACAGCTTGTCTGTAAGCGGATGCCGGGAGCAGACAAGCCCGTCAGGGCG
CGTCAGCGGGTGTTGGCGGGTGTCGGGGCTGGCTTAACTATGCGGCATCAGAGCA
GATTGTACTGAGAGTGCACCATACCACAGCTTTTCAATTCAATTCATCATTTTTTTTTT
ATTCTTTTTTTTGATTTCGGTTTCTTTGAAATTTTTTTGATTCGGTAATCTCCGAACAG
AAGGAAGAACGAAGGAAGGAGCACAGACTTAGATTGGTATATATACGCATATGTAGT
GTTGAAGAAACATGAAATTGCCCAGTATTCTTAACCCAACTGCACAGAACAAAAACC
TGCAGGAAACGAAGATAAATCATGTCGAAAGCTACATATAAGGAACGTGCTGCTACT
CATCCTAGTCCTGTTGCTGCCAAGCTATTTAATATCATGCACGAAAAGCAAACAAACT
TGTGTGCTTCATTGGATGTTCGTACCACCAAGGAATTACTGGAGTTAGTTGAAGCAT
TAGGTCCCAAAATTTGTTTACTAAAAACACATGTGGATATCTTGACTGATTTTTCCAT
GGAGGGCACAGTTAAGCGCTAAAGGCATTATCCGCCAAGTACAATTTTTTACTCTT
CGAAGACAGAAAATTTGCTGACATTGGTAATACAGTCAAATTGCAGTACTCTGCGGG
TGTATACAGAATAGCAGAATGGGCAGACATTACGAATGCACACGGTGTGGTGGGCC
CAGGTATTGTTAGCGGTTTGAAGCAGGCGGCAGAAGAAGTAACAAAGGAACCTAGA
GGCCTTTTGATGTTAGCAGAATTGTCATGCAAGGGCTCCCTATCTACTGGAGAATAT TABLE 7-continued Disclosed Nucleic Acid and Amino Acid Sequences ACTAAGGGTACTGTTGACATTGCGAAGAGCGACAAAGATTTTGTTATCGGCTTTATT
GCTCAAAGAGACATGGGTGGAAGAGATGAAGGTTACGATTGGTTGATTATGACACC
CGGTGTGGGTTTAGATGACAAGGGAGACGCATTGGGTCAACAGTATAGAACCGTGG
ATGATGTGGTCTCTACAGGATCTGACATTATTATTGTTGGAAGAGGACTATTTGCAAA
GGGAAGGGATGCTAAGGTAGAGGGTGAACGTTACAGAAAAGCAGGCTGGGAAGCA
TATTTGAGAAGATGCGGCCAGCAAAACTAAAAAACTGTATTATAAGTAAATGCATGTA
TACTAAAACTCACAAATTAGAGCTTCAATTTAATTATATCAGTTATTACCCTATGCGGTG
TGAAATACCGCACAGATGCGTAAGGAGAAAATACCGCATCAGGAAATTGTAAACGTT
AATATTTTGTTAAAATTCGCGTTAAATTTTTGTTAAATCAGCTCATTTTTTAACCAATAG
GCCGAAATCGGCAAAATCCCTTATAAATCAAAAGAATAGACCGAGATAGGGTTGAGT
GTTGTTCCAGTTTGGAACAAGAGTCCACTATTAAAGAACGTGGACTCCAACGTCAAA
GGGCGAAAAACCGTCTATCAGGGCGATGGCCCACTACGTGAACCATCACCCTAATC
AAGTTTTTTGGGGTCGAGGTGCCGTAAAGCACTAAATCGGAACCCTAAAGGGAGCC
CCCGATTTAGAGCTTGACGGGGAAAGCCGGCGAACGTGGCGAGAAAGGAAGGGAA
GAAAGCGAAAGGAGCGGGCGCTAGGGCGCTGGCAAGTGTAGCGGTCACGCTGCG
CGTAACCACCACACCCGCCGCGCTTAATGCGCCGCTACAGGGCGCGTCGCGCCAT
TCGCCATTCAGGCTGCGCAACTGTTGGGAAGGGCGATCGGTGCGGGCCTCTTCGC
TATTACGCCAGCTGATTTGCCCGGGCAGTTCAGGCTCATCAGGCGCGCCATGCAGG
ATGCATTGATCAGTTAACCCATGGGCATGCGAAGGAAAATGAGAAATATCGAGGGA
GACGATTCAGAGGAGCAGGACAAACTATAACCGACTGTTTGTTGGAGGATGCCGTA
CATAACGAACACTGCTGAAGCTACCATGTCTACAGTTTAGAGGAATGGGTACAACTC
ACAGGCGAGGGATGGTGTTCACTCGTGCTAGCAAACGCGGTGGGAGCAAAAAGTA
GAATATTATCTTTTATTCGTGAAACTTCGAACACTGTCATCTAAAGATGCTATATACTA
ATATAGGCATACTTTGATAATGAAAACTATAAATCGTAAAGACATAAGAGATCCGCGG
ATCCCCGGGTCGAGCCTGAACGGCCTCGAGGCCTGAACGGCCTCGACGAATTCAT
TATTTGTAGAGCTCATCCATGCCATGTGTAATCCCAGCAGCAGTTACAAACTCAAGA
AGGACCATGTGGTCACGCTTTTCGTTGGGATCTTTCGAAAGGGCAGATTGTGTCGA
CAGGTAATGGTTGTCTGGTAAAAGGACAGGGCCATCGCCAATTGGAGTATTTTGTTG
ATAATGGTCTGCTAGTTGAACGGATCCATCTTCAATGTTGTGGCGAATTTTGAAGTTA
GCTTTGATTCCATTCTTTTGTTTGTCTGCCGTGATGTATACATTGTGTGAGTTATAGT
TGTACTCGAGTTTGTGTCCGAGAATGTTTCCATCTTCTTTAAAATCAATACCTTTTAAC
TCGATACGATTAACAAGGGTATCACCTTCAAACTTGACTTCAGCACGCGTCTTGTAG
TTCCCGTCATCTTTGAAAGATATAGTGCGTTCCTGTACATAACCTTCGGGCATGGCA
CTCTTGAAAAAGTCATGCCGTTTCATATGATCCGGATAACGGGAAAAGCATTGAACA
CCATAAGAGAAAGTAGTGACAAGTGTTGGCCATGGAACAGGTAGTTTTCCAGTAGTG
CAAATAAATTTAAGGGTAAGCTGGCCCTGCAGGCCAAGCTTTGTTTTATATTTGTTGT
AAAAAGTAGATAATTACTTCCTTGATGATCTGTAAAAAAGAGAAAAAGAAAGCATCTA
AGAACTTGAAAAACTACGAATTAGAAAAGACCCAAATATGTATTTCTTGCATTGACCAA
TTTATGCAAGTTTATATATATGTAAATGTAAGTTTCACGAGGTTCTACTAAACTAAACC
ACCCCCTTGGTTAGAAGAAAAGAGTGTGTGAGAACAGGCTGTTGTTGTCACACGATT
CGGACAATTCTGTTTGAAAGAGAGAGTAACAGTACGATCGAACGAACTTTGCTCT
GGAGATCACAGTGGGCATCATAGCATGTGGTACTAAACCCTTTCCCGCCATTCCAG
AACCTTCGATTGCTTGTTACAAAACCTGTGAGCCGTCGCTAGGACCTTGTTGTGTGA
CGAAATTGGAAGCTGCAATCAATAGGAAGACAGGAAGTCGAGCGTGTCTGGGTTTT
TTCAGTTTTGTTCTTTTTGCAAACAAATCACGAGCGACGGTAATTTCTTTCTCGATAA
GAGGCCACGTGCTTTATGAGGGTAACATCAATTCAAGAAGGAGGGAAACACTTCCTT
TTTCTGGCCCTGATAATAGTATGAGGGTGAAGCCAAAATAAAGGATTCGCGCCCAAA
TCGGCATCTTTAAATGCAGGTATGCGATAGTTCCTCACTCTTTCCTTACTCACGAGTA
ATTCTTGCAAATGCCTATTATGCAGATGTTATAATATCTGTGCGTAGATCTGATATCC
CTGCATGGCGCGCCTGATGAGCCTGAACTGCCCGGGCAAATCAG SEQ ID NO: 64      DNA sequence from vector pEVE27735
CTGATTTGCCCGGGCAGTTCAGGCTCATCAGGCGCGCCATGCAGGGATATCAGATC
TACGCACAGATATTATAACATCTGCATAATAGGCATTTGCAAGAATTACTCGTGAGTA
AGGAAAGAGTGAGGAACTATCGCATACCTGCATTTAAAGATGCCGATTTGGGCGCGA
ATCCTTTATTTTGGCTTCACCCTCATACTATTATCAGGGCCAGAAAAAGGAAGTGTTT
CCCTCCTTCTTGAATTGATGTTACCCTCATAAAGCACGTGGCCTCTTATCGAGAAAGA
AATTACCGTCGCTCGTGATTTGTTTGCAAAAAGAACAAAACTGAAAAAACCCAGACAC
GCTCGACTTCCTGTCTTCCTATTGATTGCAGCTTCCAATTTCGTCACACAACAAGGTC
CTAGCGACGGCTCACAGGTTTTGTAACAAGCAATCGAAGGTTCTGGAATGGCGGGA
AAGGGTTTAGTACCACATGCTATGATGCCCACTGTGATCTCCAGAGCAAAGTTCGTT
CGATCGTACTGTTACTCTCTCTTTCAAACAGAATTGTCCGAATCGTGTGACAACAA
CAGCCTGTTCTCACACACTCTTTTCTTCTAACCAAGGGGGTGGTTTAGTTTAGTAGAA
CCTCGTGAAACTTACATTTACATATATATAAACTTGCATAAATTGGTCAATGCAAGAAA
TACATATTTGGTCTTTTCTAATTCGTAGTTTTTCAAGTTCTTAGATGCTTTCTTTTTCTC
TTTTTTACAGATCATCAAGGAAGTAATTATCTACTTTTTACAACAAATATAAAACAAAG
CTTAAAATGAGAATGGAAGTCGTCTTGGTCGTTTTCTTGATGTTCATTGGTACTATCA
ACTGCGAAAGATTGATCTTCAATGGTAGACCTTTGTTGCACAGAGTTACCAAAGAAGA
AACCGTTATGTTGTACCACGAATTGGAAGTTGCTGCTTCTGCTGATGAAGTTTGGTCT
GTTGAAGGTTCTCCAGAATTGGGTTTACATTTGCCAGATTTGTTGCCAGCTGGTATTT
TTGCCAAGTTCGAAATTACTGGTGATGGTGGTGAAGGTTCCATTTTGGATATGACTTT
TCCACCAGGTCAATTCCCACATCATTACAGAGAAAAGTTCGTCTTTTTCGACCACAAG
AACAGATACAAGTTGGTCGAACAAATCGATGGTGATTTCTTCAGATTTGGGTGTTACTT
ACTACATGGACACCATTAGAGTTGTTGCTACTGGTCCAGATTCTTGCGTTATTAAGTC
TACTACTGAATACCACGTCAAGCCAGAATTTGCTAAAATCGTTAAGCCATTGATCGAT
ACCGTTCCATTGGCTATTATGTCTGAAGCTATTGCCAAGGTTGTCTTGGAAAACAAAC
ACAAGTCATCTGAATGAAAGACTCCGCGGATCTCTTATGTCTTTACGATTTATAGTTTT
CATTATCAAGTATGCCTATATTAGTATATAGCATCTTTAGATGACAGTGTTCGAAGTTT TABLE 7-continued Disclosed Nucleic Acid and Amino Acid Sequences

```
CACGAATAAAAGATAATATTCTACTTTTTGCTCCCACCGCGTTTGCTAGCACGAGTGA
ACACCATCCCTCGCCTGTGAGTTGTACCCATTCCTCTAAACTGTAGACATGGTAGCTT
CAGCAGTGTTCGTTATGTACGGCATCCTCCAACAAACAGTCGGTTATAGTTTGTCCTG
CTCCTCTGAATCGTCTCCCTCGATATTTCTCATTTTCCTTCGCATGCCCATGGGTTAA
CTGATCAATGCATCCTGCATGGCGCGCCTGATGAGCCTGAACTGCCCGGGCAAATC
AGCTGGCGTAATAGCGAAGAGGCCCGCACCGATCGCCCTTCCCAACAGTTGCGCAG
CCTGAATGGCGAATGGCGCGACGCGCCCTGTAGCGGCGCATTAAGCGCGGCGGGT
GTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTA
AATCGGGGGCTCCCTTTAGGGTTCCGATTTAGTGCTTTACGGCACCTCGACCCCAAA
AAACTTGATTAGGGTGATGGTTCACGTAGTGGGCCATCGCCCTGATAGACGGTTTTT
CGCCCTTTGACGTTGGAGTCCACGTTCTTTAATAGTGGACTCTTGTTCCAAACTGGAA
CAACACTCAACCCTATCTCGGTCTATTCTTTTGATTTATAAGGGATTTTGCCGATTTCG
GCCTATTGGTTAAAAAATGAGCTGATTTAACAAAAATTTAACGCGAATTTTAACAAAAT
ATTAACGTTTACAATTTCCTGATGCGGTATTTTCTCCTTACGCATCTGTGCGGTATTTC
ACACCGCATAGGGTAATAACTGATATAATTAAATTGAAGCTCTAATTTGTGAGTTTAGT
ATACATGCATTTACTTATAATACAGTTTTTTAGTTTTGCTGGCCGCATCTTCTCAAATA
TGCTTCCCAGCCTGCTTTTCTGTAACGTTCACCCTCTACCTTAGCATCCCTTCCCTTT
GCAAATAGTCCTCTTCCAACAATAATAATGTCAGATCCTGTAGAGACCACATCATCCA
CGGTTCTATACTGTTGACCCAATGCGTCTCCCTTGTCATCTAAACCCACACCGGGTG
TCATAATCAACCAATCGTAACCTTCATCTCTTCCACCCATGTCTCTTTGAGCAATAAAG
CCGATAACAAAATCTTTGTCGCTCTTCGCAATGTCAACAGTACCCTTAGTATATTCTC
CAGTAGATAGGGAGCCCTTGCATGACAATTCTGCTAACATCAAAAGGCCTCTAGGTT
CCTTTGTTACTTCTTCTGCCGCCTGCTTCAAACCGCTAACAATACCTGGGCCCACCA
CACCGTGTGCATTCGTAATGTCTGCCCATTCTGCTATTCTGTATACACCCGCAGAGTA
CTGCAATTTGACTGTATTACCAATGTCAGCAAATTTTCTGTCTTCGAAGAGTAAAAAT
TGTACTTGGCGGATAATGCCTTTAGCGGCTTAACTGTGCCCTCCATGGAAAAATCAG
TCAAGATATCCACATGTGTTTTTAGTAAACAAATTTTGGGACCTAATGCTTCAACTAAC
TCCAGTAATTCCTTGGTGGTACGAACATCCAATGAAGCACACAAGTTTGTTTGCTTTT
CGTGCATGATATTAAATAGCTTGGCAGCAACAGGACTAGGATGAGTAGCAGCACGTT
CCTTATATGTAGCTTTCGACATGATTTATCTTCGTTTCCTGCAGGTTTTTGTTCTGTGC
AGTTGGGTTAAGAATACTGGGCAATTTCATGTTTCTTCAACACTACATATGCGTATATA
TACCAATCTAAGTCTGTGCTCCTTCCTTCGTTCTTCCTTCTGTTCGGAGATTACCGAA
TCAAAAAAATTTCAAAGAAACCGAAATCAAAAAAAAGAATAAAAAAAAAATGATGAATT
GAATTGAAAAGCTGTGGTATGGTGCACTCTCAGTACAATCTGCTCTGATGCCGCATA
GTTAAGCCAGCCCCGACACCCGCCAACACCCGCTGACGCGCCCTGACGGGCTTGTC
TGCTCCCGGCATCCGCTTACAGACAAGCTGTGACCGTCTCCGGGAGCTGCATGTGT
CAGAGGTTTTCACCGTCATCACCGAAACGCGCGAGACGAAAGGGCCTCGTGATACG
CCTATTTTTATAGGTTAATGTCATGATAATAATGGTTTCTTAGGACGGATCGCTTGCCT
GTAACTTACACGCGCCTCGTATCTTTTAATGATGGAATAATTTGGGAATTTACTCTGT
GTTTATTTATTTTTATGTTTTGTATTTGGATTTTAGAAAGTAAATAAAGAAGGTAGAAGA
GTTACGGAATGAAGAAAAAAAATAAACAAAGGTTTAAAAAATTTCAACAAAAAGCGT
ACTTTACATATATATTTATTAGACAAGAAAAGCAGATTAAATAGATATACATTCGATTAA
CGATAAGTAAAATGTAAAATCACAGGATTTTCGTGTGTGGTCTTCTACACAGACAAGA
TGAAACAATTCGGCATTAATACCTGAGAGCAGGAAGAGCAAGATAAAAGGTAGTATTT
GTTGGCGATCCCCCTAGAGTCTTTTACATCTTCGGAAAACAAAAACTATTTTTTCTTTA
ATTTCTTTTTTTACTTTCTATTTTTAATTTATATATTTATATTAAAAAATTTAAATTATAAT
TATTTTTATAGCACGTGATGAAAAGGACCCAGGTGGCACTTTTCGGGGAAATGTGCG
CGGAACCCCTATTTGTTTATTTTTCTAAATACATTCAAATATGTATCCGCTCATGAGAC
AATAACCCTGATAAATGCTTCAATAATATTGAAAAAGGAAGAGTATGAGTATTCAACAT
TTCCGTGTCGCCCTTATTCCCTTTTTTGCGGCATTTTGCCTTCCTGTTTTTGCTCACC
CAGAAACGCTGGTGAAAGTAAAAGATGCTGAAGATCAGTTGGGTGCACGAGTGGGT
TACATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCCGTA
TTGACGCCGGGCAAGAGCAACTCGGTCGCCGCATACACTATTCTCAGAATGACTTGG
TTGAGTACTCACCAGTCACAGAAAAGCATCTTACGGATGGCATGACAGTAAGAGAAT
TATGCAGTGCTGCCATAACCATGAGTGATAACACTGCGGCCAACTTACTTCTGACAA
CGATCGGAGGACCGAAGGAGCTAACCGCTTTTTTGCACAACATGGGGATCATGTAA
CTCGCCTTGATCGTTGGGAACCGGAGCTGAATGAAGCCATACCAAACGACGAGCGT
GACACCACGATGCCTGTAGCAATGGCAACAACGTTGCGCAAACTATTAACTGGCGAA
CTACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGATGGTA
AGCCCTCCCGTATCGTAGTTATCTACACGACGGGGAGTCAGGCAACTATGGATGAAC
GAAATAGACAGATCGCTGAGATAGGTGCCTCACTGATTAAGCATTGGTAACTGTCAG
ACCAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTC
GTTCCACTGAGCGTCAGACCCCGTAGAAAAGATCAAAGGATCTTCTTGAGATCCTTTT
TTTCTGCGCGTAATCTGCTGCTTGCAAACAAAAAAACCACCGCTACCAGCGGTGGTT
TGTTTGCCGGATCAAGAGCTACCAACTCTTTTTCCGAAGGTAACTGGCTTCAGCAGA
GCGCAGATACCAAATACTGTCCTTCTAGTGTAGCCGTAGTTAGGCCACCACTTCAAG
AACTCTGTAGCACCGCCTACATACCTCGCTCTGCTAATCCTGTTACCAGTGGCTGCT
GCCAGTGGCGATAAGTCGTGTCTTACCGGGTTGGACTCAAGACGATAGTTACCGGAT
AAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGGCG
```

TABLE 7-continued

Disclosed Nucleic Acid and Amino Acid Sequences

```
GAGCCTATGGAAAAACGCCAGCAACGCGGCCTTTTTACGGTTCCTGGCCTTTTGCTG
GCCTTTTGCTCACATGTTCTTTCCTGCGTTATCCCCTGATTCTGTGGATAACCGTATT
ACCGCCTTTGAGTGAGCTGATACCGCTCGCCGCAGCCGAACGACCGAGCGCAGCG
AGTCAGTGAGCGAGGAAGCGGAAGAGCGCCCAATACGCAAACCGCCTCTCCCCGC
GCGTTGGCCGATTCATTAATGCAG
```

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

SEQUENCE LISTING

<160> NUMBER OF SEQ ID NOS: 64

<210> SEQ ID NO 1
<211> LENGTH: 351
<212> TYPE: PRT
<213> ORGANISM: Saccharomyces cerevisiae

<400> SEQUENCE: 1

```
Met Pro Ser Gln Val Ile Pro Glu Lys Gln Lys Ala Ile Val Phe Tyr
1               5                   10                  15

Glu Thr Asp Gly Lys Leu Glu Tyr Lys Asp Val Thr Val Pro Glu Pro
            20                  25                  30

Lys Pro Asn Glu Ile Leu Val His Val Lys Tyr Ser Gly Val Cys His
        35                  40                  45

Ser Asp Leu His Ala Trp His Gly Asp Trp Pro Phe Gln Leu Lys Phe
    50                  55                  60

Pro Leu Ile Gly Gly His Glu Gly Ala Gly Val Val Lys Leu Gly
65                  70                  75                  80

Ser Asn Val Lys Gly Trp Lys Val Gly Asp Phe Ala Gly Ile Lys Trp
                85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270
```

```
Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
        290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
                340                 345                 350

<210> SEQ ID NO 2
<211> LENGTH: 1056
<212> TYPE: DNA
<213> ORGANISM: Saccharomyces cerevisiae

<400> SEQUENCE: 2
atgccttcgc aagtcattcc tgaaaaacaa aaggctattg tcttttatga cacagatgga      60
aaattggaat ataaagacgt cacagttccg gaacctaagc ctaacgaaat tttagtccac     120
gttaaatatt ctggtgtttg tcatagtgac ttgcacgcgt ggcacggtga ttggccattt     180
caattgaaat ttccattaat cggtggtcac gaaggtgctg tgttgttgt taagttggga      240 tctaacgtta agggctggaa agtcggtgat tttgcaggta taaatggtt gaatgggact      300 tgcatgtcct gtgaatattg tgaagtaggt aatgaatctc aatgtcctta tttggatggt     360
actggcttca cacatgatgg tactttcaa gaatacgcaa ctgccgatgc cgttcaagct      420
gcccatattc caccaaacgt caatcttgct gaagttgccc aatcttgtg tgcaggtatc      480 actgtttata aggcgttgaa aagagccaat gtgataccag ccaatgggt cactatatcc      540 ggtgcatgcg gtggcttggg ttctctggca atccaatacg cccttgctat gggttacagg     600
gtcattggta tcgatggtgg taatgccaag cgaaagttat ttgaacaatt aggcggagaa     660
atattcatcg atttcacgga agaaaaagac attgttggtg ctataataaa ggccactaat     720
ggcggttctc atggagttat taatgtgtct gtttctgaag cagctatcga ggcttctacg     780
aggtattgta ggcccaatgg tactgtcgtc ctggttggta tgccagctca tgcttactgc     840
aattccgatg ttttcaatca agttgtaaaa tcaatctcca tcgttggatc ttgtgttgga     900
aatagagctg atacaaggga ggctttagat ttcttcgcca gaggtttgat caaatctccg     960
atccacttag ctggcctatc ggatgttcct gaattttttg caaagatgga aagggtgaa    1020 attgttggta gatatgttgt tgagacttct aaatga                              1056

<210> SEQ ID NO 3
<211> LENGTH: 360
<212> TYPE: PRT
<213> ORGANISM: Saccharomyces cerevisiae

<400> SEQUENCE: 3

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
                20                  25                  30

Asp His Asp Ile Asp Ile Lys Ile Glu Ala Cys Gly Val Cys Gly Ser
            35                  40                  45

Asp Ile His Cys Ala Ala Gly His Trp Gly Asn Met Lys Met Pro Leu
        50                  55                  60
```

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360

<210> SEQ ID NO 4
<211> LENGTH: 1083
<212> TYPE: DNA
<213> ORGANISM: Saccharomyces cerevisiae

<400> SEQUENCE: 4
atgtcttatc ctgagaaatt tgaaggtatc gctattcaat cacacgaaga ttggaaaaac      60
ccaaagaaga caaagtatga cccaaaacca ttttacgatc atgacattga cattaagatc     120
gaagcatgtg tgtctgcgg tagtgatatt cattgtgcag ctggtcattg ggcaatatg      180 aagatgccgc tagtcgttgg tcatgaaatc gttggtaaag ttgtcaagct agggcccaag     240
tcaaacagtg ggttgaaagt cggtcaacgt gttggtgtag gtgctcaagt cttttcatgc     300
ttggaatgtg accgttgtaa gaatgataat gaaccatact gcaccaagtt tgttaccaca     360
tacagtcagc cttatgaaga cggctatgtg tcgcagggtg gctatgcaaa ctacgtcaga     420

-continued

```
gttcatgaac attttgtggt gcctatccca gagaatattc catcacattt ggctgctcca      480
ctattatgtg gtggtttgac tgtgtactct ccattggttc gtaacggttg cggtccaggt      540
aaaaaagttg gtatagttgg tcttggtggt atcggcagta tgggtacatt gatttccaaa      600
gccatggggg cagagacgta tgttattcct cgttcttcga gaaaaagaga agatgcaatg      660
aagatgggcg ccgatcacta cattgctaca ttagaagaag gtgattgggg tgaaaagtac      720
tttgacacct tcgacctgat tgtagtctgt gcttcctccc ttaccgacat tgacttcaac      780
attatgccaa aggctatgaa ggttggtggt agaattgtct caatctctat accagaacaa      840
cacgaaatgt tatcgctaaa gccatatggc ttaaaggctg tctccatttc ttacagtgct      900
ttaggttcca tcaaagaatt gaaccaactc ttgaaattag tctctgaaaa agatatcaaa      960
atttgggtgg aaacattacc tgttggtgaa gccggcgtcc atgaagcctt cgaaaggatg     1020
gaaaagggtg acgttagata tagatttacc ttagtcggct acgacaaaga attttcagac     1080
tag                                                                   1083
```

<210> SEQ ID NO 5
<211> LENGTH: 361
<212> TYPE: PRT
<213> ORGANISM: Saccharomyces cerevisiae

<400> SEQUENCE: 5

```
Met Leu Tyr Pro Glu Lys Phe Gln Gly Ile Gly Ile Ser Asn Ala Lys
1               5                  10                  15

Asp Trp Lys His Pro Lys Leu Val Ser Phe Asp Pro Lys Pro Phe Gly
            20                  25                  30

Asp His Asp Val Asp Val Glu Ile Glu Ala Cys Gly Ile Cys Gly Ser
        35                  40                  45

Asp Phe His Ile Ala Val Gly Asn Trp Gly Pro Val Pro Glu Asn Gln
    50                  55                  60

Ile Leu Gly His Glu Ile Ile Gly Arg Val Val Lys Val Gly Ser Lys
65                  70                  75                  80

Cys His Thr Gly Val Lys Ile Gly Asp Arg Val Gly Val Gly Ala Gln
                85                  90                  95

Ala Leu Ala Cys Phe Glu Cys Glu Arg Cys Lys Ser Asp Asn Glu Gln
            100                 105                 110

Tyr Cys Thr Asn Asp His Val Leu Thr Met Trp Thr Pro Tyr Lys Asp
        115                 120                 125

Gly Tyr Ile Ser Gln Gly Gly Phe Ala Ser His Val Arg Leu His Glu
    130                 135                 140

His Phe Ala Ile Gln Ile Pro Glu Asn Ile Pro Ser Pro Leu Ala Ala
145                 150                 155                 160

Pro Leu Leu Cys Gly Gly Ile Thr Val Phe Ser Pro Leu Leu Arg Asn
                165                 170                 175

Gly Cys Gly Pro Gly Lys Arg Val Gly Ile Val Gly Ile Gly Gly Ile
            180                 185                 190

Gly His Met Gly Ile Leu Leu Ala Lys Ala Met Gly Ala Glu Val Tyr
        195                 200                 205

Ala Phe Ser Arg Gly His Ser Lys Arg Glu Asp Ser Met Lys Leu Gly
    210                 215                 220

Ala Asp His Tyr Ile Ala Met Leu Glu Asp Lys Gly Trp Thr Glu Gln
225                 230                 235                 240
```

```
Tyr Ser Asn Ala Leu Asp Leu Leu Val Val Cys Ser Ser Ser Leu Ser
            245                 250                 255
Lys Val Asn Phe Asp Ser Ile Val Lys Ile Met Lys Ile Gly Gly Ser
        260                 265                 270
Ile Val Ser Ile Ala Ala Pro Glu Val Asn Glu Lys Leu Val Leu Lys
    275                 280                 285
Pro Leu Gly Leu Met Gly Val Ser Ile Ser Ser Ala Ile Gly Ser
290                 295                 300
Arg Lys Glu Ile Glu Gln Leu Leu Lys Leu Val Ser Glu Lys Asn Val
305                 310                 315                 320
Lys Ile Trp Val Glu Lys Leu Pro Ile Ser Glu Glu Gly Val Ser His
            325                 330                 335
Ala Phe Thr Arg Met Glu Ser Gly Asp Val Lys Tyr Arg Phe Thr Leu
        340                 345                 350
Val Asp Tyr Asp Lys Lys Phe His Lys
        355                 360

<210> SEQ ID NO 6
<211> LENGTH: 1086
<212> TYPE: DNA
<213> ORGANISM: Saccharomyces cerevisiae

<400> SEQUENCE: 6
atgctttacc cagaaaaatt tcagggcatc ggtatttcca cgcaaagga ttggaagcat      60 cctaaattag tgagttttga cccaaaaccc tttggcgatc atgacgttga tgttgaaatt     120
gaagcctgtg gtatctgcgg atctgatttt catatagccg ttggtaattg ggtccagtc    180 ccagaaaatc aaatccttgg acatgaaata attggccgcg tggtgaaggt tggatccaag    240
tgccacactg gggtaaaaat cggtgaccgt gttggtgttg gtgcccaagc cttggcgtgt    300
tttgagtgtg aacgttgcaa aagtgacaac gagcaatact gtaccaatga ccacgttttg    360
actatgtgga ctccttacaa ggacggctac atttcacaag gaggctttgc ctcccacgtg    420
aggcttcatg aacactttgc tattcaaata ccagaaaata ttccaagtcc gctagccgct    480
ccattattgt gtggtggtat tacagttttc tctccactac taagaaatgg ctgtggtcca    540
ggtaagaggg taggtattgt tggcatcggt ggtattgggc atatgggat tctgttggct    600 aaagctatgg gagccgaggt ttatgcgttt tcgcgaggcc actccaagcg ggaggattct    660
atgaaactcg gtgctgatca ctatattgct atgttggagg ataaaggctg acagaacaa    720 tactctaacg cttttggacct tcttgtcgtt tgctcatcat ctttgtcgaa agttaatttt    780
gacagtatcg ttaagattat gaagattgga ggctccatcg tttcaattgc tgctcctgaa    840
gttaatgaaa agcttgtttt aaaaccgttg ggcctaatgg gagtatcaat ctcaagcagt    900
gctatcggat ctaggaagga aatcgaacaa ctattgaaat tagttccga aaagaatgtc     960 aaaatatggg tggaaaaact tccgatcagc gaagaaggcg tcagccatgc ctttacaagg   1020
atggaaagcg gagacgtcaa atacagattt actttggtcg attatgataa gaaattccat   1080
aaatag                                                              1086

<210> SEQ ID NO 7
<211> LENGTH: 342
<212> TYPE: PRT
<213> ORGANISM: Saccharomyces cerevisiae
```

<400> SEQUENCE: 7

```
Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340
```

<210> SEQ ID NO 8
<211> LENGTH: 1029
<212> TYPE: DNA
<213> ORGANISM: Saccharomyces cerevisiae

<400> SEQUENCE: 8

```
atgtcagttt tcgtttcagg tgctaacggg ttcattgccc aacacattgt cgatctcctg    60
ttgaaggaag actataaggt catcggttct gccagaagtc aagaaaaggc cgagaattta   120
```

-continued

```
acggaggcct tggtaacaa cccaaaattc tccatggaag ttgtcccaga catatctaag      180
ctggacgcat tgaccatgt tttccaaaag cacggcaagg atatcaagat agttctacat      240
acggcctctc cattctgctt tgatatcact gacagtgaac gcgatttatt aattcctgct      300
gtgaacggtg ttaagggaat tctccactca attaaaaaat acgccgctga ttctgtagaa      360
cgtgtagttc tcacctcttc ttatgcagct gtgttcgata tggcaaaaga aaacgataag      420
tctttaacat ttaacgaaga atcctggaac ccagctacct gggagagttg ccaaagtgac      480
ccagttaacg cctactgtgg ttctaagaag tttgctaaaa aagcagcttg ggaatttcta      540
gaggagaata gagactctgt aaaattcgaa ttaactgccg ttaacccagt ttacgttttt      600
ggtccgcaaa tgtttgacaa agatgtgaaa aaacacttga acacatcttg cgaactcgtc      660
aacagcttga tgcatttatc accagaggac aagataccgg aactatttgg tggatacatt      720
gatgttcgtg atgttgcaaa ggctcattta gttgccttcc aaaagaggga acaattggt       780 caaagactaa tcgtatcgga ggccagattt actatgcagg atgttctcga tatccttaac      840
gaagacttcc ctgttctaaa aggcaatatt ccagtgggga accaggttc tggtgctacc       900 cataacaccc ttggtgctac tcttgataat aaaaagagta agaaattgtt aggtttcaag      960
ttcaggaact tgaaagagac cattgacgac actgcctccc aaattttaaa atttgagggc     1020
agaatataa                                                            1029
```

<210> SEQ ID NO 9
<211> LENGTH: 327
<212> TYPE: PRT
<213> ORGANISM: Saccharomyces cerevisiae

<400> SEQUENCE: 9

```
Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205
```

Lys Leu His Asp Ile Gln Val Val Ala Tyr Ser Ser Phe Gly Pro Gln
    210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 10
<211> LENGTH: 984
<212> TYPE: DNA
<213> ORGANISM: Saccharomyces cerevisiae

<400> SEQUENCE: 10

```
atgtcttcac tggttactct taataacggt ctgaaaatgc ccctagtcgg cttagggtgc    60
tggaaaattg acaaaaaagt ctgtgcgaat caaatttatg aagctatcaa attaggctac   120
cgtttattcg atggtgcttg cgactacggc aacgaaaagg aagttggtga aggtatcagg   180
aaagccatct ccgaaggtct tgtttctaga aggatatat ttgttgtttc aaagttatgg   240
aacaattttc accatcctga tcatgtaaaa ttagctttaa agaagacctt aagcgatatg   300
ggacttgatt atttagacct gtattatatt cacttcccaa tcgccttcaa atatgttcca   360
tttgaagaga ataccctcc aggattctat acgggcgcag atgacgagaa gaaaggtcac   420
atcaccgaag cacatgtacc aatcatagat acgtaccggg ctctggaaga atgtgttgat   480
gaaggcttga ttaagtctat tggtgttttcc aactttcagg gaagcttgat tcaagattta   540
ttacgtggtt gtagaatcaa gcccgtggct ttgcaaattg aacaccatcc ttatttgact   600
caagaacacc tagttgagtt ttgtaaatta cacgatatcc aagtagttgc ttactcctcc   660
ttcggtcctc aatcattcat tgagatggac ttacagttgg caaaaccac gccaactctg   720
ttcgagaatg atgtaatcaa gaaggtctca caaaaccatc caggcagtac cacttcccaa   780
gtattgctta gatgggcaac tcagagaggc attgccgtca ttccaaaatc ttccaagaag   840
gaaaggttac ttggcaacct agaaatcgaa aaaagttca ctttaacgga gcaagaattg   900
aaggatattt ctgcactaaa tgccaacatc agatttaatg atccatggac ctggttggat   960
ggtaaattcc ccacttttgc ctga                                           984
```

<210> SEQ ID NO 11
<211> LENGTH: 344
<212> TYPE: PRT
<213> ORGANISM: Saccharomyces cerevisiae

<400> SEQUENCE: 11

Met Ser Asn Thr Val Leu Val Ser Gly Ala Ser Gly Phe Ile Ala Leu
1               5                   10                  15

His Ile Leu Ser Gln Leu Leu Lys Gln Asp Tyr Lys Val Ile Gly Thr
            20                  25                  30

Val Arg Ser His Glu Lys Glu Ala Lys Leu Leu Arg Gln Phe Gln His
        35                  40                  45

Asn Pro Asn Leu Thr Leu Glu Ile Val Pro Asp Ile Ser His Pro Asn
    50                  55                  60

Ala Phe Asp Lys Val Leu Gln Lys Arg Gly Arg Glu Ile Arg Tyr Val
65                  70                  75                  80

Leu His Thr Ala Ser Pro Phe His Tyr Asp Thr Thr Glu Tyr Glu Lys
                85                  90                  95

Asp Leu Leu Ile Pro Ala Leu Glu Gly Thr Lys Asn Ile Leu Asn Ser
            100                 105                 110

Ile Lys Lys Tyr Ala Ala Asp Thr Val Glu Arg Val Val Val Thr Ser
        115                 120                 125

Ser Cys Thr Ala Ile Ile Thr Leu Ala Lys Met Asp Asp Pro Ser Val
    130                 135                 140

Val Phe Thr Glu Glu Ser Trp Asn Glu Ala Thr Trp Glu Ser Cys Gln
145                 150                 155                 160

Ile Asp Gly Ile Asn Ala Tyr Phe Ala Ser Lys Lys Phe Ala Glu Lys
                165                 170                 175

Ala Ala Trp Glu Phe Thr Lys Glu Asn Glu Asp His Ile Lys Phe Lys
            180                 185                 190

Leu Thr Thr Val Asn Pro Ser Leu Leu Phe Gly Pro Gln Leu Phe Asp
        195                 200                 205

Glu Asp Val His Gly His Leu Asn Thr Ser Cys Glu Met Ile Asn Gly
    210                 215                 220

Leu Ile His Thr Pro Val Asn Ala Ser Val Pro Asp Phe His Ser Ile
225                 230                 235                 240

Phe Ile Asp Val Arg Asp Val Ala Leu Ala His Leu Tyr Ala Phe Gln
                245                 250                 255

Lys Glu Asn Thr Ala Gly Lys Arg Leu Val Val Thr Asn Gly Lys Phe
            260                 265                 270

Gly Asn Gln Asp Ile Leu Asp Ile Leu Asn Glu Asp Phe Pro Gln Leu
        275                 280                 285

Arg Gly Leu Ile Pro Leu Gly Lys Pro Gly Thr Gly Asp Gln Val Ile
    290                 295                 300

Asp Arg Gly Ser Thr Thr Asp Asn Ser Ala Thr Arg Lys Ile Leu Gly
305                 310                 315                 320

Phe Glu Phe Arg Ser Leu His Glu Ser Val His Asp Thr Ala Ala Gln
                325                 330                 335

Ile Leu Lys Lys Gln Asn Arg Leu
            340

<210> SEQ ID NO 12
<211> LENGTH: 1035
<212> TYPE: DNA
<213> ORGANISM: Saccharomyces cerevisiae

<400> SEQUENCE: 12
atgtctaata cagttctagt ttctggcgct tcaggtttta ttgccttgca tatcctgtca      60
caattgttaa aacaagatta taaggttatt ggaactgtga gatcccatga aaaagaagca     120
aaattgctaa gacaatttca acataaccct aatttaactt tagaaattgt tccggacatt     180
tctcatccaa atgctttcga taaggttctg cagaaacgtg gacgtgagat taggtatgtt     240

```
ctacacacgg cctctccttt tcattatgat actaccgaat atgaaaaaga cttattgatt    300
cccgcgttag aaggtacaaa aaacatccta aattctatca agaaatatgc agcagacact    360
gtagagcgtg ttgttgtgac ttcttcttgt actgctatta taacccttgc aaagatggac    420
gatcccagtg tggtttttac agaagagagt tggaacgaag caacctggga aagctgtcaa    480
attgatggga taaatgctta ctttgcatcc aagaagtttg ctgaaaaggc tgcctgggag    540
ttcacaaaag agaatgaaga tcacatcaaa ttcaaactaa caacagtcaa cccttctctt    600
cttttttggtc ctcaactttt cgatgaagat gtgcatggcc atttgaatac ttcttgcgaa    660
atgatcaatg gcctaattca tacccccagta aatgccagtg ttcctgatttt tcattccatt    720
tttattgatg taagggatgt ggccctagct catctgtatg ctttccagaa ggaaaatacc    780
gcgggtaaaa gattagtggt aactaacggt aaatttggaa accaagatat cctggatatt    840
ttgaacgaag attttccaca attaagaggt ctcattcctt tgggtaagcc tggcacaggt    900
gatcaagtca ttgaccgcgg ttcaactaca gataatagtg caacgaggaa aatacttggc    960
tttgagttca gaagtttaca cgaaagtgtc catgatactg ctgcccaaat tttgaagaag   1020
cagaacagat tatga                                                    1035
```

<210> SEQ ID NO 13
<211> LENGTH: 376
<212> TYPE: PRT
<213> ORGANISM: Saccharomyces cerevisiae

<400> SEQUENCE: 13

```
Met Gln Val Ala Ile Pro Glu Thr Met Lys Ala Val Val Ile Glu Asp
1               5                   10                  15

Gly Lys Ala Val Val Lys Glu Gly Ile Pro Ile Pro Glu Leu Glu Glu
            20                  25                  30

Gly Phe Val Leu Ile Lys Thr Leu Ala Val Ala Gly Asn Pro Thr Asp
        35                  40                  45

Trp Ala His Ile Asp Tyr Lys Ile Gly Pro Gln Gly Ser Ile Leu Gly
    50                  55                  60

Cys Asp Ala Ala Gly Gln Ile Val Lys Leu Gly Pro Ala Val Asn Pro
65                  70                  75                  80

Lys Asp Phe Ser Ile Gly Asp Tyr Ile Tyr Gly Phe Ile His Gly Ser
                85                  90                  95

Ser Val Arg Phe Pro Ser Asn Gly Ala Phe Ala Glu Tyr Ser Ala Ile
            100                 105                 110

Ser Thr Val Val Ala Tyr Lys Ser Pro Asn Glu Leu Lys Phe Leu Gly
        115                 120                 125

Glu Asp Val Leu Pro Ala Gly Pro Val Arg Ser Leu Glu Gly Val Ala
    130                 135                 140

Thr Ile Pro Val Ser Leu Thr Thr Ala Gly Leu Val Leu Thr Tyr Asn
145                 150                 155                 160

Leu Gly Leu Asp Leu Lys Trp Glu Pro Ser Thr Pro Gln Arg Lys Gly
                165                 170                 175

Pro Ile Leu Leu Trp Gly Gly Ala Thr Ala Val Gly Gln Ser Leu Ile
            180                 185                 190

Gln Leu Ala Asn Lys Leu Asn Gly Phe Thr Lys Ile Ile Val Val Ala
        195                 200                 205

Ser Arg Lys His Glu Lys Leu Leu Lys Glu Tyr Gly Ala Asp Glu Leu
    210                 215                 220
```

```
Phe Asp Tyr His Asp Ile Asp Val Val Glu Gln Ile Lys His Lys Tyr
225                 230                 235                 240

Asn Asn Ile Ser Tyr Leu Val Asp Cys Val Ala Asn Gln Asp Thr Leu
            245                 250                 255

Gln Gln Val Tyr Lys Cys Ala Ala Asp Lys Gln Asp Ala Thr Ile Val
        260                 265                 270

Glu Leu Lys Asn Leu Thr Glu Glu Asn Val Lys Lys Glu Asn Arg Arg
    275                 280                 285

Gln Asn Val Thr Ile Asp Ile Ile Arg Leu Tyr Ser Ile Gly Gly His
290                 295                 300

Glu Val Pro Phe Gly Asn Ile Thr Leu Pro Ala Asp Ser Glu Ala Arg
305                 310                 315                 320

Lys Ala Ala Ile Lys Phe Ile Lys Phe Ile Asn Pro Lys Ile Asn Asp
                325                 330                 335

Gly Gln Ile Arg His Ile Pro Val Arg Val Tyr Lys Asn Gly Leu Cys
            340                 345                 350

Asp Val Pro His Ile Leu Lys Asp Ile Lys Tyr Gly Lys Asn Ser Gly
        355                 360                 365

Glu Lys Leu Val Ala Val Leu Asn
    370                 375
```

<210> SEQ ID NO 14
<211> LENGTH: 1131
<212> TYPE: DNA
<213> ORGANISM: Saccharomyces cerevisiae

<400> SEQUENCE: 14

```
atgcaagttg caattccaga aaccatgaag gctgtcgtca ttgaagacgg taaagcggtt      60
gttaaagagg gcattcccat tcctgaattg aagaaggat tcgtattgat taagacactc     120
gctgttgctg gtaaccccac tgattgggca cacattgact acaagatcgg gcctcaagga    180
tctattctgg gatgtgatgc tgctggccaa attgtcaaat gggcccagc tgtcaatcct    240 aaagactttt ctatcggtga ttatatttat gggttcattc acggatcttc cgtaaggttt    300
ccttccaatg tgcttttgc tgaatattct gctatttcaa ctgtggttgc ctacaaatca    360
cccaatgaac tcaaattttt gggtgaggat gttctacctg ccggccctgt caggtctttg    420
gaaggtgtag ccactatccc agtgtcactg accacagccg gcttggtgtt gacctataac    480
ttgggcttgg acctgaagtg ggagccatca accccacaaa gaaaaggccc catcttatta    540
tggggcggtg caactgcagt aggtcagtcg ctcatccaat tagccaataa attgaatggc    600
ttcaccaaga tcattgttgt ggcttctcgg aagcacgaaa aacttttgaa gaatatggt    660 gctgatgaat tatttgatta tcatgatatt gacgtggtag aacaattaa acacaagtac    720 aacaatatct cgtatttagt cgactgtgtc gcgaatcaag atacgcttca acaagtgtac    780
aaatgtgcgg ccgataaaca ggatgctaca attgttgaat aaaaaatttt gacagaagaa    840
aacgtcaaaa aagagaacag gagacaaaac gttactattg acataataag gctatattca    900
ataggtggcc atgaagtacc atttggaaac attactttac cagccgactc agaagctagg    960
aaagctgcaa taaatttat caattcatc aatccaaaga ttaatgatgg acaaattcgc    1020
catattccag taagggtcta taagaacggg ctttgtgatg ttcctcatat cctaaaagac    1080
atcaaatatg gtaagaactc tggtgaaaaa ctcgttgccg tattaaacta g            1131
```

<210> SEQ ID NO 15
<211> LENGTH: 347
<212> TYPE: PRT
<213> ORGANISM: Saccharomyces cerevisiae

<400> SEQUENCE: 15

Met Thr Thr Asp Thr Thr Val Phe Val Ser Gly Ala Thr Gly Phe Ile
1               5                   10                  15

Ala Leu His Ile Met Asn Asp Leu Leu Lys Ala Gly Tyr Thr Val Ile
            20                  25                  30

Gly Ser Gly Arg Ser Gln Glu Lys Asn Asp Gly Leu Leu Lys Lys Phe
        35                  40                  45

Asn Asn Asn Pro Lys Leu Ser Met Glu Ile Val Glu Asp Ile Ala Ala
50                  55                  60

Pro Asn Ala Phe Asp Glu Val Phe Lys Lys His Gly Lys Glu Ile Lys
65                  70                  75                  80

Ile Val Leu His Thr Ala Ser Pro Phe His Phe Glu Thr Thr Asn Phe
                85                  90                  95

Glu Lys Asp Leu Leu Thr Pro Ala Val Asn Gly Thr Lys Ser Ile Leu
            100                 105                 110

Glu Ala Ile Lys Lys Tyr Ala Ala Asp Thr Val Glu Lys Val Ile Val
        115                 120                 125

Thr Ser Ser Thr Ala Ala Leu Val Thr Pro Thr Asp Met Asn Lys Gly
130                 135                 140

Asp Leu Val Ile Thr Glu Glu Ser Trp Asn Lys Asp Thr Trp Asp Ser
145                 150                 155                 160

Cys Gln Ala Asn Ala Val Ala Ala Tyr Cys Gly Ser Lys Lys Phe Ala
                165                 170                 175

Glu Lys Thr Ala Trp Glu Phe Leu Lys Glu Asn Lys Ser Ser Val Lys
            180                 185                 190

Phe Thr Leu Ser Thr Ile Asn Pro Gly Phe Val Phe Gly Pro Gln Met
        195                 200                 205

Phe Ala Asp Ser Leu Lys His Gly Ile Asn Thr Ser Ser Gly Ile Val
210                 215                 220

Ser Glu Leu Ile His Ser Lys Val Gly Gly Glu Phe Tyr Asn Tyr Cys
225                 230                 235                 240

Gly Pro Phe Ile Asp Val Arg Asp Val Ser Lys Ala His Leu Val Ala
                245                 250                 255

Ile Glu Lys Pro Glu Cys Thr Gly Gln Arg Leu Val Leu Ser Glu Gly
            260                 265                 270

Leu Phe Cys Cys Gln Glu Ile Val Asp Ile Leu Asn Glu Glu Phe Pro
        275                 280                 285

Gln Leu Lys Gly Lys Ile Ala Thr Gly Glu Pro Ala Thr Gly Pro Ser
290                 295                 300

Phe Leu Glu Lys Asn Ser Cys Lys Phe Asp Asn Ser Lys Thr Lys Lys
305                 310                 315                 320

Leu Leu Gly Phe Gln Phe Tyr Asn Leu Lys Asp Cys Ile Val Asp Thr
                325                 330                 335

Ala Ala Gln Met Leu Glu Val Gln Asn Glu Ala
            340                 345

<210> SEQ ID NO 16
<211> LENGTH: 1044
<212> TYPE: DNA
<213> ORGANISM: Saccharomyces cerevisiae

<400> SEQUENCE: 16

```
atgactactg ataccactgt tttcgtttct ggcgcaaccg gtttcattgc tctacacatt      60
atgaacgatc tgttgaaagc tggctataca gtcatcggct caggtagatc tcaagaaaaa     120
aatgatggct tgctcaaaaa atttaataac aatcccaaac tatcgatgga aattgtggaa     180
gatattgctg ctccaaacgc ctttgatgaa gttttcaaaa acatggtaa ggaaattaag      240
attgtgctac acactgcctc cccattccat tttgaaacta ccaattttga aaaggattta     300
ctaaccctg cagtgaacgg tacaaaatct atcttggaag cgattaaaaa atatgctgca      360
gacactgttg aaaaagttat tgttacttcg tctactgctg ctctggtgac acctacagac     420
atgaacaaag gagatttggt gatcacggag gagagttgga ataaggatac atgggacagt     480
tgtcaagcca acgccgttgc cgcatattgt ggctcgaaaa agtttgctga aaaaactgct     540
tgggaatttc ttaaagaaaa caagtctagt gtcaaattca cactatccac tatcaatccg     600
ggattcgttt ttggtcctca aatgtttgca gattcgctaa acatggcat aaatacctcc      660
tcagggatcg tatctgagtt aattcattcc aaggtaggtg agaattttta taattactgt     720
ggcccattta ttgacgtgcg tgacgtttct aaagcccacc tagttgcaat tgaaaaacca     780
gaatgtaccg gccaaagatt agtattgagt gaaggtttat tctgctgtca agaaatcgtt     840
gacatcttga acgaggaatt ccctcaatta aagggcaaga tagctacagg tgaacctgcg     900
accggtccaa gctttttaga aaaaaactct tgcaagtttg acaattctaa gacaaaaaaa     960
ctactgggat ccagtttta caatttaaag gattgcatag ttgacaccgc ggcgcaaatg    1020
ttagaagttc aaaatgaagc ctaa                                          1044
```

<210> SEQ ID NO 17
<211> LENGTH: 348
<212> TYPE: PRT
<213> ORGANISM: Saccharomyces cerevisiae

<400> SEQUENCE: 17

```
Met Thr Thr Glu Lys Thr Val Val Phe Val Ser Gly Ala Thr Gly Phe
1               5                   10                  15

Ile Ala Leu His Val Val Asp Asp Leu Leu Lys Thr Gly Tyr Lys Val
            20                  25                  30

Ile Gly Ser Gly Arg Ser Gln Glu Lys Asn Asp Gly Leu Leu Lys Lys
        35                  40                  45

Phe Lys Ser Asn Pro Asn Leu Ser Met Glu Ile Val Glu Asp Ile Ala
    50                  55                  60

Ala Pro Asn Ala Phe Asp Lys Val Phe Gln Lys His Gly Lys Glu Ile
65                  70                  75                  80

Lys Val Val Leu His Ile Ala Ser Pro Val His Phe Asn Thr Thr Asp
                85                  90                  95

Phe Glu Lys Asp Leu Leu Ile Pro Ala Val Asn Gly Thr Lys Ser Ile
            100                 105                 110

Leu Glu Ala Ile Lys Asn Tyr Ala Ala Asp Thr Val Glu Lys Val Val
        115                 120                 125

Ile Thr Ser Ser Val Ala Ala Leu Ala Ser Pro Gly Asp Met Lys Asp
    130                 135                 140

Thr Ser Phe Val Val Asn Glu Glu Ser Trp Asn Lys Asp Thr Trp Glu
145                 150                 155                 160

Ser Cys Gln Ala Asn Ala Val Ser Ala Tyr Cys Gly Ser Lys Lys Phe
                165                 170                 175
```

```
Ala Glu Lys Thr Ala Trp Asp Phe Leu Glu Glu Asn Gln Ser Ser Ile
            180                 185                 190

Lys Phe Thr Leu Ser Thr Ile Asn Pro Gly Phe Val Phe Gly Pro Gln
        195                 200                 205

Leu Phe Ala Asp Ser Leu Arg Asn Gly Ile Asn Ser Ser Ser Ala Ile
    210                 215                 220

Ile Ala Asn Leu Val Ser Tyr Lys Leu Gly Asp Asn Phe Tyr Asn Tyr
225                 230                 235                 240

Ser Gly Pro Phe Ile Asp Val Arg Asp Val Ser Lys Ala His Leu Leu
                245                 250                 255

Ala Phe Glu Lys Pro Glu Cys Ala Gly Gln Arg Leu Phe Leu Cys Glu
            260                 265                 270

Asp Met Phe Cys Ser Gln Glu Ala Leu Asp Ile Leu Asn Glu Glu Phe
        275                 280                 285

Pro Gln Leu Lys Gly Lys Ile Ala Thr Gly Glu Pro Gly Ser Gly Ser
    290                 295                 300

Thr Phe Leu Thr Lys Asn Cys Cys Lys Cys Asp Asn Arg Lys Thr Lys
305                 310                 315                 320

Asn Leu Leu Gly Phe Gln Phe Asn Lys Phe Arg Asp Cys Ile Val Asp
                325                 330                 335

Thr Ala Ser Gln Leu Leu Glu Val Gln Ser Lys Ser
            340                 345
```

<210> SEQ ID NO 18
<211> LENGTH: 1047
<212> TYPE: DNA
<213> ORGANISM: Saccharomyces cerevisiae

<400> SEQUENCE: 18

```
atgactactg aaaaaaccgt tgttttttgtt tctggtgcta ctggtttcat tgctctacac    60
gtagtggacg atttattaaa aactggttac aaggtcatcg ttcgggtag gtcccaagaa    120
aagaatgatg gattgctgaa aaatttaag agcaatccca acctttcaat ggagattgtc    180
gaagacattg ctgctccaaa cgcttttgac aaagttttc aaaagcacgg caaagagatc    240
aaggttgtct tgcacatagc ttctccggtt cacttcaaca ccactgattt cgaaaaggat    300
ctgctaattc ctgctgtgaa tggtaccaag tccattctag aagcaatcaa aaattatgcc    360
gcagacacag tcgaaaaagt cgttattact tcttctgttg ctgcccttgc atctcccgga    420
gatatgaagg acactagttt cgttgtcaat gaggaaagtt ggaacaaaga tacttgggaa    480
agttgtcaag ctaacgcggt tccgcatac tgtggttcca agaaatttgc tgaaaaaact    540
gcttgggatt tctcgagga aaaccaatca agcatcaaat ttacgctatc aaccatcaac    600
ccaggatttg ttttttggccc tcagctattt gccgactctc ttagaaatgg aataaatagc    660
tcttcagcca ttattgccaa tttggttagt tataaaattag gcgacaattt ttataattac    720
agtggtcctt ttattgacgt tcgcgatgtt tcaaaagctc atttacttgc atttgagaaa    780
cccgaatgcg ctggccaaag actattctta tgtgaagata tgttttgctc tcaagaagcg    840
ctggatatct tgaatgagga atttccacag ttaaaaggca agatagcaac tggcgaacct    900
ggtagcggct caaccttttt tgacaaaaaac tgctgcaagt gcgacaaccg caaaaccaaa    960
aatttattag gattccaatt taataagttc agagattgca ttgtcgatac tgcctcgcaa    1020
ttactagaag ttcaaagtaa aagctaa    1047
```

```
<210> SEQ ID NO 19
<211> LENGTH: 368
<212> TYPE: PRT
<213> ORGANISM: Saccharomyces cerevisiae

<400> SEQUENCE: 19

Met Lys Ala Val Val Ile Glu Asp Gly Lys Ala Val Val Lys Glu Gly
1               5                   10                  15

Val Pro Ile Pro Glu Leu Glu Glu Gly Phe Val Leu Ile Lys Thr Leu
            20                  25                  30

Ala Val Ala Gly Asn Pro Thr Asp Trp Ala His Ile Asp Tyr Lys Val
        35                  40                  45

Gly Pro Gln Gly Ser Ile Leu Gly Cys Asp Ala Ala Gly Gln Ile Val
    50                  55                  60

Lys Leu Gly Pro Ala Val Asp Pro Lys Asp Phe Ser Ile Gly Asp Tyr
65                  70                  75                  80

Ile Tyr Gly Phe Ile His Gly Ser Ser Val Arg Phe Pro Ser Asn Gly
                85                  90                  95

Ala Phe Ala Glu Tyr Ser Ala Ile Ser Thr Val Val Ala Tyr Lys Ser
            100                 105                 110

Pro Asn Glu Leu Lys Phe Leu Gly Glu Asp Val Leu Pro Ala Gly Pro
        115                 120                 125

Val Arg Ser Leu Glu Gly Ala Ala Thr Ile Pro Val Ser Leu Thr Thr
    130                 135                 140

Ala Gly Leu Val Leu Thr Tyr Asn Leu Gly Leu Asn Leu Lys Trp Glu
145                 150                 155                 160

Pro Ser Thr Pro Gln Arg Asn Gly Pro Ile Leu Leu Trp Gly Gly Ala
                165                 170                 175

Thr Ala Val Gly Gln Ser Leu Ile Gln Leu Ala Asn Lys Leu Asn Gly
            180                 185                 190

Phe Thr Lys Ile Ile Val Val Ala Ser Arg Lys His Glu Lys Leu Leu
        195                 200                 205

Lys Glu Tyr Gly Ala Asp Gln Leu Phe Asp Tyr His Asp Ile Asp Val
    210                 215                 220

Val Glu Gln Ile Lys His Lys Tyr Asn Asn Ile Ser Tyr Leu Val Asp
225                 230                 235                 240

Cys Val Ala Asn Gln Asn Thr Leu Gln Gln Val Tyr Lys Cys Ala Ala
                245                 250                 255

Asp Lys Gln Asp Ala Thr Val Val Glu Leu Thr Asn Leu Thr Glu Glu
            260                 265                 270

Asn Val Lys Lys Glu Asn Arg Arg Gln Asn Val Thr Ile Asp Arg Thr
        275                 280                 285

Arg Leu Tyr Ser Ile Gly Gly His Glu Val Pro Phe Gly Gly Ile Thr
    290                 295                 300

Phe Pro Ala Asp Pro Glu Ala Arg Arg Ala Ala Thr Glu Phe Val Lys
305                 310                 315                 320

Phe Ile Asn Pro Lys Ile Ser Asp Gly Gln Ile His His Ile Pro Ala
                325                 330                 335

Arg Val Tyr Lys Asn Gly Leu Tyr Asp Val Pro Arg Ile Leu Glu Asp
            340                 345                 350

Ile Lys Ile Gly Lys Asn Ser Gly Glu Lys Leu Val Ala Val Leu Asn
        355                 360                 365

<210> SEQ ID NO 20
<211> LENGTH: 1107
```

```
<212> TYPE: DNA
<213> ORGANISM: Saccharomyces cerevisiae

<400> SEQUENCE: 20
atgaaggctg tcgtcattga agacggtaaa gcggttgtca agagggcgt tcccattcct      60
gaattggaag aaggattcgt attgattaag acactcgctg ttgctggtaa cccgactgat     120
tgggcacaca ttgactacaa ggtcgggcct caaggatcta ttctgggatg tgacgctgcc     180
ggccaaattg tcaaattggg cccagccgtc gatcctaaag actttctat tggtgattat      240
atttatgggt tcattcacgg atcttccgta aggtttcctt ccaatggtgc ttttgctgaa     300
tattctgcta tttcaactgt ggttgcctac aaatcaccca atgaactcaa attttggg      360
gaagatgttc tacctgccgg ccctgtcagg tctttggaag gggcagccac tatcccagtg     420
tcactgacca cagctggctt ggtgttgacc tataacttgg gcttgaacct gaagtgggag     480
ccatcaaccc cacaaagaaa cggccccatc ttattatggg gcggtgcaac tgcagtaggt     540
cagtcgctca tccaattagc caataaattg aatggcttca ccaagatcat tgttgtggct     600
tctcggaaac acgaaaaact gttgaaagaa tatggtgctg atcaactatt tgattaccat     660
gatattgacg tggtagaaca aattaaacac aagtacaaca atatctcgta tttagtcgac     720
tgtgtcgcga atcaaaatac gcttcaacaa gtgtacaaat gtgcggccga taaacaggat     780
gctaccgttg tcgaattaac taatttgaca gaagaaaacg tcaaaaagga aataggagg      840
caaaatgtca ctattgacag aacaagactg tattcaatag gcggccatga agtaccattt     900
ggtggcatta ctttccctgc tgacccagaa gccaggagag ctgccaccga attcgtcaag     960
ttcatcaatc caaagattag tgatgggcaa attcaccata ttccagcaag ggtctataag    1020
aacgggcttt acgatgttcc tcgtatcctg gaagacatta aaatcggtaa gaactctggt    1080
gaaaaactag ttgccgtatt aaactag                                        1107

<210> SEQ ID NO 21
<211> LENGTH: 345
<212> TYPE: PRT
<213> ORGANISM: Saccharomyces cerevisiae

<400> SEQUENCE: 21

Met Ser Val Ala Asp Leu Lys Asn Asn Ile His Lys Leu Asp Thr Gly
1               5                   10                  15

Tyr Gly Leu Met Ser Leu Thr Trp Arg Ala Glu Pro Ile Pro Gln Ser
            20                  25                  30

Gln Ala Phe Glu Ala Met His Arg Val Val Glu Leu Ser Arg Glu Arg
        35                  40                  45

Gly His Lys Ala Phe Phe Asn Val Gly Glu Phe Tyr Gly Pro Asp Phe
    50                  55                  60

Ile Asn Leu Ser Tyr Val His Asp Phe Phe Ala Lys Tyr Pro Asp Leu
65                  70                  75                  80

Arg Lys Asp Val Val Ile Ser Cys Lys Gly Gly Ala Asp Asn Ala Thr
                85                  90                  95

Leu Thr Pro Arg Gly Ser His Asp Asp Val Val Gln Ser Val Lys Asn
            100                 105                 110

Ser Val Ser Ala Ile Gly Gly Tyr Ile Asp Ile Phe Glu Val Ala Arg
        115                 120                 125

Ile Asp Thr Ser Leu Cys Thr Lys Gly Glu Val Tyr Pro Tyr Glu Ser
    130                 135                 140
```

```
Phe Glu Ala Leu Ala Glu Met Ile Ser Glu Gly Val Ile Gly Gly Ile
145                 150                 155                 160

Ser Leu Ser Glu Val Asn Glu Glu Gln Ile Arg Ala Ile His Lys Asp
                165                 170                 175

Trp Gly Lys Phe Leu Thr Cys Val Glu Val Glu Leu Ser Leu Phe Ser
            180                 185                 190

Asn Asp Ile Leu His Asn Gly Ile Ala Lys Thr Cys Ala Glu Leu Gly
        195                 200                 205

Leu Ser Ile Ile Cys Tyr Ser Pro Leu Gly Arg Gly Leu Leu Thr Gly
    210                 215                 220

Gln Leu Lys Ser Asn Ala Asp Ile Pro Glu Gly Asp Phe Arg Lys Ser
225                 230                 235                 240

Leu Lys Arg Phe Ser Asp Glu Ser Leu Lys Lys Asn Leu Thr Leu Val
            245                 250                 255

Arg Phe Leu Gln Glu Glu Ile Val Asp Lys Arg Pro Gln Asn Asn Ser
            260                 265                 270

Ile Thr Leu Ala Gln Leu Ala Leu Gly Trp Val Lys His Trp Asn Lys
        275                 280                 285

Val Pro Glu Tyr Ser Gly Ala Lys Phe Ile Pro Ile Pro Ser Gly Ser
    290                 295                 300

Ser Ile Ser Lys Val Asn Glu Asn Phe Asp Glu Gln Lys Thr Lys Leu
305                 310                 315                 320

Thr Asp Gln Glu Phe Asn Ala Ile Asn Lys Tyr Leu Thr Thr Phe His
            325                 330                 335

Thr Val Gly Asp Arg Tyr Glu Met Ala
            340                 345

<210> SEQ ID NO 22
<211> LENGTH: 1038
<212> TYPE: DNA
<213> ORGANISM: Saccharomyces cerevisiae

<400> SEQUENCE: 22
atgtctgtcg ccgatttgaa aaacaacatc cacaagttag atactggcta tggtttaatg      60
agtttgactt ggagagccga gcctatccct cagtcgcagg ctttcgaggc catgcacaga     120
gtggttgagt tatccagaga acgtgggcac aaggccttt  tcaacgttgg tgaattctat     180
ggtcccgatt ttattaattt gtcgtatgtt cacgacttct ttgcgaaata cccagatttg     240
agaaaggatg tggttatcag ttgtaaaggt ggtgcagaca atgctacctt aaccccccaga    300 ggcagtcacg atgatgttgt acaaagcgta aagaattcag ttagtgctat tggtggctac    360
atcgacatct tcgaagtcgc aagaatcgac acttccctat gcacgaaagg agaggtctac    420
ccctacgaat cgttcgaagc gcttgctgag atgatctccg aaggcgttat tggcggtatt    480
tcattaagtg aagttaatga agagcaaatt agagctattc acaaggattg ggaaagttt     540 ttgacctgcg ttgaagtgga actttctttg ttcagtaatg acatttttaca caacggaatt   600 gctaaaacat gtgctgaatt ggggttgtcc atcatctgct actccccact gggcagagga   660
ttgttgacag tcaattgaa gtcaaacgct gatatccctg agggtgactt tagaaagtcg    720
ttaaagagat ttagcgacga gtctttgaaa aaaaacctga ccttggtcag gtttctacag   780
gaagaaatag tcgacaagcg cccacaaaac aactccatta ctcttgcaca actggctttg   840
ggatgggtta agcactggaa caaagttccg aatacagtg gcgccaaatt tatcccaatt    900
ccaagtggct cttctatttc caaggttaat gaaaactttg atgaacagaa aaccaaactt    960
```

```
accgatcaag agttcaatgc cattaacaaa tatttgacta ctttccatac tgttggtgac    1020
agatacgaaa tggcgtaa                                                  1038
```

<210> SEQ ID NO 23
<211> LENGTH: 612
<212> TYPE: DNA
<213> ORGANISM: Coptis japonica

<400> SEQUENCE: 23

```
aagcttaaaa tgagaatgga agtcgtcttg gtcgttttct tgatgttcat tggtactatc     60
aactgcgaaa gattgatctt caatggtaga cctttgttgc acagagttac caaagaagaa    120
accgttatgt tgtaccacga attggaagtt gctgcttctg ctgatgaagt ttggtctgtt    180
gaaggttctc cagaattggg tttacatttg ccagatttgt tgccagctgg tattttgcc     240 aagttcgaaa ttactggtga tggtggtgaa ggttccattt tggatatgac ttttccacca    300
ggtcaattcc cacatcatta cagagaaaag ttcgtctttt tcgaccacaa gaacagatac    360
aagttggtcg aacaaatcga tggtgatttc ttcgatttgg gtgttactta ctacatggac    420
accattagag ttgttgctac tggtccagat tcttgcgtta ttaagtctac tactgaatac    480
cacgtcaagc cagaatttgc taaaatcgtt aagccattga tcgataccgt tccattggct    540
attatgtctg aagctattgc caaggttgtc ttggaaaaca acacaagtc atctgaatga     600 aagactccgc gg                                                        612
```

<210> SEQ ID NO 24
<211> LENGTH: 196
<212> TYPE: PRT
<213> ORGANISM: Coptis japonica

<400> SEQUENCE: 24

```
Met Arg Met Glu Val Val Leu Val Val Phe Leu Met Phe Ile Gly Thr
1               5                   10                  15

Ile Asn Cys Glu Arg Leu Ile Phe Asn Gly Arg Pro Leu Leu His Arg
            20                  25                  30

Val Thr Lys Glu Glu Thr Val Met Leu Tyr His Glu Leu Glu Val Ala
        35                  40                  45

Ala Ser Ala Asp Glu Val Trp Ser Val Glu Gly Ser Pro Glu Leu Gly
    50                  55                  60

Leu His Leu Pro Asp Leu Leu Pro Ala Gly Ile Phe Ala Lys Phe Glu
65                  70                  75                  80

Ile Thr Gly Asp Gly Gly Glu Gly Ser Ile Leu Asp Met Thr Phe Pro
                85                  90                  95

Pro Gly Gln Phe Pro His His Tyr Arg Glu Lys Phe Val Phe Phe Asp
            100                 105                 110

His Lys Asn Arg Tyr Lys Leu Val Glu Gln Ile Asp Gly Asp Phe Phe
        115                 120                 125

Asp Leu Gly Val Thr Tyr Tyr Met Asp Thr Ile Arg Val Val Ala Thr
    130                 135                 140

Gly Pro Asp Ser Cys Val Ile Lys Ser Thr Thr Glu Tyr His Val Lys
145                 150                 155                 160

Pro Glu Phe Ala Lys Ile Val Lys Pro Leu Ile Asp Thr Val Pro Leu
                165                 170                 175

Ala Ile Met Ser Glu Ala Ile Ala Lys Val Val Leu Glu Asn Lys His
            180                 185                 190
```

Lys Ser Ser Glu
        195

<210> SEQ ID NO 25
<211> LENGTH: 363
<212> TYPE: PRT
<213> ORGANISM: Saccharomyces cerevisiae

<400> SEQUENCE: 25

Met Ile Gly Ser Ala Ser Asp Ser Ser Lys Leu Gly Arg Leu Arg
1               5                   10                  15

Phe Leu Ser Glu Thr Ala Ala Ile Lys Val Ser Pro Leu Ile Leu Gly
            20                  25                  30

Glu Val Ser Tyr Asp Gly Ala Arg Ser Asp Phe Leu Lys Ser Met Asn
        35                  40                  45

Lys Asn Arg Ala Phe Glu Leu Leu Asp Thr Phe Tyr Glu Ala Gly Gly
50                  55                  60

Asn Phe Ile Asp Ala Ala Asn Asn Cys Gln Asn Glu Gln Ser Glu Glu
65                  70                  75                  80

Trp Ile Gly Glu Trp Ile Gln Ser Arg Arg Leu Arg Asp Gln Ile Val
                85                  90                  95

Ile Ala Thr Lys Phe Ile Lys Ser Asp Lys Lys Tyr Lys Ala Gly Glu
            100                 105                 110

Ser Asn Thr Ala Asn Tyr Cys Gly Asn His Lys Arg Ser Leu His Val
        115                 120                 125

Ser Val Arg Asp Ser Leu Arg Lys Leu Gln Thr Asp Trp Ile Asp Ile
    130                 135                 140

Leu Tyr Val His Trp Trp Asp Tyr Met Ser Ser Ile Glu Glu Phe Met
145                 150                 155                 160

Asp Ser Leu His Ile Leu Val Gln Gln Gly Lys Val Leu Tyr Leu Gly
                165                 170                 175

Val Ser Asp Thr Pro Ala Trp Val Val Ser Ala Ala Asn Tyr Tyr Ala
            180                 185                 190

Thr Ser Tyr Gly Lys Thr Pro Phe Ser Ile Tyr Gln Gly Lys Trp Asn
        195                 200                 205

Val Leu Asn Arg Asp Phe Glu Arg Asp Ile Ile Pro Met Ala Arg His
    210                 215                 220

Phe Gly Met Ala Leu Ala Pro Trp Asp Val Met Gly Gly Gly Arg Phe
225                 230                 235                 240

Gln Ser Lys Lys Ala Met Glu Glu Arg Lys Asn Gly Glu Gly Ile
                245                 250                 255

Arg Ser Phe Val Gly Ala Ser Glu Gln Thr Asp Ala Glu Ile Lys Ile
            260                 265                 270

Ser Glu Ala Leu Ala Lys Ile Ala Glu Glu His Gly Thr Glu Ser Val
        275                 280                 285

Thr Ala Ile Ala Ile Ala Tyr Val Arg Ser Lys Ala Lys Asn Phe Phe
    290                 295                 300

Pro Ser Val Glu Gly Gly Lys Ile Glu Asp Leu Lys Glu Asn Ile Lys
305                 310                 315                 320

Ala Leu Ser Ile Asp Leu Thr Pro Asp Asn Ile Lys Tyr Leu Glu Ser
                325                 330                 335

Ile Val Pro Phe Asp Ile Gly Phe Pro Asn Asn Phe Ile Val Leu Asn
            340                 345                 350

Ser Leu Thr Gln Lys Tyr Gly Thr Asn Asn Val
        355                 360

<210> SEQ ID NO 26
<211> LENGTH: 1092
<212> TYPE: DNA
<213> ORGANISM: Saccharomyces cerevisiae

<400> SEQUENCE: 26

```
atgattgggt ccgcgtccga ctcatctagc aagttaggac gcctccgatt tctttctgaa      60
actgccgcta ttaaagtatc cccgttaatc taggagaag tctcatacga tggagcacgt       120
tcggattttc tcaaatcaat gaacaagaat cgagcttttg aattgcttga tactttttac     180
gaggcaggtg gaaatttcat tgatgccgca acaactgcc aaaacgagca atcagaagaa       240
tggattggtg aatggataca gtccagaagg ttacgtgatc aaattgtcat tgcaaccaag      300
tttataaaaa gcgataaaaa gtataaagca ggtgaaagta acactgccaa ctactgtggt      360
aatcacaagc gtagtttaca tgtgagtgtg agggattctc tccgcaaatt gcaaactgat      420
tggattgata tactttacgt tcactggtgg gattatatga gttcaatcga agaatttatg      480
gatagtttgc atattctggt ccagcagggc aaggtcctct atttgggtgt atctgataca      540
cctgcttggg ttgtttctgc ggcaaactac tacgctacat cttatggtaa aactcccttt      600
agtatctacc aaggtaaatg aacgtgttg aacagagatt ttgagcgtga tattattcca      660
atggctaggc atttcggtat ggccctcgcc catgggatg tcatgggagg tggaagattt        720
cagagtaaaa aagcaatgga ggaacggagg aagaatggag agggtattcg ttctttcgtt      780
ggcgcctccg aacaaacaga tgcagaaatc aagattagtg aagcattggc caagattgct      840
gaggaacatg gcactgagtc tgttactgct attgctattg cctatgttcg ctctaaggcg      900
aaaaatttt ttccgtcggt tgaaggagga aaaattgagg atctcaaaga gaacattaag       960
gctctcagta tcgatctaac gccagacaat ataaaatact tagaaagtat agttcctttt      1020
gacatcggat ttcctaataa ttttatcgtg ttaaattcct tgactcaaaa atatggtacg     1080
aataatgttt ag                                                         1092
```

<210> SEQ ID NO 27
<211> LENGTH: 329
<212> TYPE: PRT
<213> ORGANISM: Saccharomyces cerevisiae

<400> SEQUENCE: 27

```
Met Gly Ser Met Asn Lys Glu Gln Ala Phe Glu Leu Leu Asp Ala Phe
1               5                   10                  15

Tyr Glu Ala Gly Gly Asn Cys Ile Asp Thr Ala Asn Ser Tyr Gln Asn
            20                  25                  30

Glu Glu Ser Glu Ile Trp Ile Gly Glu Trp Met Lys Ser Arg Lys Leu
        35                  40                  45

Arg Asp Gln Ile Val Ile Ala Thr Lys Phe Thr Gly Asp Tyr Lys Lys
    50                  55                  60

Tyr Glu Val Gly Gly Lys Ser Ala Asn Tyr Cys Gly Asn His Lys
65                  70                  75                  80

His Ser Leu His Val Ser Val Arg Asp Ser Leu Arg Lys Leu Gln Thr
                85                  90                  95

Asp Trp Ile Asp Ile Leu Tyr Val His Trp Trp Asp Tyr Met Ser Ser
            100                 105                 110

Ile Glu Glu Val Met Asp Ser Leu His Ile Leu Val Gln Gln Gly Lys
        115                 120                 125
```

Val Leu Tyr Leu Gly Val Ser Asp Thr Pro Ala Trp Val Val Ser Ala
130                 135                 140

Ala Asn Tyr Tyr Ala Thr Ser His Gly Lys Thr Pro Phe Ser Ile Tyr
145                 150                 155                 160

Gln Gly Lys Trp Asn Val Leu Asn Arg Asp Phe Glu Arg Asp Ile Ile
                165                 170                 175

Pro Met Ala Arg His Phe Gly Met Ala Leu Ala Pro Trp Asp Val Met
            180                 185                 190

Gly Gly Gly Arg Phe Gln Ser Lys Lys Ala Met Glu Arg Lys Lys
        195                 200                 205

Asn Gly Glu Gly Leu Arg Thr Val Ser Gly Thr Ser Lys Gln Thr Asp
210                 215                 220

Lys Glu Val Lys Ile Ser Glu Ala Leu Ala Lys Val Ala Glu Glu His
225                 230                 235                 240

Gly Thr Glu Ser Val Thr Ala Ile Ala Ile Ala Tyr Val Arg Ser Lys
                245                 250                 255

Ala Lys Asn Val Phe Pro Leu Val Gly Gly Arg Lys Ile Glu His Leu
            260                 265                 270

Lys Gln Asn Ile Glu Ala Leu Ser Ile Lys Leu Thr Pro Glu Gln Ile
        275                 280                 285

Glu Tyr Leu Glu Ser Ile Ile Pro Phe Asp Val Gly Phe Pro Thr Asn
290                 295                 300

Phe Ile Gly Asp Asp Pro Ala Val Thr Lys Lys Ala Ser Leu Leu Thr
305                 310                 315                 320

Ala Met Ser Ala Gln Ile Ser Phe Asp
                325

<210> SEQ ID NO 28
<211> LENGTH: 990
<212> TYPE: DNA
<213> ORGANISM: Saccharomyces cerevisiae

<400> SEQUENCE: 28
atgggctcta tgaataagga acaggctttt gaacttcttg atgcttttta tgaagcagga      60
ggtaattgca ttgatactgc aaacagttac caaaatgaag agtcagagat tggataggt     120 gaatggatga aatcaagaaa gttgcgtgac caaattgtaa ttgccaccaa gtttaccgga     180
gattataaga gtatgaagt aggtggcggt aaaagtgcca actattgtgg taatcacaag     240
catagtttac atgtgagtgt gagggattct ctccgcaaat tgcaaactga ttggattgat     300
atactttacg ttcactggtg ggattatatg agttcaatcg aagaagttat ggatagtttg     360
catattttag ttcagcaggg caaagtcctc tatttgggtg tgtctgatac acctgcttgg     420
gttgtttctg cggcaaacta ctacgccaca tctcatggga aaactccttt tagtatctat     480
caaggtaaat ggaatgtgtt gaacagggac tttgagcgcg atatcattcc aatggccaga     540
cattttggta tggctctagc cccatgggat gttatgggag gtggaagatt tcagagtaaa     600
aaagcaatgg aggaacggaa gaagaatgga gagggtctgc gtactgtttc gggtacttct     660
aaacagacgg ataagaggt taagatcagt gaagcattgg ccaaggttgc tgaggaacat     720
ggcactgagt ctgttactgc tattgctatt gcctatgttc gctctaaggc gaaaaatgtt     780
ttcccattgg ttggtggaag gaaaattgaa caccctcaaac agaacattga ggctttaagt     840
atcaaactga caccagaaca gatagaatac ttagaaagta ttattccttt tgatgttggt     900

```
tttcctacta attttatcgg tgatgatccg gctgttacca agaaggcttc acttctcacg    960
gcaatgtctg cgcagatttc cttcgattaa                                     990
```

<210> SEQ ID NO 29
<211> LENGTH: 375
<212> TYPE: PRT
<213> ORGANISM: Saccharomyces cerevisiae

<400> SEQUENCE: 29

```
Met Leu Arg Thr Ser Thr Leu Phe Thr Arg Arg Val Gln Pro Ser Leu
1               5                   10                  15

Phe Ser Arg Asn Ile Leu Arg Leu Gln Ser Thr Ala Ala Ile Pro Lys
            20                  25                  30

Thr Gln Lys Gly Val Ile Phe Tyr Glu Asn Lys Gly Lys Leu His Tyr
        35                  40                  45

Lys Asp Ile Pro Val Pro Glu Pro Lys Pro Asn Glu Ile Leu Ile Asn
    50                  55                  60

Val Lys Tyr Ser Gly Val Cys His Thr Asp Leu His Ala Trp His Gly
65                  70                  75                  80

Asp Trp Pro Leu Pro Val Lys Leu Pro Leu Val Gly Gly His Glu Gly
                85                  90                  95

Ala Gly Val Val Val Lys Leu Gly Ser Asn Val Lys Gly Trp Lys Val
            100                 105                 110

Gly Asp Leu Ala Gly Ile Lys Trp Leu Asn Gly Ser Cys Met Thr Cys
        115                 120                 125

Glu Phe Cys Glu Ser Gly His Glu Ser Asn Cys Pro Asp Ala Asp Leu
    130                 135                 140

Ser Gly Tyr Thr His Asp Gly Ser Phe Gln Gln Phe Ala Thr Ala Asp
145                 150                 155                 160

Ala Ile Gln Ala Ala Lys Ile Gln Gln Gly Thr Asp Leu Ala Glu Val
                165                 170                 175

Ala Pro Ile Leu Cys Ala Gly Val Thr Val Tyr Lys Ala Leu Lys Glu
            180                 185                 190

Ala Asp Leu Lys Ala Gly Asp Trp Val Ala Ile Ser Gly Ala Ala Gly
        195                 200                 205

Gly Leu Gly Ser Leu Ala Val Gln Tyr Ala Thr Ala Met Gly Tyr Arg
    210                 215                 220

Val Leu Gly Ile Asp Ala Gly Glu Glu Lys Glu Lys Leu Phe Lys Lys
225                 230                 235                 240

Leu Gly Gly Glu Val Phe Ile Asp Phe Thr Lys Thr Lys Asn Met Val
                245                 250                 255

Ser Asp Ile Gln Glu Ala Thr Lys Gly Gly Pro His Gly Val Ile Asn
            260                 265                 270

Val Ser Val Ser Glu Ala Ala Ile Ser Leu Ser Thr Glu Tyr Val Arg
        275                 280                 285

Pro Cys Gly Thr Val Val Leu Val Gly Leu Pro Ala Asn Ala Tyr Val
    290                 295                 300

Lys Ser Glu Val Phe Ser His Val Val Lys Ser Ile Asn Ile Lys Gly
305                 310                 315                 320

Ser Tyr Val Gly Asn Arg Ala Asp Thr Arg Glu Ala Leu Asp Phe Phe
                325                 330                 335

Ser Arg Gly Leu Ile Lys Ser Pro Ile Lys Ile Val Gly Leu Ser Glu
            340                 345                 350
```

```
Leu Pro Lys Val Tyr Asp Leu Met Glu Lys Gly Lys Ile Leu Gly Arg
        355                 360                 365

Tyr Val Val Asp Thr Ser Lys
    370                 375

<210> SEQ ID NO 30
<211> LENGTH: 1128
<212> TYPE: DNA
<213> ORGANISM: Saccharomyces cerevisiae

<400> SEQUENCE: 30
atgttgagaa cgtcaacatt gttcaccagg cgtgtccaac caagcctatt ttctagaaac     60
attcttagat tgcaatccac agctgcaatc cctaagactc aaaaaggtgt catcttttat    120
gagaataagg ggaagctgca ttacaaagat atccctgtcc ccgagcctaa gccaaatgaa    180
attttaatca acgttaaata ttctggtgta tgtcacaccg atttacatgc ttggcacggc    240
gattggccat tacctgttaa actaccatta gtaggtggtc atgaaggtgc tggtgtagtt    300
gtcaaactag gttccaatgt caagggctgg aaagtcggtg attagcagg tatcaaatgg    360 ctgaacggtt cttgtatgac atgcgaattc tgtgaatcag gtcatgaatc aaattgtcca    420
gatgctgatt tatctggtta cactcatgat ggttctttcc aacaatttgc gaccgctgat    480
gctattcaag ccgccaaaat tcaacagggt accgacttgg ccgaagtagc cccaatatta    540
tgtgctggtg ttactgtata taagcacta aaagaggcag acttgaaagc tggtgactgg    600
gttgccatct ctggtgctgc aggtggcttg ggttccttgg ccgttcaata tgcaactgcg    660
atgggttaca gagttctagg tattgatgca ggtgaggaaa aggaaaaact tttcaagaaa    720
ttggggggtg aagtattcat cgactttact aaaacaaaga atatggtttc tgacattcaa    780
gaagctacca aaggtggccc tcatggtgtc attaacgttt ccgtttctga agccgctatt    840
tctctatcta cggaatatgt tagaccatgt ggtaccgtcg ttttggttgg tttgcccgct    900
aacgcctacg ttaaatcaga ggtattctct catgtggtga agtccatcaa tatcaagggt    960
tcttatgttg gtaacagagc tgatacgaga gaagccttag acttctttag cagaggtttg   1020
atcaaatcac caatcaaaat tgttggatta tctgaattac caaggtttta tgacttgatg   1080
gaaaagggca agattttggg tagatacgtc gtcgatacta gtaaataa                1128

<210> SEQ ID NO 31
<211> LENGTH: 382
<212> TYPE: PRT
<213> ORGANISM: Saccharomyces cerevisiae

<400> SEQUENCE: 31

Met Ser Ser Val Thr Gly Phe Tyr Ile Pro Pro Ile Ser Phe Phe Gly
1               5                   10                  15

Glu Gly Ala Leu Glu Glu Thr Ala Asp Tyr Ile Lys Asn Lys Asp Tyr
            20                  25                  30

Lys Lys Ala Leu Ile Val Thr Asp Pro Gly Ile Ala Ala Ile Gly Leu
        35                  40                  45

Ser Gly Arg Val Gln Lys Met Leu Glu Glu Arg Asp Leu Asn Val Ala
    50                  55                  60

Ile Tyr Asp Lys Thr Gln Pro Asn Pro Asn Ile Ala Asn Val Thr Ala
65                  70                  75                  80

Gly Leu Lys Val Leu Lys Glu Gln Asn Ser Glu Ile Val Val Ser Ile
                85                  90                  95
```

Gly Gly Gly Ser Ala His Asp Asn Ala Lys Ala Ile Ala Leu Leu Ala
            100                 105                 110

Thr Asn Gly Gly Glu Ile Gly Asp Tyr Glu Gly Val Asn Gln Ser Lys
            115                 120                 125

Lys Ala Ala Leu Pro Leu Phe Ala Ile Asn Thr Thr Ala Gly Thr Ala
130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
                165                 170                 175

Asp Pro Ser Thr Met Phe Gly Leu Pro Pro Ala Leu Thr Ala Ala Thr
            180                 185                 190

Gly Leu Asp Ala Leu Thr His Cys Ile Glu Ala Tyr Val Ser Thr Ala
            195                 200                 205

Ser Asn Pro Ile Thr Asp Ala Cys Ala Leu Lys Gly Ile Asp Leu Ile
            210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
            260                 265                 270

Phe Tyr His Leu Pro His Gly Val Cys Asn Ala Val Leu Leu Pro His
            275                 280                 285

Val Gln Glu Ala Asn Met Gln Cys Pro Lys Ala Lys Lys Arg Leu Gly
290                 295                 300

Glu Ile Ala Leu His Phe Gly Ala Ser Gln Glu Asp Pro Glu Glu Thr
305                 310                 315                 320

Ile Lys Ala Leu His Val Leu Asn Arg Thr Met Asn Ile Pro Arg Asn
                325                 330                 335

Leu Lys Glu Leu Gly Val Lys Thr Glu Asp Phe Glu Ile Leu Ala Glu
            340                 345                 350

His Ala Met His Asp Ala Cys His Leu Thr Asn Pro Val Gln Phe Thr
            355                 360                 365

Lys Glu Gln Val Val Ala Ile Ile Lys Lys Ala Tyr Glu Tyr
370                 375                 380

<210> SEQ ID NO 32
<211> LENGTH: 1149
<212> TYPE: DNA
<213> ORGANISM: Saccharomyces cerevisiae

<400> SEQUENCE: 32
atgtcttccg ttactgggtt ttacattcca ccaatctctt tctttggtga aggtgcttta      60
gaagaaaccg ctgattacat caaaaacaag gattacaaaa aggctttgat cgttactgat     120
cctggtattg cagctattgg tctctccggt agagtccaaa agatgttgga agaacgtgac     180
ttaaacgttg ctatctatga caaaactcaa ccaaacccaa atattgccaa tgtcacagct     240
ggtttgaagg ttttgaagga acaaaactct gaaattgttg tttccattgg tggtggttct     300
gctcacgaca atgctaaggc cattgcttta ttggctacta cggtggggga aatcggagac     360
tatgaaggtg tcaatcaatc taagaaggct gctttaccac tatttgccat caacactact     420
gctggtactg cttccgaaat gaccagattc actattatct ctaatgaaga aagaaaatc       480 aagatggcta tcattgacaa caacgtcact ccagctgttg ctgtcaacga tccatctacc     540

-continued

```
atgtttggtt tgccacctgc tttgactgct gctactggtc tagatgcttt gactcactgt    600
atcgaagctt atgtttccac cgcctctaac ccaatcaccg atgcctgtgc tttgaagggt    660
attgatttga tcaatgaaag cttagtcgct gcatacaaag acggtaaaga caagaaggcc    720
agaactgaca tgtgttacgc tgaatacttg gcaggtatgg ctttcaacaa tgcttctcta    780
ggttatgttc atgcccttgc tcatcaactt ggtggtttct accacttgcc tcatggtgtt    840
tgtaacgctg tcttgttgcc tcatgttcaa gaggccaaca tgcaatgtcc aaaggccaag    900
aagagattag gtgaaattgc tttgcatttc ggtgcttctc aagaagatcc agaagaaacc    960
atcaaggctt gcacgttttt aaacagaacc atgaacattc aagaaacttg aaagaatta   1020
ggtgttaaaa ccgaagattt tgaaattttg gctgaacacg ccatgcatga tgcctgccat   1080
ttgactaacc cagttcaatt caccaaagaa caagtggttg ccattatcaa gaaagcctat   1140
gaatattaa                                                          1149
```

<210> SEQ ID NO 33
<211> LENGTH: 500
<212> TYPE: PRT
<213> ORGANISM: Saccharomyces cerevisiae

<400> SEQUENCE: 33

```
Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255
```

```
Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500

<210> SEQ ID NO 34
<211> LENGTH: 1503
<212> TYPE: DNA
<213> ORGANISM: Saccharomyces cerevisiae

<400> SEQUENCE: 34
atgactaagc tacactttga cactgctgaa ccagtcaaga tcacacttcc aaatggtttg      60
acatacgagc aaccaaccgg tctattcatt aacaacaagt ttatgaaagc tcaagacggt     120
aagacctatc ccgtcgaaga tccttccact gaaaacaccg tttgtgaggt ctcttctgcc     180
accactgaag atgttgaata tgctatcgaa tgtgccgacc gtgctttcca cgacactgaa     240
tgggctaccc aagacccaag agaaagaggc cgtctactaa gtaagttggc tgacgaattg     300
gaaagccaaa ttgacttggt ttcttccatt gaagctttgg acaatggtaa actttggcc      360 ttagcccgtg gggatgttac cattgcaatc aactgtctaa gagatgctgc tgcctatgcc     420
gacaaagtca cggtagaac aatcaacacc ggtgacggct acatgaactt caccaccta      480 gagccaatcg gtgtctgtgg tcaaattatt ccatggaact ttccaataat gatgttggct     540
tggaagatcg ccccagcatt ggccatgggt aacgtctgta tcttgaaacc cgctgctgtc     600
acacctttaa atgccctata ctttgcttct ttatgtaaga aggttggtat tccagctggt     660
gtcgtcaaca tcgttccagg tcctggtaga actgttggtg ctgctttgac caacgaccca     720
```

-continued

```
agaatcagaa agctggcttt taccggttct acagaagtcg gtaagagtgt tgctgtcgac      780
tcttctgaat ctaacttgaa gaaaatcact ttggaactag tggtaagtc cgcccatttg       840 gtctttgacg atgctaacat taagaagact ttaccaaatc tagtaaacgg tattttcaag      900
aacgctggtc aaatttgttc ctctggttct agaatttacg ttcaagaagg tatttacgac     960
gaactattgg ctgctttcaa ggcttacttg gaaaccgaaa tcaaagttgg taatccattt    1020
gacaaggcta acttccaagg tgctatcact aaccgtcaac aattcgacac aattatgaac    1080
tacatcgata tcggtaagaa agaaggcgcc aagatcttaa ctggtggcga aaaagttggt    1140
gacaagggtt acttcatcag accaaccgtt ttctacgatg ttaatgaaga catgagaatt    1200
gttaaggaag aaattttggg accagttgtc actgtcgcaa agttcaagac tttagaagaa    1260
ggtgtcgaaa tggctaacag ctctgaattc ggtctaggtt ctggtatcga aacagaatct   1320
ttgagcacag gtttgaaggt ggccaagatg ttgaaggccg gtaccgtctg gatcaacaca    1380
tacaacgatt ttgactccag agttccattc ggtggtgtta agcaatctgg ttacggtaga    1440
gaaatgggtg aagaagtcta ccatgcatac actgaagtaa aagctgtcag aattaagttg    1500
taa                                                                   1503
```

<210> SEQ ID NO 35
<211> LENGTH: 382
<212> TYPE: PRT
<213> ORGANISM: Saccharomyces cerevisiae

<400> SEQUENCE: 35

```
Met Arg Ala Leu Ala Tyr Phe Lys Lys Gly Asp Ile His Phe Thr Asn
1               5                   10                  15

Asp Ile Pro Arg Pro Glu Ile Gln Thr Asp Asp Glu Val Ile Ile Asp
            20                  25                  30

Val Ser Trp Cys Gly Ile Cys Gly Ser Asp Leu His Glu Tyr Leu Asp
        35                  40                  45

Gly Pro Ile Phe Met Pro Lys Asp Gly Glu Cys His Lys Leu Ser Asn
    50                  55                  60

Ala Ala Leu Pro Leu Ala Met Gly His Glu Met Ser Gly Ile Val Ser
65                  70                  75                  80

Lys Val Gly Pro Lys Val Thr Lys Val Lys Val Gly Asp His Val Val
                85                  90                  95

Val Asp Ala Ala Ser Ser Cys Ala Asp Leu His Cys Trp Pro His Ser
            100                 105                 110

Lys Phe Tyr Asn Ser Lys Pro Cys Asp Ala Cys Gln Arg Gly Ser Glu
        115                 120                 125

Asn Leu Cys Thr His Ala Gly Phe Val Gly Leu Gly Val Ile Ser Gly
    130                 135                 140

Gly Phe Ala Glu Gln Val Val Val Ser Gln His His Ile Ile Pro Val
145                 150                 155                 160

Pro Lys Glu Ile Pro Leu Asp Val Ala Ala Leu Val Glu Pro Leu Ser
                165                 170                 175

Val Thr Trp His Ala Val Lys Ile Ser Gly Phe Lys Lys Gly Ser Ser
            180                 185                 190

Ala Leu Val Leu Gly Ala Gly Pro Ile Gly Leu Cys Thr Ile Leu Val
        195                 200                 205

Leu Lys Gly Met Gly Ala Ser Lys Ile Val Val Ser Glu Ile Ala Glu
    210                 215                 220
```

```
Arg Arg Ile Glu Met Ala Lys Lys Leu Gly Val Glu Val Phe Asn Pro
225                 230                 235                 240

Ser Lys His Gly His Lys Ser Ile Glu Ile Leu Arg Gly Leu Thr Lys
            245                 250                 255

Ser His Asp Gly Phe Asp Tyr Ser Tyr Asp Cys Ser Gly Ile Gln Val
            260                 265                 270

Thr Phe Glu Thr Ser Leu Lys Ala Leu Thr Phe Lys Gly Thr Ala Thr
        275                 280                 285

Asn Ile Ala Val Trp Gly Pro Lys Pro Val Pro Phe Gln Pro Met Asp
        290                 295                 300

Val Thr Leu Gln Glu Lys Val Met Thr Gly Ser Ile Gly Tyr Val Val
305                 310                 315                 320

Glu Asp Phe Glu Glu Val Val Arg Ala Ile His Asn Gly Asp Ile Ala
                325                 330                 335

Met Glu Asp Cys Lys Gln Leu Ile Thr Gly Lys Gln Arg Ile Glu Asp
                340                 345                 350

Gly Trp Glu Lys Gly Phe Gln Glu Leu Met Asp His Lys Glu Ser Asn
            355                 360                 365

Val Lys Ile Leu Leu Thr Pro Asn Asn His Gly Glu Met Lys
370                 375                 380

<210> SEQ ID NO 36
<211> LENGTH: 1149
<212> TYPE: DNA
<213> ORGANISM: Saccharomyces cerevisiae

<400> SEQUENCE: 36
atgagagctt tggcatattt caagaagggt gatattcact tcactaatga tatccctagg      60
ccagaaatcc aaaccgacga tgaggttatt atcgacgtct cttggtgtgg gatttgtggc    120
tcggatcttc acgagtactt ggatggtcca atcttcatgc taaagatgg agagtgccat     180 aaattatcca acgctgcttt acctctggca atgggccatg agatgtcagg aattgtttcc    240
aaggttggtc ctaaagtgac aaaggtgaag gttggcgacc acgtggtcgt tgatgctgcc    300
agcagttgtg cggacctgca ttgctggcca cactccaaat tttacaattc caaaccatgt    360
gatgcttgtc agaggggcag tgaaaatcta tgtacccacg ccggttttgt aggactaggt    420
gtgatcagtg gtggctttgc tgaacaagtc gtagtctctc aacatcacat tatcccggtt    480
ccaaaggaaa ttcctctaga tgtggctgct ttagttgagc ctctttctgt cacctggcat    540
gctgttaaga tttctggttt caaaaaaggc agttcagcct tggttcttgg tgcaggtccc    600
attgggttgt gtaccatttt ggtacttaag ggaatggggg ctagtaaaat tgtagtgtct    660
gaaattgcag agaagaat agaaatggcc aagaaactgg gcgttgaggt gttcaatccc     720
tccaagcacg gtcataaatc tatagagata ctacgtggtt tgaccaagag ccatgatggg   780
tttgattaca gttatgattg ttctggtatt caagttactt cgaaacctc tttgaaggca    840 ttaacattca aggggacagc caccaacatt gcagtttggg gtccaaaacc tgtcccattc    900
caaccaatgg atgtgactct ccaagagaaa gttatgactg gttcgatcgg ctatgttgtc    960
gaagacttcg aagaagttgt tcgtgccatc acaacggag acatcgccat ggaagattgt    1020
aagcaactaa tcactggtaa gcaaaggatt gaggacggtt gggaaaaggg attccaagag  1080
ttgatggatc acaaggaatc caacgttaag attctattga cgcctaacaa tcacggtgaa  1140
atgaagtaa                                                           1149
```

<210> SEQ ID NO 37
<211> LENGTH: 417
<212> TYPE: PRT
<213> ORGANISM: Saccharomyces cerevisiae

<400> SEQUENCE: 37

Met Arg Ala Leu Ala Tyr Phe Gly Lys Gly Asn Ile Arg Phe Thr Asn
1               5                   10                  15

His Leu Lys Glu Pro His Ile Val Ala Pro Asp Glu Leu Val Ile Asp
            20                  25                  30

Ile Glu Trp Cys Gly Ile Cys Gly Thr Asp Leu His Glu Tyr Thr Asp
        35                  40                  45

Gly Pro Ile Phe Phe Pro Glu Asp Gly His Thr His Glu Ile Ser His
    50                  55                  60

Asn Pro Leu Pro Gln Ala Met Gly His Glu Met Ala Gly Thr Val Leu
65                  70                  75                  80

Glu Val Gly Pro Gly Val Lys Asn Leu Lys Val Gly Asp Lys Val Val
                85                  90                  95

Val Glu Pro Thr Gly Thr Cys Arg Asp Arg Tyr Arg Trp Pro Leu Ser
            100                 105                 110

Pro Asn Val Asp Lys Glu Trp Cys Ala Ala Cys Lys Lys Gly Tyr Tyr
        115                 120                 125

Asn Ile Cys Ser Tyr Leu Gly Leu Cys Gly Ala Gly Val Gln Ser Gly
    130                 135                 140

Gly Phe Ala Glu Arg Val Val Met Asn Glu Ser His Cys Tyr Lys Val
145                 150                 155                 160

Pro Asp Phe Val Pro Leu Asp Val Ala Ala Leu Ile Gln Pro Leu Ala
                165                 170                 175

Val Cys Trp His Ala Ile Arg Val Cys Glu Phe Lys Ala Gly Ser Thr
            180                 185                 190

Ala Leu Ile Ile Gly Ala Gly Pro Ile Gly Leu Gly Thr Ile Leu Ala
        195                 200                 205

Leu Asn Ala Ala Gly Cys Lys Asp Ile Val Val Ser Glu Pro Ala Lys
    210                 215                 220

Val Arg Arg Glu Leu Ala Glu Lys Met Gly Ala Arg Val Tyr Asp Pro
225                 230                 235                 240

Thr Ala His Ala Ala Lys Glu Ser Ile Asp Tyr Leu Arg Ser Ile Ala
                245                 250                 255

Asp Gly Gly Asp Gly Phe Asp Tyr Thr Phe Asp Cys Ser Gly Leu Glu
            260                 265                 270

Val Thr Leu Asn Ala Ala Ile Gln Cys Leu Thr Phe Arg Gly Thr Ala
        275                 280                 285

Val Asn Leu Ala Met Trp Gly His His Lys Ile Gln Phe Ser Pro Met
    290                 295                 300

Asp Ile Thr Leu His Glu Arg Lys Tyr Thr Gly Ser Met Cys Tyr Thr
305                 310                 315                 320

His His Asp Phe Glu Ala Val Ile Glu Ala Leu Glu Glu Gly Arg Ile
                325                 330                 335

Asp Ile Asp Arg Ala Arg His Met Ile Thr Gly Arg Val Asn Ile Glu
            340                 345                 350

Asp Gly Leu Asp Gly Ala Ile Met Lys Leu Ile Asn Glu Lys Glu Ser
        355                 360                 365

Thr Ile Lys Ile Ile Leu Thr Pro Asn Asn His Gly Glu Leu Asn Arg
    370                 375                 380

Glu Ala Asp Asn Glu Lys Lys Glu Ile Ser Glu Leu Ser Ser Arg Lys
385                 390                 395                 400

Asp Gln Glu Arg Leu Arg Glu Ser Ile Asn Glu Ala Lys Leu Arg His
            405                 410                 415

Thr

<210> SEQ ID NO 38
<211> LENGTH: 1254
<212> TYPE: DNA
<213> ORGANISM: Saccharomyces cerevisiae

<400> SEQUENCE: 38

```
atgagagcct tagcgtattt cggtaaaggt aacatcagat tcaccaacca tttaaaggag      60
ccacatattg tggcgcccga tgagcttgtg attgatatcg aatggtgtgg tatttgcggt     120
acggacctgc atgagtacac agatggtcct atcttttttcc cagaagatgg acacacacat    180
gagattagtc ataacccatt gccacaggcg atgggccacg aaatggctgg taccgttttg     240
gaggtgggcc ctggtgtgaa aaacttgaaa gtgggagaca aggtagttgt cgagcccaca     300
ggtacatgca gagaccggta tcgttggccc ctgtcgccaa cgttgacaa ggaatggtgc      360
gctgcttgca aaaagggcta ctataacatt tgttcatatt tggggctttg tggtgcgggt     420
gtgcagagcg gtggatttgc agaacgtgtt gtgatgaacg aatctcactg ctacaaagta     480
ccggacttcg tgcccttaga cgttgcagct ttgattcaac cgttggctgt gtgctggcat     540
gcaattagag tctgcgagtt caaagcaggc tctacggctt tgatcattgg tgctggcccc     600
atcggactgg gcacgatact ggcgttgaac gctgcaggtt gcaaggacat cgtcgtttca     660
gagcctgcca aggtaagaag agaactggct gaaaaaatgg gtgccagggt ttacgaccca     720
actgcgcacg ctgccaagga gagcattgat tatctgaggt cgattgctga tggtggagac     780
ggcttcgatt acacatttga ttgctccggg ttggaagtca cattgaatgc tgctattcag     840
tgtctcactt tcagaggcac cgcagtgaac ttggccatgt ggggccatca aagatacag      900
ttttctccga tggacatcac attgcatgaa agaaagtaca cagggtccat gtgctacaca     960
caccacgatt tgaggcagt aatagaagct ttggaagaag caggattga cattgataga     1020
gcaagacata tgataacggg cagagtcaac attgaggacg gccttgatgg cgccatcatg    1080
aagctgataa cgagaaggga gtctacaatc aagattattc tgactccaaa caatcacgga    1140
gagttgaaca gggaagccga taatgagaag aaagaaattt ccgagctgag cagtcggaaa    1200
gatcaagaaa gactacgaga atcaataaac gaggctaaac tgcgtcacac atga          1254
```

<210> SEQ ID NO 39
<211> LENGTH: 900
<212> TYPE: PRT
<213> ORGANISM: Saccharomyces cerevisiae

<400> SEQUENCE: 39

Met Pro Gly Asn Leu Ser Phe Lys Asp Arg Val Val Ile Thr Gly
1               5                   10                  15

Ala Gly Gly Gly Leu Gly Lys Val Tyr Ala Leu Ala Tyr Ala Ser Arg
            20                  25                  30

Gly Ala Lys Val Val Val Asn Asp Leu Gly Gly Thr Leu Gly Gly Ser
            35                  40                  45

Gly His Asn Ser Lys Ala Ala Asp Leu Val Val Asp Glu Ile Lys Lys
    50                  55                  60

```
Ala Gly Gly Ile Ala Val Ala Asn Tyr Asp Ser Val Asn Glu Asn Gly
 65                  70                  75                  80

Glu Lys Ile Ile Glu Thr Ala Ile Lys Glu Phe Gly Arg Val Asp Val
                 85                  90                  95

Leu Ile Asn Asn Ala Gly Ile Leu Arg Asp Val Ser Phe Ala Lys Met
                100                 105                 110

Thr Glu Arg Glu Phe Ala Ser Val Val Asp Val His Leu Thr Gly Gly
                115                 120                 125

Tyr Lys Leu Ser Arg Ala Ala Trp Pro Tyr Met Arg Ser Gln Lys Phe
            130                 135                 140

Gly Arg Ile Ile Asn Thr Ala Ser Pro Ala Gly Leu Phe Gly Asn Phe
145                 150                 155                 160

Gly Gln Ala Asn Tyr Ser Ala Ala Lys Met Gly Leu Val Gly Leu Ala
                165                 170                 175

Glu Thr Leu Ala Lys Glu Gly Ala Lys Tyr Asn Ile Asn Val Asn Ser
            180                 185                 190

Ile Ala Pro Leu Ala Arg Ser Arg Met Thr Glu Asn Val Leu Pro Pro
            195                 200                 205

His Ile Leu Lys Gln Leu Gly Pro Glu Lys Ile Val Pro Leu Val Leu
210                 215                 220

Tyr Leu Thr His Glu Ser Thr Lys Val Ser Asn Ser Ile Phe Glu Leu
225                 230                 235                 240

Ala Ala Gly Phe Phe Gly Gln Leu Arg Trp Glu Arg Ser Ser Gly Gln
                245                 250                 255

Ile Phe Asn Pro Asp Pro Lys Thr Tyr Thr Pro Glu Ala Ile Leu Asn
            260                 265                 270

Lys Trp Lys Glu Ile Thr Asp Tyr Arg Asp Lys Pro Phe Asn Lys Thr
            275                 280                 285

Gln His Pro Tyr Gln Leu Ser Asp Tyr Asn Asp Leu Ile Thr Lys Ala
            290                 295                 300

Lys Lys Leu Pro Pro Asn Glu Gln Gly Ser Val Lys Ile Lys Ser Leu
305                 310                 315                 320

Cys Asn Lys Val Val Val Thr Gly Ala Gly Gly Leu Gly Lys
                325                 330                 335

Ser His Ala Ile Trp Phe Ala Arg Tyr Gly Ala Lys Val Val Val Asn
            340                 345                 350

Asp Ile Lys Asp Pro Phe Ser Val Val Glu Glu Ile Asn Lys Leu Tyr
            355                 360                 365

Gly Glu Gly Thr Ala Ile Pro Asp Ser His Asp Val Val Thr Glu Ala
            370                 375                 380

Pro Leu Ile Ile Gln Thr Ala Ile Ser Lys Phe Gln Arg Val Asp Ile
385                 390                 395                 400

Leu Val Asn Asn Ala Gly Ile Leu Arg Asp Lys Ser Phe Leu Lys Met
                405                 410                 415

Lys Asp Glu Glu Trp Phe Ala Val Leu Lys Val His Leu Phe Ser Thr
            420                 425                 430

Phe Ser Leu Ser Lys Ala Val Trp Pro Ile Phe Thr Lys Gln Lys Ser
            435                 440                 445

Gly Phe Ile Ile Asn Thr Thr Ser Thr Ser Gly Ile Tyr Gly Asn Phe
            450                 455                 460

Gly Gln Ala Asn Tyr Ala Ala Lys Ala Ala Ile Leu Gly Phe Ser
465                 470                 475                 480
```

```
Lys Thr Ile Ala Leu Glu Gly Ala Lys Arg Gly Ile Val Asn Val
                485                 490                 495

Ile Ala Pro His Ala Glu Thr Ala Met Thr Lys Thr Ile Phe Ser Glu
            500                 505                 510

Lys Glu Leu Ser Asn His Phe Asp Ala Ser Gln Val Ser Pro Leu Val
                515                 520                 525

Val Leu Leu Ala Ser Glu Glu Leu Gln Lys Tyr Ser Gly Arg Arg Val
            530                 535                 540

Ile Gly Gln Leu Phe Glu Val Gly Gly Trp Cys Gly Gln Thr Arg
545                 550                 555                 560

Trp Gln Arg Ser Ser Gly Tyr Val Ser Ile Lys Glu Thr Ile Glu Pro
                565                 570                 575

Glu Glu Ile Lys Glu Asn Trp Asn His Ile Thr Asp Phe Ser Arg Asn
            580                 585                 590

Thr Ile Asn Pro Ser Ser Thr Glu Glu Ser Ser Met Ala Thr Leu Gln
                595                 600                 605

Ala Val Gln Lys Ala His Ser Ser Lys Glu Leu Asp Asp Gly Leu Phe
            610                 615                 620

Lys Tyr Thr Thr Lys Asp Cys Ile Leu Tyr Asn Leu Gly Leu Gly Cys
625                 630                 635                 640

Thr Ser Lys Glu Leu Lys Tyr Thr Tyr Glu Asn Asp Pro Asp Phe Gln
                645                 650                 655

Val Leu Pro Thr Phe Ala Val Ile Pro Phe Met Gln Ala Thr Ala Thr
            660                 665                 670

Leu Ala Met Asp Asn Leu Val Asp Asn Phe Asn Tyr Ala Met Leu Leu
                675                 680                 685

His Gly Glu Gln Tyr Phe Lys Leu Cys Thr Pro Thr Met Pro Ser Asn
690                 695                 700

Gly Thr Leu Lys Thr Leu Ala Lys Pro Leu Gln Val Leu Asp Lys Asn
705                 710                 715                 720

Gly Lys Ala Ala Leu Val Val Gly Gly Phe Glu Thr Tyr Asp Ile Lys
                725                 730                 735

Thr Lys Lys Leu Ile Ala Tyr Asn Glu Gly Ser Phe Phe Ile Arg Gly
            740                 745                 750

Ala His Val Pro Pro Glu Lys Glu Val Arg Asp Gly Lys Arg Ala Lys
            755                 760                 765

Phe Ala Val Gln Asn Phe Glu Val Pro His Gly Lys Val Pro Asp Phe
770                 775                 780

Glu Ala Glu Ile Ser Thr Asn Lys Asp Gln Ala Ala Leu Tyr Arg Leu
785                 790                 795                 800

Ser Gly Asp Phe Asn Pro Leu His Ile Asp Pro Thr Leu Ala Lys Ala
                805                 810                 815

Val Lys Phe Pro Thr Pro Ile Leu His Gly Leu Cys Thr Leu Gly Ile
            820                 825                 830

Ser Ala Lys Ala Leu Phe Glu His Tyr Gly Pro Tyr Glu Glu Leu Lys
            835                 840                 845

Val Arg Phe Thr Asn Val Val Phe Pro Gly Asp Thr Leu Lys Val Lys
850                 855                 860

Ala Trp Lys Gln Gly Ser Val Val Phe Gln Thr Ile Asp Thr Thr
865                 870                 875                 880

Arg Asn Val Ile Val Leu Asp Asn Ala Ala Val Lys Leu Ser Gln Ala
                885                 890                 895
```

Lys Ser Lys Leu
900

<210> SEQ ID NO 40
<211> LENGTH: 2703
<212> TYPE: DNA
<213> ORGANISM: Saccharomyces cerevisiae

<400> SEQUENCE: 40

| | | | | |
|---|---|---|---|---|
| atgcctggaa atttatcctt caaagataga gttgttgtaa tcacgggcgc tggaggggc | | | | 60 |
| ttaggtaagg tgtatgcact agcttacgca agcagaggtg caaaagtggt cgtcaatgat | | | | 120 |
| ctaggtggca cttttgggtgg ttcaggacat aactccaaag ctgcagactt agtggtggat | | | | 180 |
| gagataaaaa aagccggagg tatagctgtg gcaaattacg actctgttaa tgaaaatgga | | | | 240 |
| gagaaaataa ttgaaacggc tataaaagaa ttcggcaggg ttgatgtact aattaacaac | | | | 300 |
| gctggaatat taagggatgt ttcatttgca aagatgacag aacgtgagtt tgcatctgtg | | | | 360 |
| gtagatgttc atttgacagg tggctataag ctatcgcgtg ctgcttggcc ttatatgcgc | | | | 420 |
| tctcagaaat ttggtagaat cattaacacc gcttcccctg ccggtctatt tggaaatttt | | | | 480 |
| ggtcaagcta attattcagc agctaaaatg ggcttagttg gtttggcgga aaccctcgcg | | | | 540 |
| aaggagggtg ccaaatacaa cattaatgtt aattcaattg cgccattggc tagatcacgt | | | | 600 |
| atgacagaaa acgtgttacc accacatatc ttgaaacagt taggaccgga aaaaattgtt | | | | 660 |
| cccttagtac tctatttgac acacgaaagt acgaaagtgt caaactccat ttttgaactc | | | | 720 |
| gctgctggat tctttggaca gctcagatgg gagaggtctt ctggacaaat tttcaatcca | | | | 780 |
| gaccccaaga catatactcc tgaagcaatt ttaaataagt ggaaggaaat cacagactat | | | | 840 |
| agggacaagc catttaacaa aactcagcat ccatatcaac tctcggatta taatgattta | | | | 900 |
| atcaccaaag caaaaaaatt acctcccaat gaacaaggct cagtgaaaat caagtcgctt | | | | 960 |
| tgcaacaaag tcgtagtagt tacgggtgca ggaggtggtc ttgggaagtc tcatgcaatc | | | | 1020 |
| tggtttgcac ggtacggtgc gaaggtagtt gtaaatgaca tcaaggatcc ttttttcagtt | | | | 1080 |
| gttgaagaaa taaataaact atatggtgaa ggcacagcca ttccagattc ccatgatgtg | | | | 1140 |
| gtcaccgaag ctcctctcat tatccaaact gcaataagta agtttcagag agtagacatc | | | | 1200 |
| ttggtcaata cgctggtat tttgcgtgac aaatctttttt taaaaatgaa agatgaggaa | | | | 1260 |
| tggtttgctg tcctgaaagt ccaccttttt tccacatttt cattgtcaaa agcagtatgg | | | | 1320 |
| ccaatattta ccaaacaaaa gtctggattt attatcaata ctacttctac ctcaggaatt | | | | 1380 |
| tatggtaatt ttgacaggc caattatgcc gctgcaaaag ccgccatttt aggattcagt | | | | 1440 |
| aaaactattg cactggaagg tgccaagaga ggaattattg ttaatgttat cgctcctcat | | | | 1500 |
| gcagaaacgg ctatgacaaa gactatattc tcggagaagg aattatcaaa ccactttgat | | | | 1560 |
| gcatctcaag tctccccact tgttgttttg ttggcatctg aagaactaca aaagtattct | | | | 1620 |
| ggaagaaggg ttattggcca attattcgaa gttggcggtg gttggtgtgg caaaccaga | | | | 1680 |
| tggcaaagaa gttccggtta tgtttctatt aaagagacta ttgaaccgga gaaaattaaa | | | | 1740 |
| gaaaattgga accacatcac tgatttcagt cgcaacacta tcaacccgag ctccacagag | | | | 1800 |
| gagtcttcta tggcaaccct tgcaagccgt gcaaaaagcgc actcttcaaa ggagttggat | | | | 1860 |
| gatggattat tcaagtacac taccaaggat tgtatcttgt acaatttagg acttggatgc | | | | 1920 |
| acaagcaaag agcttaagta cacctacgag aatgatccag acttccaagt tttgcccacg | | | | 1980 |
| ttcgccgtca ttccatttat gcaagctact gccacactag ctatggacaa tttagtcgat | | | | 2040 |

-continued

```
aacttcaatt atgcaatgtt actgcatgga gaacaatatt ttaagctctg cacgccgaca    2100
atgccaagta atggaactct aaagacactt gctaaacctt acaagtact tgacaagaat     2160 ggtaaagccg ctttagttgt tggtggcttc gaaacttatg acattaaaac taagaaactc    2220
atagcttata acgaaggatc gttcttcatc aggggcgcac atgtacctcc agaaaaggaa    2280
gtgagggatg ggaaaagagc caagtttgct gtccaaaatt ttgaagtgcc acatggaaag    2340
gtaccagatt tgaggcgga gattctacg aataaagatc aagccgcatt gtacaggtta      2400
tctggcgatt tcaatccttt acatatcgat cccacgctag ccaaagcagt taaatttcct    2460
acgccaattc tgcatgggct ttgtacatta ggtattagtg cgaaagcatt gtttgaacat    2520
tatggtccat atgaggagtt gaaagtgaga tttaccaatg ttgttttccc aggtgatact    2580
ctaaaggtta aagcttggaa gcaaggctcg gttgtcgttt ttcaaacaat tgatacgacc    2640
agaaacgtca ttgtattgga taacgccgct gtaaaactat cgcaggcaaa atctaaacta    2700
taa                                                                  2703
```

<210> SEQ ID NO 41
<211> LENGTH: 312
<212> TYPE: PRT
<213> ORGANISM: Saccharomyces cerevisiae

<400> SEQUENCE: 41

```
Met Pro Ala Thr Leu His Asp Ser Thr Lys Ile Leu Ser Leu Asn Thr
 1               5                  10                  15

Gly Ala Gln Ile Pro Gln Ile Gly Leu Gly Thr Trp Gln Ser Lys Glu
                20                  25                  30

Asn Asp Ala Tyr Lys Ala Val Leu Thr Ala Leu Lys Asp Gly Tyr Arg
            35                  40                  45

His Ile Asp Thr Ala Ala Ile Tyr Arg Asn Glu Asp Gln Val Gly Gln
        50                  55                  60

Ala Ile Lys Asp Ser Gly Val Pro Arg Glu Glu Ile Phe Val Thr Thr
 65                  70                  75                  80

Lys Leu Trp Cys Thr Gln His Glu Pro Glu Val Ala Leu Asp Gln
                85                  90                  95

Ser Leu Lys Arg Leu Gly Leu Asp Tyr Val Asp Leu Tyr Leu Met His
               100                 105                 110

Trp Pro Ala Arg Leu Asp Pro Ala Tyr Ile Lys Asn Glu Asp Ile Leu
           115                 120                 125

Ser Val Pro Thr Lys Lys Asp Gly Ser Arg Ala Val Asp Ile Thr Asn
       130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Leu
                165                 170                 175

Lys Asp Leu Leu Ala Ser Gln Gly Asn Lys Leu Thr Pro Ala Ala Asn
            180                 185                 190

Gln Val Glu Ile His Pro Leu Leu Pro Gln Asp Glu Leu Ile Asn Phe
        195                 200                 205

Cys Lys Ser Lys Gly Ile Val Val Glu Ala Tyr Ser Pro Leu Gly Ser
    210                 215                 220

Thr Asp Ala Pro Leu Leu Lys Glu Pro Val Ile Leu Glu Ile Ala Lys
225                 230                 235                 240

Lys Asn Asn Val Gln Pro Gly His Val Val Ile Ser Trp His Val Gln
                245                 250                 255
```

Arg Gly Tyr Val Val Leu Pro Lys Ser Val Asn Pro Asp Arg Ile Lys
            260                 265                 270

Thr Asn Arg Lys Ile Phe Thr Leu Ser Thr Glu Asp Phe Glu Ala Ile
        275                 280                 285

Asn Asn Ile Ser Lys Glu Lys Gly Glu Lys Arg Val Val His Pro Asn
    290                 295                 300

Trp Ser Pro Phe Glu Val Phe Lys
305                 310

<210> SEQ ID NO 42
<211> LENGTH: 939
<212> TYPE: DNA
<213> ORGANISM: Saccharomyces cerevisiae

<400> SEQUENCE: 42
atgcctgcta ctttacatga ttctacgaaa atcctttctc taaatactgg agcccaaatc      60
cctcaaatag gtttaggtac gtggcagtcg aaagagaacg atgcttataa ggctgtttta     120
accgctttga agatggcta ccgacacatt gatactgctg ctatttaccg taatgaagac      180
caagtcggtc aagccatcaa ggattcaggt gttcctcggg aagaaatctt tgttactaca     240
aagttatggt gtacacaaca ccacgaacct gaagtagcgc tggatcaatc actaaagagg     300
ttaggattgg actacgtaga cttatatttg atgcattggc ctgccagatt agatccagcc     360
tacatcaaaa atgaagacat cttgagtgtg ccaacaaaga aggatggttc tcgtgcagtg     420
gatatcacca attggaattt catcaaaacc tgggaattaa tgcaggaact accaaagact     480
ggtaaaacta aggccgttgg agtctccaac ttttctataa ataacctgaa agatctatta     540
gcatctcaag gtaataagct tacgccagct gctaaccaag tcgaaataca tccattacta     600
cctcaagacg aattgattaa ttttttgtaaa agtaaaggca ttgtggttga agcttattct     660
ccgttaggta gtaccgatgc tccactattg aaggaaccgg ttatccttga aattgcgaag     720
aaaaataacg ttcaacccgg acacgttgtt attagctggc acgtccaaag aggttatgtt     780
gtcttgccaa aatctgtgaa tcccgatcga atcaaaacga acaggaaaat atttactttg     840
tctactgagg actttgaagc tatcaataac atatcgaagg aaaagggcga aaaaggggtt     900
gtacatccaa attggtctcc tttcgaagta ttcaagtaa                            939

<210> SEQ ID NO 43
<211> LENGTH: 350
<212> TYPE: PRT
<213> ORGANISM: Saccharomyces cerevisiae

<400> SEQUENCE: 43

Met Ser Lys Lys Pro Ile Val Leu Lys Leu Gly Lys Asp Ala Phe Gly
1               5                   10                  15

Asp Gln Ala Trp Gly Glu Leu Glu Lys Ile Ala Asp Val Ile Thr Ile
            20                  25                  30

Pro Glu Ser Thr Thr Arg Glu Gln Phe Leu Arg Glu Val Lys Asp Pro
        35                  40                  45

Gln Asn Lys Leu Ser Gln Val Gln Val Ile Thr Arg Thr Ala Arg Ser
    50                  55                  60

Val Lys Asn Thr Gly Arg Phe Asp Glu Glu Leu Ala Leu Ala Leu Pro
65                  70                  75                  80

Ser Ser Val Val Ala Val Cys His Thr Gly Ala Gly Tyr Asp Gln Ile
                85                  90                  95

-continued

```
Asp Val Glu Pro Phe Lys Lys Arg His Ile Gln Val Ala Asn Val Pro
            100                 105                 110
Asp Leu Val Ser Asn Ala Thr Ala Asp Thr His Val Phe Leu Leu Leu
        115                 120                 125
Gly Ala Leu Arg Asn Phe Gly Ile Gly Asn Arg Arg Leu Ile Glu Gly
    130                 135                 140
Asn Trp Pro Glu Ala Gly Pro Ala Cys Gly Ser Pro Phe Gly Tyr Asp
145                 150                 155                 160
Pro Glu Gly Lys Thr Val Gly Ile Leu Gly Leu Gly Arg Ile Gly Arg
                165                 170                 175
Cys Ile Leu Glu Arg Leu Lys Pro Phe Gly Phe Glu Asn Phe Ile Tyr
            180                 185                 190
His Asn Arg His Gln Leu Pro Ser Glu Glu Glu His Gly Cys Glu Tyr
        195                 200                 205
Val Gly Phe Glu Glu Phe Leu Lys Arg Ser Asp Ile Val Ser Val Asn
    210                 215                 220
Val Pro Leu Asn His Asn Thr His His Leu Ile Asn Ala Glu Thr Ile
225                 230                 235                 240
Glu Lys Met Lys Asp Gly Val Val Ile Val Asn Thr Ala Arg Gly Ala
                245                 250                 255
Val Ile Asp Glu Gln Ala Met Thr Asp Ala Leu Arg Ser Gly Lys Ile
            260                 265                 270
Arg Ser Ala Gly Leu Asp Val Phe Glu Tyr Glu Pro Lys Ile Ser Lys
        275                 280                 285
Glu Leu Leu Ser Met Ser Gln Val Leu Gly Leu Pro His Met Gly Thr
    290                 295                 300
His Ser Val Glu Thr Arg Lys Lys Met Glu Glu Leu Val Val Glu Asn
305                 310                 315                 320
Ala Lys Asn Val Ile Leu Thr Gly Lys Val Leu Thr Ile Val Pro Glu
                325                 330                 335
Leu Gln Asn Glu Asp Trp Pro Asn Glu Ser Lys Pro Leu Val
            340                 345                 350

<210> SEQ ID NO 44
<211> LENGTH: 1053
<212> TYPE: DNA
<213> ORGANISM: Saccharomyces cerevisiae

<400> SEQUENCE: 44
atgagtaaga aaccaattgt tttgaaatta ggaaaggatg cctttggtga ccaagcctgg      60
ggggaattgg aaaagattgc ggatgtaatt accatccctg aatccaccac tagagaacag     120
tttttgcggg aggtaaaaga cccacaaaat aagctctccc aagtacaagt cattactaga     180
acagcaagga gtgtgaaaaa caccggtaga tttgatgaag agcttgctct tgctttgccc     240
tcctccgtag tggctgtatg tcatactggt gctggttatg accaaattga tgttgagcca     300
ttcaagaaaa ggcacatcca ggttgccaat gttcctgatt tagttagcaa tgctaccgct     360
gatacgcatg tattttttgct attgggtgcc ctaagaaact tcggtattgg taacagaagg     420
ttgatcgagg gaaactggcc ggaggcagga cccgcatgtg gttctccctt ggatacgac      480 cctgaaggga aaacagttgg tatactgggt ctaggtagga ttggtcgttg tattttagag     540
agattgaagc cgtttgggtt cgagaatttc atatatcata acagacacca gcttccttcc     600
gaagaagagc atggttgtga atatgtagga ttcgaggagt ttttgaagcg ttctgatata     660
gtatctgtaa acgtcccact gaaccacaat actcaccatc taatcaatgc agagactatt     720
```

```
gaaaaaatga aagatggtgt agttattgtt aacacagcgc gtggtgccgt gatagacgaa    780
caagccatga ctgatgcttt gcgttctgga agattagaa gtgctggttt ggacgttttc    840
gaatatgagc caaaaatatc caagagtta ttatcgatgt cccaagtctt aggactgcct    900
catatgggca cacatagtgt agaaacaaga aagaaatgg aagaactggt cgttgaaaat    960
gcaaagaatg tgatattgac cgggaaagtc ttgactattg ttccggaatt acaaaatgaa   1020
gactggccca atgaatctaa gccattagtt tga                                1053

<210> SEQ ID NO 45
<211> LENGTH: 391
<212> TYPE: PRT
<213> ORGANISM: Saccharomyces cerevisiae

<400> SEQUENCE: 45
```

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

```
Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
        340                 345                 350

Thr Cys Gly Ser Val Glu Asp Phe Pro Leu Phe Glu Ala Val Tyr Gln
    355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 46
<211> LENGTH: 1176
<212> TYPE: DNA
<213> ORGANISM: Saccharomyces cerevisiae

<400> SEQUENCE: 46
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact     300 ctacccgaca atttggttgc taatccagac ttgattgatt cagtcaagga tgtcgacatc     360
atcgttttca acattccaca tcaattttg ccccgtatct gtagccaatt gaaaggtcat     420
gttgattcac acgtcagagc tatctcctgt ctaaagggtt tgaagttgg tgctaaaggt     480 gtccaattgc tatcctctta catcactgag gaactaggta ttcaatgtgg tgctctatct     540
ggtgctaaca ttgccaccga agtcgctcaa gaacactggc tgaaacaac agttgcttac     600 cacattccaa aggattcag aggcgagggc aaggacgtcg accataaggt tctaaaggcc     660
ttgttccaca gacctacttt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaaaga gtcggtttgg gtgagatcat cagattcggt     840
caaatgtttt tcccagaatc tagagaagaa acatactacc aagagtctgc tggtgttgct     900
gatttgatca ccacctgcgc tggtggtaga aacgtcaagg ttgctaggct aatggctact     960
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                               1176

<210> SEQ ID NO 47
<211> LENGTH: 799
<212> TYPE: PRT
<213> ORGANISM: Saccharomyces cerevisiae

<400> SEQUENCE: 47

Met Val Leu Pro Ile Leu Pro Leu Ile Asp Asp Leu Ala Ser Trp Asn
1               5                   10                  15

Ser Lys Lys Glu Tyr Val Ser Leu Val Gly Gln Val Leu Leu Asp Gly
            20                  25                  30
```

```
Ser Ser Leu Ser Asn Glu Glu Ile Leu Gln Phe Ser Lys Glu Glu Glu
        35                  40                  45

Val Pro Leu Val Ala Leu Ser Leu Pro Ser Gly Lys Phe Ser Asp Asp
 50                  55                  60

Glu Ile Ile Ala Phe Leu Asn Asn Gly Val Ser Ser Leu Phe Ile Ala
 65                  70                  75                  80

Ser Gln Asp Ala Lys Thr Ala Glu His Leu Val Glu Gln Leu Asn Val
                 85                  90                  95

Pro Lys Glu Arg Val Val Glu Glu Asn Gly Val Phe Ser Asn Gln
                 100                 105                 110

Phe Met Val Lys Gln Lys Phe Ser Gln Asp Lys Ile Val Ser Ile Lys
         115                 120                 125

Lys Leu Ser Lys Asp Met Leu Thr Lys Glu Val Leu Gly Glu Val Arg
         130                 135                 140

Thr Asp Arg Pro Asp Gly Leu Tyr Thr Thr Leu Val Val Asp Gln Tyr
145                 150                 155                 160

Glu Arg Cys Leu Gly Leu Val Tyr Ser Ser Lys Lys Ser Ile Ala Lys
                 165                 170                 175

Ala Ile Asp Leu Gly Arg Gly Val Tyr Tyr Ser Arg Ser Arg Asn Glu
             180                 185                 190

Ile Trp Ile Lys Gly Glu Thr Ser Gly Asn Gly Gln Lys Leu Leu Gln
             195                 200                 205

Ile Ser Thr Asp Cys Asp Ser Asp Ala Leu Lys Phe Ile Val Glu Gln
         210                 215                 220

Glu Asn Val Gly Phe Cys His Leu Glu Thr Met Ser Cys Phe Gly Glu
225                 230                 235                 240

Phe Lys His Gly Leu Val Gly Leu Glu Ser Leu Leu Lys Gln Arg Leu
                 245                 250                 255

Gln Asp Ala Pro Glu Glu Ser Tyr Thr Arg Arg Leu Phe Asn Asp Ser
             260                 265                 270

Ala Leu Leu Asp Ala Lys Ile Lys Glu Glu Ala Glu Leu Thr Glu
         275                 280                 285

Ala Lys Gly Lys Lys Glu Leu Ser Trp Glu Ala Ala Asp Leu Phe Tyr
290                 295                 300

Phe Ala Leu Ala Lys Leu Val Ala Asn Asp Val Ser Leu Lys Asp Val
305                 310                 315                 320

Glu Asn Asn Leu Asn Met Lys His Leu Lys Val Thr Arg Arg Lys Gly
                 325                 330                 335

Asp Ala Lys Pro Lys Phe Val Gly Gln Pro Lys Ala Glu Glu Lys
             340                 345                 350

Leu Thr Gly Pro Ile His Leu Asp Val Val Lys Ala Ser Asp Lys Val
         355                 360                 365

Gly Val Gln Lys Ala Leu Ser Arg Pro Ile Gln Lys Thr Ser Glu Ile
370                 375                 380

Met His Leu Val Asn Pro Ile Ile Glu Asn Val Arg Asp Lys Gly Asn
385                 390                 395                 400

Ser Ala Leu Leu Glu Tyr Thr Glu Lys Phe Asp Gly Val Lys Leu Ser
                 405                 410                 415

Asn Pro Val Leu Asn Ala Pro Phe Pro Glu Glu Tyr Phe Glu Gly Leu
             420                 425                 430

Thr Glu Glu Met Lys Glu Ala Leu Asp Leu Ser Ile Glu Asn Val Arg
         435                 440                 445
```

```
Lys Phe His Ala Ala Gln Leu Pro Thr Glu Thr Leu Glu Val Glu Thr
450                 455                 460

Gln Pro Gly Val Leu Cys Ser Arg Phe Pro Arg Pro Ile Glu Lys Val
465                 470                 475                 480

Gly Leu Tyr Ile Pro Gly Gly Thr Ala Ile Leu Pro Ser Thr Ala Leu
                485                 490                 495

Met Leu Gly Val Pro Ala Gln Val Ala Gln Cys Lys Glu Ile Val Phe
            500                 505                 510

Ala Ser Pro Pro Arg Lys Ser Asp Gly Lys Val Ser Pro Glu Val Val
            515                 520                 525

Tyr Val Ala Glu Lys Val Gly Ala Ser Lys Ile Val Leu Ala Gly Gly
530                 535                 540

Ala Gln Ala Val Ala Ala Met Ala Tyr Gly Thr Glu Thr Ile Pro Lys
545                 550                 555                 560

Val Asp Lys Ile Leu Gly Pro Gly Asn Gln Phe Val Thr Ala Ala Lys
                565                 570                 575

Met Tyr Val Gln Asn Asp Thr Gln Ala Leu Cys Ser Ile Asp Met Pro
            580                 585                 590

Ala Gly Pro Ser Glu Val Leu Val Ile Ala Asp Glu Asp Ala Asp Val
            595                 600                 605

Asp Phe Val Ala Ser Asp Leu Leu Ser Gln Ala Glu His Gly Ile Asp
610                 615                 620

Ser Gln Val Ile Leu Val Gly Val Asn Leu Ser Glu Lys Lys Ile Gln
625                 630                 635                 640

Glu Ile Gln Asp Ala Val His Asn Gln Ala Leu Gln Leu Pro Arg Val
                645                 650                 655

Asp Ile Val Arg Lys Cys Ile Ala His Ser Thr Ile Val Leu Cys Asp
            660                 665                 670

Gly Tyr Glu Glu Ala Leu Glu Met Ser Asn Gln Tyr Ala Pro Glu His
            675                 680                 685

Leu Ile Leu Gln Ile Ala Asn Ala Asn Asp Tyr Val Lys Leu Val Asp
690                 695                 700

Asn Ala Gly Ser Val Phe Val Gly Ala Tyr Thr Pro Glu Ser Cys Gly
705                 710                 715                 720

Asp Tyr Ser Ser Gly Thr Asn His Thr Leu Pro Thr Tyr Gly Tyr Ala
                725                 730                 735

Arg Gln Tyr Ser Gly Ala Asn Thr Ala Thr Phe Gln Lys Phe Ile Thr
            740                 745                 750

Ala Gln Asn Ile Thr Pro Glu Gly Leu Glu Asn Ile Gly Arg Ala Val
            755                 760                 765

Met Cys Val Ala Lys Lys Glu Gly Leu Asp Gly His Arg Asn Ala Val
770                 775                 780

Lys Ile Arg Met Ser Lys Leu Gly Leu Ile Pro Lys Asp Phe Gln
785                 790                 795

<210> SEQ ID NO 48
<211> LENGTH: 2400
<212> TYPE: DNA
<213> ORGANISM: Saccharomyces cerevisiae

<400> SEQUENCE: 48
atggttttgc cgattctacc gttaattgat gatctggcct catggaatag taagaaggaa      60
tacgtttcac ttgttggtca ggtacttttg gatggctcga gcctgagtaa tgaagagatt     120
ctccagttct ccaaagagga agaagttcca ttggtggctt tgtccttgcc aagtggtaaa     180
```

```
ttcagcgatg atgaaatcat tgccttcttg aacaacggag tttcttctct gttcattgct    240
agccaagatg ctaaaacagc cgaacacttg gttgaacaat tgaatgtacc aaaggagcgt    300
gttgttgtgg aagagaacgg tgttttctcc aatcaattca tggtaaaaca aaaattctcg    360
caagataaaa ttgtgtccat aaagaaatta agcaaggata tgttgaccaa agaagtgctt    420
ggtgaagtac gtacagaccg tcctgacggt ttatatacca ccctagttgt cgaccaatat    480
gagcgttgtc tagggttggt gtattcttcg aagaaatcta tagcaaaggc catcgatttg    540
ggtcgtggcg tttattattc tcgttctagg aatgaaatct ggatcaaggg tgaaacttct    600
ggcaatggcc aaaagctttt acaaatctct actgactgtg attcggatgc cttaaagttt    660
atcgttgaac aagaaaacgt tggattttgc cacttggaga ccatgtcttg ctttggtgaa    720
ttcaagcatg gtttggtggg ctagaatct ttactaaaac aaaggctaca ggacgctcca    780
gaggaatctt atactagaag actattcaac gactctgcat tgttagatgc caagatcaag    840
gaagaagctg aagaactgac tgaggcaaag ggtaagaagg agctttcttg ggaggctgcc    900
gatttgttct actttgcact ggccaaatta gtggccaacg atgtttcatt gaaggacgtc    960
gagaataatc tgaatatgaa gcatctgaag gttacaagac ggaaaggtga tgctaagcca   1020
aagtttgttg acaaccaaa ggctgaagaa gaaaaactga ccggtccaat tcacttggac   1080
gtggtgaagg cttccgacaa agttggtgtg cagaaggctt tgagcagacc aatccaaaag   1140
acttctgaaa ttatgcattt agtcaatccg atcatcgaaa atgttagaga caaaggtaac   1200
tctgcccttt tggagtacac agaaaagttt gatggtgtaa aattatccaa tcctgttctt   1260
aatgctccat tcccagaaga atactttgaa ggtttaaccg aggaaatgaa ggaagctttg   1320
gacctttcaa ttgaaaacgt ccgcaaattc catgctgctc aattgccaac agagactctt   1380
gaagttgaaa cccaacctgg tgtcttgtgt tccagattcc ctcgtcctat tgaaaaagtt   1440
ggtttgtata tccctggtgg cactgccatt ttaccaagta ctgcattaat gcttggtgtt   1500
ccagcacaag ttgcccaatg taaggagatt gtgtttgcat ctccaccaag aaaatctgat   1560
ggtaaagttt cacccgaagt tgtttatgtc gcagaaaaag ttggcgcttc aagattgtt   1620 ctagctggtg gtgcccaagc cgttgctgct atggcttacg gacagaaaac tattcctaaa   1680
gtggataaga tcttgggtcc aggtaatcaa tttgtgactg ccgccaaaat gtatgttcaa   1740
aatgacactc aagctctatg ttccattgat atgccagctg gcccaagtga agttttggtt   1800
attgccgatg aagatgccga tgtggatttt gttgcaagtg atttgctatc gcaagctgaa   1860
cacggtattg actcccaagt tatccttgtt ggtgttaact tgagcgaaaa gaaaattcaa   1920
gagattcaag atgctgtcca caatcaagct ttacaactgc cacgtgtgga tattgttcgt   1980
aaatgtattg ctcacagtac gatcgttctt tgtgacggtt acgaagaagc ccttgaaatg   2040
tccaaccaat atgcaccaga acatttgatt ctacaaatcg ccaatgctaa cgattatgtt   2100
aaattggttg acaatgcagg gtccgtattt gtgggtgctt acactccaga atcgtgcggt   2160
gactattcaa gtggtactaa ccatacatta ccaacctatg gttacgctag gcagtacagt   2220
ggtgccaaca ctgcaacctt ccaaaagttt atcactgccc aaaacattac ccctgaaggt   2280
ttagaaaaca tcggtagagc tgttatgtgc gttgccaaga aggagggtct agacggtcac   2340
agaaacgctg tgaaaatcag aatgagtaag cttgggttga tcccaaagga tttccagtag   2400
```

<210> SEQ ID NO 49
<211> LENGTH: 1054
<212> TYPE: PRT

<213> ORGANISM: Saccharomyces cerevisiae

<400> SEQUENCE: 49

```
Met Pro Pro Leu Phe Lys Gly Leu Lys Gln Met Ala Lys Pro Ile Ala
1               5                   10                  15
Tyr Val Ser Arg Phe Ser Ala Lys Arg Pro Ile His Ile Ile Leu Phe
            20                  25                  30
Ser Leu Ile Ile Ser Ala Phe Ala Tyr Leu Ser Val Ile Gln Tyr Tyr
        35                  40                  45
Phe Asn Gly Trp Gln Leu Asp Ser Asn Ser Val Phe Glu Thr Ala Pro
    50                  55                  60
Asn Lys Asp Ser Asn Thr Leu Phe Gln Glu Cys Ser His Tyr Tyr Arg
65                  70                  75                  80
Asp Ser Ser Leu Asp Gly Trp Val Ser Ile Thr Ala His Glu Ala Ser
                85                  90                  95
Glu Leu Pro Ala Pro His His Tyr Tyr Leu Leu Asn Leu Asn Phe Asn
            100                 105                 110
Ser Pro Asn Glu Thr Asp Ser Ile Pro Glu Leu Ala Asn Thr Val Phe
        115                 120                 125
Glu Lys Asp Asn Thr Lys Tyr Ile Leu Gln Asp Leu Ser Val Ser
    130                 135                 140
Lys Glu Ile Ser Ser Thr Asp Gly Thr Lys Trp Arg Leu Arg Ser Asp
145                 150                 155                 160
Arg Lys Ser Leu Phe Asp Val Lys Thr Leu Ala Tyr Ser Leu Tyr Asp
                165                 170                 175
Val Phe Ser Glu Asn Val Thr Gln Ala Asp Pro Phe Asp Val Leu Ile
            180                 185                 190
Met Val Thr Ala Tyr Leu Met Met Phe Tyr Thr Ile Phe Gly Leu Phe
        195                 200                 205
Asn Asp Met Arg Lys Thr Gly Ser Asn Phe Trp Leu Ser Ala Ser Thr
    210                 215                 220
Val Val Asn Ser Ala Ser Ser Leu Phe Leu Ala Leu Tyr Val Thr Gln
225                 230                 235                 240
Cys Ile Leu Gly Lys Glu Val Ser Ala Leu Thr Leu Phe Glu Gly Leu
                245                 250                 255
Pro Phe Ile Val Val Val Gly Phe Lys His Lys Ile Lys Ile Ala
            260                 265                 270
Gln Tyr Ala Leu Glu Lys Phe Glu Arg Val Gly Leu Ser Lys Arg Ile
        275                 280                 285
Thr Thr Asp Glu Ile Val Phe Glu Ser Val Ser Glu Glu Gly Gly Arg
    290                 295                 300
Leu Ile Gln Asp His Leu Leu Cys Ile Phe Ala Phe Ile Gly Cys Ser
305                 310                 315                 320
Met Tyr Ala His Gln Leu Lys Thr Leu Thr Asn Phe Cys Ile Leu Ser
                325                 330                 335
Ala Phe Ile Leu Ile Phe Glu Leu Ile Leu Thr Pro Thr Phe Tyr Ser
            340                 345                 350
Ala Ile Leu Ala Leu Arg Leu Glu Met Asn Val Ile His Arg Ser Thr
        355                 360                 365
Ile Ile Lys Gln Thr Leu Glu Glu Asp Gly Val Val Pro Ser Thr Ala
    370                 375                 380
Arg Ile Ile Ser Lys Ala Glu Lys Lys Ser Val Ser Ser Phe Leu Asn
385                 390                 395                 400
```

-continued

```
Leu Ser Val Val Val Ile Ile Met Lys Leu Ser Val Ile Leu Leu Phe
                405                 410                 415
Val Phe Ile Asn Phe Tyr Asn Phe Gly Ala Asn Trp Val Asn Asp Ala
            420                 425                 430
Phe Asn Ser Leu Tyr Phe Asp Lys Glu Arg Val Ser Leu Pro Asp Phe
        435                 440                 445
Ile Thr Ser Asn Ala Ser Glu Asn Phe Lys Glu Gln Ala Ile Val Ser
    450                 455                 460
Val Thr Pro Leu Leu Tyr Tyr Lys Pro Ile Lys Ser Tyr Gln Arg Ile
465                 470                 475                 480
Glu Asp Met Val Leu Leu Leu Arg Asn Val Ser Val Ala Ile Arg
                485                 490                 495
Asp Arg Phe Val Ser Lys Leu Val Leu Ser Ala Leu Val Cys Ser Ala
            500                 505                 510
Val Ile Asn Val Tyr Leu Leu Asn Ala Ala Arg Ile His Thr Ser Tyr
        515                 520                 525
Thr Ala Asp Gln Leu Val Lys Thr Glu Val Thr Lys Lys Ser Phe Thr
    530                 535                 540
Ala Pro Val Gln Lys Ala Ser Thr Pro Val Leu Thr Asn Lys Thr Val
545                 550                 555                 560
Ile Ser Gly Ser Lys Val Lys Ser Leu Ser Ser Ala Gln Ser Ser Ser
                565                 570                 575
Ser Gly Pro Ser Ser Ser Ser Glu Glu Asp Asp Ser Arg Asp Ile Glu
            580                 585                 590
Ser Leu Asp Lys Lys Ile Arg Pro Leu Glu Glu Leu Glu Ala Leu Leu
        595                 600                 605
Ser Ser Gly Asn Thr Lys Gln Leu Lys Asn Lys Glu Val Ala Ala Leu
    610                 615                 620
Val Ile His Gly Lys Leu Pro Leu Tyr Ala Leu Glu Lys Lys Leu Gly
625                 630                 635                 640
Asp Thr Thr Arg Ala Val Ala Val Arg Arg Lys Ala Leu Ser Ile Leu
                645                 650                 655
Ala Glu Ala Pro Val Leu Ala Ser Asp Arg Leu Pro Tyr Lys Asn Tyr
            660                 665                 670
Asp Tyr Asp Arg Val Phe Gly Ala Cys Cys Glu Asn Val Ile Gly Tyr
        675                 680                 685
Met Pro Leu Pro Val Gly Val Ile Gly Pro Leu Val Ile Asp Gly Thr
    690                 695                 700
Ser Tyr His Ile Pro Met Ala Thr Thr Glu Gly Cys Leu Val Ala Ser
705                 710                 715                 720
Ala Met Arg Gly Cys Lys Ala Ile Asn Ala Gly Gly Gly Ala Thr Thr
                725                 730                 735
Val Leu Thr Lys Asp Gly Met Thr Arg Gly Pro Val Val Arg Phe Pro
            740                 745                 750
Thr Leu Lys Arg Ser Gly Ala Cys Lys Ile Trp Leu Asp Ser Glu Glu
        755                 760                 765
Gly Gln Asn Ala Ile Lys Lys Ala Phe Asn Ser Thr Ser Arg Phe Ala
    770                 775                 780
Arg Leu Gln His Ile Gln Thr Cys Leu Ala Gly Asp Leu Leu Phe Met
785                 790                 795                 800
Arg Phe Arg Thr Thr Thr Gly Asp Ala Met Gly Met Asn Met Ile Ser
                805                 810                 815
```

Lys Gly Val Glu Tyr Ser Leu Lys Gln Met Val Glu Tyr Gly Trp
                820                 825                 830

Glu Asp Met Glu Val Val Ser Val Ser Gly Asn Tyr Cys Thr Asp Lys
            835                 840                 845

Lys Pro Ala Ala Ile Asn Trp Ile Glu Gly Arg Gly Lys Ser Val Val
        850                 855                 860

Ala Glu Ala Thr Ile Pro Gly Asp Val Val Arg Lys Val Leu Lys Ser
865                 870                 875                 880

Asp Val Ser Ala Leu Val Glu Leu Asn Ile Ala Lys Asn Leu Val Gly
                885                 890                 895

Ser Ala Met Ala Gly Ser Val Gly Gly Phe Asn Ala His Ala Ala Asn
            900                 905                 910

Leu Val Thr Ala Val Phe Leu Ala Leu Gly Gln Asp Pro Ala Gln Asn
        915                 920                 925

Val Glu Ser Ser Asn Cys Ile Thr Leu Met Lys Glu Val Asp Gly Asp
        930                 935                 940

Leu Arg Ile Ser Val Ser Met Pro Ser Ile Glu Val Gly Thr Ile Gly
945                 950                 955                 960

Gly Gly Thr Val Leu Glu Pro Gln Gly Ala Met Leu Asp Leu Leu Gly
                965                 970                 975

Val Arg Gly Pro His Ala Thr Ala Pro Gly Thr Asn Ala Arg Gln Leu
            980                 985                 990

Ala Arg Ile Val Ala Cys Ala Val Leu Ala Gly Glu Leu Ser Leu Cys
        995                 1000                1005

Ala Ala Leu Ala Ala Gly His Leu Val Gln Ser His Met Thr His
        1010                1015                1020

Asn Arg Lys Pro Ala Glu Pro Thr Lys Pro Asn Asn Leu Asp Ala
        1025                1030                1035

Thr Asp Ile Asn Arg Leu Lys Asp Gly Ser Val Thr Cys Ile Lys
        1040                1045                1050

Ser

<210> SEQ ID NO 50
<211> LENGTH: 3165
<212> TYPE: DNA
<213> ORGANISM: Saccharomyces cerevisiae

<400> SEQUENCE: 50

```
atgccgccgc tattcaaggg actgaaacag atggcaaagc caattgccta tgtttcaaga      60
ttttcggcga acgaccaat tcatataata cttttttctc taatcatatc cgcattcgct     120
tatctatccg tcattcagta ttacttcaat ggttggcaac tagattcaaa tagtgttttt     180
gaaactgctc caaataaaga ctccaacact ctatttcaag aatgttccca ttactacaga     240
gattcctctc tagatggttg ggtatcaatc accgcgcatg aagctagtga gttaccagcc     300
ccacaccatt actatctatt aaacctgaac ttcaatagtc ctaatgaaac tgactccatt     360
ccagaactag ctaacacggt ttttgagaaa gataatacaa aatatattct gcaagaagat     420
ctcagtgttt ccaaagaaat tcttctact gatggaacga atggaggtt aagaagtgac     480
agaaaaagtc ttttcgacgt aaagacgtta gcatattctc tctacgatgt atttcagaa     540
aatgtaaccc aagcagaccc gtttgacgtc cttattatgg ttactgccta cctaatgatg     600
ttctacacca tattcggcct cttcaatgac atgaggaaga ccgggtcaaa ttttggttg     660
agcgcctcta cagtggtcaa ttctgcatca tcactttct tagcattgta tgtcacccaa     720
```

```
tgtattctag gcaaagaagt ttccgcatta actcttttg aaggtttgcc tttcattgta    780
gttgttgttg gtttcaagca caaaatcaag attgcccagt atgccctgga gaaatttgaa    840
agagtcggtt tatctaaaag gattactacc gatgaaatcg tttttgaatc cgtgagcgaa    900
gagggtggtc gtttgattca agaccatttg cttttgtattt ttgcctttat cggatgctct    960
atgtatgctc accaattgaa gactttgaca aacttctgca tattatcagc atttatccta   1020
attttgaat tgattttaac tcctacattt tattctgcta tcttagcgct tagactggaa   1080
atgaatgtta tccacagatc tactattatc aagcaaacat tagaagaaga cggtgttgtt   1140
ccatctacag caagaatcat ttctaaagca gaaagaaat ccgtatcttc tttcttaaat   1200
ctcagtgtgg ttgtcattat catgaaactc tctgtcatac tgttgtttgt cttcatcaac   1260
ttttataact ttggtgcaaa ttgggtcaat gatgccttca attcattgta cttcgataag   1320
gaacgtgttt ctctaccaga ttttattacc tcgaatgcct ctgaaaactt taaagagcaa   1380
gctattgtta gtgtcacccc attattatat tacaaaccca ttaagtccta ccaacgcatt   1440
gaggatatgg ttcttctatt gcttcgtaat gtcagtgttg ccattcgtga taggttcgtc   1500
agtaaattag ttcttttccgc cttagtatgc agtgctgtca tcaatgtgta tttattgaat   1560
gctgctagaa ttcataccag ttatactgca gaccaattgg tgaaaactga agtcaccaag   1620
aagtctttta ctgctcctgt acaaaaggct tctacaccag ttttaaccaa taaaacagtc   1680
atttctggat cgaaagtcaa aagtttatca tctgcgcaat cgagctcatc aggaccttca   1740
tcatctagtg aggaagatga ttcccgcgat attgaaagct ggataagaa atacgtcct   1800
ttagaagaat tagaagcatt attaagtagt ggaaatacaa acaattgaa gaacaaagag   1860
gtcgctgcct tggttattca cggtaagtta ccttttgtacg ctttggagaa aaaattaggt   1920
gatactacga gagcggttgc ggtacgtagg aaggctcttt caattttggc agaagctcct   1980
gtattagcat ctgatcgttt accatataaa aattatgact acgaccgcgt atttggcgct   2040
tgttgtgaaa atgttatagg ttacatgcct ttgcccgttg gtgttatagg ccccttggtt   2100
atcgatggta catcttatca tataccaatg gcaactacag agggttgttt ggtagcttct   2160
gccatgcgtg gctgtaaggc aatcaatgct ggcggtggtg caacaactgt tttaactaag   2220
gatggtatga caagaggccc agtagtccgt ttcccaactt tgaaagatc tggtgcctgt   2280
aagatatggt tagactcaga agagggacaa aacgcaatta aaaaagcttt taactctaca   2340
tcaagatttg cacgtctgca acatattcaa acttgtctag caggagattt actcttcatg   2400
agatttagaa caactactgg tgacgcaatg ggtatgaata tgatttctaa aggtgtcgaa   2460
tactcattaa agcaaatggt agaagagtat ggctgggaag atatggaggt tgtctccgtt   2520
tctggtaact actgtaccga caaaaaacca gctgccatca actggatcga aggtcgtggt   2580
aagagtgtcg tcgcagaagc tactattcct ggtgatgttg tcagaaaagt gttaaaaagt   2640
gatgtttccg cattggttga gttgaacatt gctaagaatt tggttggatc tgcaatggct   2700
gggtctgttg gtggatttaa cgcacatgca gctaatttag tgacagctgt tttcttggca   2760
ttaggacaag atcctgcaca aaatgttgaa agttccaact gtataacatt gatgaaagaa   2820
gtggacggtg atttgagaat ttccgtatcc atgccatcca tcgaagtagg taccatcggt   2880
ggtggtactg ttctagaacc acaaggtgcc atgttggact tattaggtgt aagaggcccg   2940
catgctaccg ctcctggtac caacgcacgt caattagcaa gaatagttgc ctgtgccgtc   3000
ttggcaggtg aattatcctt atgtgctgcc ctagcagccg gccatttggt tcaaagtcat   3060
```

-continued

```
atgacccaca acaggaaacc tgctgaacca acaaaaccta acaatttgga cgccactgat      3120
ataaatcgtt tgaaagatgg gtccgtcacc tgcattaaat cctaa                     3165
```

<210> SEQ ID NO 51
<211> LENGTH: 428
<212> TYPE: PRT
<213> ORGANISM: Saccharomyces cerevisiae

<400> SEQUENCE: 51

Met Ser Met Leu Ser Arg Arg Leu Phe Ser Thr Ser Arg Leu Ala Ala
1               5                   10                  15

Phe Ser Lys Ile Lys Val Lys Gln Pro Val Val Glu Leu Asp Gly Asp
                20                  25                  30

Glu Met Thr Arg Ile Ile Trp Asp Lys Ile Lys Lys Lys Leu Ile Leu
            35                  40                  45

Pro Tyr Leu Asp Val Asp Leu Lys Tyr Tyr Asp Leu Ser Val Glu Ser
        50                  55                  60

Arg Asp Ala Thr Ser Asp Lys Ile Thr Gln Asp Ala Ala Glu Ala Ile
65                  70                  75                  80

Lys Lys Tyr Gly Val Gly Ile Lys Cys Ala Thr Ile Thr Pro Asp Glu
                85                  90                  95

Ala Arg Val Lys Glu Phe Asn Leu His Lys Met Trp Lys Ser Pro Asn
            100                 105                 110

Gly Thr Ile Arg Asn Ile Leu Gly Gly Thr Val Phe Arg Glu Pro Ile
        115                 120                 125

Val Ile Pro Arg Ile Pro Arg Leu Val Pro Arg Trp Glu Lys Pro Ile
130                 135                 140

Ile Ile Gly Arg His Ala His Gly Asp Gln Tyr Lys Ala Thr Asp Thr
145                 150                 155                 160

Leu Ile Pro Gly Pro Gly Ser Leu Glu Leu Val Tyr Lys Pro Ser Asp
                165                 170                 175

Pro Thr Thr Ala Gln Pro Gln Thr Leu Lys Val Tyr Asp Tyr Lys Gly
            180                 185                 190

Ser Gly Val Ala Met Ala Met Tyr Asn Thr Asp Glu Ser Ile Glu Gly
        195                 200                 205

Phe Ala His Ser Ser Phe Lys Leu Ala Ile Asp Lys Lys Leu Asn Leu
210                 215                 220

Phe Leu Ser Thr Lys Asn Thr Ile Leu Lys Lys Tyr Asp Gly Arg Phe
225                 230                 235                 240

Lys Asp Ile Phe Gln Glu Val Tyr Glu Ala Gln Tyr Lys Ser Lys Phe
                245                 250                 255

Glu Gln Leu Gly Ile His Tyr Glu His Arg Leu Ile Asp Asp Met Val
            260                 265                 270

Ala Gln Met Ile Lys Ser Lys Gly Gly Phe Ile Met Ala Leu Lys Asn
        275                 280                 285

Tyr Asp Gly Asp Val Gln Ser Asp Ile Val Ala Gln Gly Phe Gly Ser
290                 295                 300

Leu Gly Leu Met Thr Ser Ile Leu Val Thr Pro Asp Gly Lys Thr Phe
305                 310                 315                 320

Glu Ser Glu Ala Ala His Gly Thr Val Thr Arg His Tyr Arg Lys Tyr
                325                 330                 335

Gln Lys Gly Glu Glu Thr Ser Thr Asn Ser Ile Ala Ser Ile Phe Ala
            340                 345                 350

Trp Ser Arg Gly Leu Leu Lys Arg Gly Glu Leu Asp Asn Thr Pro Ala
            355                 360                 365

Leu Cys Lys Phe Ala Asn Ile Leu Glu Ser Ala Thr Leu Asn Thr Val
    370                 375                 380

Gln Gln Asp Gly Ile Met Thr Lys Asp Leu Ala Leu Ala Cys Gly Asn
385                 390                 395                 400

Asn Glu Arg Ser Ala Tyr Val Thr Thr Glu Glu Phe Leu Asp Ala Val
            405                 410                 415

Glu Lys Arg Leu Gln Lys Glu Ile Lys Ser Ile Glu
            420                 425

<210> SEQ ID NO 52
<211> LENGTH: 1287
<212> TYPE: DNA
<213> ORGANISM: Saccharomyces cerevisiae

<400> SEQUENCE: 52
atgagtatgt tatctagaag attattttcc acctctcgcc ttgctgcttt cagtaagatt      60
aaggtcaaac aacccgttgt cgagttggac ggtgatgaaa tgacccgtat catttgggat     120
aagatcaaga gaaaattgat tctaccctac ttggacgtag atttgaagta ctacgactta     180
tctgtcgaat ctcgtgacgc cacctccgac aagattactc aggatgctgc tgaggcgatc     240
aagaagtatg tgttggtat caatgtgcc accatcactc tgatgaagc tcgtgtgaag       300 gaattcaacc tgcacaagat gtggaaatct cctaatggta ccatcagaaa cattctcggc     360
ggtacagtgt tcagagagcc cattgtgatt cctagaattc ctagactggt cccacgttgg     420
gaaaaaccaa tcattattgg aagacacgcc acggtgatc aatataaagc tacggacaca      480
ctgatcccag gcccaggatc tttggaactg gtctacaagc catccgaccc tacgactgct     540
caaccacaaa ctttgaaagt gtatgactac aagggcagtg gtgtggccat ggccatgtac     600
aatactgacg aatccatcga agggtttgct cattcgtctt tcaagctggc cattgacaaa     660
aagctaaatc ttttcttgtc aaccaagaac actattttga agaaatatga cggtcggttc     720
aaagacattt tccaagaagt ttatgaagct caatataaat ccaaattcga caactaggg     780 atccactatg aacaccgttt aattgatgat atggtcgctc aaatgataaa atctaaaggt     840
ggctttatca tggcgctaaa gaactatgac ggtgatgtcc aatctgacat cgtcgctcaa     900
ggatttggct cctaggtttt gatgacttct atcttagtta caccagacgg taaaactttc     960
gaaagtgaag ctgctcatgg taccgtgaca agacattata gaaagtacca aaagggtgaa    1020
gaaacttcta caaactccat tgcatccatt ttcgcgtggt cgagaggtct attgaagaga    1080
ggtgaattgg acaatactcc tgctttgtgt aaatttgcca atattttgga atccgccact    1140
ttgaacacag ttcagcaaga cggtatcatg acgaaggact ggctttggc ttgcggtaac     1200 aacgaaagat ctgcttatgt taccacagaa gaattttgg atgccgttga aaaagacta     1260 caaaaagaaa tcaagtcgat cgagtaa                                        1287

<210> SEQ ID NO 53
<211> LENGTH: 371
<212> TYPE: PRT
<213> ORGANISM: Saccharomyces cerevisiae

<400> SEQUENCE: 53

Met Phe Arg Ser Val Ala Thr Arg Leu Ser Ala Cys Arg Gly Leu Ala
1               5                   10                  15

-continued

```
Ser Asn Ala Ala Arg Lys Ser Leu Thr Ile Gly Leu Ile Pro Gly Asp
             20                  25                  30

Gly Ile Gly Lys Glu Val Ile Pro Ala Gly Lys Gln Val Leu Glu Asn
         35                  40                  45

Leu Asn Ser Lys His Gly Leu Ser Phe Asn Phe Ile Asp Leu Tyr Ala
 50                  55                  60

Gly Phe Gln Thr Phe Gln Glu Thr Gly Lys Ala Leu Pro Asp Glu Thr
 65                  70                  75                  80

Val Lys Val Leu Lys Glu Gln Cys Gln Gly Ala Leu Phe Gly Ala Val
                 85                  90                  95

Gln Ser Pro Thr Thr Lys Val Glu Gly Tyr Ser Ser Pro Ile Val Ala
                100                 105                 110

Leu Arg Arg Glu Met Gly Leu Phe Ala Asn Val Arg Pro Val Lys Ser
            115                 120                 125

Val Glu Gly Glu Lys Gly Lys Pro Ile Asp Met Val Ile Val Arg Glu
        130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175

Ala Thr Arg Arg Ile Ala Thr Ile Ala Leu Asp Ile Ala Leu Lys Arg
            180                 185                 190

Leu Gln Thr Arg Gly Gln Ala Thr Leu Thr Val Thr His Lys Ser Asn
        195                 200                 205

Val Leu Ser Gln Ser Asp Gly Leu Phe Arg Glu Ile Cys Lys Glu Val
    210                 215                 220

Tyr Glu Ser Asn Lys Asp Lys Tyr Gly Gln Ile Lys Tyr Asn Glu Gln
225                 230                 235                 240

Ile Val Asp Ser Met Val Tyr Arg Leu Phe Arg Glu Pro Gln Cys Phe
                245                 250                 255

Asp Val Ile Val Ala Pro Asn Leu Tyr Gly Asp Ile Leu Ser Asp Gly
            260                 265                 270

Ala Ala Ala Leu Val Gly Ser Leu Gly Val Val Pro Ser Ala Asn Val
        275                 280                 285

Gly Pro Glu Ile Val Ile Gly Glu Pro Cys His Gly Ser Ala Pro Asp
    290                 295                 300

Ile Ala Gly Lys Gly Ile Ala Asn Pro Ile Ala Thr Ile Arg Ser Thr
305                 310                 315                 320

Ala Leu Met Leu Glu Phe Leu Gly His Asn Glu Ala Ala Gln Asp Ile
                325                 330                 335

Tyr Lys Ala Val Asp Ala Asn Leu Arg Glu Gly Ser Ile Lys Thr Pro
            340                 345                 350

Asp Leu Gly Gly Lys Ala Ser Thr Gln Gln Val Val Asp Asp Val Leu
        355                 360                 365

Ser Arg Leu
    370

<210> SEQ ID NO 54
<211> LENGTH: 1116
<212> TYPE: DNA
<213> ORGANISM: Saccharomyces cerevisiae
```

```
<400> SEQUENCE: 54
atgtttagat ctgttgctac tagattatct gcctgccgtg ggttagcatc taacgctgct      60
cgcaaatcac tcactattgg tcttatcccc ggtgacggta tcggtaagga agtcattcct     120
gctggtaagc aagttttgga aaaccttaac tccaagcacg gcctaagctt caactttatt     180
gatctctacg ccggtttcca acattccaa gaaacaggaa aggcgttgcc tgatgagact     240
gttaaagtgt tgaaggaaca atgtcaaggt gctcttttcg gtgcagttca gtctccaact     300
actaaggtgg aaggttactc ctcaccaatt gttgctctaa ggagggaaat gggccttttc     360
gctaatgttc gtcctgttaa gtctgtagag ggagaaaagg gtaaaccaat tgacatggtt     420
atcgtcagag aaaatactga ggacctgtac attaaaattg aaaaaacata cattgacaag     480
gccacaggta caagagttgc tgatgccaca aagagaatat ccgaaattgc aacaagaaga     540
attgcaacca ttgcattaga tattgccttg aaaagattac aacaagagg ccaagccact      600
ttgacagtga ctcataaatc aaatgttcta tctcaaagtg atggtctatt cagagaaatc     660
tgtaaggaag tctacgaatc taacaaggac aagtacggtc aaatcaaata taacgaacaa     720
attgtggatt ccatggttta taggctgttc agagaaccac aatgttttga tgtgatagtg     780
gcaccaaacc tatacgggga tatattatct gacggtgctg ctgctttagt cggttcatta     840
ggtgttgttc aagcgccaa cgtaggtcca gaaattgtca ttggtgaacc atgccatggt     900
tctgcaccag atattgctgg taaaggtatt gctaacccaa tcgccactat aagatctact     960
gctttgatgt tggaattctt gggccacaac gaagctgccc aagatatcta caaggctgtt    1020
gatgctaact aagagaggg ttctatcaag acaccagatt taggtggtaa ggcttctact     1080
caacaagtcg ttgacgacgt tttgtcgaga ttatag                               1116

<210> SEQ ID NO 55
<211> LENGTH: 469
<212> TYPE: PRT
<213> ORGANISM: Saccharomyces cerevisiae

<400> SEQUENCE: 55

Met Ser Tyr Ser Ala Ala Asp Asn Leu Gln Asp Ser Phe Gln Arg Ala
1               5                   10                  15

Met Asn Phe Ser Gly Ser Pro Gly Ala Val Ser Thr Ser Pro Thr Gln
            20                  25                  30

Ser Phe Met Asn Thr Leu Pro Arg Arg Val Ser Ile Thr Lys Gln Pro
        35                  40                  45

Lys Ala Leu Lys Pro Phe Ser Thr Gly Asp Met Asn Ile Leu Leu Leu
    50                  55                  60

Glu Asn Val Asn Ala Thr Ala Ile Lys Ile Phe Lys Asp Gln Gly Tyr
65                  70                  75                  80

Gln Val Glu Phe His Lys Ser Ser Leu Pro Glu Asp Glu Leu Ile Glu
                85                  90                  95

Lys Ile Lys Asp Val His Ala Ile Gly Ile Arg Ser Lys Thr Arg Leu
            100                 105                 110

Thr Glu Lys Ile Leu Gln His Ala Arg Asn Leu Val Cys Ile Gly Cys
        115                 120                 125

Phe Cys Ile Gly Thr Asn Gln Val Asp Leu Lys Tyr Ala Ala Ser Lys
    130                 135                 140

Gly Ile Ala Val Phe Asn Ser Pro Phe Ser Asn Ser Arg Ser Val Ala
145                 150                 155                 160
```

Glu Leu Val Ile Gly Glu Ile Ile Ser Leu Ala Arg Gln Leu Gly Asp
            165                 170                 175

Arg Ser Ile Glu Leu His Thr Gly Thr Trp Asn Lys Val Ala Ala Arg
        180                 185                 190

Cys Trp Glu Val Arg Gly Lys Thr Leu Gly Ile Ile Gly Tyr Gly His
        195                 200                 205

Ile Gly Ser Gln Leu Ser Val Leu Ala Glu Ala Met Gly Leu His Val
    210                 215                 220

Leu Tyr Tyr Asp Ile Val Thr Ile Met Ala Leu Gly Thr Ala Arg Gln
225                 230                 235                 240

Val Ser Thr Leu Asp Glu Leu Leu Asn Lys Ser Asp Phe Val Thr Leu
                245                 250                 255

His Val Pro Ala Thr Pro Glu Thr Glu Lys Met Leu Ser Ala Pro Gln
            260                 265                 270

Phe Ala Ala Met Lys Asp Gly Ala Tyr Val Ile Asn Ala Ser Arg Gly
        275                 280                 285

Thr Val Val Asp Ile Pro Ser Leu Ile Gln Ala Val Lys Ala Asn Lys
    290                 295                 300

Ile Ala Gly Ala Ala Leu Asp Val Tyr Pro His Glu Pro Ala Lys Asn
305                 310                 315                 320

Gly Glu Gly Ser Phe Asn Asp Glu Leu Asn Ser Trp Thr Ser Glu Leu
                325                 330                 335

Val Ser Leu Pro Asn Ile Ile Leu Thr Pro His Ile Gly Gly Ser Thr
            340                 345                 350

Glu Glu Ala Gln Ser Ser Ile Gly Ile Glu Val Ala Thr Ala Leu Ser
        355                 360                 365

Lys Tyr Ile Asn Glu Gly Asn Ser Val Gly Ser Val Asn Phe Pro Glu
    370                 375                 380

Val Ser Leu Lys Ser Leu Asp Tyr Asp Gln Glu Asn Thr Val Arg Val
385                 390                 395                 400

Leu Tyr Ile His Arg Asn Val Pro Gly Val Leu Lys Thr Val Asn Asp
                405                 410                 415

Ile Leu Ser Asp His Asn Ile Glu Lys Gln Phe Ser Asp Ser His Gly
            420                 425                 430

Glu Ile Ala Tyr Leu Met Ala Asp Ile Ser Ser Val Asn Gln Ser Glu
        435                 440                 445

Ile Lys Asp Ile Tyr Glu Lys Leu Asn Gln Thr Ser Ala Lys Val Ser
    450                 455                 460

Ile Arg Leu Leu Tyr
465

<210> SEQ ID NO 56
<211> LENGTH: 1410
<212> TYPE: DNA
<213> ORGANISM: Saccharomyces cerevisiae

<400> SEQUENCE: 56
atgtcttatt cagctgccga taatttacaa gattcattcc aacgtgccat gaacttttct      60
ggctctcctg gtgcagtctc aacctcacca actcagtcat ttatgaacac actacctcgt    120
cgtgtaagca ttacaaagca accaaaggct ttaaaacctt tttctactgg tgacatgaat    180
attctactgt tggaaaatgt caatgcaact gcaatcaaaa tcttcaagga tcagggttac    240
caagtagagt tccacaagtc ttctctacct gaggatgaat tgattgaaaa atcaaagac     300 gtacacgcta tcggtataag atccaaaact agattgactg aaaaaatact acagcatgcc    360

-continued

```
aggaatctag tttgtattgg ttgtttttgc ataggtacca atcaagtaga cctaaaatat    420
gccgctagta aaggtattgc tgttttcaat tcgccattct ccaattcaag atccgtagca    480
gaattggtaa ttggtgagat cattagttta gcaagacaat taggtgatag atccattgaa    540
ctgcatacag gtacatggaa taaagtcgct gctaggtgtt gggaagtaag aggaaaaact    600
ctcggtatta ttgggtatgg tcacattggt tcgcaattat cagttcttgc agaagctatg    660
ggcctgcatg tgctatacta tgatatcgtg acaattatgg ccttaggtac tgccagacaa    720
gtttctacat tagatgaatt gttgaataaa tctgattttg taacactaca tgtaccagct    780
actccagaaa ctgaaaaaat gttatctgct ccacaattcg ctgctatgaa ggacggggct    840
tatgttatta atgcctcaag aggtactgtc gtggacattc catctctgat ccaagccgtc    900
aaggccaaca aaattgcagg tgctgcttta gatgtttatc cacatgaacc agctaagaac    960
ggtgaaggtt catttaacga tgaacttaac agctggactt ctgagttggt ttcattacca   1020
aatataatcc tgacaccaca tattggtggc tctacagaag aagctcaaag ttcaatcggt   1080
attgaggtgg ctactgcatt gtccaaatac atcaatgaag gtaactctgt cggttctgtg   1140
aacttcccag aagtcagttt gaagtctttg gactacgatc aagagaacac agtacgtgtc   1200
ttgtatattc atcgtaacgt tcctggtgtt ttgaagaccg ttaatgatat cttatccgat   1260
cataatatcg agaaacagtt ttctgattct cacggcgaga tcgcttatct aatggcagac   1320
atctcttctg ttaatcaaag tgaaatcaag gatatatatg aaaagttgaa ccaaacttct   1380
gccaaagttt ccatcaggtt attatactaa                                    1410
```

<210> SEQ ID NO 57
<211> LENGTH: 505
<212> TYPE: PRT
<213> ORGANISM: Saccharomyces cerevisiae

<400> SEQUENCE: 57

```
Met Ser Glu Gly Pro Val Lys Phe Glu Lys Asn Thr Val Ile Ser Val
1               5                   10                  15

Phe Gly Ala Ser Gly Asp Leu Ala Lys Lys Lys Thr Phe Pro Ala Leu
            20                  25                  30

Phe Gly Leu Phe Arg Glu Gly Tyr Leu Asp Pro Ser Thr Lys Ile Phe
        35                  40                  45

Gly Tyr Ala Arg Ser Lys Leu Ser Met Glu Glu Asp Leu Lys Ser Arg
    50                  55                  60

Val Leu Pro His Leu Lys Lys Pro His Gly Glu Ala Asp Asp Ser Lys
65                  70                  75                  80

Val Glu Gln Phe Phe Lys Met Val Ser Tyr Ile Ser Gly Asn Tyr Asp
                85                  90                  95

Thr Asp Glu Gly Phe Asp Glu Leu Arg Thr Gln Ile Glu Lys Phe Glu
            100                 105                 110

Lys Ser Ala Asn Val Asp Val Pro His Arg Leu Phe Tyr Leu Ala Leu
        115                 120                 125

Pro Pro Ser Val Phe Leu Thr Val Ala Lys Gln Ile Lys Ser Arg Val
    130                 135                 140

Tyr Ala Glu Asn Gly Ile Thr Arg Val Ile Val Glu Lys Pro Phe Gly
145                 150                 155                 160

His Asp Leu Ala Ser Ala Arg Glu Leu Gln Lys Asn Leu Gly Pro Leu
                165                 170                 175
```

Phe Lys Glu Glu Leu Tyr Arg Ile Asp His Tyr Leu Gly Lys Glu
                180                 185                 190

Leu Val Lys Asn Leu Leu Val Leu Arg Phe Gly Asn Gln Phe Leu Asn
        195                 200                 205

Ala Ser Trp Asn Arg Asp Asn Ile Gln Ser Val Gln Ile Ser Phe Lys
        210                 215                 220

Glu Arg Phe Gly Thr Glu Gly Arg Gly Gly Tyr Phe Asp Ser Ile Gly
225                 230                 235                 240

Ile Ile Arg Asp Val Met Gln Asn His Leu Leu Gln Ile Met Thr Leu
                245                 250                 255

Leu Thr Met Glu Arg Pro Val Ser Phe Asp Pro Glu Ser Ile Arg Asp
        260                 265                 270

Glu Lys Val Lys Val Leu Lys Ala Val Ala Pro Ile Asp Thr Asp Asp
        275                 280                 285

Val Leu Leu Gly Gln Tyr Gly Lys Ser Glu Asp Gly Ser Lys Pro Ala
        290                 295                 300

Tyr Val Asp Asp Thr Val Asp Lys Asp Ser Lys Cys Val Thr Phe
305                 310                 315                 320

Ala Ala Met Thr Phe Asn Ile Glu Asn Glu Arg Trp Glu Gly Val Pro
                325                 330                 335

Ile Met Met Arg Ala Gly Lys Ala Leu Asn Glu Ser Lys Val Glu Ile
            340                 345                 350

Arg Leu Gln Tyr Lys Ala Val Ala Ser Gly Val Phe Lys Asp Ile Pro
        355                 360                 365

Asn Asn Glu Leu Val Ile Arg Val Gln Pro Asp Ala Ala Val Tyr Leu
        370                 375                 380

Lys Phe Asn Ala Lys Thr Pro Gly Leu Ser Asn Ala Thr Gln Val Thr
385                 390                 395                 400

Asp Leu Asn Leu Thr Tyr Ala Ser Arg Tyr Gln Asp Phe Trp Ile Pro
                405                 410                 415

Glu Ala Tyr Glu Val Leu Ile Arg Asp Ala Leu Leu Gly Asp His Ser
            420                 425                 430

Asn Phe Val Arg Asp Asp Glu Leu Asp Ile Ser Trp Gly Ile Phe Thr
        435                 440                 445

Pro Leu Leu Lys His Ile Glu Arg Pro Asp Gly Pro Thr Pro Glu Ile
450                 455                 460

Tyr Pro Tyr Gly Ser Arg Gly Pro Lys Gly Leu Lys Glu Tyr Met Gln
465                 470                 475                 480

Lys His Lys Tyr Val Met Pro Glu Lys His Pro Tyr Ala Trp Pro Val
                485                 490                 495

Thr Lys Pro Glu Asp Thr Lys Asp Asn
        500                 505

<210> SEQ ID NO 58
<211> LENGTH: 1518
<212> TYPE: DNA
<213> ORGANISM: Saccharomyces cerevisiae

<400> SEQUENCE: 58
atgagtgaag gccccgtcaa attcgaaaaa ataccgtca tatctgtctt tggtgcgtca      60
ggtgatctgg caaagaagaa gactttttccc gccttatttg ggcttttcag agaaggttac    120
cttgatccat ctaccaagat cttcggttat gcccggtcca aattgtccat ggaggaggac    180
ctgaagtccc cgtgtcctacc ccacttgaaa aaacctcacg gtgaagccga tgactctaag    240

```
gtcgaacagt tcttcaagat ggtcagctac atttcgggaa attacgacac agatgaaggc    300
ttcgacgaat taagaacgca gatcgagaaa ttcgagaaaa gtgccaacgt cgatgtccca    360
caccgtctct tctatctggc cttgccgcca agcgtttttt tgacggtggc caagcagatc    420
aagagtcgtg tgtacgcaga gaatggcatc acccgtgtaa tcgtagagaa acctttcggc    480
cacgacctgg cctctgccag ggagctgcaa aaaaacctgg ggcccctctt taagaagaa     540
gagttgtaca gaattgacca ttacttgggt aaagagttgg tcaagaatct tttagtcttg    600
aggttcggta accagttttt gaatgcctcg tggaatagag acaacattca aagcgttcag    660
atttcgttta aagagaggtt cggcaccgaa ggccgtggcg gctatttcga ctctataggc    720
ataatcagag acgtgatgca gaaccatctg ttacaaatca tgactctctt gactatggaa    780
agaccggtgt cttttgaccc ggaatctatt cgtgacgaaa aggttaaggt tctaaaggcc    840
gtggccccca tcgacacgga cgacgtcctc ttgggccagt acggtaaatc tgaggacggg    900
tctaagcccg cctacgtgga tgatgacact gtagacaagg actctaaatg tgtcactttt    960
gcagcaatga ctttcaacat cgaaaacgag cgttgggagg gcgtccccat catgatgcgt   1020
gccggtaagg ctttgaatga gtccaaggtg gagatcagac tgcagtacaa agcggtcgca   1080
tcgggtgtct tcaaagacat tccaaataac gaactggtca tcagagtgca gcccgatgcc   1140
gctgtgtacc taaagtttaa tgctaagacc cctggtctgt caaatgctac ccaagtcaca   1200
gatctgaatc taacttacgc aagcaggtac caagacttt ggattccaga ggcttacgag    1260
gtgttgataa gagacgccct actgggtgac cattccaact ttgtcagaga tgacgaattg   1320
gatatcagtt ggggcatatt caccccatta ctgaagcaca tagagcgtcc ggacggtcca   1380
acaccggaaa tttaccccta cggatcaaga ggtccaaagg gattgaagga atatatgcaa   1440
aaacacaagt atgttatgcc cgaaaagcac ccttacgctt ggcccgtgac taagccagaa   1500
gatacgaagg ataattag                                                  1518

<210> SEQ ID NO 59
<211> LENGTH: 342
<212> TYPE: PRT
<213> ORGANISM: Saccharomyces cerevisiae

<400> SEQUENCE: 59

Met Val Leu Val Lys Gln Val Arg Leu Gly Asn Ser Gly Leu Lys Ile
1               5                   10                  15

Ser Pro Ile Val Ile Gly Cys Met Ser Tyr Gly Ser Lys Lys Trp Ala
            20                  25                  30

Asp Trp Val Ile Glu Asp Lys Thr Gln Ile Phe Lys Ile Met Lys His
        35                  40                  45

Cys Tyr Asp Lys Gly Leu Arg Thr Phe Asp Thr Ala Asp Phe Tyr Ser
    50                  55                  60

Asn Gly Leu Ser Glu Arg Ile Ile Lys Glu Phe Leu Glu Tyr Tyr Ser
65                  70                  75                  80

Ile Lys Arg Glu Thr Val Val Ile Met Thr Lys Ile Tyr Phe Pro Val
                85                  90                  95

Asp Glu Thr Leu Asp Leu His His Asn Phe Thr Leu Asn Glu Phe Glu
            100                 105                 110

Glu Leu Asp Leu Ser Asn Gln Arg Gly Leu Ser Arg Lys His Ile Ile
        115                 120                 125

Ala Gly Val Glu Asn Ser Val Lys Arg Leu Gly Thr Tyr Ile Asp Leu
    130                 135                 140
```

```
Leu Gln Ile His Arg Leu Asp His Glu Thr Pro Met Lys Glu Ile Met
145                 150                 155                 160

Lys Ala Leu Asn Asp Val Val Glu Ala Gly His Val Arg Tyr Ile Gly
                165                 170                 175

Ala Ser Ser Met Leu Ala Thr Glu Phe Ala Glu Leu Gln Phe Thr Ala
            180                 185                 190

Asp Lys Tyr Gly Trp Phe Gln Phe Ile Ser Ser Gln Ser Tyr Tyr Asn
        195                 200                 205

Leu Leu Tyr Arg Glu Asp Arg Glu Leu Ile Pro Phe Ala Lys Arg
    210                 215                 220

His Asn Ile Gly Leu Leu Pro Trp Ser Pro Asn Ala Arg Gly Met Leu
225                 230                 235                 240

Thr Arg Pro Leu Asn Gln Ser Thr Asp Arg Ile Lys Ser Asp Pro Thr
                245                 250                 255

Phe Lys Ser Leu His Leu Asp Asn Leu Glu Glu Gln Lys Glu Ile
            260                 265                 270

Ile Asn Arg Val Glu Lys Val Ser Lys Asp Lys Val Ser Met Ala
        275                 280                 285

Met Leu Ser Ile Ala Trp Val Leu His Lys Gly Cys His Pro Ile Val
290                 295                 300

Gly Leu Asn Thr Thr Ala Arg Val Asp Glu Ala Ile Ala Ala Leu Gln
305                 310                 315                 320

Val Thr Leu Thr Glu Glu Ile Lys Tyr Leu Glu Glu Pro Tyr Lys
                325                 330                 335

Pro Gln Arg Gln Arg Cys
            340

<210> SEQ ID NO 60
<211> LENGTH: 1029
<212> TYPE: DNA
<213> ORGANISM: Saccharomyces cerevisiae

<400> SEQUENCE: 60
atggttttag ttaagcaggt aagactcggt aactcaggtc ttaagatatc accgatagtg      60
ataggatgta tgtcatacgg gtccaagaaa tgggcggact gggtcataga ggacaagacc     120
caaattttca agattatgaa gcattgttac gataaaggtc ttcgtacttt tgacacagca     180 gattttatt ctaatggttt gagtgaaaga taattaagg agtttctgga gtactacagt      240
ataaagagag aaacggtggt gattatgacc aaaatttact tcccagttga tgaaacgctt     300
gatttgcatc ataacttcac tttaaatgaa tttgaagaat tggacttgtc caaccagcgg     360
ggtttatcca gaaagcatat aattgctggt gtcgagaact ctgtgaaaag actgggcaca     420
tatatagacc ttttacaaat tcacagatta gatcatgaaa cgccaatgaa agagatcatg     480
aaggcattga atgatgttgt tgaagcgggc cacgttagat acattggggc ttcgagtatg     540
ttggcaactg aatttgcaga actgcagttc acagccgata aatatggctg tttcagttc      600 atttcttcgc agtcttacta caatttgctc tatcgtgaag atgaacgcga attgattcct     660
tttgccaaaa gacacaatat tggtttactt ccatggtctc ctaacgcacg aggcatgttg     720
actcgtcctc tgaaccaaag cacggacagg attaagagtg atccaacttt caagtcgtta     780
catttggata atctcgaaga gaacaaaag gaaattataa atcgtgtgga aaaggtgtcg     840
aaggacaaaa aagtctcgat ggctatgctc tccattgcat gggttttgca taaggatgt      900 caccctattg tgggattgaa cactacagca agagtagacg aagcgattgc cgcactacaa     960
```

```
gtaactctaa cagaagaaga gataaagtac ctcgaggagc cctacaaacc ccagaggcaa    1020
agatgttaa                                                            1029
```

<210> SEQ ID NO 61
<211> LENGTH: 344
<212> TYPE: PRT
<213> ORGANISM: Saccharomyces cerevisiae

<400> SEQUENCE: 61

```
Met Ser Ser Ser Val Ala Ser Thr Glu Asn Ile Val Glu Asn Met Leu
1               5                   10                  15

His Pro Lys Thr Thr Glu Ile Tyr Phe Ser Leu Asn Asn Gly Val Arg
            20                  25                  30

Ile Pro Ala Leu Gly Leu Gly Thr Ala Asn Pro His Glu Lys Leu Ala
        35                  40                  45

Glu Thr Lys Gln Ala Val Lys Ala Ala Ile Lys Ala Gly Tyr Arg His
    50                  55                  60

Ile Asp Thr Ala Trp Ala Tyr Glu Thr Glu Pro Phe Val Gly Glu Ala
65                  70                  75                  80

Ile Lys Glu Leu Leu Glu Asp Gly Ser Ile Lys Arg Glu Asp Leu Phe
                85                  90                  95

Ile Thr Thr Lys Val Trp Pro Val Leu Trp Asp Glu Val Asp Arg Ser
            100                 105                 110

Leu Asn Glu Ser Leu Lys Ala Leu Gly Leu Glu Tyr Val Asp Leu Leu
        115                 120                 125

Leu Gln His Trp Pro Leu Cys Phe Glu Lys Ile Lys Asp Pro Lys Gly
    130                 135                 140

Ile Ser Gly Leu Val Lys Thr Pro Val Asp Asp Ser Gly Lys Thr Met
145                 150                 155                 160

Tyr Ala Ala Asp Gly Asp Tyr Leu Glu Thr Tyr Lys Gln Leu Glu Lys
                165                 170                 175

Ile Tyr Leu Asp Pro Asn Asp His Arg Val Arg Ala Ile Gly Val Ser
            180                 185                 190

Asn Phe Ser Ile Glu Tyr Leu Glu Arg Leu Ile Lys Glu Cys Arg Val
        195                 200                 205

Lys Pro Thr Val Asn Gln Val Glu Thr His Pro His Leu Pro Gln Met
    210                 215                 220

Glu Leu Arg Lys Phe Cys Phe Met His Asp Ile Leu Leu Thr Ala Tyr
225                 230                 235                 240

Ser Pro Leu Gly Ser His Gly Ala Pro Asn Leu Lys Ile Pro Leu Val
                245                 250                 255

Lys Lys Leu Ala Glu Lys Tyr Asn Val Thr Gly Asn Asp Leu Leu Ile
            260                 265                 270

Ser Tyr His Ile Arg Gln Gly Thr Ile Val Ile Pro Arg Ser Leu Asn
        275                 280                 285

Pro Val Arg Ile Ser Ser Ile Glu Phe Ala Ser Leu Thr Lys Asp
    290                 295                 300

Glu Leu Gln Glu Leu Asn Asp Phe Gly Glu Lys Tyr Pro Val Arg Phe
305                 310                 315                 320

Ile Asp Glu Pro Phe Ala Ala Ile Leu Pro Glu Phe Thr Gly Asn Gly
                325                 330                 335

Pro Asn Leu Asp Asn Leu Lys Tyr
            340
```

<210> SEQ ID NO 62
<211> LENGTH: 1035
<212> TYPE: DNA
<213> ORGANISM: Saccharomyces cerevisiae

<400> SEQUENCE: 62

```
atgtcttctt cagtagcctc aaccgaaaac atagtcgaaa atatgttgca tccaaagact    60
acagaaatat acttttcact caacaatggt gttcgtatcc cagcactggg tttggggaca   120
gcaaatcctc acgaaaagtt agctgaaaca aaacaagccg taaaagctgc aatcaaagct   180
ggatacaggc acattgatac tgcttgggcc tacgagacag agccattcgt aggtgaagcc   240
atcaaggagt tattagaaga tggatctatc aaaaggagg atcttttcat aaccacaaaa    300
gtgtggccgg ttctatggga cgaagtggac agatcattga atgaatcttt gaaagcttta   360
ggcttggaat acgtcgactt gctcttgcaa cattggccgc tatgttttga aaagattaag   420
gaccctaagg ggatcagcgg actggtgaag actccggttg atgattctgg aaaaacaatg   480
tatgctgccg acggtgacta tttagaaact acaagcaat tggaaaaaat ttaccttgat    540
cctaacgatc atcgtgtgag agccattggt gtctcaaatt tttccattga gtatttggaa   600
cgtctcatta aggaatgcag agttaagcca acggtgaacc aagtggaaac tcaccctcac   660
ttaccacaaa tggaactaag aaagttctgc tttatgcacg acattctgtt aacagcatac   720
tcaccattag gttcccatgg cgcaccaaac ttgaaaatcc cactagtgaa aaagcttgcc   780
gaaaagtaca atgtcacagg aaatgacttg ctaatttctt accatattag acaaggcact   840
atcgtaattc cgagatcctt gaatccagtt aggatttcct cgagtattga attcgcatct   900
ttgacaaagg atgaattaca agagttgaac gacttcggtg aaaaatacc agtgagattc    960
atcgatgagc catttgcagc catccttcca gagtttactg gtaacggacc aaacttggac  1020
aatttaaagt attaa                                                   1035
```

<210> SEQ ID NO 63
<211> LENGTH: 6311
<212> TYPE: DNA
<213> ORGANISM: Artificial Sequence
<220> FEATURE:
<223> OTHER INFORMATION: vector pEVE2120

<400> SEQUENCE: 63

```
ctgcattaat gaatcggcca acgcgcgggg agaggcggtt tgcgtattgg gcgctcttcc    60
gcttcctcgc tcactgactc gctgcgctcg gtcgttcggc tgcggcgagc ggtatcagct   120
cactcaaagg cggtaatacg gttatccaca gaatcagggg ataacgcagg aaagaacatg   180
tgagcaaaag gccagcaaaa ggccaggaac cgtaaaaagg ccgcgttgct ggcgtttttc   240
cataggctcc gcccccctga cgagcatcac aaaaatcgac gctcaagtca gaggtggcga   300
aacccgacag gactataaag ataccaggcg tttccccctg gaagctccct cgtgcgctct   360
cctgttccga ccctgccgct taccggatac ctgtccgcct ttctcccttc gggaagcgtg   420
gcgctttctc atagctcacg ctgtaggtat ctcagttcgg tgtaggtcgt tcgctccaag   480
ctgggctgtg tgcacgaacc ccccgttcag cccgaccgct gcgccttatc cggtaactat   540
cgtcttgagt ccaacccggt aagacacgac ttatcgccac tggcagcagc cactggtaac   600
aggattagca gagcgaggta tgtaggcggt gctacagagt tcttgaagtg gtggcctaac   660
tacggctaca ctagaaggac agtatttggt atctgcgctc tgctgaagcc agttaccttc   720
ggaaaaagag ttggtagctc ttgatccggc aaacaaacca ccgctggtag cggtggtttt   780
```

```
tttgtttgca agcagcagat tacgcgcaga aaaaaaggat ctcaagaaga tcctttgatc      840
ttttctacgg ggtctgacgc tcagtggaac gaaaactcac gttaagggat tttggtcatg      900
agattatcaa aaaggatctt cacctagatc cttttaaatt aaaaatgaag ttttaaatca      960
atctaaagta tatatgagta aacttggtct gacagttacc aatgcttaat cagtgaggca     1020
cctatctcag cgatctgtct atttcgttca tccatagttg cctgactccc cgtcgtgtag     1080
ataactacga tacgggaggg cttaccatct ggccccagtg ctgcaatgat accgcgagac     1140
ccacgctcac cggctccaga tttatcagca ataaaccagc cagccggaag ggccgagcgc     1200
agaagtggtc ctgcaacttt atccgcctcc atccagtcta ttaattgttg ccgggaagct     1260
agagtaagta gttcgccagt taatagtttg cgcaacgttg ttgccattgc tacaggcatc     1320
gtggtgtcac gctcgtcgtt tggtatggct tcattcagct ccggttccca acgatcaagg     1380
cgagttacat gatcccccat gttgtgcaaa aaagcggtta gctccttcgg tcctccgatc     1440
gttgtcagaa gtaagttggc cgcagtgtta tcactcatgg ttatggcagc actgcataat     1500
tctcttactg tcatgccatc cgtaagatgc ttttctgtga ctggtgagta ctcaaccaag     1560
tcattctgag aatagtgtat gcggcgaccg agttgctctt gcccggcgtc aatacgggat     1620
aataccgcgc cacatagcag aactttaaaa gtgctcatca ttggaaaacg ttcttcgggg     1680
cgaaaactct caaggatctt accgctgttg agatccagtt cgatgtaacc cactcgtgca     1740
cccaactgat cttcagcatc ttttactttc accagcgttt ctgggtgagc aaaaacagga     1800
aggcaaaatg ccgcaaaaaa gggaataagg gcgacacgga aatgttgaat actcatactc     1860
ttcctttttc aatattattg aagcatttat cagggttatt gtctcatgag cggatacata     1920
tttgaatgta tttagaaaaa taaacaaata ggggttccgc gcacatttcc ccgaaaagtg     1980
ccacctgggc ccttttcatc acgtgctata aaaataatta aatttaaat ttttaatat     2040 aaatatataa attaaaaata gaaagtaaaa aagaaatta agaaaaaat gttttttgtt     2100 ttccgaagat gtaaaagact ctagggggat cgccaacaaa tactaccttt tatcttgctc     2160
ttcctgctct caggtattaa tgccgaattg tttcatcttg tctgtgtaga agaccacaca     2220
cgaaaatcct gtgattttac attttactta tcgttaatcg aatgtatatc tatttaatct     2280
gcttttcttg tctaataaat atatatgtaa agtacgcttt ttgttgaaat ttttaaacc     2340 tttgtttatt tttttttctt cattccgtaa ctcttctacc ttctttatt actttctaaa     2400 atccaaatac aaaacataaa aataaataaa cacagagtaa attcccaaat tattccatca     2460
ttaaaagata cgaggcgcgt gtaagttaca ggcaagcgat ccgtcctaag aaaccattat     2520
tatcatgaca ttaacctata aaaataggcg tatcacgagg ccctttcgtc tcgcgcgttt     2580
cggtgatgac ggtgaaaacc tctgacacat gcagctcccg gagacggtca cagcttgtct     2640
gtaagcggat gccgggagca gacaagcccg tcagggcgcg tcagcgggtg ttggcgggtg     2700
tcggggctgg cttaactatg cggcatcaga gcagattgta ctgagagtgc accataccac     2760
agcttttcaa ttcaattcat catttttttt ttattctttt ttttgatttc ggtttctttg     2820 aaatttttt gattcggtaa tctccgaaca gaaggaagaa cgaaggaagg agcacagact     2880
tagattggta tatatacgca tatgtagtgt tgaagaaaca tgaaattgcc cagtattctt     2940
aacccaactg cacagaacaa aaacctgcag gaaacgaaga taaatcatgt cgaaagctac     3000
atataaggaa cgtgctgcta ctcatcctag tcctgttgct gccaagctat ttaatatcat     3060
gcacgaaaag caaacaaact tgtgtgcttc attggatgtt cgtaccacca aggaattact     3120
ggagttagtt gaagcattag gtcccaaaat ttgtttacta aaaacacatg tggatatctt     3180
```

```
gactgatttt tccatggagg gcacagttaa gccgctaaag gcattatccg ccaagtacaa   3240
ttttttactc ttcgaagaca gaaaatttgc tgacattggt aatacagtca aattgcagta   3300
ctctgcgggt gtatacagaa tagcagaatg ggcagacatt acgaatgcac acggtgtggt   3360
gggcccaggt attgttagcg gtttgaagca ggcggcagaa gaagtaacaa aggaacctag   3420
aggccttttg atgttagcag aattgtcatg caagggctcc ctatctactg gagaatatac   3480
taagggtact gttgacattg cgaagagcga caaagatttt gttatcggct ttattgctca   3540
aagagacatg ggtggaagag atgaaggtta cgattggttg attatgacac ccggtgtggg   3600
tttagatgac aagggagacg cattgggtca acagtataga accgtggatg atgtggtctc   3660
tacaggatct gacattatta ttgttggaag aggactattt gcaaagggaa gggatgctaa   3720
ggtagagggt gaacgttaca gaaaagcagg ctgggaagca tatttgagaa gatgcggcca   3780
gcaaaactaa aaaactgtat tataagtaaa tgcatgtata ctaaactcac aaattagagc   3840
ttcaatttaa ttatatcagt tattacccta tgcggtgtga ataccgcac agatgcgtaa   3900 ggagaaaata ccgcatcagg aaattgtaaa cgttaatatt ttgttaaaat tcgcgttaaa   3960
tttttgttaa atcagctcat tttttaacca ataggccgaa atcggcaaaa tcccttataa   4020
atcaaaagaa tagaccgaga tagggttgag tgttgttcca gtttggaaca agagtccact   4080
attaaagaac gtggactcca acgtcaaagg gcgaaaaacc gtctatcagg gcgatggccc   4140
actacgtgaa ccatcaccct aatcaagttt ttggggtcg aggtgccgta aagcactaaa   4200
tcggaaccct aaagggagcc ccgatttag agcttgacgg ggaaagccgg cgaacgtggc   4260
gagaaaggaa gggaagaaag cgaaaggagc gggcgctagg gcgctggcaa gtgtagcggt   4320
cacgctgcgc gtaaccacca cacccgccgc gcttaatgcg ccgctacagg gcgcgtcgcg   4380
ccattcgcca ttcaggctgc gcaactgttg ggaagggcga tcggtgcggg cctcttcgct   4440
attacgccag ctgatttgcc cgggcagttc aggctcatca ggcgcgccat gcaggatgca   4500
ttgatcagtt aacccatggg catgcgaagg aaaatgagaa atatcgaggg agacgattca   4560
gaggagcagg acaaactata accgactgtt tgttggagga tgccgtacat aacgaacact   4620
gctgaagcta ccatgtctac agtttagagg aatgggtaca actcacaggc gagggatggt   4680
gttcactcgt gctagcaaac gcggtgggag caaaaagtag aatattatct tttattcgtg   4740
aaacttcgaa cactgtcatc taaagatgct atatactaat ataggcatac ttgataatga   4800
aaactataaa tcgtaaagac ataagagatc cgcggatccc cgggtcgagc ctgaacggcc   4860
tcgaggcctg aacggcctcg acgaattcat tatttgtaga gctcatccat gccatgtgta   4920
atcccagcag cagttacaaa ctcaagaagg accatgtggt cacgcttttc gttgggatct   4980
ttcgaaaggg cagattgtgt cgacaggtaa tggttgtctg gtaaaaggac agggccatcg   5040
ccaattggag tattttgttg ataatggtct gctagttgaa cggatccatc ttcaatgttg   5100
tggcgaattt tgaagttagc tttgattcca ttctttttgtt tgtctgccgt gatgtataca   5160
ttgtgtgagt tatagttgta ctcgagtttg tgtccgagaa tgtttccatc ttcttttaaaa   5220 tcaataccttt ttaactcgat acgattaaca agggtatcac cttcaaactt gacttcagca   5280
cgcgtcttgt agttcccgtc atctttgaaa gatatagtgc gttcctgtac ataaccttcg   5340
ggcatggcac tcttgaaaaa gtcatgccgt ttcatatgat ccggataacg ggaaaagcat   5400
tgaacaccat aagagaaagt agtgacaagt gttggccatg gaacaggtag ttttccagta   5460
gtgcaaataa atttaagggt aagctggccc tgcaggccaa gctttgtttt atatttgttg   5520
```

| | |
|---|---|
| taaaaagtag ataattactt ccttgatgat ctgtaaaaaa gagaaaaaga aagcatctaa | 5580 |
| gaacttgaaa aactacgaat tagaaaagac caaatatgta tttcttgcat tgaccaattt | 5640 |
| atgcaagttt atatatatgt aaatgtaagt ttcacgaggt tctactaaac taaaccaccc | 5700 |
| ccttggttag aagaaaagag tgtgtgagaa caggctgttg ttgtcacacg attcggacaa | 5760 |
| ttctgtttga aagagagaga gtaacagtac gatcgaacga actttgctct ggagatcaca | 5820 |
| gtgggcatca tagcatgtgg tactaaaccc tttcccgcca ttccagaacc ttcgattgct | 5880 |
| tgttacaaaa cctgtgagcc gtcgctagga ccttgttgtg tgacgaaatt ggaagctgca | 5940 |
| atcaatagga agacaggaag tcgagcgtgt ctgggttttt tcagttttgt tcttttttgca | 6000 |
| aacaaatcac gagcgacggt aatttctttc tcgataagag gccacgtgct ttatgagggt | 6060 |
| aacatcaatt caagaaggag ggaaacactt cctttttctg gccctgataa tagtatgagg | 6120 |
| gtgaagccaa ataaaggat tcgcgcccaa atcggcatct ttaaatgcag gtatgcgata | 6180 |
| gttcctcact ctttccttac tcacgagtaa ttcttgcaaa tgcctattat gcagatgtta | 6240 |
| taatatctgt gcgtagatct gatatccctg catggcgcgc ctgatgagcc tgaactgccc | 6300 |
| gggcaaatca g | 6311 |

<210> SEQ ID NO 64
<211> LENGTH: 6248
<212> TYPE: DNA
<213> ORGANISM: Artificial Sequence
<220> FEATURE:
<223> OTHER INFORMATION: vector pEVE27735

<400> SEQUENCE: 64

| | |
|---|---|
| ctgatttgcc cgggcagttc aggctcatca ggcgcgccat gcagggatat cagatctacg | 60 |
| cacagatatt ataacatctg cataataggc atttgcaaga attactcgtg agtaaggaaa | 120 |
| gagtgaggaa ctatcgcata cctgcattta aagatgccga tttgggcgcg aatcctttat | 180 |
| tttggcttca ccctcatact attatcaggg ccagaaaaag gaagtgtttc cctccttctt | 240 |
| gaattgatgt taccctcata aagcacgtgg cctcttatcg agaaagaaat taccgtcgct | 300 |
| cgtgatttgt ttgcaaaaag aacaaaactg aaaaaaccca gacacgctcg acttcctgtc | 360 |
| ttcctattga ttgcagcttc caatttcgtc acacaacaag gtcctagcga cggctcacag | 420 |
| gttttgtaac aagcaatcga aggttctgga atggcgggaa agggtttagt accacatgct | 480 |
| atgatgccca ctgtgatctc cagagcaaag ttcgttcgat cgtactgtta ctctctctct | 540 |
| ttcaaacaga attgtccgaa tcgtgtgaca acaacagcct gttctcacac actctttttct | 600 |
| tctaaccaag ggggtggttt agtttagtag aacctcgtga aacttacatt tacatatata | 660 |
| taaacttgca taaattggtc aatgcaagaa atacatattt ggtcttttct aattcgtagt | 720 |
| ttttcaagtt cttagatgct ttcttttttct cttttttaca gatcatcaag gaagtaatta | 780 |
| tctacttttt acaacaaata taaaacaaag cttaaaatga aatgaaagt cgtcttggtc | 840 |
| gttttcttga tgttcattgg tactatcaac tgcgaaagat tgatcttcaa tggtagacct | 900 |
| ttgttgcaca gagttaccaa agaagaaacc gttatgttgt accacgaatt ggaagttgct | 960 |
| gcttctgctg atgaagtttg gtctgttgaa ggttctccag aattgggttt acatttgcca | 1020 |
| gatttgttgc cagctggtat ttttgccaag ttcgaaatta ctggtgatgg tggtgaaggt | 1080 |
| tccattttgg atatgacttt tccaccaggt caattcccac atcattacag agaaaagttc | 1140 |
| gtcttttttcg accacaagaa cagatacaag ttggtcgaac aaatcgatgg tgatttcttc | 1200 |
| gatttgggtg ttacttacta catggacacc attagagttg ttgctactgg tccagattct | 1260 |

```
tgcgttatta agtctactac tgaataccac gtcaagccag aatttgctaa aatcgttaag    1320
ccattgatcg ataccgttcc attggctatt atgtctgaag ctattgccaa ggttgtcttg    1380
gaaaacaaac acaagtcatc tgaatgaaag actccgcgga tctcttatgt ctttacgatt    1440
tatagttttc attatcaagt atgcctatat tagtatatag catctttaga tgacagtgtt    1500
cgaagtttca cgaataaaag ataatattct acttttttgct cccaccgcgt ttgctagcac    1560
gagtgaacac catccctcgc ctgtgagttg tacccattcc tctaaactgt agacatggta    1620
gcttcagcag tgttcgttat gtacggcatc ctccaacaaa cagtcggtta tagtttgtcc    1680
tgctcctctg aatcgtctcc ctcgatattt ctcattttcc ttcgcatgcc catgggttaa    1740
ctgatcaatg catcctgcat ggcgcgcctg atgagcctga actgcccggg caaatcagct    1800
ggcgtaatag cgaagaggcc cgcaccgatc gcccttccca acagttgcgc agcctgaatg    1860
gcgaatggcg cgacgcgccc tgtagcggcg cattaagcgc ggcgggtgtg gtggttacgc    1920
gcagcgtgac cgctacactt gccagcgccc tagcgcccgc tcctttcgct ttcttccctt    1980
cctttctcgc cacgttcgcc ggctttcccc gtcaagctct aaatcggggg ctccctttag    2040
ggttccgatt tagtgcttta cggcacctcg accccaaaaa acttgattag ggtgatggtt    2100
cacgtagtgg gccatcgccc tgatagacgg ttttcgccc tttgacgttg gagtccacgt    2160
tctttaatag tggactcttg ttccaaactg gaacaacact caaccctatc tcggtctatt    2220
cttttgattt ataagggatt ttgccgattt cggcctattg gttaaaaaat gagctgattt    2280
aacaaaaatt taacgcgaat tttaacaaaa tattaacgtt tacaatttcc tgatgcggta    2340
ttttctcctt acgcatctgt gcggtatttc acaccgcata gggtaataac tgatataatt    2400
aaattgaagc tctaatttgt gagtttagta tacatgcatt tacttataat acagttttt    2460 agttttgctg gccgcatctt ctcaaatatg cttcccagcc tgcttttctg taacgttcac    2520
cctctacctt agcatccctt ccctttgcaa atagtcctct tccaacaata taatgtcag    2580 atcctgtaga gaccacatca tccacggttc tatactgttg acccaatgcg tctcccttgt    2640
catctaaacc cacaccgggt gtcataatca accaatcgta accttcatct cttccaccca    2700
tgtctctttg agcaataaag ccgataacaa atctttgtc gctcttcgca atgtcaacag    2760 taccccttagt atattctcca gtagataggg agccttgca tgacaattct gctaacatca    2820
aaaggcctct aggttccttt gttacttctt ctgccgcctg cttcaaaccg ctaacaatac    2880
ctgggcccac cacaccgtgt gcattcgtaa tgtctgccca ttctgctatt ctgtatacac    2940
ccgcagagta ctgcaatttg actgtattac caatgtcagc aaattttctg tcttcgaaga    3000
gtaaaaaatt gtacttggcg gataatgcct ttagcggctt aactgtgccc tccatggaaa    3060
aatcagtcaa gatatccaca tgtgttttta gtaaacaaat tttgggacct aatgcttcaa    3120
ctaactccag taattccttg gtggtacgaa catccaatga agcacacaag tttgtttgct    3180
tttcgtgcat gatattaaat agcttggcag caacaggact aggatgagta gcagcacgtt    3240
ccttatatgt agctttcgac atgatttatc ttcgtttcct gcaggttttt gttctgtgca    3300
gttgggttaa gaatactggg caatttcatg tttcttcaac actacatatg cgtatatata    3360
ccaatctaag tctgtgctcc ttccttcgtt cttccttctg ttcggagatt accgaatcaa    3420
aaaaatttca agaaaccga atcaaaaaa aagaataaaa aaaaatgat gaattgaatt    3480 gaaaagctgt ggtatggtgc actctcagta caatctgctc tgatgccgca tagttaagcc    3540
agccccgaca cccgccaaca cccgctgacg cgccctgacg ggcttgtctg ctcccggcat    3600
```

```
ccgcttacag acaagctgtg accgtctccg ggagctgcat gtgtcagagg tttttcaccgt    3660 catcaccgaa acgcgcgaga cgaaagggcc tcgtgatacg cctattttta taggttaatg    3720
tcatgataat aatggtttct taggacggat cgcttgcctg taacttacac gcgcctcgta    3780
tcttttaatg atggaataat ttgggaattt actctgtgtt tatttatttt tatgttttgt    3840
atttggattt tagaaagtaa ataaagaagg tagaagagtt acggaatgaa gaaaaaaaaa    3900
taaacaaagg tttaaaaaat ttcaacaaaa agcgtacttt acatatatat ttattagaca    3960
agaaaagcag attaaataga tatacattcg attaacgata agtaaaatgt aaaatcacag    4020
gattttcgtg tgtggtcttc tacacagaca agatgaaaca attcggcatt aatacctgag    4080
agcaggaaga gcaagataaa aggtagtatt tgttggcgat cccctagag tcttttacat      4140 cttcggaaaa caaaaactat ttttctttta atttcttttt ttactttcta ttttaatttt     4200
atatatttat attaaaaaat ttaaattata attattttta tagcacgtga tgaaaaggac    4260
ccaggtggca cttttcgggg aaatgtgcgc ggaaccccta tttgtttatt tttctaaata    4320
cattcaaata tgtatccgct catgagacaa taaccctgat aaatgcttca ataatattga    4380
aaaaggaaga gtatgagtat tcaacatttc cgtgtcgccc ttattccctt ttttgcggca    4440
ttttgccttc ctgtttttgc tcacccagaa acgctggtga agtaaaagatgctgaagat      4500 cagttgggtg cacgagtggg ttacatcgaa ctggatctca acagcggtaa gatccttgag    4560
agttttcgcc ccgaagaacg ttttccaatg atgagcactt taaagttct gctatgtggc     4620 gcggtattat cccgtattga cgccgggcaa gagcaactcg gtcgccgcat acactattct    4680
cagaatgact tggttgagta ctcaccagtc acagaaaagc atcttacgga tggcatgaca    4740
gtaagagaat tatgcagtgc tgccataacc atgagtgata acactgcggc caacttactt    4800
ctgacaacga tcggaggacc gaaggagcta accgcttttt tgcacaacat gggggatcat    4860
gtaactcgcc ttgatcgttg ggaaccggag ctgaatgaag ccataccaaa cgacgagcgt    4920
gacaccacga tgcctgtagc aatggcaaca acgttgcgca aactattaac tggcgaacta    4980
cttactctag cttcccggca acaattaata gactggatgg aggcggataa agttgcagga    5040
ccacttctgc gctcggccct tccggctggc tggtttattg ctgataaatc tggagccggt    5100
gagcgtgggt ctcgcggtat cattgcagca ctggggccag atggtaagcc ctcccgtatc    5160
gtagttatct acacgacggg gagtcaggca actatggatg aacgaaatag acagatcgct    5220
gagataggtg cctcactgat taagcattgg taactgtcag accaagttta ctcatatata    5280
ctttagattg atttaaaact tcatttttaa tttaaaagga tctaggtgaa gatccttttt    5340
gataatctca tgaccaaaat cccttaacgt gagttttcgt tccactgagc gtcagacccc    5400
gtagaaaaga tcaaaggatc ttcttgagat cctttttttc tgcgcgtaat ctgctgcttg    5460
caaacaaaaa aaccaccgct accagcggtg gtttgtttgc cggatcaaga gctaccaact    5520
ctttttccga aggtaactgg cttcagcaga gcgcagatac caaatactgt ccttctagtg    5580
tagccgtagt taggccacca cttcaagaac tctgtagcac cgcctacata cctcgctctg    5640
ctaatcctgt taccagtggc tgctgccagt ggcgataagt cgtgtcttac cgggttggac    5700
tcaagacgat agttaccgga taaggcgcag cggtcgggct gaacggggggttcgtgcaca    5760 cagcccagct tggagcgaac gacctacacc gaactgagat acctacagcg tgagctatga    5820
gaaagcgcca cgcttcccga agggagaaag gcggacaggt atccggtaag cggcagggtc    5880
ggaacaggag agcgcacgag ggagcttcca ggggggaaacg cctggtatct ttatagtcct    5940
gtcgggtttc gccacctctg acttgagcgt cgatttttgt gatgctcgtc agggggggcgg    6000
```

```
agcctatgga aaaacgccag caacgcggcc tttttacggt tcctggcctt ttgctggcct    6060
tttgctcaca tgttctttcc tgcgttatcc cctgattctg tggataaccg tattaccgcc    6120
tttgagtgag ctgataccgc tcgccgcagc cgaacgaccg agcgcagcga gtcagtgagc    6180
gaggaagcgg aagagcgccc aatacgcaaa ccgcctctcc ccgcgcgttg gccgattcat    6240
taatgcag                                                            6248
```

The invention claimed is:

1. A recombinant yeast cell capable of producing one or more benzylisoquinoline alkaloids or benzylisoquinoline alkaloid precursors, or both, comprising:
  (a) reduced or eliminated enzymatic activity of Genes de Respuesta a Estres 2 (GRE2) comprising the amino acid sequence of SEQ ID NO: 7, or an amino acid sequence having at least 90% identity to SEQ ID NO: 7; and, optionally,
  (b) reduced or eliminated enzymatic activity of one or more alcohol dehydrogenases or other aldehyde reductases, or a combination thereof,
wherein the activity of each of the enzymes in (a) and (b) is reduced or eliminated, and whereby the recombinant yeast cell is thereby capable of increased production of one or more benzylisoquinoline alkaloids or benzylisoquinoline alkaloid precursors, or both, than are produced in cells without reduced or eliminated activity of the enzymes.

2. The recombinant cell according to claim 1, wherein the cell produces one or more benzylisoquinoline alkaloid precursors.

3. The recombinant cell according to claim 1, wherein the cell produces (S)-reticuline.

4. The recombinant cell according to claim 1, wherein the cell produces (S)-norcoclaurine.

5. The recombinant cell according to claim 1, wherein GRE2 is encoded by a sequence sharing at least 90% sequence identity to the nucleic acid sequence of SEQ ID NO:8.

6. The recombinant cell according to claim 1, wherein GRE2 is encoded by the nucleotide sequence of SEQ ID NO:8.

7. The recombinant yeast cell of claim 1, wherein the one or more alcohol dehydrogenases or other aldehyde reductases, or combination thereof, is: Alcohol Dehydrogenase 3 (ADH3) comprising the amino acid sequence of SEQ ID NO:29, Alcohol Dehydrogenase 4 (ADH4) comprising the amino acid sequence of SEQ ID NO: 31, Alcohol Dehydrogenase 5 (ADH5) comprising the amino acid sequence of SEQ ID NO: 1, Alcohol Dehydrogenase 6 (ADH6) comprising the amino acid sequence of SEQ ID NO:3, Alcohol Dehydrogenase 7 (ADH7) comprising the amino acid sequence of SEQ ID NO:5, Aryl-alcohol Dehydrogenase 3 (AAD3) comprising the amino acid sequence of SEQ ID NO:25, Aryl-alcohol Dehydrogenase 3 (AAD4) comprising the amino acid sequence of SEQ ID NO:27, Butanediol dehydrogenase 1 (BDH1) comprising the amino acid sequence of SEQ ID NO:35, Butanediol dehydrogenase 2 (BDH2) comprising the amino acid sequence of SEQ ID NO:37, arabinose dehydrogenase ARA1 (ARA1) comprising the amino acid sequence of SEQ ID NO:61, glycerol dehydrogenase GCY1 (GCY1) comprising the amino acid sequence of SEQ ID NO:41, 3-hydroxyacyl-CoA dehydrogenase FOX2 comprising the amino acid sequence of SEQ ID NO:39, Aryl-alcohol Dehydrogenase YPL088W comprising the amino acid sequence of SEQ ID NO:59, glucose-6-phosphate dehydrogenase ZWF1 comprising the amino acid sequence of SEQ ID NO:57, Glycerol-3-Phosphate Dehydrogenase (GPD1) comprising the amino acid sequence of SEQ ID NO:45, HIS4 comprising the amino acid sequence of SEQ ID NO:47, NADP-specific Isocitrate Dehydrogenase (IDP1) comprising the amino acid sequence of SEQ ID NO:51, homo-isocitrate dehydrogenase (LYS12) comprising the amino acid sequence of SEQ ID NO:53, Genes de Respuesta a Estres 3 (GRE3) comprising the amino acid sequence of SEQ ID NO:9, aldehyde reductase YCR102C comprising the amino acid sequence of SEQ ID NO:19, SER33 comprising the amino acid sequence of SEQ ID NO:55, aldehyde reductase YGL039W comprising the amino acid sequence of SEQ ID NO:17, aldehyde reductase YLR460C comprising the amino acid sequence of SEQ ID NO:13, aldehyde reductase YPR127W comprising the amino acid sequence of SEQ ID NO:21, aldehyde dehydrogenase 6 (ALD6) comprising the amino acid sequence of SEQ ID NO:33, GlyOxylate Reductase (GOR1) comprising the amino acid sequence of SEQ ID NO:43, 3-Hydroxy-3-MethylGlutaryl-coenzyme a reductase (HMG1) comprising the amino acid sequence of SEQ ID NO:49, or an amino acid sequence having at least 90% identity to SEQ ID NO: 29, 31, 1, 3, 5, 25, 27, 35, 37, 61, 41, 39, 59, 57, 45, 47, 51, 53, 9, 19, 55, 17, 13, 21, 33, 43, or 49, and wherein the recombinant yeast cell comprises a native gene of the corresponding one or more alcohol dehydrogenases or other aldehyde reductases.

8. The recombinant yeast cell of claim 7, wherein: ADH3 is encoded by SEQ ID NO: 30 or a sequence sharing at least 90% sequence identity to the sequence of SEQ ID NO:30, ADH4 is encoded by SEQ ID NO:32 or a sequence sharing at least 90% sequence identity to the sequence of SEQ ID NO:32, ADH5 is encoded by SEQ ID NO:2 or a sequence sharing at least 90% sequence identity to the sequence of SEQ ID NO:2, ADH6 is encoded by SEQ ID NO:4 or a sequence sharing at least 90% sequence identity to the sequence of SEQ ID NO:4, ADH7 is encoded by SEQ ID NO:6 or a sequence sharing at least 90% sequence identity to the sequence of SEQ ID NO:6, AAD3 is encoded by SEQ ID NO:26 or a sequence sharing at least 90% sequence identity to the sequence of SEQ ID NO:26, AAD4 is encoded by SEQ ID NO:28 or a sequence sharing at least 90% sequence identity to the sequence of SEQ ID NO:28, BDH1 is encoded by SEQ ID NO:36 or a sequence sharing at least 90% sequence identity to the sequence of SEQ ID NO:36, BDH2 is encoded by SEQ ID NO:38 or a sequence sharing at least 90% sequence identity to the sequence of SEQ ID NO:38, ARA1 is encoded by SEQ ID NO:62 or a sequence sharing at least 90% sequence identity to the sequence of SEQ ID NO:62, GCY1 is encoded by SEQ ID NO:42 or a sequence sharing at least 90% sequence identity to the sequence of SEQ ID NO:42, 3-hydroxyacyl-CoA dehydrogenase FOX2 is encoded by SEQ ID NO:40 or a sequence sharing at least 90% sequence identity to the sequence of SEQ ID NO:40, Aryl-alcohol Dehydrogenase YPL088W is encoded by SEQ ID NO:60 or a sequence sharing at least 90% sequence identity to the sequence of SEQ ID NO:60, glucose-6-phosphate dehydrogenase ZWF1 is encoded by SEQ ID NO:58 or a sequence sharing at least 90% sequence identity to the sequence of SEQ ID NO:58, GPD1 is encoded by SEQ ID NO:46 or a sequence sharing at least 90% sequence identity to the sequence of SEQ ID NO:46, HIS4 is encoded by SEQ ID NO:48 or a sequence sharing at least 90% sequence identity to the sequence of SEQ ID NO:48, IDP1 is encoded by SEQ ID NO:52 or a sequence sharing at least 90% sequence identity to the sequence of SEQ ID NO:52, LYS12 is encoded by SEQ ID NO:54 or a sequence sharing at least 90% sequence identity to the sequence of SEQ ID NO:54, GRE3 is encoded by SEQ ID NO:10 or a sequence sharing at least 90% sequence identity to the sequence of SEQ ID NO:10, aldehyde reductase YCR102C is encoded by SEQ ID NO:20 or a sequence sharing at least 90% sequence identity to the sequence of SEQ ID NO:20, SER33 is encoded by SEQ ID NO:56 or a sequence sharing at least 90% sequence identity to the sequence of SEQ ID NO:56, aldehyde reductase YGL039W is encoded by SEQ ID NO:18 or a sequence sharing at least 90% sequence identity to the sequence of SEQ ID NO:18, aldehyde reductase YLR460C is encoded by SEQ ID NO:14 or a sequence sharing at least 90% sequence identity to the sequence of SEQ ID NO:14, aldehyde reductase YPR127W is encoded by SEQ ID NO:22 or a sequence sharing at least 90% sequence identity to the sequence of SEQ ID NO:22, ALD6 is encoded by SEQ ID NO:34 or a sequence sharing at least 90% sequence identity to the sequence of SEQ ID NO:34, GOR1 is encoded by SEQ ID NO:44 or a sequence sharing at least 90% sequence identity to the sequence of SEQ ID NO:44, and HMG1 is encoded by SEQ ID NO:50 or a sequence sharing at least 90% sequence identity to the sequence of SEQ ID NO:50.

9. The recombinant yeast cell of claim 1, wherein the recombinant yeast cell is *Saccharomyces cerevisiae, Schizosaccharomyces pombe*, or *Yarrowia lipolytica*.

10. The recombinant yeast cell of claim 1, wherein the recombinant yeast cell produces one or more benzylisoquinoline alkaloids selected from thebaine, morphine, neomorphine, hydrocodone, Codeine, Oxycodone, Oxymorphone, and Dihydromorphine.

11. A method for producing of a benzylisoquinoline alkaloid or a benzylisoquinoline alkaloid precursor, or both, comprising:
(a) providing a recombinant yeast cell capable of producing one or more benzylisoquinoline alkaloids or benzylisoquinoline alkaloid precursors, or both, that has reduced or eliminated enzymatic activity of Genes de Respuesta a Estres 2 (GRE2) comprising the amino acid sequence of SEQ ID NO: 7, or an amino acid sequence having at least 90% identity to SEQ ID NO: 7; and, optionally, (ii) one or more alcohol dehydrogenases or other aldehyde reductases, or a combination thereof,
(b) cultivating the recombinant yeast cell for a time sufficient for the recombinant yeast cell to produce a benzylisoquinoline alkaloid and/or a benzylisoquinoline alkaloid precursor; and, optionally,
(c) isolating the benzylisoquinoline alkaloid and/or a benzylisoquinoline alkaloid precursor from the recombinant yeast cell or from the cultivation supernatant, thereby producing a benzylisoquinoline alkaloid and/or a benzylisoquinoline alkaloid precursor.

12. The method of claim 11, wherein the recombinant yeast cell produces one or more benzylisoquinoline alkaloid precursors.

13. The method of claim 11, wherein the recombinant yeast cell produces (S)-reticuline.

14. The method of claim 11, wherein the recombinant yeast cell produces (S)-norcoclaurine.

15. The method of claim 11, wherein GRE2 is encoded by a sequence sharing at least 90% sequence identity to the nucleic acid sequence of SEQ ID NO:8.

16. The method of claim 11, wherein GRE2 is encoded by the nucleotide sequence of SEQ ID NO:8.

17. The method of claim 11, wherein the one or more alcohol dehydrogenases or other aldehyde reductases, or combination thereof, is Alcohol Dehydrogenase 3 (ADH3) comprising the amino acid sequence of SEQ ID NO:29, Alcohol Dehydrogenase 4 (ADH4) comprising the amino acid sequence of SEQ ID NO: 31, Alcohol Dehydrogenase 5 (ADH5) comprising the amino acid sequence of SEQ ID NO: 1, Alcohol Dehydrogenase 6 (ADH6) comprising the amino acid sequence of SEQ ID NO:3, Alcohol Dehydrogenase 7 (ADH7) comprising the amino acid sequence of SEQ ID NO:5, Aryl-alcohol Dehydrogenase 3 (AAD3) comprising the amino acid sequence of SEQ ID NO:25, Aryl-alcohol Dehydrogenase 3 (AAD4) comprising the amino acid sequence of SEQ ID NO:27, Butanediol dehydrogenase 1 (BDH1) comprising the amino acid sequence of SEQ ID NO:35, Butanediol dehydrogenase 2 (BDH2) comprising the amino acid sequence of SEQ ID NO:37, arabinose dehydrogenase ARA1 (ARA1) comprising the amino acid sequence of SEQ ID NO:61, glycerol dehydrogenase GCY1 (GCY1) comprising the amino acid sequence of SEQ ID NO:41, 3-hydroxyacyl-CoA dehydrogenase FOX2 comprising the amino acid sequence of SEQ ID NO:39, Aryl-alcohol Dehydrogenase YPL088W comprising the amino acid sequence of SEQ ID NO:59, glucose-6-phosphate dehydrogenase ZWF1 comprising the amino acid sequence of SEQ ID NO:57, Glycerol-3-Phosphate Dehydrogenase (GPD1) comprising the amino acid sequence of SEQ ID NO:45, HIS4 comprising the amino acid sequence of SEQ ID NO:47, NADP-specific Isocitrate Dehydrogenase (IDP1) comprising the amino acid sequence of SEQ ID NO:51, homo-isocitrate dehyrogenase (LYS12) comprising the amino acid sequence of SEQ ID NO:53, Genes de Respuesta a Estres 3 (GRE3) comprising the amino acid sequence of SEQ ID NO:9, aldehyde reductase YCR102C comprising the amino acid sequence of SEQ ID NO:19, SER33 comprising the amino acid sequence of SEQ ID NO:55, aldehyde reductase YGL039W comprising the amino acid sequence of SEQ ID NO:17, aldehyde reductase YLR460C comprising the amino acid sequence of SEQ ID NO:13, aldehyde reductase YPR127W comprising the amino acid sequence of SEQ ID NO:21, aldehyde dehydrogenase 6 (ALD6) comprising the amino acid sequence of SEQ ID NO:33, Gly-Oxylate Reductase (GOR1) comprising the amino acid sequence of SEQ ID NO:43, 3-Hydroxy-3-MethylGlutaryl-coenzyme a reductase (HMG1) comprising the amino acid sequence of SEQ ID NO:49, or an amino acid sequence having at least 90% identity to SEQ ID NO: 29, 31, 1, 3, 5, 25, 27, 35, 37, 61, 41, 39, 59, 57, 45, 47, 51, 53, 9, 19, 55, 17, 13, 21, 33, 43, or 49, and wherein the recombinant yeast cell comprises a native gene of the corresponding one or more alcohol dehydrogenases or other aldehyde reductases.

18. The method of claim 13, wherein: ADH3 is encoded by SEQ ID NO: 30 or a sequence sharing at least 90% sequence identity to the sequence of SEQ ID NO:30, ADH4 is encoded by SEQ ID NO:32 or a sequence sharing at least 90% sequence identity to the sequence of SEQ ID NO:32, ADH5 is encoded by SEQ ID NO:2 or a sequence sharing at least 90% sequence identity to the sequence of SEQ ID NO:2, ADH6 is encoded by SEQ ID NO:4 or a sequence sharing at least 90% sequence identity to the sequence of SEQ ID NO:4, ADH7 is encoded by SEQ ID NO:6 or a sequence sharing at least 90% sequence identity to the sequence of SEQ ID NO:6, AAD3 is encoded by SEQ ID NO:26 or a sequence sharing at least 90% sequence identity to the sequence of SEQ ID NO:26, AAD4 is encoded by SEQ ID NO:28 or a sequence sharing at least 90% sequence identity to the sequence of SEQ ID NO:28, BDH1 is encoded by SEQ ID NO:36 or a sequence sharing at least 90% sequence identity to the sequence of SEQ ID NO:36, BDH2 is encoded by SEQ ID NO:38 or a sequence sharing at least 90% sequence identity to the sequence of SEQ ID NO:38, ARA1 is encoded by SEQ ID NO:62 or a sequence sharing at least 90% sequence identity to the sequence of SEQ ID NO:62, GCY1 is encoded by SEQ ID NO:42 or a sequence sharing at least 90% sequence identity to the sequence of SEQ ID NO:42, 3-hydroxyacyl-CoA dehydrogenase FOX2 is encoded by SEQ ID NO:40 or a sequence sharing at least 90% sequence identity to the sequence of SEQ ID NO:40, Aryl-alcohol Dehydrogenase YPL088W is encoded by SEQ ID NO:60 or a sequence sharing at least 90% sequence identity to the sequence of SEQ ID NO:60, glucose-6-phosphate dehydrogenase ZWF1 is encoded by SEQ ID NO:58 or a sequence sharing at least 90% sequence identity to the sequence of SEQ ID NO:58, GPD1 is encoded by SEQ ID NO:46 or a sequence sharing at least 90% sequence identity to the sequence of SEQ ID NO:46, HIS4 is encoded by SEQ ID NO:48 or a sequence sharing at least 90% sequence identity to the sequence of SEQ ID NO:48, IDP1 is encoded by SEQ ID NO:52 or a sequence sharing at least 90% sequence identity to the sequence of SEQ ID NO:52, LYS12 is encoded by SEQ ID NO:54 or a sequence sharing at least 90% sequence identity to the sequence of SEQ ID NO:54, GRE3 is encoded by SEQ ID NO:10 or a sequence sharing at least 90% sequence identity to the sequence of SEQ ID NO:10, aldehyde reductase YCR102C is encoded by SEQ ID NO:20 or a sequence sharing at least 90% sequence identity to the sequence of SEQ ID NO:20, SER33 is encoded by SEQ ID NO:56 or a sequence sharing at least 90% sequence identity to the sequence of SEQ ID NO:56, aldehyde reductase YGL039W is encoded by SEQ ID NO:18 or a sequence sharing at least 90% sequence identity to the sequence of SEQ ID NO:18, aldehyde reductase YLR460C is encoded by SEQ ID NO:14 or a sequence sharing at least 90% sequence identity to the sequence of SEQ ID NO:14, aldehyde reductase YPR127W is encoded by SEQ ID NO:22 or a sequence sharing at least 90% sequence identity to the sequence of SEQ ID NO:22, ALD6 is encoded by SEQ ID NO:34 or a sequence sharing at least 90% sequence identity to the sequence of SEQ ID NO:34, GOR1 is encoded by SEQ ID NO:44 or a sequence sharing at least 90% sequence identity to the sequence of SEQ ID NO:44, and HMG1 is encoded by SEQ ID NO:50 or a sequence sharing at least 90% sequence identity to the sequence of SEQ ID NO:50.

19. The method of claim 10, wherein the recombinant yeast cell is *Saccharomyces cerevisiae, Schizosaccharomyces pombe*, or *Yarrowia lipolytica*.

20. The method of claim 10, wherein the recombinant yeast cell produces one or more benzylisoquinoline alkaloid selected from thebaine, morphine, neomorphine, hydrocodone, Codeine, Oxycodone, Oxymorphone, and Dihydromorphine.

* * * * *

UNITED STATES PATENT AND TRADEMARK OFFICE
CERTIFICATE OF CORRECTION

| | |
|---|---|
| PATENT NO. | : 11,965,181 B2 |
| APPLICATION NO. | : 17/351381 |
| DATED | : April 23, 2024 |
| INVENTOR(S) | : Hansen et al. |

It is certified that error appears in the above-identified patent and that said Letters Patent is hereby corrected as shown below:

On the Title Page

Please delete the following:
"(71) Applicant: RIVER STONE BIOTECH LLC,"

And replace with the following:
-- (71) Applicant: RIVER STONE BIOTECH, INC., --

Signed and Sealed this
Eighteenth Day of June, 2024

Katherine Kelly Vidal
*Director of the United States Patent and Trademark Office*